US012495999B2

(12) United States Patent
Al-Ali et al.

(10) Patent No.: US 12,495,999 B2
(45) Date of Patent: Dec. 16, 2025

(54) WEARABLE BAND FOR HEALTH MONITORING DEVICE

(71) Applicant: Masimo Corporation, Irvine, CA (US)

(72) Inventors: Ammar Al-Ali, San Juan Capistrano, CA (US); Chad A. DeJong, Los Angeles, CA (US); Hee Seung Lim, Irvine, CA (US); Jinwoo Kim, Los Angeles, CA (US)

(73) Assignee: Masimo Corporation, Irvine, CA (US)

( * ) Notice: Subject to any disclaimer, the term of this patent is extended or adjusted under 35 U.S.C. 154(b) by 750 days.

(21) Appl. No.: 17/813,917

(22) Filed: Jul. 20, 2022

(65) Prior Publication Data

US 2023/0058052 A1 Feb. 23, 2023

Related U.S. Application Data

(60) Provisional application No. 63/277,058, filed on Nov. 8, 2021, provisional application No. 63/275,674, filed (Continued)

(51) Int. Cl.
*A61B 5/1455* (2006.01)
*A61B 5/00* (2006.01)

(52) U.S. Cl.
CPC .......... *A61B 5/14552* (2013.01); *A61B 5/681* (2013.01); *A61B 5/7221* (2013.01); *A61B 5/742* (2013.01)

(58) Field of Classification Search
CPC .............. A61B 5/1455; A61B 5/14551; A61B 5/14552; A61B 5/681; A61B 5/7221; A61B 5/742
See application file for complete search history.

(56) References Cited

U.S. PATENT DOCUMENTS 1,750,125 A 3/1930 Prestinari
1,817,475 A 8/1931 Becker
(Continued)

FOREIGN PATENT DOCUMENTS

CA 2 454 130 2/2003
CN 1190337 8/1998
(Continued)

OTHER PUBLICATIONS

US 2024/0016391 A1, 01/2024, Lapotko et al. (withdrawn)
(Continued)

*Primary Examiner* — Eric F Winakur
(74) *Attorney, Agent, or Firm* — Knobbe, Martens, Olson & Bear, LLP

(57) ABSTRACT

A wearable device configured to monitor physiological parameters of a wearer can include: a physiological parameter measurement sensor configured to monitor a plurality of physiological parameters; a hardware processor; a display in communication with the processor; and a band configured to secure the physiological parameter measurement sensor on a wrist of the wearer. In some implementations, the hardware processor is configured to: obtain a first plurality of signals from the physiological parameter measurement sensor when the band is secured on the wrist at a first tightness; determine a signal quality responsive to the first plurality of signals; and output an indication on the display to adjust tightness of the band with respect to the wrist from the first tightness to a second tightness based on the determined signal quality.

11 Claims, 101 Drawing Sheets

Related U.S. Application Data on Nov. 4, 2021, provisional application No. 63/263,324, filed on Oct. 29, 2021, provisional application No. 63/236,164, filed on Aug. 23, 2021, provisional application No. 63/224,347, filed on Jul. 21, 2021.

(56) References Cited

U.S. PATENT DOCUMENTS

| | | | |
|---|---|---|---|
| 1,898,402 | A | 2/1933 | Smith |
| 2,505,044 | A | 4/1950 | Heinrich |
| 3,747,171 | A | 7/1973 | Montague, Jr. |
| 4,059,267 | A | 11/1977 | Noble |
| 4,197,618 | A | 4/1980 | Bourguignon |
| 4,249,267 | A | 2/1981 | Voss |
| 4,266,400 | A | 5/1981 | Tabata |
| 4,447,238 | A | 5/1984 | Eldridge, Jr. |
| 4,847,820 | A | 7/1989 | Thinesen et al. |
| 4,941,236 | A | 7/1990 | Sherman et al. |
| 4,960,128 | A | 10/1990 | Gordon et al. |
| 4,964,408 | A | 10/1990 | Hink et al. |
| 5,319,355 | A | 6/1994 | Russek |
| 5,337,744 | A | 8/1994 | Branigan |
| 5,341,805 | A | 8/1994 | Stavridi et al. |
| 5,377,676 | A | 1/1995 | Vari et al. |
| 5,431,170 | A | 7/1995 | Mathews |
| 5,436,499 | A | 7/1995 | Namavar et al. |
| 5,456,252 | A | 10/1995 | Vari et al. |
| 5,479,934 | A | 1/1996 | Imran |
| 5,482,036 | A | 1/1996 | Diab et al. |
| 5,494,043 | A | 2/1996 | O'Sullivan et al. |
| 5,533,511 | A | 7/1996 | Kaspari et al. |
| 5,590,649 | A | 1/1997 | Caro et al. |
| 5,602,924 | A | 2/1997 | Durand et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,914 | A | 9/1997 | Kalkhoran et al. |
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,758,644 | A | 6/1998 | Diab et al. |
| 5,760,910 | A | 6/1998 | Lepper, Jr. et al. |
| D407,342 | S | 3/1999 | Ishizaka |
| D408,314 | S | 4/1999 | Kojima et al. |
| 5,890,929 | A | 4/1999 | Mills et al. |
| 5,919,134 | A | 7/1999 | Diab |
| 5,987,343 | A | 11/1999 | Kinast |
| 5,997,343 | A | 12/1999 | Mills et al. |
| 6,002,952 | A | 12/1999 | Diab et al. |
| 6,010,937 | A | 1/2000 | Karam et al. |
| 6,027,452 | A | 2/2000 | Flaherty et al. |
| 6,040,578 | A | 3/2000 | Malin et al. |
| 6,066,204 | A | 5/2000 | Haven |
| 6,088,607 | A | 7/2000 | Diab et al. |
| 6,115,673 | A | 9/2000 | Malin et al. |
| 6,124,597 | A | 9/2000 | Shehada et al. |
| 6,128,521 | A | 10/2000 | Marro et al. |
| 6,129,675 | A | 10/2000 | Jay |
| 6,144,868 | A | 11/2000 | Parker |
| 6,152,754 | A | 11/2000 | Gerhardt et al. |
| 6,184,521 | B1 | 2/2001 | Coffin, IV et al. |
| 6,232,609 | B1 | 5/2001 | Snyder et al. |
| 6,241,683 | B1 | 6/2001 | Macklem et al. |
| 6,253,097 | B1 | 6/2001 | Aronow et al. |
| 6,255,708 | B1 | 7/2001 | Sudharsanan et al. |
| 6,280,381 | B1 | 8/2001 | Malin et al. |
| 6,285,896 | B1 | 9/2001 | Tobler et al. |
| 6,301,754 | B1 | 10/2001 | Grunberger et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,334,065 | B1 | 12/2001 | Al-Ali et al. |
| 6,360,114 | B1 | 3/2002 | Diab et al. |
| 6,368,283 | B1 | 4/2002 | Xu et al. |
| 6,408,491 | B2 | 6/2002 | Guyard |
| 6,411,373 | B1 | 6/2002 | Garside et al. |
| 6,415,167 | B1 | 7/2002 | Blank et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,487,429 | B2 | 11/2002 | Hockersmith et al. |
| 6,505,059 | B1 | 1/2003 | Kollias et al. |
| 6,525,386 | B1 | 2/2003 | Mills et al. |
| 6,526,300 | B1 | 2/2003 | Kiani et al. |
| 6,534,012 | B1 | 3/2003 | Hazen et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,587,196 | B1 | 7/2003 | Stippick et al. |
| 6,587,199 | B1 | 7/2003 | Luu |
| 6,597,932 | B2 | 7/2003 | Tian et al. |
| 6,606,511 | B1 | 8/2003 | Ali et al. |
| 6,635,559 | B2 | 10/2003 | Greenwald et al. |
| 6,639,668 | B1 | 10/2003 | Trepagnier |
| 6,640,116 | B2 | 10/2003 | Diab |
| 6,640,117 | B2 | 10/2003 | Makarewicz et al. |
| 6,647,597 | B2 | 11/2003 | Reiter |
| 6,650,917 | B2 | 11/2003 | Diab et al. |
| 6,658,276 | B2 | 12/2003 | Kiani et al. |
| 6,661,161 | B1 | 12/2003 | Lanzo et al. |
| 6,697,656 | B1 | 2/2004 | Al-Ali |
| 6,697,658 | B2 | 2/2004 | Al-Ali |
| RE38,476 | E | 3/2004 | Diab et al. |
| 6,699,194 | B1 | 3/2004 | Diab et al. |
| RE38,492 | E | 4/2004 | Diab et al. |
| 6,738,652 | B2 | 5/2004 | Mattu et al. |
| 6,760,607 | B2 | 7/2004 | Al-Ali |
| 6,788,965 | B2 | 9/2004 | Ruchti et al. |
| 6,816,241 | B2 | 11/2004 | Grubisic |
| 6,822,564 | B2 | 11/2004 | Al-Ali |
| 6,850,787 | B2 | 2/2005 | Weber et al. |
| 6,850,788 | B2 | 2/2005 | Al-Ali |
| 6,876,931 | B2 | 4/2005 | Lorenz et al. |
| 6,880,364 | B1 | 4/2005 | Vidolin |
| 6,920,345 | B2 | 7/2005 | Al-Ali et al. |
| 6,934,570 | B2 | 8/2005 | Kiani et al. |
| 6,943,348 | B1 | 9/2005 | Coffin IV |
| 6,956,649 | B2 | 10/2005 | Acosta et al. |
| 6,961,598 | B2 | 11/2005 | Diab |
| 6,970,792 | B1 | 11/2005 | Diab |
| 6,985,764 | B2 | 1/2006 | Mason et al. |
| 6,990,364 | B2 | 1/2006 | Ruchti et al. |
| 6,991,364 | B2 | 1/2006 | Yang |
| 6,998,247 | B2 | 2/2006 | Monfre et al. |
| 7,003,338 | B2 | 2/2006 | Weber et al. |
| 7,015,451 | B2 | 3/2006 | Dalke et al. |
| 7,027,849 | B2 | 4/2006 | Al-Ali |
| D522,900 | S | 6/2006 | Yamamoto et al. |
| D526,719 | S | 8/2006 | Richie, Jr. et al. |
| 7,096,052 | B2 | 8/2006 | Mason et al. |
| 7,096,054 | B2 | 8/2006 | Abdul-Hafiz et al. |
| D529,616 | S | 10/2006 | Deros et al. |
| 7,133,710 | B2 | 11/2006 | Acosta et al. |
| 7,142,901 | B2 | 11/2006 | Kiani et al. |
| 7,146,731 | B2 | 12/2006 | Kraus et al. |
| 7,225,006 | B2 | 5/2007 | Al-Ali et al. |
| RE39,672 | E | 6/2007 | Shehada et al. |
| D549,602 | S | 8/2007 | Oberrieder et al. |
| 7,254,429 | B2 | 8/2007 | Schurman et al. |
| 7,254,431 | B2 | 8/2007 | Al-Ali et al. |
| 7,254,434 | B2 | 8/2007 | Schulz et al. |
| 7,274,955 | B2 | 9/2007 | Kiani et al. |
| D554,263 | S | 10/2007 | Al-Ali et al. |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| D560,520 | S | 1/2008 | Oberrieder et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,356,365 | B2 | 4/2008 | Schurman |

(56) References Cited

U.S. PATENT DOCUMENTS 7,363,687 B2 4/2008 Kraus et al.
7,371,981 B2 5/2008 Abdul-Hafiz
7,373,193 B2 5/2008 Al-Ali et al.
7,377,794 B2 5/2008 Al-Ali et al.
7,395,158 B2 7/2008 Monfre et al.
7,415,297 B2 8/2008 Al-Ali et al.
7,438,683 B2 10/2008 Al-Ali et al.
7,483,729 B2 1/2009 Al-Ali et al.
D587,657 S 3/2009 Al-Ali et al.
7,500,950 B2 3/2009 Al-Ali et al.
7,509,494 B2 3/2009 Al-Ali
7,510,849 B2 3/2009 Schurman et al.
7,514,725 B2 4/2009 Wojtczuk et al.
7,519,406 B2 4/2009 Blank et al.
D592,507 S 5/2009 Wachman et al.
7,530,942 B1 5/2009 Diab
7,593,230 B2 9/2009 Abul-Haj et al.
7,596,398 B2 9/2009 Al-Ali et al.
7,606,608 B2 10/2009 Blank et al.
7,620,674 B2 11/2009 Ruchti et al.
D606,659 S 12/2009 Kiani et al.
7,629,039 B2 12/2009 Eckerbom et al.
7,640,140 B2 12/2009 Ruchti et al.
7,640,632 B2 1/2010 Lazarus
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,761,127 B2 7/2010 Al-Ali et al.
7,764,982 B2 7/2010 Dalke et al.
D621,516 S 8/2010 Kiani et al.
7,791,155 B2 9/2010 Diab
RE41,912 E 11/2010 Parker
D631,780 S 2/2011 Levy
7,880,626 B2 2/2011 Al-Ali et al.
7,909,772 B2 3/2011 Popov et al.
7,919,713 B2 4/2011 Al-Ali et al.
7,937,128 B2 5/2011 Al-Ali
7,937,129 B2 5/2011 Mason et al.
7,941,199 B2 5/2011 Kiani
7,957,780 B2 6/2011 Lamego et al.
7,962,188 B2 6/2011 Kiani et al.
7,976,472 B2 7/2011 Kiani
7,990,382 B2 8/2011 Kiani
8,008,088 B2 8/2011 Bellott et al.
RE42,753 E 9/2011 Kiani-Azarbayjany et al.
8,028,701 B2 10/2011 Al-Ali et al.
8,029,185 B2 10/2011 Faucher et al.
8,048,040 B2 11/2011 Kiani
8,050,728 B2 11/2011 Al-Ali et al.
RE43,169 E 2/2012 Parker
8,118,620 B2 2/2012 Al-Ali et al.
8,130,105 B2 3/2012 Al-Ali et al.
8,182,443 B1 5/2012 Kiani
8,190,223 B2 5/2012 Al-Ali et al.
8,203,438 B2 6/2012 Kiani et al.
8,203,704 B2 6/2012 Merritt et al.
8,219,172 B2 7/2012 Schurman et al.
8,224,411 B2 7/2012 Al-Ali et al.
8,229,532 B2 7/2012 Davis
8,233,955 B2 7/2012 Al-Ali et al.
8,235,585 B2 8/2012 Speichinger
8,255,026 B1 8/2012 Al-Ali
8,261,416 B2 9/2012 Rothbaum et al.
8,265,723 B1 9/2012 McHale et al.
8,274,360 B2 9/2012 Sampath et al.
8,280,473 B2 10/2012 Al-Ali
8,315,683 B2 11/2012 Al-Ali et al.
8,316,515 B2 11/2012 Slank
RE43,860 E 12/2012 Parker
8,346,330 B2 1/2013 Lamego
8,353,842 B2 1/2013 Al-Ali et al.
8,355,766 B2 1/2013 MacNeish, III et al.
8,374,665 B2 2/2013 Lamego
8,388,353 B2 3/2013 Kiani et al.
8,401,602 B2 3/2013 Kiani
8,414,499 B2 4/2013 Al-Ali et al.
8,418,524 B2 4/2013 Al-Ali
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,707 B2 6/2013 Kiani
8,471,713 B2 6/2013 Poeze et al.
8,473,020 B2 6/2013 Kiani et al.
8,509,867 B2 8/2013 Workman et al.
8,515,509 B2 8/2013 Bruinsma et al.
8,523,781 B2 9/2013 Al-Ali
D692,145 S 10/2013 Al-Ali et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,584,345 B2 11/2013 Al-Ali et al.
8,588,880 B2 11/2013 Abdul-Hafiz et al.
8,630,691 B2 1/2014 Lamego et al.
8,641,631 B2 2/2014 Sierra et al.
8,652,060 B2 2/2014 Al-Ali
8,666,468 B1 3/2014 Al-Ali
8,670,811 B2 3/2014 O'Reilly
RE44,823 E 4/2014 Parker
RE44,875 E 4/2014 Kiani et al.
8,688,183 B2 4/2014 Bruinsma et al.
8,690,799 B2 4/2014 Telfort et al.
8,702,627 B2 4/2014 Telfort et al.
8,712,494 B1 4/2014 MacNeish, III et al.
8,715,206 B2 5/2014 Telfort et al.
8,723,677 B1 5/2014 Kiani
8,740,792 B1 6/2014 Kiani et al.
8,755,535 B2 6/2014 Telfort et al.
8,755,872 B1 6/2014 Marinow
8,764,671 B2 7/2014 Kiani
8,768,423 B2 7/2014 Shakespeare et al.
8,771,204 B2 7/2014 Telfort et al.
8,781,544 B2 7/2014 Al-Ali et al.
8,790,268 B2 7/2014 Al-Ali
D711,760 S 8/2014 Savoy
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,840,549 B2 9/2014 Al-Ali et al.
D715,668 S 10/2014 Roush et al.
8,852,094 B2 10/2014 Al-Ali et al.
8,852,994 B2 10/2014 Wojtczuk et al.
8,893,938 B2 11/2014 Grossenbacher et al.
8,897,847 B2 11/2014 Al-Ali
8,911,377 B2 12/2014 Al-Ali
8,989,831 B2 3/2015 Al-Ali et al.
8,997,318 B2 4/2015 Nicolas et al.
8,998,484 B2 4/2015 Savoy
8,998,809 B2 4/2015 Kiani
9,066,666 B2 6/2015 Kiani
9,066,680 B1 6/2015 Al-Ali et al.
9,095,316 B2 8/2015 Welch et al.
9,106,038 B2 8/2015 Telfort et al.
9,107,625 B2 8/2015 Telfort et al.
9,131,881 B2 9/2015 Diab et al.
9,138,180 B1 9/2015 Coverston et al.
9,153,112 B1 10/2015 Kiani et al.
9,192,329 B2 11/2015 Al-Ali
9,192,351 B1 11/2015 Telfort et al.
9,195,385 B2 11/2015 Al-Ali et al.
9,211,095 B1 12/2015 Al-Ali
9,218,454 B2 12/2015 Kiani et al.
9,245,668 B1 1/2016 Vo et al.
9,267,572 B2 2/2016 Barker et al.
9,277,880 B2 3/2016 Poeze et al.
9,307,928 B1 4/2016 Al-Ali et al.
9,323,894 B2 4/2016 Kiani

(56) References Cited

U.S. PATENT DOCUMENTS

| | | | |
|---|---|---|---|
| D755,392 | S | 5/2016 | Hwang et al. |
| 9,326,712 | B1 | 5/2016 | Kiani |
| 9,392,945 | B2 | 7/2016 | Al-Ali et al. |
| 9,408,542 | B1 | 8/2016 | Kinast et al. |
| 9,436,645 | B2 | 9/2016 | Al-Ali et al. |
| 9,445,759 | B1 | 9/2016 | Lamego et al. |
| 9,474,474 | B2 | 10/2016 | Lamego et al. |
| 9,480,435 | B2 | 11/2016 | Olsen |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,560,996 | B2 | 2/2017 | Kiani |
| 9,579,039 | B2 | 2/2017 | Jansen et al. |
| 9,585,445 | B2 | 3/2017 | Qian et al. |
| 9,622,692 | B2 | 4/2017 | Lamego et al. |
| D788,312 | S | 5/2017 | Al-Ali et al. |
| 9,649,054 | B2 | 5/2017 | Lamego et al. |
| 9,697,928 | B2 | 7/2017 | Al-Ali et al. |
| D795,731 | S | 8/2017 | Bayley et al. |
| 9,717,458 | B2 | 8/2017 | Lamego et al. |
| 9,724,016 | B1 | 8/2017 | Al-Ali et al. |
| 9,724,024 | B2 | 8/2017 | Al-Ali |
| 9,724,025 | B1 | 8/2017 | Kiani et al. |
| 9,749,232 | B2 | 8/2017 | Sampath et al. |
| 9,750,442 | B2 | 9/2017 | Olsen |
| 9,750,461 | B1 | 9/2017 | Telfort |
| D800,594 | S | 10/2017 | Lasserre |
| 9,775,545 | B2 | 10/2017 | Al-Ali et al. |
| 9,778,079 | B1 | 10/2017 | Al-Ali et al. |
| 9,782,077 | B2 | 10/2017 | Lamego et al. |
| 9,787,568 | B2 | 10/2017 | Lamego et al. |
| 9,808,188 | B1 | 11/2017 | Perea et al. |
| 9,839,379 | B2 | 12/2017 | Al-Ali et al. |
| 9,839,381 | B1 | 12/2017 | Weber et al. |
| 9,847,749 | B2 | 12/2017 | Kiani et al. |
| 9,848,800 | B1 | 12/2017 | Lee et al. |
| 9,861,298 | B2 | 1/2018 | Eckerbom et al. |
| 9,861,305 | B1 | 1/2018 | Weber et al. |
| 9,877,650 | B2 | 1/2018 | Muhsin et al. |
| 9,891,079 | B2 | 2/2018 | Dalvi |
| 9,907,345 | B2 | 3/2018 | O'Neill |
| 9,924,897 | B1 | 3/2018 | Abdul-Hafiz |
| 9,936,917 | B2 | 4/2018 | Poeze et al. |
| 9,955,937 | B2 | 5/2018 | Telfort |
| 9,965,946 | B2 | 5/2018 | Al-Ali et al. |
| D820,865 | S | 6/2018 | Muhsin et al. |
| 9,986,952 | B2 | 6/2018 | Dalvi et al. |
| D822,215 | S | 7/2018 | Al-Ali et al. |
| D822,216 | S | 7/2018 | Barker et al. |
| 10,010,276 | B2 | 7/2018 | Al-Ali et al. |
| 10,086,138 | B1 | 10/2018 | Novak, Jr. |
| 10,098,422 | B2 | 10/2018 | Fiedler et al. |
| 10,111,591 | B2 | 10/2018 | Dyell et al. |
| D833,624 | S | 11/2018 | DeJong et al. |
| 10,123,729 | B2 | 11/2018 | Dyell et al. |
| D835,282 | S | 12/2018 | Barker et al. |
| D835,283 | S | 12/2018 | Barker et al. |
| D835,284 | S | 12/2018 | Barker et al. |
| D835,285 | S | 12/2018 | Barker et al. |
| 10,149,518 | B1 | 12/2018 | De Iuliis et al. |
| 10,149,616 | B2 | 12/2018 | Al-Ali et al. |
| 10,154,815 | B2 | 12/2018 | Al-Ali et al. |
| 10,159,412 | B2 | 12/2018 | Lamego et al. |
| 10,188,348 | B2 | 1/2019 | Al-Ali et al. |
| RE47,218 | E | 2/2019 | Al-Ali |
| RE47,244 | E | 2/2019 | Kiani et al. |
| RE47,249 | E | 2/2019 | Kiani et al. |
| 10,205,291 | B2 | 2/2019 | Scruggs et al. |
| 10,206,463 | B2 | 2/2019 | de Jong |
| 10,226,187 | B2 | 3/2019 | Al-Ali et al. |
| 10,231,657 | B2 | 3/2019 | Al-Ali et al. |
| 10,231,670 | B2 | 3/2019 | Blank et al. |
| RE47,353 | E | 4/2019 | Kiani et al. |
| 10,279,247 | B2 | 5/2019 | Kiani |
| 10,292,664 | B2 | 5/2019 | Al-Ali |
| 10,299,720 | B2 | 5/2019 | Brown et al. |
| D850,317 | S | 6/2019 | Hinds et al. |
| 10,327,337 | B2 | 6/2019 | Schmidt et al. |
| 10,327,713 | B2 | 6/2019 | Barker et al. |
| 10,332,630 | B2 | 6/2019 | Al-Ali |
| D854,960 | S | 7/2019 | Yu et al. |
| D857,545 | S | 8/2019 | Akana et al. |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| D862,459 | S | 10/2019 | Choplin et al. |
| D863,095 | S | 10/2019 | Akana et al. |
| D863,985 | S | 10/2019 | Viry |
| D864,120 | S | 10/2019 | Forrest et al. |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali et al. |
| 10,456,038 | B2 | 10/2019 | Lamego et al. |
| 10,463,119 | B1 | 11/2019 | Chambers et al. |
| 10,463,340 | B2 | 11/2019 | Telfort et al. |
| 10,471,159 | B1 | 11/2019 | Lapotko et al. |
| 10,505,311 | B2 | 12/2019 | Al-Ali et al. |
| 10,524,738 | B2 | 1/2020 | Olsen |
| 10,532,174 | B2 | 1/2020 | Al-Ali |
| 10,537,285 | B2 | 1/2020 | Shreim et al. |
| 10,542,903 | B2 | 1/2020 | Al-Ali et al. |
| D874,311 | S | 2/2020 | Connor et al. |
| 10,555,678 | B2 | 2/2020 | Dalvi et al. |
| 10,568,553 | B2 | 2/2020 | O'Neil et al. |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,287 | S | 6/2020 | Kong |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| D901,492 | S | 11/2020 | Gao |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| D904,919 | S | 12/2020 | Barczak et al. |
| D905,584 | S | 12/2020 | Register et al. |
| 10,849,554 | B2 | 12/2020 | Shreim et al. |
| 10,856,750 | B2 | 12/2020 | Indorf et al. |
| D906,970 | S | 1/2021 | Forrest et al. |
| D908,213 | S | 1/2021 | Abdul-Hafiz et al. |
| 10,918,281 | B2 | 2/2021 | Al-Ali et al. |
| D912,563 | S | 3/2021 | Akana et al. |
| 10,932,705 | B2 | 3/2021 | Muhsin et al. |
| 10,932,729 | B2 | 3/2021 | Kiani et al. |
| 10,939,878 | B2 | 3/2021 | Kiani et al. |
| 10,956,950 | B2 | 3/2021 | Al-Ali et al. |
| D916,135 | S | 4/2021 | Indorf et al. |
| D917,046 | S | 4/2021 | Abdul-Hafiz et al. |
| D917,550 | S | 4/2021 | Indorf et al. |
| D917,564 | S | 4/2021 | Indorf et al. |
| D917,704 | S | 4/2021 | Al-Ali et al. |
| 10,987,066 | B2 | 4/2021 | Chandran et al. |
| 10,991,135 | B2 | 4/2021 | Al-Ali et al. |
| D919,094 | S | 5/2021 | Al-Ali et al. |
| D919,100 | S | 5/2021 | Al-Ali et al. |
| D919,619 | S | 5/2021 | Kozlovskaya et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |
| D925,597 | S | 7/2021 | Chandran et al. |
| D927,699 | S | 8/2021 | Al-Ali et al. |
| 11,076,777 | B2 | 8/2021 | Lee et al. |

(56) References Cited

U.S. PATENT DOCUMENTS 11,114,188 B2 9/2021 Poeze et al.
D932,321 S 10/2021 Jung
D933,232 S 10/2021 Al-Ali et al.
D933,233 S 10/2021 Al-Ali et al.
D933,234 S 10/2021 Al-Ali et al.
11,145,408 B2 10/2021 Sampath et al.
11,147,518 B1 10/2021 Al-Ali et al.
11,185,262 B2 11/2021 Al-Ali et al.
D939,360 S 12/2021 Qu
11,191,484 B2 12/2021 Kiani et al.
D946,596 S 3/2022 Ahmed
D946,597 S 3/2022 Ahmed
D946,598 S 3/2022 Ahmed
D946,617 S 3/2022 Ahmed
11,266,349 B2 3/2022 Mizuno et al.
11,272,839 B2 3/2022 Al-Ali et al.
11,289,199 B2 3/2022 Al-Ali
RE49,034 E 4/2022 Al-Ali
D948,057 S 4/2022 Rahman
11,298,021 B2 4/2022 Muhsin et al.
D950,580 S 5/2022 Ahmed
D950,599 S 5/2022 Ahmed
D950,738 S 5/2022 Al-Ali et al.
D952,499 S 5/2022 Akana et al.
D957,648 S 7/2022 Al-Ali
D957,977 S 7/2022 Cao
11,382,567 B2 7/2022 O'Brien et al.
11,389,093 B2 7/2022 Triman et al.
D959,993 S 8/2022 Qin
D961,437 S 8/2022 Tian
11,406,286 B2 8/2022 Al-Ali et al.
11,417,426 B2 8/2022 Muhsin et al.
11,439,329 B2 9/2022 Lamego
11,445,948 B2 9/2022 Scruggs et al.
D965,789 S 10/2022 Al-Ali et al.
D967,433 S 10/2022 Al-Ali et al.
11,464,410 B2 10/2022 Muhsin
11,504,058 B1 11/2022 Sharma et al.
11,504,066 B1 11/2022 Dalvi et al.
D971,769 S 12/2022 Yi
D971,933 S 12/2022 Ahmed
D972,431 S 12/2022 Huang
D973,072 S 12/2022 Ahmed
D973,532 S 12/2022 Zheng
D973,685 S 12/2022 Ahmed
D973,686 S 12/2022 Ahmed
D974,185 S 1/2023 He et al.
D974,193 S 1/2023 Forrest et al.
D975,572 S 1/2023 Akana et al.
D979,516 S 2/2023 Al-Ali et al.
11,589,815 B1 * 2/2023 Williams ............... A61B 5/681
D980,091 S 3/2023 Forrest et al.
11,596,363 B2 3/2023 Lamego
11,627,919 B2 4/2023 Kiani et al.
11,637,437 B2 4/2023 Al-Ali et al.
D985,498 S 5/2023 Al-Ali et al.
11,653,862 B2 5/2023 Dalvi et al.
D989,112 S 6/2023 Muhsin et al.
D989,327 S 6/2023 Al-Ali et al.
11,678,829 B2 6/2023 Al-Ali et al.
11,679,579 B2 6/2023 Al-Ali
11,684,296 B2 6/2023 Vo et al.
11,692,934 B2 7/2023 Normand et al.
11,701,043 B2 7/2023 Al-Ali et al.
D997,365 S 8/2023 Hwang
11,721,105 B2 8/2023 Ranasinghe et al.
11,730,379 B2 8/2023 Ahmed et al.
D998,625 S 9/2023 Indorf et al.
D998,630 S 9/2023 Indorf et al.
D998,631 S 9/2023 Indorf et al.
D999,244 S 9/2023 Indorf et al.
D999,245 S 9/2023 Indorf et al.
D999,246 S 9/2023 Indorf et al.
11,766,198 B2 9/2023 Pauley et al.
D1,000,975 S 10/2023 Al-Ali et al.
11,803,623 B2 10/2023 Kiani et al.
11,832,940 B2 12/2023 Diab et al.
D1,013,179 S 1/2024 Al-Ali et al.
11,872,156 B2 1/2024 Telfort et al.
11,879,960 B2 1/2024 Ranasinghe et al.
11,883,129 B2 1/2024 Olsen
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
2001/0016971 A1 8/2001 Guyard
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0133080 A1 9/2002 Apruzzese et al.
2003/0013975 A1 1/2003 Kiani
2003/0018243 A1 1/2003 Gerhardt et al.
2003/0026170 A1 2/2003 Yang
2003/0144582 A1 7/2003 Cohen et al.
2003/0156288 A1 8/2003 Barnum et al.
2003/0212312 A1 11/2003 Coffin, IV et al.
2003/0229974 A1 12/2003 Zemer et al.
2004/0106163 A1 6/2004 Workman, Jr. et al.
2005/0055276 A1 3/2005 Kiani et al.
2005/0102802 A1 5/2005 Sitbon et al.
2005/0234317 A1 10/2005 Kiani
2006/0073719 A1 4/2006 Kiani
2006/0189871 A1 8/2006 Al-Ali et al.
2007/0073116 A1 3/2007 Kiani et al.
2007/0167106 A1 7/2007 Hoover
2007/0180140 A1 8/2007 Welch et al.
2007/0244377 A1 10/2007 Cozad et al.
2008/0064965 A1 3/2008 Jay et al.
2008/0094228 A1 4/2008 Welch et al.
2008/0103375 A1 5/2008 Kiani
2008/0221418 A1 9/2008 Al-Ali et al.
2009/0010110 A1 1/2009 Chariton
2009/0036759 A1 2/2009 Ault et al.
2009/0049667 A1 2/2009 Takahashi
2009/0093687 A1 4/2009 Telfort et al.
2009/0095926 A1 4/2009 MacNeish, III
2009/0113870 A1 5/2009 Rejzner
2009/0182216 A1 7/2009 Roushey, III et al.
2009/0247984 A1 10/2009 Lamego et al.
2009/0275844 A1 11/2009 Al-Ali
2009/0289090 A1 11/2009 Fullerton et al.
2010/0004518 A1 1/2010 Vo et al.
2010/0030040 A1 2/2010 Poeze et al.
2010/0099964 A1 4/2010 O'Reilly et al.
2010/0200627 A1 8/2010 Shen
2010/0234718 A1 9/2010 Sampath et al.
2010/0243688 A1 9/2010 Gutierrez et al.
2010/0270257 A1 10/2010 Wachman et al.
2010/0302914 A1 12/2010 Faucher et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0083254 A1 4/2011 Trutna et al.
2011/0087081 A1 4/2011 Kiani et al.
2011/0099771 A1 5/2011 Grossenbacher et al.
2011/0118561 A1 5/2011 Tari et al.
2011/0137297 A1 6/2011 Kiani et al.
2011/0172498 A1 7/2011 Olsen et al.
2012/0113760 A1 5/2012 Pagrani
2012/0123231 A1 5/2012 O'Reilly
2012/0165629 A1 6/2012 Merritt et al.
2012/0209084 A1 8/2012 Olsen et al.
2012/0226117 A1 9/2012 Lamego et al.
2012/0283524 A1 11/2012 Kiani et al.
2013/0023775 A1 1/2013 Lamego et al.
2013/0060147 A1 3/2013 Welch et al.
2013/0074545 A1 3/2013 Moloney
2013/0096405 A1 4/2013 Garfio
2013/0205476 A1 8/2013 Gentile et al.
2013/0235546 A1 9/2013 Sedillo et al.

(56) References Cited

U.S. PATENT DOCUMENTS

| | | | |
|---|---|---|---|
| 2013/0296672 | A1 | 11/2013 | O'Neil et al. |
| 2013/0326790 | A1 | 12/2013 | Cauwels et al. |
| 2013/0345921 | A1 | 12/2013 | Al-Ali et al. |
| 2014/0000312 | A1 | 1/2014 | Nicolas et al. |
| 2014/0078871 | A1 | 3/2014 | Savoy |
| 2014/0166076 | A1 | 6/2014 | Kiani et al. |
| 2014/0180160 | A1 | 6/2014 | Brown et al. |
| 2014/0187973 | A1 | 7/2014 | Brown et al. |
| 2014/0257050 | A1 | 9/2014 | Kuroda et al. |
| 2014/0275871 | A1 | 9/2014 | Lamego et al. |
| 2014/0275872 | A1 | 9/2014 | Merritt et al. |
| 2014/0276119 | A1 | 9/2014 | Venkatraman et al. |
| 2014/0316217 | A1 | 10/2014 | Purdon et al. |
| 2014/0316218 | A1 | 10/2014 | Purdon et al. |
| 2014/0323897 | A1 | 10/2014 | Brown et al. |
| 2014/0323898 | A1 | 10/2014 | Purdon et al. |
| 2015/0005600 | A1 | 1/2015 | Blank et al. |
| 2015/0011907 | A1 | 1/2015 | Purdon et al. |
| 2015/0073241 | A1 | 3/2015 | Lamego |
| 2015/0080754 | A1 | 3/2015 | Purdon et al. |
| 2015/0099950 | A1 | 4/2015 | Al-Ali et al. |
| 2016/0026215 | A1 | 1/2016 | Armstrong |
| 2016/0066842 | A1 | 3/2016 | Kokkoneva et al. |
| 2016/0128209 | A1 | 5/2016 | Yoon et al. |
| 2017/0024748 | A1 | 1/2017 | Haider |
| 2017/0086535 | A1 | 3/2017 | De Iuliis et al. |
| 2017/0105682 | A1* | 4/2017 | MacDonald ........... A61B 5/681 |
| 2017/0119314 | A1 | 5/2017 | Just et al. |
| 2017/0251974 | A1 | 9/2017 | Shreim et al. |
| 2018/0168293 | A1 | 6/2018 | Leiggener |
| 2018/0184920 | A1 | 7/2018 | Rabinovich et al. |
| 2018/0242926 | A1 | 8/2018 | Muhsin et al. |
| 2018/0247712 | A1 | 8/2018 | Muhsin et al. |
| 2018/0338721 | A1 | 11/2018 | Wang et al. |
| 2019/0320906 | A1 | 10/2019 | Olsen |
| 2020/0060869 | A1 | 2/2020 | Telfort et al. |
| 2020/0111552 | A1 | 4/2020 | Ahmed |
| 2020/0113520 | A1 | 4/2020 | Abdul-Hafiz et al. |
| 2020/0138368 | A1 | 5/2020 | Kiani et al. |
| 2020/0163597 | A1 | 5/2020 | Dalvi et al. |
| 2020/0253474 | A1 | 8/2020 | Muhsin et al. |
| 2020/0253544 | A1 | 8/2020 | Belur Nagaraj et al. |
| 2020/0275841 | A1 | 9/2020 | Telfort et al. |
| 2020/0288983 | A1 | 9/2020 | Telfort et al. |
| 2020/0323440 | A1 | 10/2020 | Vule et al. |
| 2020/0329983 | A1 | 10/2020 | Al-Ali et al. |
| 2020/0329993 | A1 | 10/2020 | Al-Ali et al. |
| 2021/0022628 | A1 | 1/2021 | Telfort et al. |
| 2021/0104173 | A1 | 4/2021 | Pauley et al. |
| 2021/0113121 | A1 | 4/2021 | Diab et al. |
| 2021/0117525 | A1 | 4/2021 | Kiani et al. |
| 2021/0121582 | A1 | 4/2021 | Krishnamani et al. |
| 2021/0161465 | A1 | 6/2021 | Barker et al. |
| 2021/0181012 | A1 | 6/2021 | Simmendinger |
| 2021/0236729 | A1 | 8/2021 | Kiani et al. |
| 2021/0256835 | A1 | 8/2021 | Ranasinghe et al. |
| 2021/0275101 | A1 | 9/2021 | Vo et al. |
| 2021/0275103 | A1* | 9/2021 | Ishikawa ................ A61B 5/681 |
| 2021/0290072 | A1 | 9/2021 | Forrest |
| 2021/0290080 | A1 | 9/2021 | Ahmed |
| 2021/0290120 | A1 | 9/2021 | Al-Ali |
| 2021/0290177 | A1 | 9/2021 | Novak, Jr. |
| 2021/0290184 | A1 | 9/2021 | Ahmed |
| 2021/0296008 | A1 | 9/2021 | Novak, Jr. |
| 2021/0330228 | A1 | 10/2021 | Olsen et al. |
| 2021/0386382 | A1 | 12/2021 | Olsen et al. |
| 2021/0402110 | A1 | 12/2021 | Pauley et al. |
| 2022/0039707 | A1 | 2/2022 | Sharma et al. |
| 2022/0053892 | A1 | 2/2022 | Al-Ali et al. |
| 2022/0071562 | A1 | 3/2022 | Kiani |
| 2022/0096603 | A1 | 3/2022 | Kiani et al. |
| 2022/0148724 | A1 | 5/2022 | Pasternak et al. |
| 2022/0151521 | A1 | 5/2022 | Krishnamani et al. |
| 2022/0218244 | A1 | 7/2022 | Kiani et al. |
| 2022/0287574 | A1 | 9/2022 | Telfort et al. |
| 2022/0296161 | A1 | 9/2022 | Al-Ali et al. |
| 2022/0361819 | A1 | 11/2022 | Al-Ali et al. |
| 2022/0379059 | A1 | 12/2022 | Yu et al. |
| 2022/0392610 | A1 | 12/2022 | Kiani et al. |
| 2023/0028745 | A1 | 1/2023 | Al-Ali |
| 2023/0038389 | A1 | 2/2023 | Vo |
| 2023/0045647 | A1 | 2/2023 | Vo |
| 2023/0058342 | A1 | 2/2023 | Kiani |
| 2023/0069789 | A1 | 3/2023 | Koo et al. |
| 2023/0087671 | A1 | 3/2023 | Telfort et al. |
| 2023/0110152 | A1 | 4/2023 | Forrest et al. |
| 2023/0111198 | A1 | 4/2023 | Yu et al. |
| 2023/0115397 | A1 | 4/2023 | Vo et al. |
| 2023/0116371 | A1 | 4/2023 | Mills et al. |
| 2023/0135297 | A1 | 5/2023 | Kiani et al. |
| 2023/0138098 | A1 | 5/2023 | Telfort et al. |
| 2023/0145155 | A1 | 5/2023 | Krishnamani et al. |
| 2023/0147750 | A1 | 5/2023 | Barker et al. |
| 2023/0210417 | A1 | 7/2023 | Al-Ali et al. |
| 2023/0222805 | A1 | 7/2023 | Muhsin et al. |
| 2023/0222887 | A1 | 7/2023 | Muhsin et al. |
| 2023/0226331 | A1 | 7/2023 | Kiani et al. |
| 2023/0284916 | A1 | 9/2023 | Telfort |
| 2023/0284943 | A1 | 9/2023 | Scruggs et al. |
| 2023/0301562 | A1 | 9/2023 | Scruggs et al. |
| 2023/0346993 | A1 | 11/2023 | Kiani et al. |
| 2023/0368221 | A1 | 11/2023 | Haider |
| 2023/0371893 | A1 | 11/2023 | Al-Ali et al. |
| 2023/0389837 | A1 | 12/2023 | Krishnamani et al. |
| 2024/0016418 | A1 | 1/2024 | Devadoss et al. |
| 2024/0016419 | A1 | 1/2024 | Devadoss et al. |
| 2024/0047061 | A1 | 2/2024 | Al-Ali et al. |
| 2024/0049310 | A1 | 2/2024 | Al-Ali et al. |
| 2024/0049986 | A1 | 2/2024 | Al-Ali et al. |
| 2024/0081656 | A1 | 3/2024 | DeJong et al. |
| 2024/0122486 | A1 | 4/2024 | Kiani |

FOREIGN PATENT DOCUMENTS

| | | | |
|---|---|---|---|
| CN | 1309938 | | 8/2001 |
| CN | 1221195 | | 10/2005 |
| CN | 101836780 | | 7/2014 |
| CN | 102854793 | | 4/2017 |
| CN | 107106907 | A | 8/2017 |
| CN | 103376734 | | 9/2017 |
| CN | 107411248 | | 12/2017 |
| CN | 206960868 | | 2/2018 |
| CN | 105392418 | | 5/2018 |
| CN | 108464585 | | 8/2018 |
| CN | 107106907 | B | 10/2018 |
| CN | 208972735 | | 6/2019 |
| EP | 0 198 279 | | 10/1986 |
| EP | 0 824 328 | | 2/1999 |
| EP | 2 098 131 | | 9/2009 |
| EP | 2 316 298 | A1 | 5/2011 |
| EP | 2 382 890 | A2 | 11/2011 |
| EP | 2 316 298 | B1 | 5/2012 |
| EP | 2 382 890 | B1 | 7/2015 |
| EP | 3 015 948 | | 5/2016 |
| FR | 2 579 426 | | 10/1986 |
| FR | 2 946 159 | | 12/2010 |
| GB | 361942 | | 11/1931 |
| GB | 2 223 665 | | 4/1990 |
| GB | 2 384 162 | | 7/2003 |
| IN | 201003219(I4) | | 7/2011 |
| JP | 11300864 | | 11/1999 |
| JP | 11-342010 | | 12/1999 |
| JP | 11-342011 | | 12/1999 |
| JP | 2001-178525 | | 7/2001 |
| JP | 2001-272479 | | 10/2001 |
| JP | 2004-537802 | | 12/2004 |
| JP | 2006-034654 | | 2/2006 |
| JP | 3947768 | | 4/2007 |
| JP | 2016-045207 | | 4/2016 |
| JP | 2016-114600 | | 6/2016 |
| JP | 6182583 | | 7/2017 |
| KR | 10-2011-0047163 | | 5/2011 |
| KR | 10-2011-0055419 | | 5/2011 |
| KR | 10-2016-0088157 | | 7/2016 |

(56) References Cited

FOREIGN PATENT DOCUMENTS

| | | |
|---|---|---|
| WO | WO 03/012615 | 2/2003 |
| WO | WO 2014/184649 | 11/2014 |
| WO | WO 2020/019192 | 1/2020 |
| WO | WO 2021/028840 | 2/2021 |
| WO | WO 2022/040231 | 2/2022 |
| WO | WO 2023/003980 | 1/2023 |

OTHER PUBLICATIONS

AIVAnet, "Garmin Vivofit Jr Release Date, Price and Specs—CNET", Sep. 29, 2016, https://blog.aivanet.com/2016/09/29/garmin-vivofit-jr-release-date-price-and-specs-cnet/ in 3 pages.
Apollo, "Apollo® Wearable", as archived Oct. 3, 2022, https://web.archive.org/web/20221003190714/https://apolloneuro.com/products/apollo-wearable?variant=41447575945413, pp. 8.
"Batfree, World First Power Strap for Apple Watch", as uploaded Dec. 18, 2018, https://www.youtube.com/watch?v=v38-9wJyBoE, in 1 page.
Comstock, Jonah, "Whoop, a wearable for athletes, raises $12 million", https://www.mobihealthnews.com/46964/whoop-a-wearable-for-athletes-raises-12-million, Sep. 22, 2015, pp. 2.
DC Rainmaker, "Garmin Vivofit Jr. 2: Everything you ever wanted to know", DC Rainmaker, Sep. 27, 2017, https://www.dcrainmaker.com/2017/09/garmin-vivofit-jr-2-review-everything-you-ever-wanted-to-know.html in 52 pages.
Duffy, Jill, "MIO Alpha BLE Review", PC Magazine, Jan. 28, 2013, https://www.pcmag.com/reviews/mio-alpha-ble in 7 pages.
Faust, Erik, "The Togvu Batfree is an Apple Watch band that charges your watch while you wear it", May 1, 2019, https://the-gadgeteer.com/2019/05/01/the-togvu-batfree-is-an-apple-watch-band-that-charges-your-watch-while-you-wear-it/ in 4 pages.
Flex Watches, "Black Band", as printed Oct. 4, 2023, https://flexwatches.com/products/black-silicone-replaceable-band?variant=410473941&currency=USD&utm_medium=product_sync&utm_source=google&utm_content=sag_organic&utm_campaign=sag_organic&srsltid=ASuE1wRzDWxvsf2DTXquBCKplYT15e4vfPv6argqpEJ9yDqBWOS2zjk5zs&com_cvv=a0ca8cf311e059d8bc8090c0d8ed53ef9363e1dc2aeea0d3bd8c43122e608eab in 2 pages.
Flex Watches, "The Black Band", as archived Dec. 29, 2011, https://web.archive.org/web/20111229082626/http:/flexwatches.com/store/the-black-band.html in 2 pages.
Gadgetsin, "Batfree Apple Watch Power Strap with Built-in Batteries", Mar. 16, 2019, https://gadgetsin.com/batfree-apple-watch-power-strap-with-built-in-batteries.htm in 5 pages.
Garmin Vivofit Jr. 3, Fitness Tracker for Kids, Includes Interactive App Experience, Swim-Friendly, Up To 1-year Battery Life, Blue Stars, Date first available: Oct. 15, 2020, as archived Oct. 4, 2023, https://web.archive.org/web/20231004210347/https://www.amazon.com/Garmin-Interactive-Experience-Swim-Friendly-010-02441-22/dp/B08JWZ5WY2/ref=sr_1_2?keywords=garmin%2Bvivofit%2Bjr%2B3&qid=1689620317&sr=8-2&th=1 in 4 pages.
Garmin, Blue Stars Band, Accessory Band for Vivofit® Jr. 3, Date first available: Oct. 15, 2020, as printed Oct. 4, 2023, https://web.archive.org/web/20231004204515/https://www.garmin.com/en-US/p/742671 in 3 pages.
Garmin Vivofit Jr. 3: Accessory Band, Disney The Little Mermaid, Date first available: Apr. 26, 2021, as archived Oct. 4, 2023, https://web.archive.org/web/20231004203105/https://www.amazon.com/Garmin-Vivofit-Accessory-Mermaid-010-12666-43/dp/B093JR6LD7/ref=asc_df_B093JR6LD7/?tag=hyprod-20&linkCode=df0&hvadid=649684855167&hvpos=&hvnetw=g&hvrand=6991608940390168035&hvpone=&hvptwo=&hvqmt=&hvdev=c&hvdvcmdl=&hvlocint=&hvlocphy=9031529&hvtargid=pla-1679549217739&psc=1 in 3 pages.
Iiteeology, Compatible with Apple Watch Band 44mm SE/Series 6 5 4, Upgraded Stainless Steel Link Replacement Band with iWatch Screen Protector Case Silver/Silver, Date first available: Jul. 10, 2020, as printed Oct. 4, 2023, https://www.amazon.com/iiteeology-Compatible-Stainless-Replacement-Protector/dp/B08CRSLF4V?th=1 in 7 pages.
International Search Report and Written Opinion as received in PCT Application No. PCT/US2021/046369, as mailed Nov. 25, 2021 in 15 pages.
International Search Report and Written Opinion as received in PCT Application No. PCT/US2022/037764, as mailed Sep. 23, 2022 in 15 pages.
JXVM for Apple Watch Band 45mm 44mm 42mm 41mm 40mm 38mm with Case, Uni-body Protective Bumper Band, Crystal Clear Sporty Case, with Adjustable Strap for iWatch Ultra & Series 9 8 7 6 5 4 3 2 1 / SE, Date first available: Jun. 3, 2023, as archived Oct. 4, 2023, https://web.archive.org/web/20231004232401/https://www.amazon.com/dp/B096TLY3QT/ref=sspa_dk_detail_1?pd_rd_i=B096TLY3QT&pd_rd_w=DHOJE&content-id=amzn1.sym.386c274b-4bfe-4421-9052-a1a56db557ab&pf_rd_p=386c274b-4bfe-4421-9052-A1a56db557ab&pf_rd_r=18BQQRTPDVFBCCVA1WE2&pd_rd_wg=jYoke&pd_rd_r=c500a4bf-770c-46aa-9e76-ba98c1a39918&s=apparel&sp_csd=d2lkZ2VOTmFtZT1zcF9kZXRhaWxfdGhlbWF0aWM&spLa=ZW5jcn IwdGVkUXVhbGlmaWVyPUFSSFFRMVpaWKNQM0ImZW5jcnlwdGVkSWQ9QTAxOTMyNDExOEc1RkdLRkNRSUVNJmVuY3J5cHRlZEFkSWQ9QTA5MDY2NDQxS05ZODNOUkQxSUNBJndpZGdldE5hbWU9c3BfZGVOYWlsX3RoZW1hdGljJmFjdGlvbj1jbGlja1JlZGlyZWNOJmRvTm90TG9nQ2xpY2s9dHJ1ZQ&th=1&psc=1 in 5 pages.
"Magnetic Milanese Stainless Steel Strap Band And Frame for Apple Watch Series 42mm-Silver",iSank, Date first available: Jun. 28, 2021, as printed Oct. 4, 2023, https://www.amazon.eg/-/en/Magnetic-Milanese-Stainless-Steel-Silver/dp/B09841V2KX in 3 pages.
"M5 Band Sport Silicone Wrist Strap (M5/M6), For Office", as printed Nov. 2, 2023, https://www.indiamart.com/proddetail/m5-band-sport-silicone-wrist-strap-m5-m6-23772599055.html, pp. 5.
O'Kane, Sean, "Whoop's New Fitness Tracker is Better Thanks to a Battery Breakthrough", The Verge, Sep. 8, 2021, https://www.theverge.com/2021/9/8/22662979/whoop-fitness-tracker-sila-silicon-anode-battery-electric-cars, pp. 4.
PROATL Compatible with Apple Watch Bands Series SE 8 7 6 5 4 3 2 1, Women& Men Sport Clear Soft Silicone Strap with Bumper Protective Cases for Apple Watch Series 45mm 44mm 42mm 41mm 40mm 38mm, Date first available: May 18, 2021, as archived Oct. 4, 2023,|https://web.archive.org/web/20231004215422/https://www.amazon.com/dp/B0957P42R5?asc_source=verso&asc_campaign=6220f63a9621fbc9faf148e3%7Cc53mEFfLxx2tam8KkPY43X&asc_refurl=https%3A%2F%2Fwww.wired.com%2Fgallery%2Fbest-apple-watch-accessories%2F&ascsubtag=6220f63a9621fbc9faf148e3&tag=w050b-20 in 3 pages.
"Replacement Bands Compatible with Xiaomi Mi Band 3/Xiaomi Mi band4 Bands, Silicone Wristbands for Women Men", https://www.amazon.com/Replacement-Compatible-Xiaomi-Silicone-Wristbands/dp/B08GLV1B4H?th=1, Aug. 25, 2020, pp. 5.
Ritche Silicone Watch Band 18mm 20mm 22mm Quick Release Rubber Watch Bands for Men Women, first available May 26, 2021, Amazon.com, pp. 10, https://www.amazon.com/Ritche-Silicone-Watch-Release-Rubber/dp/B095KG8PRY/ref=sr%201%208?crid=1%20NZTZ03COTGPC&keywords=rubber%2Bwatch%2Bband&qid=1678448896&sprefix=rubber%2Bwatch%2Bband%2Caps%2C108&sr=8-8&th=1.
SEC Filing for Whoop, Inc. noting incorporation in 2011, CIK #0001582746, https://www.sec.gov/Archives/edgar/data/1582746/000158274614000002/xslFormDX01/primary_doc.xml, dated Jun. 20, 2014, pp. 5.
Stuart, S.C., "24 Hours With the Apollo Mood-Altering Wearable", PC Magazine, Dec. 10, 2019, https://www.pcmag.com/news/24-hours-with-the-apollo-mood-altering-wearable, pp. 10.
Whoop, "The Whoop Strap 3.0", as archived Feb. 3, 2021, https://web.archive.org/web/20210203174156/https://www.whoop.com/membership/strap/, pp. 6.
"Xiaomi Mi Band", Release Date Jul. 22, 2014, Wikipedia, https://en.wikipedia.org/wiki/Xiaomi_Mi_Band, pp. 5.

(56) References Cited

OTHER PUBLICATIONS

"Xiaomi Mi Band 3/4 Silicone Strap", Believed to be available on/before Apr. 15, 2019 based on customer review date, https://judge.me/reviews/www.penguin.com.bd/products/xiaomi-mi-band-3-4-silicone-strap-orange, pp. 4.
"Z Create Design strap Strap Smart Sports Bracelet Replacement Strap Wrist Protector Frame ShellReplacement watch strap", https://www.amazon.com/Create-Design-Bracelet-Replacement-Protector/dp/BOB6ZMDJBG?th=1, First available Jul. 19, 2022, pp. 4.

* cited by examiner

WEARABLE BAND FOR HEALTH MONITORING DEVICE

INCORPORATION BY REFERENCE TO ANY PRIORITY APPLICATIONS

The present application claims priority to U.S. Provisional Application No. 63/275,674, filed Nov. 4, 2021, U.S. Provisional Application No. 63/277,058, filed Nov. 8, 2021, U.S. Provisional Application No. 63/263,324, filed Oct. 29, 2021, U.S. Provisional Application No. 63/236,164, filed Aug. 23, 2021, and U.S. Provisional Application No. 63/224,347, filed Jul. 21, 2021. All of the above-listed applications and any and all other applications for which a foreign or domestic priority claim is identified in the Application Data Sheet as filed with the present application, are hereby incorporated by reference under 37 CFR 1.57.

FIELD

The present disclosure relates to a wearable band for securing a health monitoring device incorporating a plurality of sensors to a portion of a user's body.

BACKGROUND

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\varepsilon_{i,\lambda}$ at a particular wavelength $\lambda$.

In generalized form, the Beer-Lambert law is expressed as:

$$I_\lambda = I_{0,\lambda} e^{-d_\lambda \cdot \mu_{a,\lambda}} \quad (1)$$

$$\mu_{a,\lambda} = \sum_{i=1}^{n} \varepsilon_{i,\lambda} \cdot c_i \quad (2)$$

where $\mu_{\alpha,\lambda}$ is the bulk absorption coefficient and represents the probability of absorption per unit length. The minimum number of discrete wavelengths that are required to solve equations 1 and 2 is the number of significant absorbers that are present in the solution.

A practical application of this technique is pulse oximetry or plethysmography, which utilizes a noninvasive sensor to measure oxygen saturation and pulse rate, among other physiological parameters. Pulse oximetry or plethysmography relies on a sensor attached externally to the patient (typically for example, at the fingertip, foot, ear, forehead, or other measurement sites) to output signals indicative of various physiological parameters, such as a patient's blood constituents and/or analytes, including for example a percent value for arterial oxygen saturation, among other physiological parameters. The sensor has at least one emitter that transmits optical radiation of one or more wavelengths into a tissue site and at least one detector that responds to the intensity of the optical radiation (which can be reflected from or transmitted through the tissue site) after absorption by pulsatile arterial blood flowing within the tissue site. Based upon this response, a processor determines the relative concentrations of oxygenated hemoglobin ($HbO_2$) and deoxygenated hemoglobin (Hb) in the blood so as to derive oxygen saturation, which can provide early detection of potentially hazardous decreases in a patient's oxygen supply, and other physiological parameters.

A patient monitoring device can include a plethysmograph sensor. The plethysmograph sensor can calculate oxygen saturation ($SpO_2$), pulse rate, a plethysmograph waveform, perfusion index (PI), pleth variability index (PVI), methemoglobin (MetHb), carboxyhemoglobin (CoHb), total hemoglobin (tHb), respiration rate, glucose, and/or otherwise. The parameters measured by the plethysmograph sensor can display on one or more monitors the foregoing parameters individually, in groups, in trends, as combinations, or as an overall wellness or other index.

A pulse oximetry sensor is described in U.S. Pat. No. 6,088,607 entitled Low Noise Optical Probe; pulse oximetry signal processing is described in U.S. Pat. Nos. 6,650,917 and 6,699,194 entitled Signal Processing Apparatus and Signal Processing Apparatus and Method, respectively; a pulse oximeter monitor is described in U.S. Pat. No. 6,584,336 entitled Universal/Upgrading Pulse Oximeter; all of which are assigned to Masimo Corporation, Irvine, CA, and each is incorporated by reference herein in its entirety.

SUMMARY

A draw back to current pulse oximetry sensors is a need to be located near significant capillary beds on the body, including fingers, ears, toes, nose and forehead. Such locations are often inconvenient for monitoring a user during normal activities, outside of a healthcare facility. Further, although measuring through motion oxygen saturation technology exists, it is directed to the healthcare facility context and is not reliable for normal routines, which include sporting activities or other significant daily movement. Accordingly, the present disclosure provides a sensor which allows for measuring pulse oximetry at sparse capillary bed locations, including the wrist. The present disclosure also provides algorithms for measuring pulse oximetry though higher exertion everyday motion.

A physiological monitoring sensor or module, also referred to herein as a physiological parameter measurement sensor or module, or a module, can be integrated into a wearable device that is secured to a wrist of a person (the "wearer"), such as a wristwatch or watch. The sensor on the watch can be used to monitor the wearer's physiological parameters. The sensor can detect pulse rate, oxygen saturation, hydration status, respiratory rate, and/or other parameters, such as the parameters disclosed herein, of the wearer. The sensor can include a convex protrusion to improve pressure and contact, and therefore optical coupling, between the wearer's skin and the physiological parameter measurement sensor. The curvature of the sensor can be designed to balance the desired pressure by the watch on the wearer's wrist and the wearer's comfort. The sensor can include a light barrier between emitters and detectors of the module and/or light diffusing materials surrounding the emitters and the detectors, among other features, to improve signal strength and reduce noise. The sensor or the watch can include a connection port to receive another sensor, which can be configured to be coupled to the wearer at a different measurement site of the wearer's body than the wrist. The sensor can be configured to continuously, at certain time intervals, and/or upon the wearer's request, measure one or more of the physiological parameters. For example, the sensor can be configured to continuously measure the wearer's oxygen saturation and/or pulse rate when the watch is worn on the wearer's wrist.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a first emitter grouping comprising a first plurality of light emitting diodes (LEDs) at a first location; a second emitter grouping comprising a second plurality of LEDs at a second location different from the first location, wherein the second emitter grouping can comprise the same number and type of LEDs as the first emitter groupings; one or more light blocks separating the first emitter grouping from the second emitter grouping; light diffusing material configured to diffuse light emitted by each of the first and second pluralities of LEDs; a plurality of detectors including four or more photodiodes; and a convex surface configured to be positioned between (i) the first and second emitter groupings and the four or more photodiodes and (ii) the tissue of the wearer, the convex surface comprising one or more surface materials.

In some configurations, the one or more surface materials can comprise at least a portion of the one or more light blocks and a light transmission material.

In some configurations, the emitters in the first or second emitter groupings may not be electrically connected to one another.

In some configurations, the first or second emitter groupings can define a group of emitters located in close proximity.

In some configurations, the plurality of detectors can be individually both a near detector and far detector for each emitter grouping.

In some configurations, the first and second emitter groups can be located at non-central locations of a printed circuit board (PCB) of the sensor.

In some configurations, the one or more light blocks can extend from a surface of the sensor positioning the first and second pluralities of LEDs towards a tissue of the wearer when the watch is worn.

In some configurations, each of the first or second emitter grouping can be surrounded by its own diffusing material.

In some configurations, the light diffusing material surrounding the first emitter grouping can be different from the light diffusing material surrounding the second emitter grouping.

In some configurations, at least some of the plurality of detectors can extend around a circumference of the sensor.

In some configurations, the plurality of detectors can be positioned in a grid pattern and/or across from one another.

In some configurations, locations of the emitter groupings can be interleaved with the plurality of detectors.

In some configurations, at least one of the plurality of detectors can be located between the first plurality of LEDs and the second plurality of LEDs, and at least one of the plurality of detectors can be located on each of at least two sides of each of the first plurality of LEDs and the second plurality of LEDs.

In some configurations, the sensor can further comprise a processor configured to determine an oxygen saturation measurement based on signals from the optical physiological sensor.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a plurality of emitters, the emitters configured to emit light of a plurality of different wavelengths, the plurality of different wavelengths comprising at least three different wavelengths; a plurality of detectors, the detectors configured to detect light emitted by the plurality of emitters and attenuated by tissue of the user when the watch is worn on the wrist of the wearer and output signals to a sensor processor for determining the physiological parameters of the wearer; and a sensor housing, the plurality of emitters and the plurality of detectors enclosed within the housing, wherein the sensor housing can comprise: a convex skin-facing light transmissive cover extending over the plurality of emitters and the plurality of detectors, the cover located at a first side of sensor housing, and a printed circuit board (PCB) located at a second side of the sensor housing opposite the first side, the plurality of emitters and detectors located on a skin-facing side of the PCB; and a plurality of light barriers extending from the PCB to the cover, the plurality of light barriers configured to form walls of chambers to block light or substantially all the light between the chambers, each chamber enclosing one or more emitters without detectors, or one or more detectors without emitters, wherein a skin-facing surface of the cover and at least one of the light barriers can define a skin-facing surface of the sensor, a surface area of the cover extending over the chambers that enclose one or more detectors is at least 50% of a surface area of the skin-facing surface of the sensor.

In some configurations, the surface area of the cover extending over the chambers that enclose one or more detectors can be at least 100 $mm^2$.

In some configurations, the surface area of the cover extending over the chambers that enclose one or more detectors can be at least 150 $mm^2$.

In some configurations, the surface area of the cover extending over the chambers that enclose one or more detectors can be at least 165 $mm^2$.

In some configurations, a surface area of the light transmissive cover that extends over the chambers that enclose one or more emitters can be at least 25 $mm^2$.

In some configurations, the surface area of the light transmissive cover that extends over the chambers that enclose one or more detectors can be at least 35 $mm^2$.

In some configurations, the skin-facing surface of the sensor can have a longer side and a shorter side, the longer side configured to be along a width of the wearer's wrist when the watch is worn.

In some configurations, more of the plurality of detectors can be located along the longer side than along the shorter side.

In some configurations, the plurality of emitters can comprise a first group of emitters and a second group of emitters, the chambers comprising a first emitter chamber enclosing the first group and a second emitter chamber enclosing the second group.

In some configurations, the plurality of detectors can comprise a first ring of detectors and a second ring of detectors, the first ring of detectors surrounding the first group of emitters and the second ring of detectors surrounding the second group of emitters.

In some configurations, at least one of the plurality of detectors can be located between the first and second group of emitters and can be shared by the first and second rings of detectors.

In some configurations, some of the plurality of detectors can be closer to the first group of emitters than a remainder of the plurality of detectors and some of the plurality of detectors can be closer to the second group of emitters than a remainder of the plurality of detectors.

In some configurations, the plurality of light barriers can extend to a skin-facing surface of the cover.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a plurality of emitters, the emitters configured to emit light of a plurality of different wavelengths, the plurality of different wavelengths comprising at least three different wavelengths; a plurality of detectors, the detectors configured to detect light emitted by the plurality of emitters and attenuated by tissue of the user when the watch is worn on the wrist of the wearer and output signals to a sensor processor for determining the physiological parameters of the wearer; and a sensor housing, the plurality of emitters and the plurality of detectors enclosed within the housing, wherein the sensor housing can comprise: a convex skin-facing light transmissive cover extending over the plurality of emitters and the plurality of detectors, the cover located at a first side of sensor housing, and a printed circuit board (PCB) located at a second side of the sensor housing opposite the first side, the plurality of emitters and detectors located on a skin-facing side of the PCB; and a plurality of light barriers extending from the PCB to the cover, the plurality of light barriers configured to form walls of chambers to block light or substantially all the light between the chambers, each chamber enclosing one or more emitters without detectors, or one or more detectors without emitters, wherein at least one of the plurality of light barriers can extend to a skin-facing surface of the cover.

In some configurations, all of the plurality of light barriers can extend to the skin-facing surface of the cover.

In some configurations, the skin-facing surface of the cover and the at least one of the light barriers can define a skin-facing surface of the sensor.

In some configurations, the skin-facing surface of the sensor can comprise a continuous curvature.

In some configurations, the cover can be a single lens or cover.

In some configurations, the cover can comprise individual lenses, each lens or cover covering a single chamber.

In some configurations, the cover can comprise a lens or cover covering all the chambers that extend over one or more detectors.

In some configurations, the lens or cover covering all the chambers that extend over one or more detectors may not cover a chamber that extends over one or more emitters.

In some configurations, the plurality of light barriers can comprise colored sapphire glass.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a first emitter comprising a first a plurality of light emitting diodes (LEDs) positioned on a surface of a substrate; a first photodiode positioned on the surface of the substrate; a curved surface extending over all the first plurality of LEDs and the first photodiode; and a first light barrier positioned between the first emitter and the first photodiode, and extending from the surface of the substrate to the curved surface.

In some configurations, the first light barrier can comprise one or more portions that together extend from the surface of the substrate to the curved surface.

In some configurations, the sensor can further comprise: a second emitter comprising a second plurality of LEDs positioned on the surface of the substrate; a second photodiode positioned on the surface of the substrate; a second light barrier positioned between (i) both the first and second emitters and (ii) the second photodiode, and extending from the surface of the substrate to the curved surface, wherein the curved surface can extend over all the second plurality of LEDs and the second photodiode.

In some configurations, the second light barrier can comprise one or more portions that together extend from the surface of the substrate to the curved surface.

In some configurations, portions of the curved surface positioned above the first and second emitters can comprise at least a first material, portions of the curved surface positioned and the first and second photodiodes can comprise at least a second material, and portions of the first and second barriers extending to the curved surface can comprise at least a third material different from the first and second materials.

In some configurations, at least the first, second, and third materials together can make up the curved surface.

In some configurations, the first and second materials can comprise the same material.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a plurality of light-emitting diodes (LEDs) configured to emit light to tissue of a wearer; a wall dividing the plurality of LEDs into at least a first group of LEDs and a second group of LEDs, the wall blocking at least some of the light emitted by the first group of LEDs from contacting the second group of LEDs; four or more photodiodes configured to detect the light emitted by the plurality of LEDs after attenuation by the tissue; and one or more covers covering the plurality of LEDs and the four or more photodiodes, the one or more covers together forming part of a convex surface configured to contact the tissue.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a plurality of emitters, the emitters configured to emit light of a plurality of different wavelengths, the plurality of different wavelengths comprising at least three different wavelengths; a plurality of detectors, the detectors configured to detect light emitted by the plurality of emitters and attenuated by tissue of the user when the watch is worn on the wrist of the wearer and output signals to a sensor processor for determining the physiological parameters of the wearer; and a sensor housing, the plurality of emitters and the plurality of detectors enclosed within the housing, wherein the sensor housing can comprise: a convex skin-facing light transmissive cover extending over the plurality of emitters and the plurality of detectors, the cover located at a first side of sensor housing, and a printed circuit board (PCB) located at a second side of the sensor housing opposite the first side, the plurality of emitters and detectors located on a skin-facing side of the PCB; and a plurality of light barriers extending from the PCB to the cover, the plurality of light barriers configured to form walls of chambers to block light or substantially all the light between the chambers, each chamber enclosing one or more emitters without detectors, or one or more detectors without emitters, wherein the plurality of detectors can comprise a plurality of far detectors that are further from at least some of the plurality of emitters than a remainder of the plurality of detectors.

In some configurations, the plurality of emitters can comprise a first group of emitters and a second group of emitters, the chambers comprising a first emitter chamber enclosing the first group and a second emitter chamber enclosing the second group.

In some configurations, the plurality of detectors can comprise a first ring of detectors and a second ring of detectors, the first ring of detectors surrounding the first group of emitters and the second ring of detectors surrounding the second group of emitters.

In some configurations, at least one of the plurality of detectors can be located between the first and second group of emitters and is shared by the first and second rings of detectors.

In some configurations, some of the plurality of detectors can be closer to the first group of emitters than a remainder of the plurality of detectors and some of the plurality of detectors are closer to the second group of emitters than a remainder of the plurality of detectors.

In some configurations, the sensor can further comprise the sensor processor, wherein the sensor processor is configured to determine a hydration status of a user based on signals from the plurality of far detectors.

In some configurations, at least one of the emitters can be configured to emit light of a wavelength more sensitive to water than a remainder of the different wavelengths.

In some configurations, the wavelength more sensitive to water can be about 970 nm.

In some configurations, the sensor processor can be configured to compare signals of the reflected light of the wavelength more sensitive to water and another wavelength less sensitive to water from the plurality of far detectors.

In some configurations, the sensor processor can be configured to selectively drive some of the plurality of emitters and/or activate or deactivate some of the plurality of detectors.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a plurality of emitters, the emitters configured to emit light of a plurality of different wavelengths, wherein at least one of the emitters can be configured to emit light of a reference wavelength; a plurality of detectors, the detectors configured to detect light emitted by the plurality of emitters and attenuated by tissue of the user when the watch is worn on the wrist of the wearer; a sensor processor, wherein the plurality of detectors can be configured to output signals to the sensor processor for determining at least some of the physiological parameters of the wearer based in part on a signal of the reflected light of the reference wavelength; and a sensor housing, the plurality of emitters and the plurality of detectors enclosed within the housing, wherein the sensor housing can comprise: a convex skin-facing light transmissive cover extending over the plurality of emitters and the plurality of detectors, the cover located at a first side of sensor housing, and a printed circuit board (PCB) located at a second side of the sensor housing opposite the first side, the plurality of emitters and detectors located on a skin-facing side of the PCB; and a plurality of light barriers extending from the printed circuit board to the cover, the plurality of light barriers configured to form walls of chambers to block light or substantially all the light between the chambers, each chamber enclosing one or more emitters without detectors, or one or more detectors without emitters.

In some configurations, the reference wavelength can be about 525 nm.

In some configurations, the light of the reference wavelength can be green or yellow.

In some configurations, the sensor processor can be configured to extract features from signals of other wavelengths based on the signal of the reflected light of the reference wavelength and calculate the at least some of the physiological parameters based on the extracted features.

In some configurations, at least one of the emitters can be configured to emit light of a wavelength more sensitive to oxygen saturation.

In some configurations, at least one of the emitters can be configured to emit light of a wavelength more sensitive to water.

In some configurations, at least one of the emitters can be configured to emit light of a normalizing wavelength.

In some configurations, the sensor processor can be configured to determine a hydration status of a user based on signals of the reflected light of the wavelength more sensitive to water and of the normalizing wavelength.

In some configurations, one or more physiological parameters can comprise a pulse rate, respiration rate, SpO2, PVI, PI, RRP, hydration, or a combination thereof.

In some configurations, the sensor can further comprise a thermistor located near the plurality of emitters.

In some configurations, the sensor can further comprise an accelerometer and/or gyroscope.

In some configurations, the sensor processor can be configured to selectively drive some of the plurality of emitters and/or activate or deactivate some of the plurality of detectors.

An example optical physiological sensor of the present disclosure can be integrated into a watch configured to monitor health of a wearer. The optical physiological sensor can be configured to face tissue of the wearer when the watch is worn by the wearer and to measure physiological parameters of the wearer using information from the optical physiological sensor. The optical physiological sensor can comprise a plurality of emitters, the emitters configured to emit light of a plurality of different wavelengths, the plurality of different wavelengths comprising at least three different wavelengths; a plurality of detectors, the detectors configured to detect light emitted by the plurality of emitters and attenuated by tissue of the user when the watch is worn on the wrist of the wearer and output signals to a sensor processor for determining the physiological parameters of the wearer; and a sensor housing, the plurality of emitters and the plurality of detectors enclosed within the housing, wherein the sensor housing can comprise: a convex skin-facing light transmissive cover extending over the plurality of emitters and the plurality of detectors, the cover located at a first side of sensor housing, and a printed circuit board (PCB) located at a second side of the sensor housing opposite the first side, the plurality of emitters and detectors located on a skin-facing side of the PCB; a plurality of light barriers extending from the PCB to the cover, the plurality of light barriers configured to form walls of chambers to block light or substantially all the light between the chambers, each chamber enclosing one or more emitters without detectors, or one or more detectors without emitters, wherein each chamber that encloses one or more emitters can be filled with a diffusing material such that there is no air gap between the plurality of emitters and the cover.

In some configurations, the light diffusing material can comprise glass microspheres.

In some configurations, the cover can comprise glass microspheres.

In some configurations, the sensor housing can comprise one or more openings configured to receive a flow of light diffusing solution.

In some configurations, the light diffusion solution can be UV-cured after being injected into each chamber that encloses one or more emitters.

In some configurations, the sensor housing can comprise one or more air vent openings configured to receive air displaced from the chamber(s) by the flow of light diffusing solution.

In some configurations, each chamber that encloses one or more detectors can be filled with the diffusing material such that there is no air gap between the plurality of detectors and the cover.

In some configurations, the diffusing material in each chamber that encloses one or more emitters can be configured to improve mixing of light such that light emitted by one of the emitter in the same chamber appears to be emitted from the entire same chamber.

An example watch of the present disclosure can be configured to monitor physiological parameters of a wearer. The watch can comprise any of the optical sensor or physiological parameter measurement sensor configurations disclosed above; a watch processor separate from and in electrical communication with the sensor processor; a power source configured to power the watch and the sensor, and a display in communication with the processor, the display configured to display the plurality of physiological parameters monitored by the sensor.

In some configurations, the display can be configured to display the wearer's SpO2 and pulse rate that are monitored by the sensor.

In some configurations, the sensor can be configured to continuously monitor the wearer's SpO2 and pulse rate.

In some configurations, the display can be configured to continuously display the wearer's SpO2 and pulse rate.

In some configurations, the watch can further comprise an ECG sensor.

In some configurations, the ECG sensor can comprise a reference electrode, a negative electrode, and a positive electrode.

In some configurations, the reference and negative electrodes can be located on the sensor.

In some configurations, a portion of a housing of the watch can form the positive electrode.

In some configurations, the ECG sensor can be in electrical communication with the sensor processor.

In some configurations, the watch can further comprise a wireless transmitter such that the watch is configured to wireless connect to external devices and/or external sensors.

In some configurations, the wireless transmitter can be a Bluetooth chip.

In some configurations, the external devices and/or external sensors can comprise a bedside monitor, a mobile communication device, a tablet, a nurses' station system, or a different medical device.

A health monitoring watch of the present disclosure can comprise a strap and a housing. The housing can comprise: a first chamber comprising a first well comprising a first depth below a first surface configured to be in contact with a skin of a user; a first plurality of light emitting diodes positioned at the first depth inside the first well, said first plurality of light emitting diodes comprising a first light emitting diode configured to emit light at a first wavelength, a second light emitting diode configured to emit light at a second wavelength different than the first wavelength, and a third light emitting diode configured to emit light at a third wavelength different than the first wavelength and the second wavelength, and a first wall surrounding the first well; a second chamber comprising a second well comprising a second depth below a second surface configured to be in contact with the skin of the user, a second plurality of light emitting diodes positioned at the second depth inside the second well, said second plurality of light emitting diodes comprising a fourth light emitting diode configured to emit light at the first wavelength, a fifth light emitting diode configured to emit light at the second wavelength different than the first wavelength, and a sixth light emitting diode configured to emit light at the third wavelength different than the first wavelength and the second wavelength, and a second wall surrounding the second well; and four or more light sensors.

A wearable health monitoring device can be configured to be worn on a wrist of a user and monitor one or more physiological parameters indicative of the user's health. The wearable health monitoring device can comprise: a first emitter grouping, the first emitter grouping comprising a first plurality of light-emitting diodes (LEDs) configured to emit light of one or more wavelengths, wherein the first emitter grouping can be arranged at a first location, the first location being spaced from an axis extending through a center of the wearable health monitoring device; a second emitter grouping, the second emitter grouping comprising a second plurality of LEDs configured to emit light of one or more wavelengths, wherein the second emitter grouping can be arranged at a second location, the second location being spaced from the first location and spaced from the axis extending through the center of the wearable health monitoring device; one or more light blocks separating the first emitter grouping from the second emitter grouping; a first light diffusing material, the first light diffusing material configured to be positioned between the first emitter grouping and tissue of the user when the wearable health monitoring device is in use, wherein the first light diffusing material can be configured to spread light emitted from one or more of the first plurality of LEDs before the emitted light reaches the tissue; a second light diffusing material, the second light diffusing material configured to be positioned between the second emitter grouping and the tissue of the user when the wearable health monitoring device is in use, wherein the second light diffusing material can be configured to spread light emitted from one or more of the second plurality of LEDs before the emitted light reaches the tissue; a plurality of photodiodes configured to detect at least a portion of the light emitted from one or more of the first plurality of LEDs or one or more of the second plurality of LEDs after attenuation through the user's tissue, the plurality of photodiodes configured to output one or more signals responsive to the detected light; and a processor configured to receive and process one or more signals responsive to the one or more signals outputted by the plurality of photodiodes and further configured to determine a physiological parameter of the user based on the received and processed one or more signals.

It is noted that "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood. Moreover, "oximetry" as used herein encompasses its broad ordinary meaning known to one of skill in the art, which includes at least those noninvasive procedures for measuring parameters of circulating blood through spectroscopy.

Also disclosed herein are examples of a watch or electronic device that can be configured to monitor physiological parameters of a wearer, and can include a physiological parameter measurement sensor, a processor, a power source configured to power at least the watch and the sensor, a display in communication with the processor, the display configured to display the plurality of physiological parameters monitored by the sensor, and a watch band. In some examples, the processor can be configured to analyze a quality level of the signals from the optical physiological sensor, determine if the quality level of the signals from the optical physiological sensor is below, at, or above a threshold quality level, and output a result related to the quality level to the user.

Any examples of the watches or electronic devices disclosed herein can include, in additional examples, one or more of the following features, components, and/or details, in any combination with any of the other features, components, and/or details of any other examples disclosed herein: wherein the watch comprises an adjustable watch band; wherein the adjustable watch band comprises a reel and cable system; wherein the adjustable watch band comprises a constant tension mechanism; wherein the adjustable watch band comprises a mechanical adjustment mechanism; wherein the adjustable watch band comprises a rack and pinion adjustment mechanism; wherein the adjustable watch band comprises an adjustment dial that can be moved between a first position in which the adjustment dial extends away from the watch band and a second position in which the adjustment dial does not extend away from the watch band; and/or wherein the adjustable watch band comprises an adjustment dial that can be moved between a first position in which the adjustment dial extends away from the watch band and a second position in which the adjustment dial is positioned within a recess formed in the watch band.

Also disclosed herein are examples of a wearable band configured to improve contact between one or more sensors of a physiological monitoring system with a tissue site on a wrist of a user that can include a buckle unit configured to secure the wearable band to the wrist of the user and a mechanical adjustment unit configured tighten the wearable band on the wrist of the user. Any examples of the wearable band disclosed herein can include, in additional examples, one or more of the following features, components, and/or details, in any combination with any of the other features, components, and/or details of any other examples disclosed herein: wherein said tightening is configured to improve contact between one or more sensors of the physiological monitoring system with the tissue site; wherein the mechanical adjustment unit comprises a rack and pinion adjustment mechanism; wherein the rack and pinion adjustment mechanism comprises a dial, a first gear rotationally coupled with the dial, and a rack having a plurality of teeth configured to engage with the first gear, the rack being configured to move in a lengthwise direction to shorten or lengthen the wearable band when the first gear is rotated; wherein the rack and pinion adjustment mechanism comprises a dial, a first gear rotationally coupled with the dial, a second gear rotationally engaged with the first gear, a third gear rotationally engaged with the second gear, and a rack having a plurality of teeth configured to engage with the third gear, the rack being configured to move in a lengthwise direction to shorten or lengthen the wearable band when the third gear is rotated; further comprising a locking mechanism configured to at least selectively inhibit a movement of the mechanical adjustment unit when the locking mechanism is engaged; wherein the adjustable watch band comprises an adjustment dial that can be moved between a first position in which the adjustment dial extends away from the watch band and a second position in which the adjustment dial does not extend away from the watch band; wherein the adjustable watch band comprises an adjustment dial that can be moved between a first position in which the adjustment dial extends away from the watch band and a second position in which the adjustment dial is positioned within a recess formed in the watch band; and/or wherein the wearable band comprises a first strap comprising a first end configured to be secured to a first portion of the health monitoring device, a second end opposite the first end, and a length extending between the first and second ends; and a second strap comprising a first end configured to be secured to a second portion of the health monitoring device, a second end opposite the first end, and a length extending between the first and second ends, wherein the first strap and the second strap are configured to be secured with one another to form a closed loop around a portion of the user's body wherein the first strap and the second strap further comprise a stretchable material; said stretchable material comprising a plurality of holes or ridges, or both, configured to stretch the first strap and the second strap evenly when the first strap and the second strap are secured with one another around a portion of the user's body.

Also disclosed herein are examples of a method of analyzing and notifying a user of a tension level of a strap of a watch configured to monitor physiological parameters of a wearer, wherein the method can include analyzing a quality of a signal data from a physiological parameter measurement sensor of the watch, determining if the quality of the signal data is below a predefined threshold or desired value, and outputting a message to a user to (i) instruct the user to change a tension level of the strap if the quality of the signal data is below a predefined threshold or desired value, or (ii) notify the user that the tension level of the strap is adequate or optimal if the quality of the signal data is above a predefined threshold or desired value.

The wearable health monitoring device can include an adjustable strap configured to releasably secure the device around a wrist of a wearer. In some cases, to ensure accurate and reliable measurements, it can be important for the user to secure the adjustable strap around the wrist at an adequate tightness, such that the adjustable strap is not too loose or too tight. Disclosed herein are systems and methods for electronically assessing the tightness of the adjustable strap using a non-invasive sensor. Furthermore, disclosed herein are systems and methods for providing an indication of a tightness condition, such as whether the tightness of the adjustable strap is adequate, too tight, or too loose. By electronically assessing the tightness of the adjustable strap, the wearable plethysmography monitoring device can advantageously improve reliability and accuracy of measurements.

Disclosed herein is a wearable device configured to monitor physiological parameters of a wearer, the wearable device comprising: a physiological parameter measurement sensor configured to monitor a plurality of physiological parameters; a hardware processor; a display in communication with the processor; and a band configured to secure the physiological parameter measurement sensor on a wrist of the wearer; wherein the hardware processor is configured to: obtain a first plurality of signals from the physiological parameter measurement sensor when the band is secured on the wrist at a first tightness; determine a signal quality responsive to the first plurality of signals; and output an indication on the display to adjust tightness of the band with respect to the wrist from the first tightness to a second tightness based on the determined signal quality In some implementations, the band comprises an adjustable watch band. In some implementations the adjustable watch band comprises a reel and cable system. In some implementations the adjustable watch band comprises a mechanical adjustment mechanism. In some implementations the adjustable watch band comprises a rack and pinion adjustment mechanism. In some implementations the adjustable watch band comprises an adjustment dial that can be moved between a first position in which the adjustment dial extends away from the adjustable watch band and a second position in which the adjustment dial does not extend away from the adjustable watch band. In some implementations the adjustable watch band comprises an adjustment dial that can move between a first position in which the adjustment dial extends away from the adjustable watch band and a second position in which the adjustment dial is positioned within a recess formed in the adjustable watch band.

Disclosed herein is a wearable device configured to monitor physiological parameters of a wearer, the wearable device comprising: a physiological parameter measurement sensor configured to monitor a plurality of physiological parameters; a hardware processor; a power source configured to power at least the wearable device and the physiological parameter measurement sensor; a display in communication with the hardware processor, the display configured to display the plurality of physiological parameters monitored by the physiological parameter measurement sensor; and a band comprising a plurality of characters and configured to secure the physiological parameter measurement sensor to the wearer; wherein the hardware processor is configured to: obtain a first plurality of signals from the physiological parameter measurement sensor when the band is secured to the wearer at a first tightness; determine a signal quality responsive to the first plurality of signals; and output an indication on the display to adjust tightness of the band with respect to a wrist from the first tightness to a second tightness based on the determined signal quality.

In some implementations, the first tightness comprises a tighter configuration than the second tightness. In some implementations, the second tightness comprises a tighter configuration than the second tightness. In some implementations, the band is adjustable. In some implementations, the band comprises a reel and cable system. In some implementations, band comprises a constant tension mechanism. In some implementations, the band comprises a mechanical adjustment mechanism. In some implementations, the band comprises a rack and pinion adjustment mechanism. In some implementations, the band comprises an adjustment dial that can be moved between a first position in which the adjustment dial extends away from the band and a second position in which the adjustment dial does not extend away from the band. In some implementations, the band comprises an adjustment dial that can be moved between a first position in which the adjustment dial extends away from the band and a second position in which the adjustment dial is positioned within a recess formed in the band. In some implementations, each of the plurality of characters comprise at least one of a number, a letter, a symbol, or a combination thereof. In some implementations, the band comprises a first strap and a second strap, at least one of the first strap and the second strap comprising a plurality of holes configured to receive a securing mechanism. In some implementations, each of the plurality of characters is associated with at least one of the plurality of holes of the first strap and the second strap. In some implementations, each of the plurality of characters is displayed adjacent to each one of the plurality of holes of the first strap and the second strap. In some implementations, the hardware processor is further configured to provide an indication to a user to secure the securing mechanism to at least one of the plurality of holes. In some implementations, the indication comprises displaying at least one of the plurality of characters on the display In some implementations, the plurality of holes extend along a length of the first strap and second strap, and wherein each of the plurality of characters is positioned adjacent to each of the plurality of holes.

Disclosed herein is a wearable band configured to improve contact between one or more sensors of a physiological monitoring system with a tissue site of a user, said wearable band comprising: a buckle unit configured to secure the wearable band to the user; and a mechanical adjustment unit configured to tighten the wearable band on the user, said tightening configured to improve contact between one or more sensors of the physiological monitoring system with the tissue site.

In some implementations, the mechanical adjustment unit comprises a at least one of a rack and pinion adjustment mechanism, a reel and cable system. In some implementations, the rack and pinion adjustment mechanism comprises a dial, a first gear rotationally coupled with the dial, and a rack having a plurality of teeth configured to engage with the first gear, the rack being configured to move in a lengthwise direction to shorten or lengthen the wearable band when the first gear is rotated. In some implementations, the rack and pinion adjustment mechanism comprises a dial, a first gear rotationally coupled with the dial, a second gear rotationally engaged with the first gear, a third gear rotationally engaged with the second gear, and a rack having a plurality of teeth configured to engage with the third gear, the rack being configured to move in a lengthwise direction to shorten or lengthen the wearable band when the third gear is rotated. In some implementations, the wearable band comprises a locking mechanism configured to at least selectively inhibit a movement of the mechanical adjustment unit when the locking mechanism is engaged. In some implementations, the mechanical adjustment unit comprises an adjustment dial that can be moved between a first position in which the adjustment dial extends away from the wearable band and a second position in which the adjustment dial does not extend away from the wearable band. In some implementations, the wearable band comprises an adjustment dial that can be moved between a first position in which the adjustment dial extends away from the wearable band and a second position in which the adjustment dial is positioned within a recess formed in the wearable band.

Disclosed herein is a method of analyzing and notifying a user of a tension level of a strap of a wearable device configured to monitor physiological parameters of a wearer, comprising: obtaining a first plurality of signals from a physiological parameter measurement sensor when the strap is secured to the user at a first tightness; determining a signal quality responsive to the first plurality of signals using a hardware processor; and outputting a message to a user to adjust the tightness of the strap from the first tightness to a second tightness based on the determined signal quality.

In some cases, the method further comprises providing a strap having a plurality of holes and a plurality of characters associated to each of the plurality of holes. In some cases, the plurality of characters comprises at least one of a number, a letter, a symbol, or a combination thereof. In some cases, the method further comprises instructing the user to secure the strap to a specific hole of the plurality of holes associated to a specific character of the plurality of characters. In some instructing the user to secure the strap to a specific hole of the plurality of holes further comprises displaying, on a display of the wearable device, at least one of the plurality of characters.

Disclosed herein is a wearable band configured to improve contact between one or more sensors of a health monitoring device with a tissue site on a wrist of a user, said wearable band comprising: a first strap comprising a first end configured to be secured to a first portion of the health monitoring device, a second end opposite the first end, and a length extending between the first and second ends; and a second strap comprising a first end configured to be secured to a second portion of the health monitoring device, a second end opposite the first end, and a length extending between the first and second ends, wherein the first strap and the second strap are configured to be secured with one another to form a closed loop around a portion of the user, wherein the first strap or the second strap, or both, further comprise a stretchable material; said stretchable material comprising a plurality of holes or ridges, or both, configured to stretch the first strap and the second strap evenly when the first strap and the second strap are secured with one another around a portion of the user's body. In some implementations, the plurality of ridges of the first and second straps extend along substantially an entirety of the length of the first strap and the second strap. In some implementations, the plurality of ridges of the first and second straps are spaced evenly. In some implementations, the plurality of holes of the first and second straps extend along substantially an entirety of the length of the first strap and the second strap. In some implementations, the plurality of holes of the first and second straps extend along substantially a portion of the length of the first strap and the second strap. In some implementations, the plurality of holes of the first and second straps are spaced evenly. In some implementations, at least a portion of the plurality of holes of the first and second straps are covered. In some implementations, the second end of the first strap comprises a securing mechanism. In some implementations, the first and second straps further comprise a plurality of openings, and wherein said plurality of openings extend substantially an entirety of the length of the first strap and the second strap. In some implementations, the plurality of openings of the second strap is configured to receive at least one portion of the securing mechanism of the first strap to form a closed loop around a portion of the user's body. In some implementations, the health monitoring device is configured to measure one or more physiological parameters of the user. In some implementations, the health monitoring device is configured to measure at least one of oxygen saturation and pulse rate of the user.

Disclosed herein is a strap for a wearable device configured to secure to a portion of a body of a user, the strap comprising: a first band comprising a first end configured to be secured to a portion of the wearable device, a second end opposite the first end, a length extending between the first and second ends, and a hollow interior extending along at least a portion of the length, wherein the first band comprises a first material; and a second band secured to the first band, the second band positioned within the hollow interior of the first band and extending outward from the hollow interior beyond the second end of the first band, wherein at least a portion of the second band comprises a second material that is different than the first material and that is configured to allow the second band to stretch, thereby allowing a total length of the strap to vary.

In some implementations, a portion of the second band positioned within the hollow interior of the first band substantially fills the hollow interior. In some implementations, an entirety of a portion of the second band positioned within the hollow interior of the first band is surrounded by the first band. In some implementations, the hollow interior extends along substantially an entirety of the length of the first band. In some implementations, the second band comprises a first end positioned within the hollow interior of the first band and a second end opposite the first end of the second band and positioned outside the hollow interior. In some implementations, the first end of the second band is secured to the first band. In some implementations, only the first end of the second band is secured to the first band. In some implementations, the second band further comprises first and second sides opposite one another and extending between the first and second ends of the second band, and wherein portions of the first and second sides are secured to the first band within the hollow interior. In some implementations, the second band further comprises first and second sides opposite one another and extending between the first and second ends of the second band, and wherein the first and second sides are not secured to the first band within the hollow interior. In some implementations, the second band further comprises top and bottom surfaces opposite one another and extending between the first and second ends of the second band, and wherein portions of the top and bottom surfaces are secured to the first band within the hollow interior. In some implementations, the second band further comprises top and bottom surfaces opposite one another and extending between the first and second ends of the second band, and wherein the top and bottom surfaces are not secured to the first band within the hollow interior. In some implementations, the second end of the second band is coupled with a buckle. In some implementations, the first material comprises leather or suede. In some implementations, the second material comprises silicone. In some implementations, the second material comprises stretchable fabric. In some implementations, the second material comprises nylon. In some implementations, the second material is more stretchable than the first material. In some implementations, the first end of the first band comprises a coupling portion configured to be secured to the portion of the wearable device via a pin connection. In some implementations, an entirety of the second band comprises the second material. In some implementations, a first portion of the second band comprises the second material and a second portion of the second band comprises a third material that is different than the second material. In some implementations, the third material is less stretchable than the second material. In some implementations, the third material and the first material are the same. In some implementations, the first portion of the second band is greater than the second portion of the second band. In some implementations, the first portion of the second band is less than the second portion of the second band. In some implementations, the third material comprises silicone. In some implementations, the third material comprises a stretchable fabric. Disclosed herein is a wearable device comprising any of the straps described above or elsewhere herein and also comprising an additional strap configured to be secured with one another to form a closed loop around a portion of the user's body. In some implementations, the wearable device is configured to be secured to a wrist of the user. In some implementations, the wearable device is configured to measure one or more physiological parameters of the user. In some implementations, the wearable device is configured to measure at least one of oxygen saturation and pulse rate of the user.

Disclosed herein is a strap for a wearable device configured to secure to a portion of a body of a user, the strap comprising: a first band comprising a first portion and a second portion, the second portion configured to be secured to a portion of the wearable device; and a second band secured to the first and second portions of the first band, wherein at least a portion of the second band is configured to allow the second band to stretch relative to at least one of the first and second portions of the first band. In some implementations: the strap has a first state in which the strap has a first length and a second state in which the strap has a second length that is greater than the first length; and the first and second portions of the first band are spaced farther apart from one another when the strap is in the second state than when in the first state.

In some implementations, the strap is biased toward the first state. In some implementations, there is no gap between the first and second portions of the first band when the strap is in the first state. In some implementations, when the strap is in the first state, the first and second portions are in contact with one another. In some implementations: when the strap is in the first state, the first and second portions of the first band are separated from one another by a first gap; when the strap is in the second state, the first and second portions are separated from one another by a second gap; and the first gap is smaller than the second gap. In some implementations, the first gap is between about 0 inch and about 0.2 inch. In some implementations, the first gap is less than about 0.2 inch. In some implementations, the first portion of the first band is coupled with a buckle. In some implementations, a first portion of the second band is positioned within an interior of the first portion of the first band and wherein a second portion of the second band is positioned within an interior of the second portion of the first band. In some implementations, the first band comprises a first material and at least a portion of the second band comprises a second material that is different than the first material. In some implementations, the second material is more stretchable than the first material. In some implementations, an entirety of the second band comprises the second material. In some implementations, only a portion of the second band comprises the second material. In some implementations, the first material comprises leather or fabric. In some implementations, the second material comprises silicone or stretchable fabric. In some implementations, when the strap is in the first state, the second band is substantially hidden from view, and wherein, when the strap is in the second state, the second band is visible. In some implementations: the second band comprises a first portion and a second portion; an entire cross-section of the first portion of the second band is surrounded by the first portion of the first band; and an entire cross-section of the second portion of the second band is surrounded by the second portion of the first band. Disclosed herein is a wearable device comprising any of the straps described above or elsewhere herein and also comprising an additional strap configured to be secured with one another to form a closed loop around a portion of the user's body. In some implementations, the wearable device is configured to secure to a wrist of the user. In some implementations, the wearable device is configured to measure one or more physiological parameters of the user. In some implementations, the wearable device is configured to measure at least one of oxygen saturation and pulse rate of the user.

For purposes of summarization, certain aspects, advantages and novel features are described herein. Of course, it is to be understood that not necessarily all such aspects, advantages or features need to be present in any particular example.

BRIEF DESCRIPTION OF THE DRAWINGS

The drawings and the associated descriptions are provided to illustrate examples of the disclosure and not to limit the scope of the claims. In the present disclosure, "bottom" refers to the side facing a wearer's wrist when an example wearable device disclosed herein is worn on the wearer's wrist and "top" refers to the side facing away from the wearer's wrist.

FIGS. 75I-75J illustrates views of a strap of the wearable device of FIGS. 75A-75B in a second state in accordance with aspects of this disclosure.

FIGS. 75K-75L illustrate views of another implementation of a strap in first and second states in accordance with aspects of this disclosure.

FIG. 76A illustrates another implementation of a wearable device in accordance with aspects of this disclosure.

FIG. 76B illustrates an enlarged view of a strap of the wearable device of FIG. 76A in a first state in accordance with aspects of this disclosure.

FIG. 76C illustrates an enlarged view of the strap of the wearable device of FIG. 76A in a second state in accordance with aspects of this disclosure.

FIGS. 76D-76F illustrate views of the wearable device of FIG. 76A being secured and/or secured to a user's wrist in accordance with aspects of this disclosure.

FIG. 77A illustrates a bottom perspective view of a wearable device in accordance with aspects of this disclosure.

FIG. 77B illustrates an enlarged view of the strap of the wearable device of FIG. 76A in accordance with aspects of this disclosure.

FIGS. 78A-80E illustrate additional implementations of wearable devices and straps therefor, in accordance with aspects of this disclosure.

DETAILED DESCRIPTION

Figure 1C:
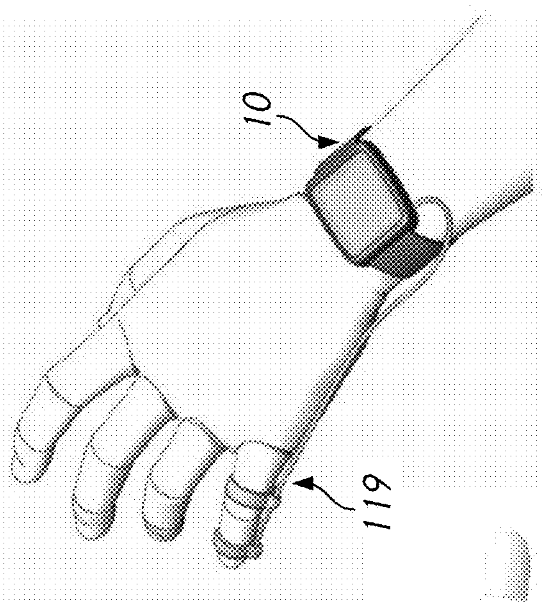
FIG. 1C illustrates an example fingertip sensor that can be coupled to the wearable device of the present disclosure.
Figure 1B:
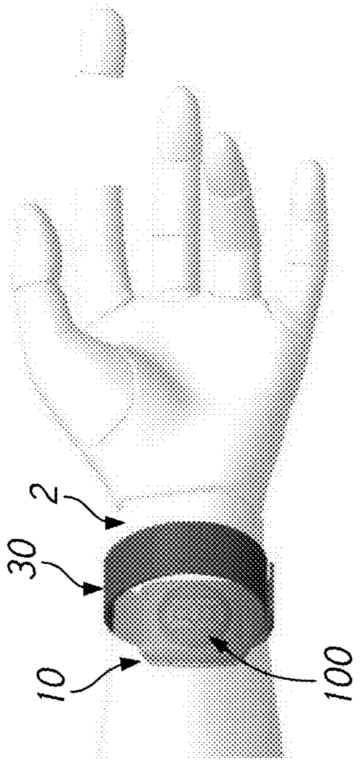
FIG. 1B illustrates a second view of the example wearable device of FIG. 1A worn on the wrist.
Figure 1A:
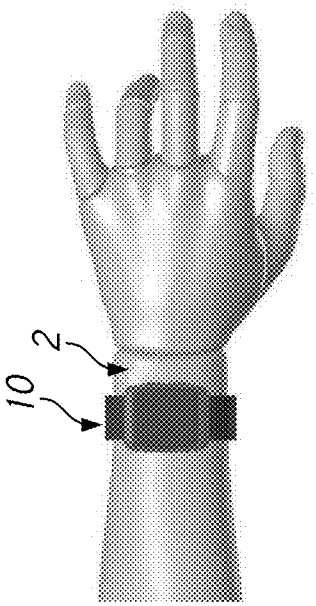
FIG. 1A illustrates a first view of an example wearable device including a physiological parameter measurement sensor or module worn on a wrist using straps.

Although certain examples and examples are described below, those of skill in the art will appreciate that the disclosure extends beyond the specifically disclosed examples and/or uses and obvious modifications and equivalents thereof based on the disclosure herein. Thus, it is intended that the scope of the disclosure herein disclosed should not be limited by any particular examples described below.

Overview of Wearable Device Including a Physiological Parameter Measurement Sensor or Module Daily use of a wearable healthcare monitoring device, which can include oximetry- or plethmosmograph-based and/or ECG physiological parameters, can be beneficial to the wearer. The device, such as a device 10 as shown in FIGS. 1A-1H, can be a wristwatch incorporating a physiological parameter measurement sensor or module 100 or a wrist-worn physiological parameter measurement sensor with built-in watch or time-indicating functions. The device 10 can include an adjustable strap 30. Accordingly, the wearer needs not wear an additional sensor when going about daily activities and the appearance of the device attracts less attention from the general public so that the wearer may feel less self-conscious about wearing a pulse oximeter sensor on the wearer's body. The wearer can also connect additional sensors (for example, a fingertip plethysmograph sensor shown in FIG. 1C) and/or other physiological monitoring devices to the wearable device to expand the functionality of the wearable device.

The wearer can be informed of physiological parameters, such as vital signs including but not limited to heart rate (or pulse rate), and oxygen saturation by the wearable device 10. The device 10 can display one or more of the measured physiological parameters on its display screen 12. The information can be helpful in providing feedback to the wearer and/or a third party user, for example, a healthcare professional or the wearer's family member, when the wearer is exercising, or otherwise for warning the wearer of possible health-related conditions, including but not limited to changes in the wearer's physiological parameters in response to medication that is being administered to the wearer.

As shown in FIGS. 1A-1H, the wearable device 10 can be a watch, which can include a physiological parameter measurement sensor or module 100 configured to measure an indication of the wearer's physiological parameters, which can include, for example, pulse rate, respiration rate, oxygen saturation (SpO2), Pleth Variability Index (PVI), Perfusion Index (PI), Respiration from the pleth (RRp), hydration, glucose, blood pressure, and/or other parameters. The physiological parameter measurement sensor or module 100 can be an optical sensor. Additionally, the sensor or module 100 can optionally calculate a wellness index based on more than one individual physiological parameter measured by the module and/or received by the sensor or module 100 based on externally connected sensors and/or patient monitoring devices. The sensor or module 100 can perform intermittent and/or continuous monitoring of the measured parameters. The sensor or module 100 can additionally and/or alternatively perform a spot check of the measured parameters, for example, upon request by the wearer.

Figure 1E:
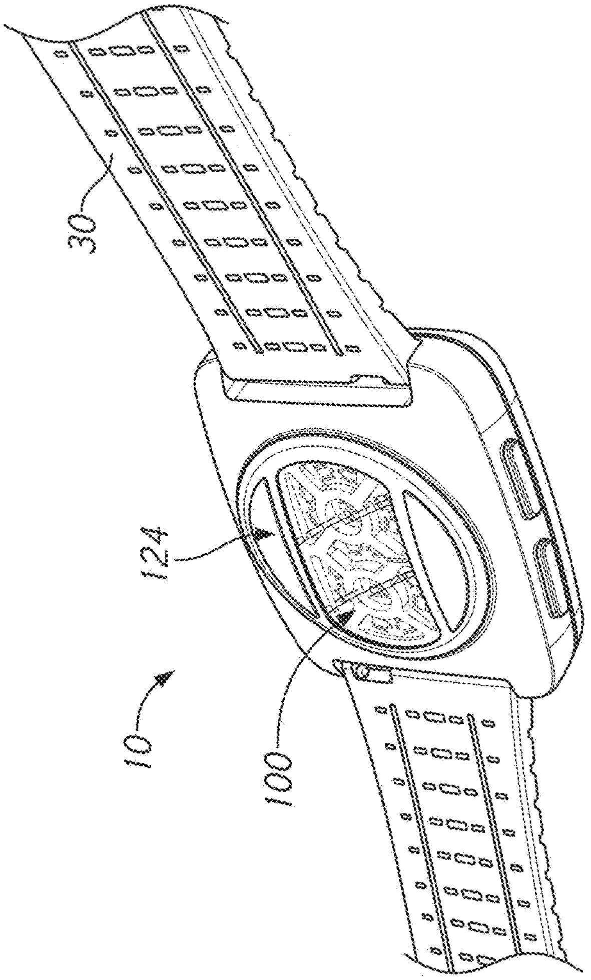
FIG. 1E illustrates a bottom perspective view of the example wearable device of FIG. 1D.
Figure 1D:
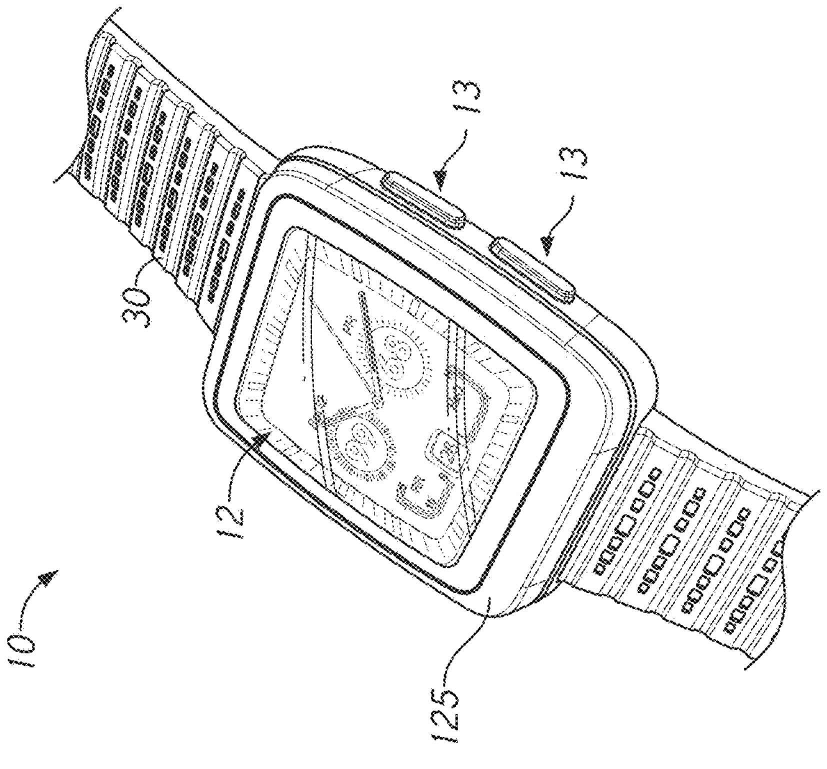
FIG. 1D illustrates a top perspective view of the example wearable device of FIGS. 1A-1C with a partial view of the straps.
Figure 1G:
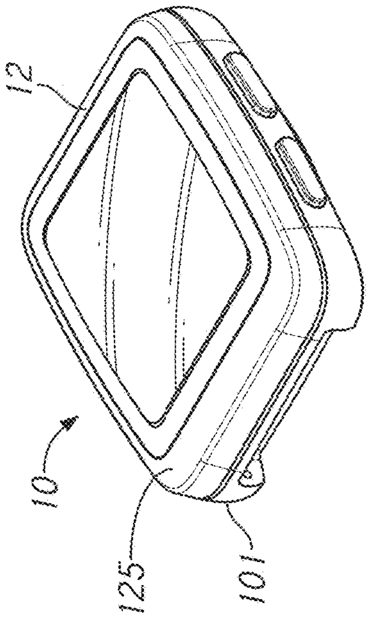
FIG. 1G illustrates a top perspective view of the example wearable device of FIG. 1F.
Figure 1H:
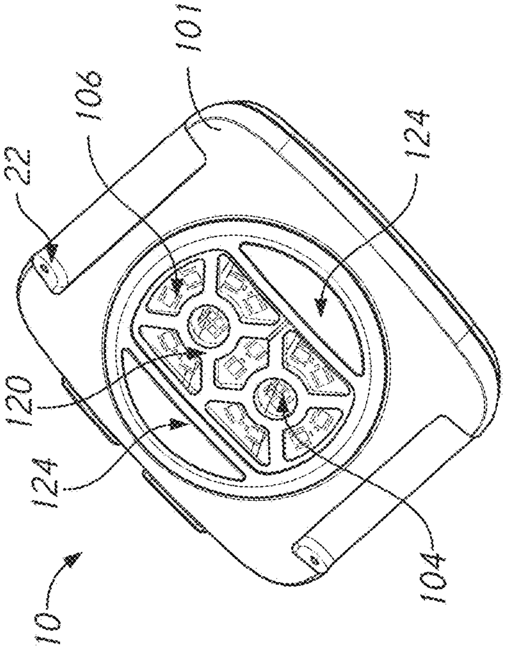
FIG. 1H illustrates a bottom perspective view of an example wearable device.
Figure 1F:
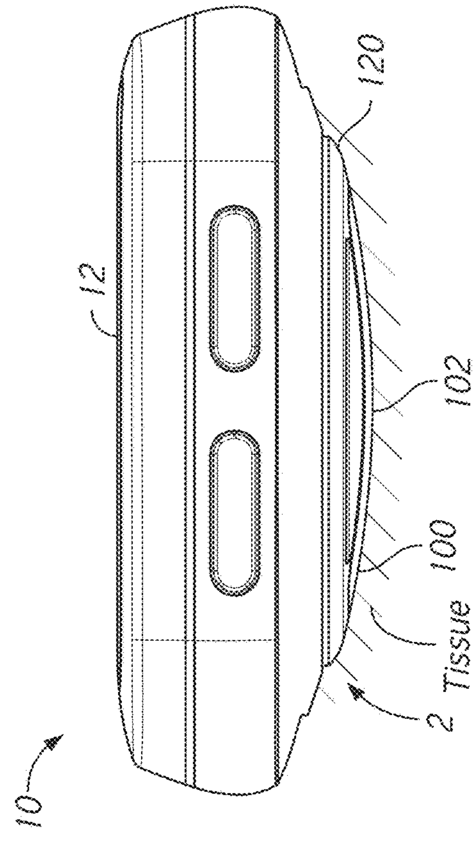
FIG. 1F illustrates a side view of an example wearable device without the straps when the device is interfacing with a wearer's skin.

As shown in FIGS. 1E and 1H, a bottom side of a device (or watch) housing 101 can include an opening sized to retain the physiological parameter measurement sensor or module 100 while still allowing the tissue-facing surface of the sensor or module 100 to be exposed. The retaining of the sensor or module 100 in the device housing 101 can be aided by any suitable retaining mechanisms. As shown in FIGS. 1F and 1H, the physiological parameter measurement sensor or module 100 can include a skin-interfacing light transmissive cover 102 that encloses a plurality of light emitters 104 (such as LEDs) and one or more photodetectors (also referred to as "detectors") 106. Additionally, the sensor or module 100 can optionally include an electrocardiogram (ECG) sensor, which can include a plurality of ECG electrodes 124, 125. As shown in FIGS. 1G and 1H, some of the ECG electrodes 125 can be located away from the sensor or module 100 and some of the ECG electrodes 124 can be located on the sensor or module 100. The cover 102 can include a plurality of lenses or covers or a single construct of lens or cover. The physiological parameter measurement sensor or module 100 is designed to reduce noise in the signals detected by the detectors 106, for example, by reducing mixing of the emitted light and the reflected light using light barriers that are substantially opaque. As shown in FIG. 1F, the light barrier 120 can include a first light barrier which can be placed between the emitters and the detectors of the sensor or module 100. The first light barrier can extend (for example, entirely extend) along an inner portion of the cover 102. The first light barrier can also suppress light emitted by the emitters at an angle. The sensor or module 100 can include additional light barriers, including for example, a side perimeter wall and additional light barriers to separate the detectors from the emitters, and/or separate different detector groups from one another.

FIG. 1F illustrates the device 10 being worn on the wrist 2 of the wearer, with the physiological parameter measurement sensor or module 100 facing the wrist 2. The physiological parameter measurement sensor or module 100 on the device 10 is designed so as to reduce and/or eliminate a gap between a surface of the physiological parameter measurement sensor or module 100 and the wearer's skin at the measurement site where the device 10 is worn. At the wrist, if the device 10 is worn too loosely (which can be the case when the device 10 is able to slide over the skin when the device 10 is moved), the gap between the tissue-facing surface of the physiological parameter measurement sensor or module 100 and the wearer's skin can cause inaccurate measurements. This is because the gap can result in both light-piping and in the emitted light not penetrating deep enough into the wearer's tissue, for example, by going no deeper than within a top skin layer (for example, the epidermis) of the wearer's tissue, which typically does not have any blood vessels present. Therefore, light cannot reach and or interact with tissues, such as the arterial blood in the dermis, located below the top skin layer. The gap can also result in loss of the attenuated and reflected light through the gap so that less of the attenuated and reflected light can arrive at the detectors 106.

Figure 1I:
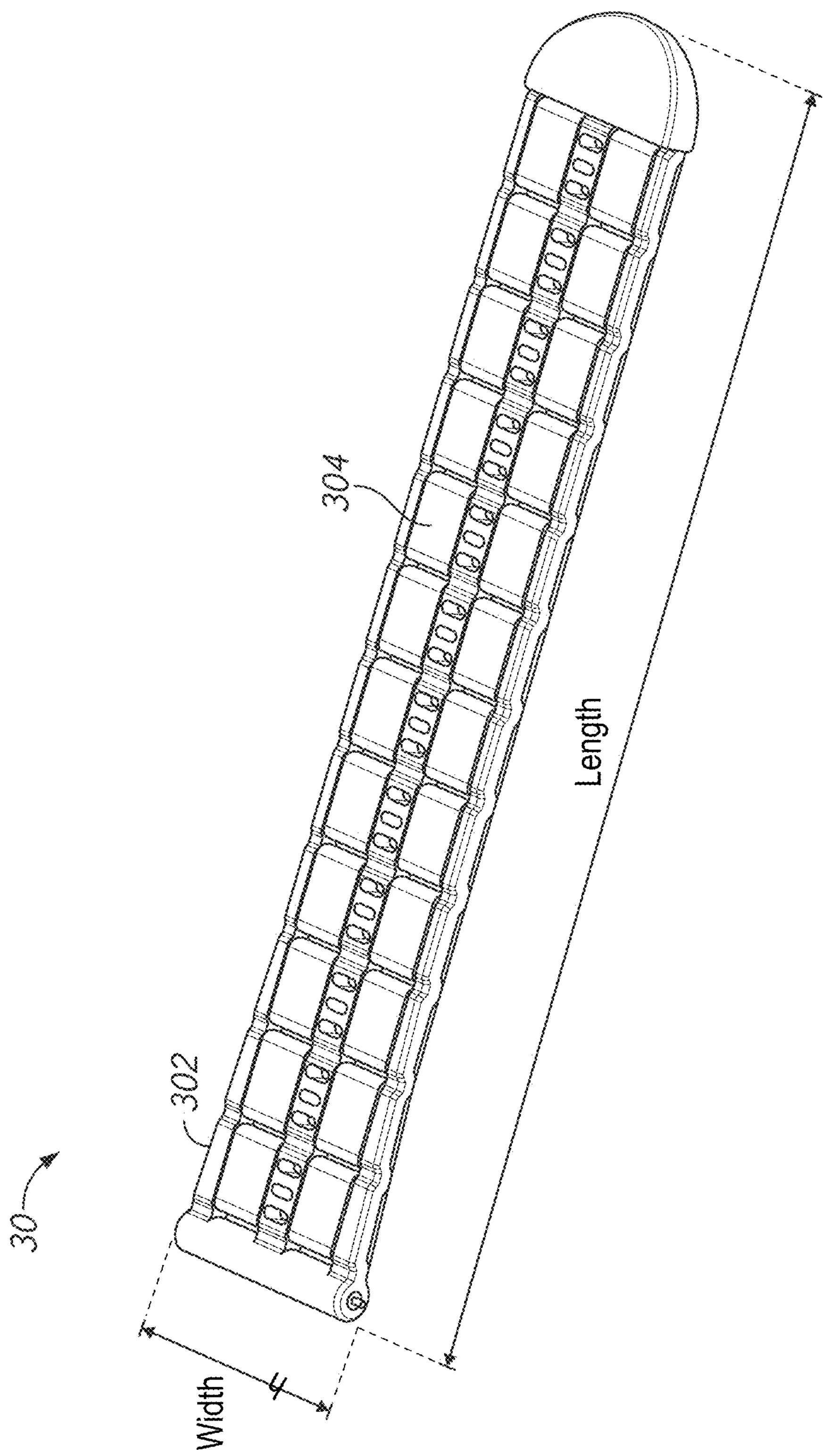
FIG. 1I illustrates a perspective view of an example strap configured to secure the wearable device disclosed herein to a wearer's wrist.

The tightness of the device 10 on the wearer's body (for example, the wrist) can be adjusted by adjusting any suitable strap(s) 30 used to secure the device to the wearer's body. The strap(s) can be connected to the device 10 using any suitable strap connections 22. For example, the strap connections 22 can be compatible with third party watch bands, wearable blood pressure monitors, and/or the like. As shown in FIG. 1I, an example strap 30 can be stretchable and evenly distribute the pressure of the device 10 around the wrist so as to provide better contact between the sensor or module 100 and the wrist 2 while not compromising the comfort of the wearer and/or reducing the blood flow across the wrist 2 in a way that reduces the accuracy of the measurement by the sensor or module 100. As shown in FIG. 1L, a rubber base 302 can be molded through a plurality of metal loops 304 arranged along a length of a strap 30 to form the strap 30. The metal loops 304 can include a thin (for example, less than about 1 mm) wall of metal forming a closed loop with a through-hole in a direction generally transverse to the length (that is, along a width) of the strap 30 and perpendicular to a thickness of the strap 30. During the overmolding process, the rubber material can fill up or substantially fill up the space in the through-hole. The metal loops 304 can be arranged in two rows along the length of the strap 30. Alternatively, the metal loops can include a partial loop with an opening, or the strap may include more than one partial metal loop snapped onto each other around the rubber base. Additional details of the strap 30 are described in U.S. Provisional Application No. 63/068,256, filed Aug. 20, 2020 and titled "WEARABLE PHYSIOLOGICAL MONITORING DEVICE WITH ADJUSTABLE STRAPS", the entire of which is incorporated herein by reference.

In the present disclosure, reference is made to a tightness of the adjustable strap. As used herein, the term "tightness" is used broadly to define the fit, position, orientation, pressure, etc. of the adjustable strap around the limb of the wearer. Accordingly, an adequate tightness can correspond to an adequate or optimal fit, position, orientation, pressure, etc. of the adjustable strap, and inadequate tightness correspond to an unsatisfactory or unacceptable fit, position, orientation, pressure, etc. of the adjustable strap. Furthermore, in some cases, the terms "adequate tightness" or "inadequate tightness" can be relative determinations based on measurement reliability. For example, a tightness that has a relatively high likelihood of being associated with a reliable measurement can be considered adequate. As a corollary, a tightness that has a relatively low likelihood of being associated with a reliable measurement can be considered inadequate.

In light of the description herein, it will be understood that the examples disclosed herein substantially improve wrist-based pulse oximetry and pulse oximetry in the presence of motion. Specifically, the examples disclosed herein enable a wearable device to determine a tightness condition of its adjustable strap, including determining whether the adjustable strap is too tight or too loose for the wearable device to obtain an accurate, consistent, or reliable measurement. The ability to electronically assess the fit of the adjustable strap 30 using a non-invasive sensor of the wearable device advantageously allow a wearer of the device to receive an indication of the tightness condition and readjust the tightness of the strap, if necessary, based on the tightness condition, which increases the usability and reliability of the wrist-based pulse oximetry of the wearable device. In some cases, the wearable device may automatically self-adjust the tightness of the strap based on the tightness condition. For example, the wearable device can include and control a motor, a rack and pinion gear system, etc. to tighten or loosen the strap. By providing an automatic adjustment of the strap tightness, the wearable device advantageously improves results of any wrist-based pulse oximetry performed by the device.

Additionally, the gap between a surface of the physiological parameter measurement sensor or module 100 and the wearer's skin at the measurement site can be reduced by the design of the light transmissive cover 102. As shown in FIG. 1F, a cover 102 of the physiological parameter measurement sensor or module 100 can include a convex curvature or convex protrusion on its skin-interfacing cover 102. As will be described in greater detail below, the curvature of the cover 102 of the sensor or module 100, which can include a plurality of lenses or covers or a single lens or cover, can be discontinuous or continuous.

As shown in FIG. 1F, when the device 10 is worn by the wearer, the convex cover 102 can be pressed onto the skin and the tissue 2 of the wearer can conform around the convex curvature. The contact between the convex cover 102 and the tissue 2 of the wearer can leave no air gaps between the tissue 2 and the convex cover 102. And as the emitters and/or detectors can be surrounded by a light-diffusing material (as will be described below), the physiological parameter measurement sensor or module 100 may leave no air gap between the tissue 2 and any of the emitters and/or detectors. Optionally, certain portion(s) of the cover 102 can protrude more into the skin than the remainder of the cover. The pressure exerted by the curvature of the cover 102 on the skin and/or the absence of air gap can increase a light illuminated and/or detection area, improve the optical coupling of the emitted light and the blood vessels and/or of the reflected light and the detectors, reduce light piping, and/or reduce stagnation of the blood. The cover curvature can be configured so as to balance the pressure needed to improve contact between the cover 102 and the skin, and the comfort of the wearer.

Figure 2:
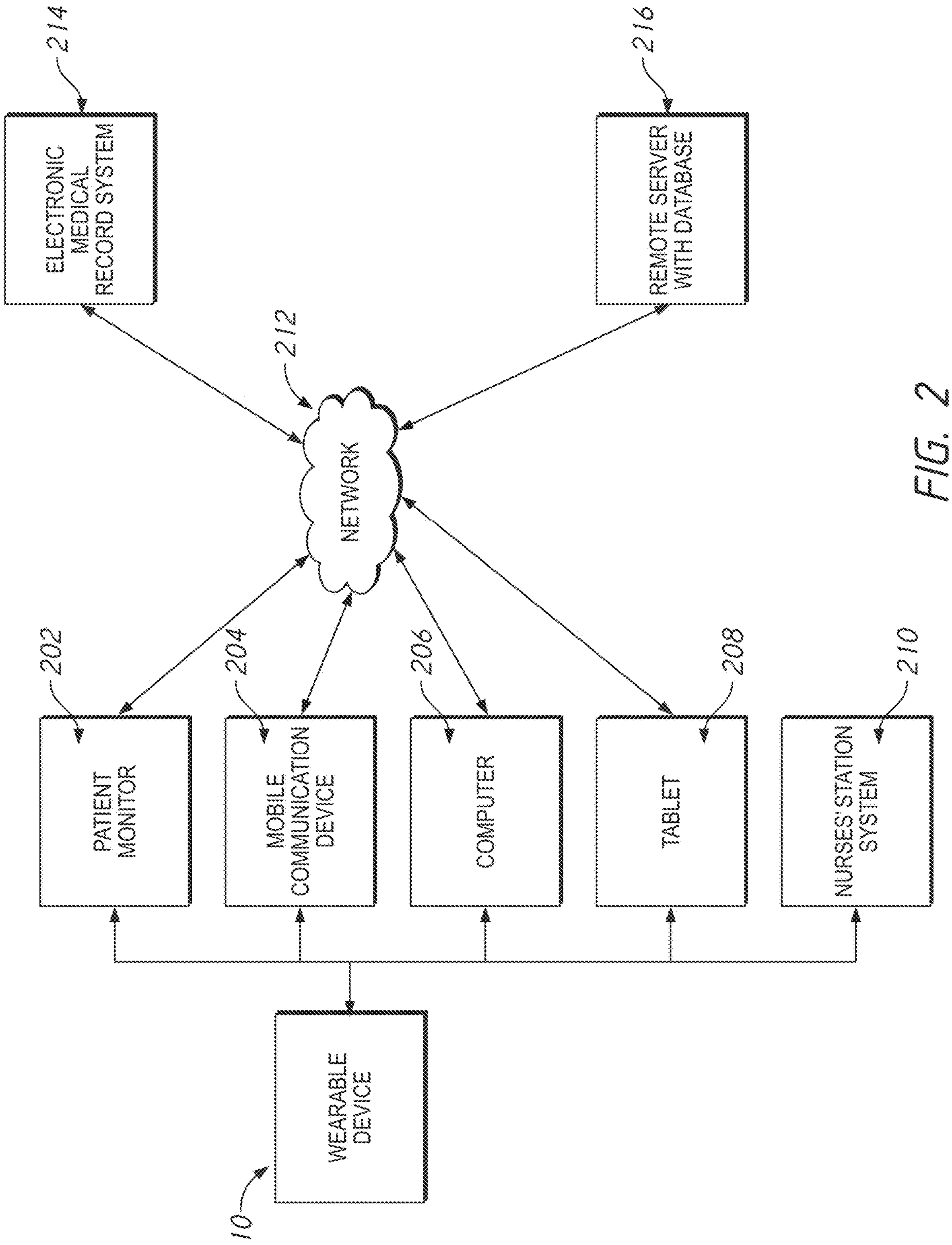
FIG. 2 is a diagram illustrating schematically a network of non-limiting examples of devices that can communicate with the wearable device disclosed herein.

The wearable device 10 can be used in a standalone manner and/or in combination with other devices and/or sensors. As shown in FIG. 2, the device 10 can connect (for example, wirelessly) with a plurality of devices, including but not limited to a patient monitor 202 (for example, a bedside monitor such as Masimo's Radical-7®, Rad-97® (optionally with noninvasive blood pressure or NomoLine capnography), and Rad-8® bedside monitors, a patient monitoring and connectivity hub such as Masimo's Root® Platform, any handheld patient monitoring devices, and any other wearable patient monitoring devices), a mobile communication device 204 (for example, a smartphone), a computer 207 (which can be a laptop or a desktop), a tablet 208, a nurses' station system 210, and/or the like. The wireless connection can be based on Bluetooth technology, near-field communication (NFC) technology, and/or the like. Additionally, the wearable device 10 can connect to a computing network 212 (for example, via any of the connected devices disclosed herein, or directly). The wearable device 10 can establish connection via the computing network 212 to one or more electronic medical record system 214, a remote server with a database 217, and/or the like.

Optionally, the device 10 can be integrated with more sensors and/or configured to connect to a plurality of external sensors, wirelessly or with a connecting cable. The connecting cable can be a universal connector configured to connect to any of the medical devices and/or sensors disclosed herein to provide communication between the wearable device 10 and the connected medical devices and/or sensors. The cable can optionally include a board-in-cable device that includes its own processor, but may not include its own display.

The device 10 can act as hub for the external sensors, for example, the sensors described in U.S. Patent Publication No. 2020/0138288, published on May 7, 2020 (the entirety of which is hereby incorporated herein by reference). The sensors described in U.S. Patent Publication No. 2020/0138288 can collect patient physiological data and provide power for a reusable pairing device. The reusable pairing device can establish wireless communication with a patient monitoring device. The wearable device 10 can replace the patient monitoring device in U.S. Patent Publication No. 2020/0138288. As another example, the device 10 can replace a patient monitor device described in U.S. Patent Publication No. 2020/0329993, published on Oct. 22, 2020, the entirety of which is hereby incorporated herein by reference. By replacing the patient monitor device in U.S. Patent Publication No. 2020/0329993, the wearable device 10 performs all the computations based on the sensor data so that the connected external sensors, for example, the ECG sensors disclosed in U.S. Patent Publication No. 2020/0329993, do not require heavy computing power.

The device 10 can include open architecture to allow connection of third party wireless sensor, and/or allow third party access to a plurality of sensors on the wearable device 10 or connected to the wearable device 10. The plurality of sensors can include, for example, a temperature sensor, an altimeter, a gyroscope, an accelerometer, emitters, LEDs, etc. Third party applications can be installed on the wearable device 10 and can use data from one or more of the sensors on the wearable device 10 and/or in electrical communication with the wearable device.

Optionally, the wearable device 10 can communicate with any other suitable noninvasive sensor, such as an acoustic sensor, a blood pressure sensor, temperature sensor, movement sensor, ECG sensor, etc. Examples of some of these devices include Masimo's Radius PPG™ sensor, Radius T™ sensor, and Centroid™ sensor, or otherwise. One or more of those sensors, for example, the Centroid™ sensor, can be used for stroke detection. The wearable device 10 can output an alert of stroke detection of the wearer and/or automatically initiate communication with a first respondent and/or the wearer's guardian or next-of-kin upon stroke detection.

The wearable device 10 can optionally communicate with chemical sensors, which can detect, for example, chemicals on the wearer's skin, and/or sweat, and/or the odor of certain chemicals in the air. The chemical sensors can include electrochemical sensors or any other suitable types of chemical sensors. A chemical sensor configured to analyze compositions of sweat can output measurements aiding the wearable device 10 in detecting stress and/or the wearer's hydration status. The wearable device 10 can optionally communicate with a skin impedance sensor, which can be used for monitoring the hydration status of the wearer.

Another example sensor that can be integrated into or connected to the device 10 and/or the sensor or module 100 can include a toxin and/or radiation detector configured to detect toxins in air (for example, pollution or contaminant particulates, carbon monoxide, smoke, and the like in the air). The toxin detection can aid care providers and/or firefighters who wear the device 10. Alternatively, the device 10 can be connected wirelessly to an external toxin and/or radiation detector. The toxin and/or radiation detector can be used with a smart mask. For example, the external toxin and/or radiation detector can be located on the mask, which can allow the mask to output a warning to the wearer of the mask when the mask filter or cartridge needs replacement.

Optionally, the wearable device 10 can communicate with glucose monitors, which can be invasive or minimally invasive such as finger prick type of glucose monitors, or a continuous noninvasive glucose monitor. The wearable device 10 can receive and display the wearer's glucose level from the glucose monitor. The wearable device 10 can also optionally be in communication with an insulin pump. The wearable device 10 can send a control signal to dispense insulin from the insulin pump to the wearer based on the monitored glucose level of the wearer.

Figure 3:
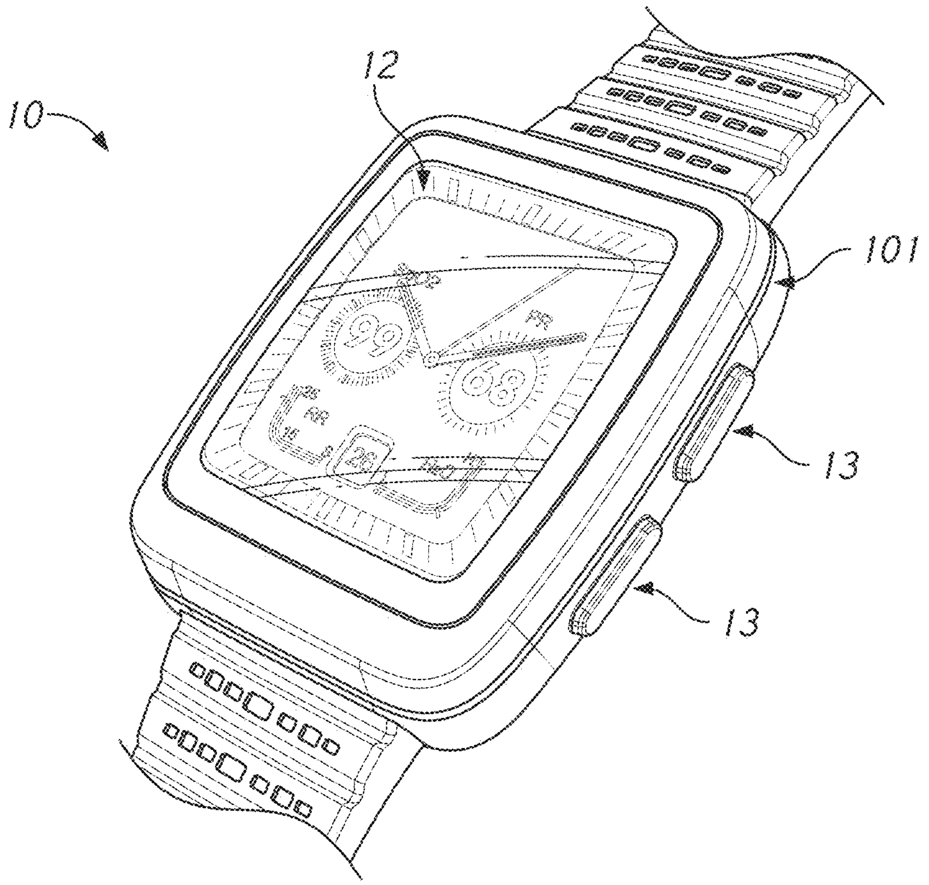
FIG. 3 illustrates an example display of physiological parameter measurements on the wearable device disclosed herein.

As shown in FIG. 3, the device 10 can include a display screen 12 positioned at a top side of the device housing 101. In addition to time and date indicators, one display layout (for example, the default display layout) of the display screen 12 can display the wearer's SpO2 measurement, the pulse rate (PR) measurement, the respiration rate (RR) measurement, and/or hydration status (H2O). The format of the measurement displayed is not limiting. For example, some measurements, such as the SpO2 measurement and the PR measurements, can be displayed as numerical values. As another example, some measurements, such as the RR measurements and hydration status, can be displayed as a sliding scale. In the illustrated example, the hydration status can be displayed as having three levels from low (L) to high (H). In the illustrated example, the respiration rate can be displayed as ranging from 5 bpm to 25 bpm. The wearer can optionally view individual display layouts for each measurements or a group of measurements by tapping on the display screen 12, which can be a touch screen, and/or pressing a button on the device 10. Each of the measurements can be displayed constantly, at certain intervals, and/or upon receiving instructions for display (for example, by the wearer tapping on the display screen 12 and/or pressing a button on the device 10). Each of the measurements can be configured to be displayed with different or the same frequencies. Time and certain physiological parameters (for example, SpO2 and pulse rate) can be immediately and/or intermittently available, and/or continuously measured (for example, at least every 5 to 10 measurements per minute or more) and the displayed values constantly updated. Optionally, the display screen 12 can further show a trend line for some parameters, such as SpO2 and pulse rate. In one example, the display screen 12 of the wearable device 10 can be configured to display only time, SpO2, and pulse rate.

Figure 4:
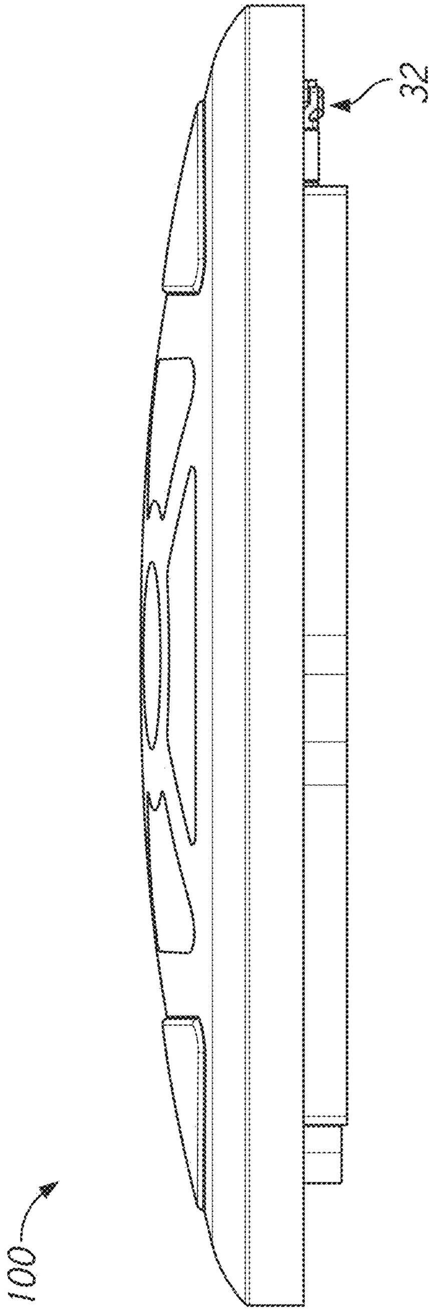
FIG. 4 illustrates an example physiological parameter measurement module of the wearable device.
Figure 5B:
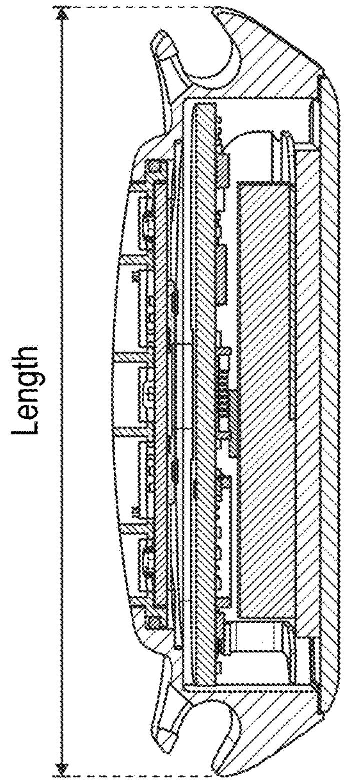
FIG. 5B illustrates a cross-sectional view of the example wearable device of FIG. 5A.
Figure 5D:
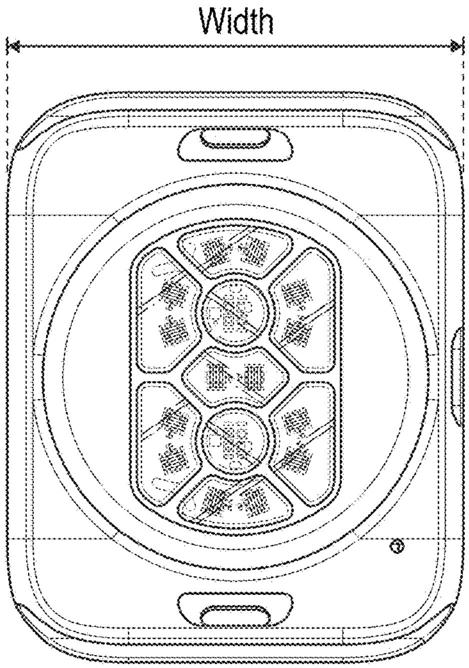
FIG. 5D illustrates a bottom view of the wearable device of FIG. 5A.
Figure 5A:
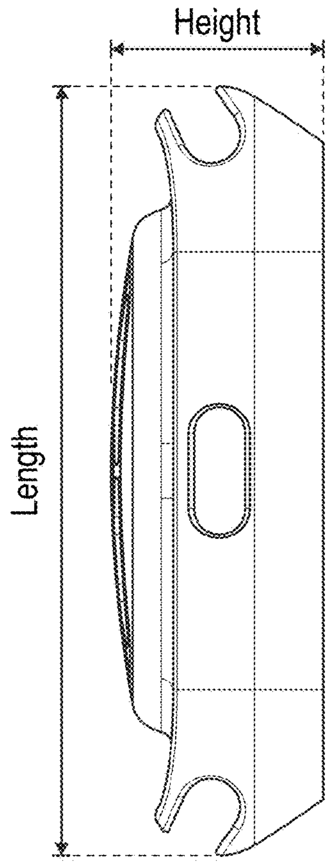
FIG. 5A illustrates a side view of an example wearable device incorporating an example physiological parameter measurement module.
Figure 5C:
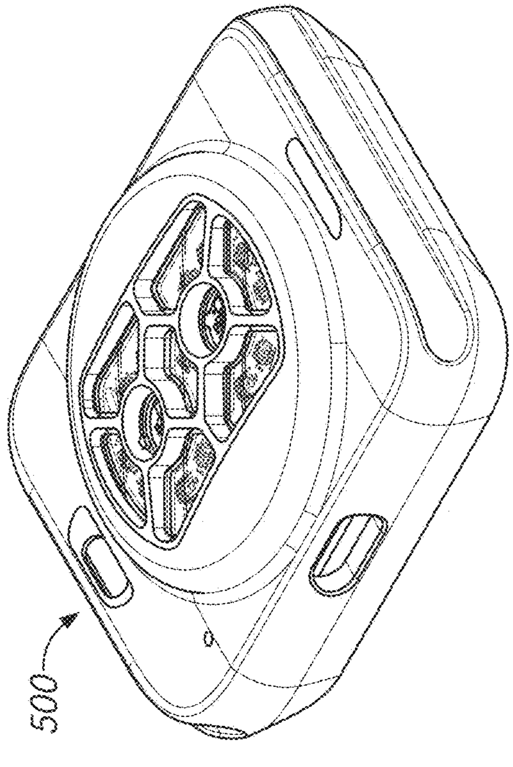
FIG. 5C illustrates a perspective view of the wearable device of FIG. 5A.

As shown in FIG. 4, the physiological parameter measurement sensor or module 100 can be preassembled before being integrated into the device 10. The physiological parameter measurement sensor or module 100 can be characterized before being assembled with the rest of the device 10. The preassembled physiological parameter measurement sensor or module 100 can be secured within the device housing 101 using various mechanical assembly mechanisms, for example, one or more screws or other fasteners. The sensor or module 100 of a wearable device 10 can be interchangeable and be replaced without replacing the memory in the device 10. For example, the sensor or module 100 can include a quick-connect (and/or quick-release) feature for attaching the sensor or module 100 to the remainder of the device 10, such as being attachable to the device 10 by magnets. An electrical connection can be established between the physiological parameter measurement sensor or module processor board and the circuit of the rest of the device 10, including for example, a device processor and the display screen 12. Optionally, the electrical connection can include a connector 32 on the sensor or module 100. The connector 32 is configured to be electrically connected to a flex circuit. The wearable device 10 and the sensor or module 100 are portable and can be moved from place to place. As described above, the functionality of the wearable device 10 can be integrated and/or interchangeable with various other patient monitoring devices, displays, etc.

The sensor or module 100 can be applied to locations on the body other than the wrist. Alternatively or additionally, multiple sensors or modules 100 can be applied to different locations of the body of the wearer. Other types of straps or fastening mechanism may be used to attach the multiple sensors or modules 100 onto other parts of the body. The other types of straps or fastening mechanism can optionally include a power source (for example, battery) to power a sensor or module 100 that is not integrated into the wearable device 10, but may not have its own display. For example, an optical sensor can be placed on the wearer's neck to measure arterial and venous oxygen saturation, which can be transmitted to and displayed on the wearable device 10. The wearer can view his or her oxygen consumption information on the wearable device 10 based on the signals from the optical sensor on the neck and/or the signals from the sensor or module 100 that is located on the wearable device 10.

As shown in FIGS. 5A-5D, an example wearable device 500 can include a watch housing 501. Features of the wearable device 500 can be incorporated into features of the device 10 and features of the device 10 can be incorporated into features of the wearable device 500. The watch housing 501 can have a length, for example, between about 40 mm and 50 mm, or between about 42 mm and 46 mm. The watch housing can have a width, for example, between about 32 mm to about 40 mm, or between about 35 mm to about 38 mm. When fully assembled, the wearable device 500 can have a thickness or height, for example, between 10 mm to about 15 mm, or between 12 mm to about 14 mm.

Figure 6:
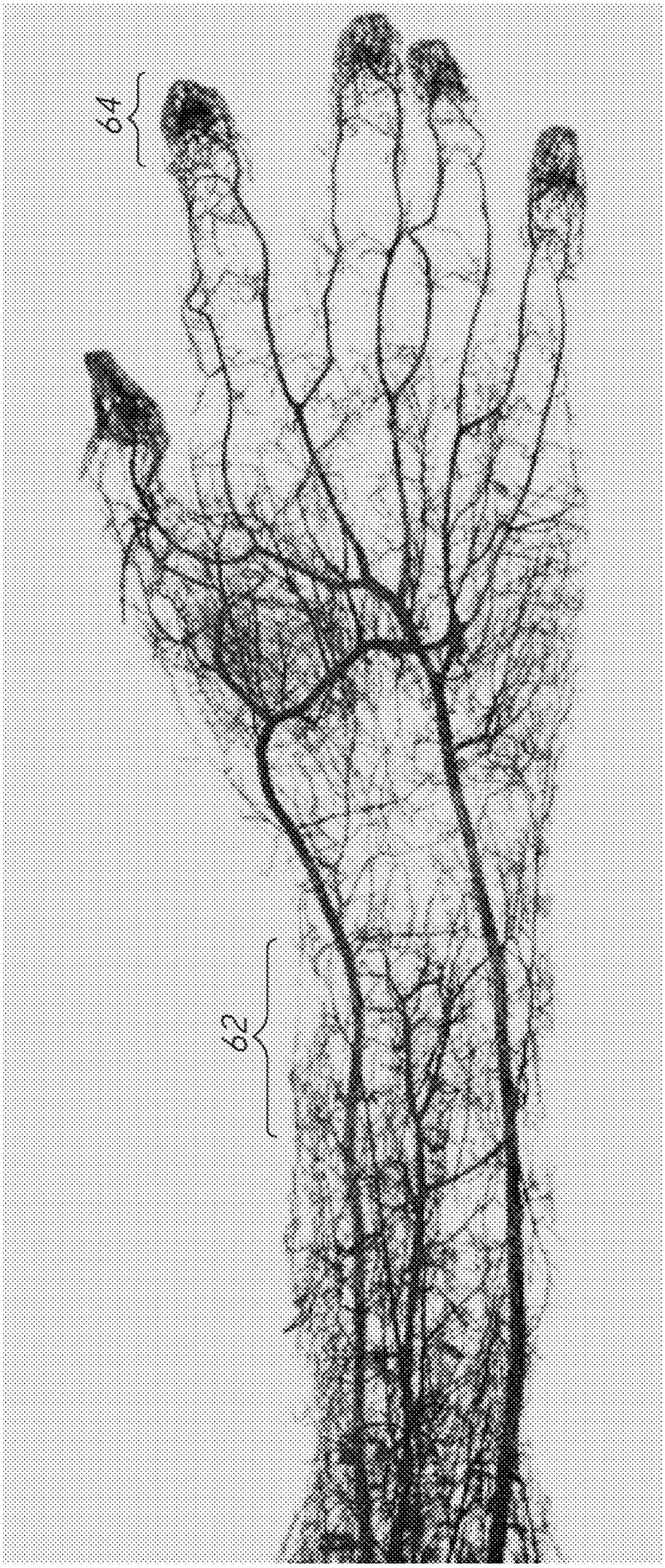
FIG. 6 illustrates schematically arteries and capillaries of a human hand and a proximal portion of a human forearm.

As described above, the physiological parameter measurement module can include a plurality of emitters and a plurality of detectors. The emitters can transmit optical radiation of a plurality of wavelengths into a tissue site (near the wrist of the wearer) and the detectors can respond to the intensity of the optical radiation (which can be reflected from the tissue site) after absorption by pulsatile arterial blood flowing within the tissue site. In addition to the light being attenuated by blood in the arteries, light interaction also happens at the capillary level. Arteries are located deeper below the skin surface than the capillaries, requiring LED emitters of greater light intensity and thus greater power consumption in order for the emitted light to reach the arteries. Moreover, measuring the light intensities signal of the light after attenuation by blood in the artery requires more selective placement of the emitters and detectors directly above the arteries to capture the pulsation of the blood. The physiological parameter measurement module disclosed herein is designed to utilize attenuation by blood in the capillaries and is not reliant on the blood flow in arteries. The patient parameter measurements made by the module disclosed herein can be accurate enough for clinical use. The module disclosed herein can provide plethysmograph-based patient parameter measurements with an accuracy of within about 4% error, or about 2% error. As shown in FIG. 6, the wrist 62 has fewer capillaries per volume than the fingertip 64. Accordingly, the module is designed to have a width to provide greater coverage area of the wearer's wrist, which can boost the signal from the sensors located on the module (which will be described in greater detail below).

When measuring oxygen saturation based on attenuation by blood in the capillaries, it is desirable to avoid veins. Because venous blood contains less oxygen, intensity signals of light attenuated by venous blood can cause errant readings oxygen saturation measurement. Optionally, the sensor or module processor of the physiological parameter measurement modules disclosed herein can reduce the effect of pulsing vein on the signal by comparing the signals from the plurality of detectors to determine which detectors receive better and/or clearer signals and deactivating the detectors that are more likely to cover and/or be around the pulsing veins. The sensor or module processor can dynamically adjust which detectors to deactivate. Deactivating the detectors can include deactivating operation of that detector and/or ignoring signals from that detector.

Optionally, the sensor or module processor of the physiological parameter measurement module can map the physiological parameter measurements calculated from signals received at the detectors and/or clusters of detectors located at different regions of the module. Variations (for example, if outside a certain range) in the mapped measurements can be an indication that the pressure distribution of the wearable device on the body of the wearer is unbalanced, and therefore the pressure of the device on the wearer is either too high or too low and/or the wearable device is tilted on the wrist. The wearable device can output an instruction to the wearer to readjust the tightness of the straps and/or to re-center of the wearable device on the wrist. Variations (for example, if outside a certain range) in the mapped measurements can additionally or alternatively provide an indication that a certain detector or cluster of detectors is/are placed over a large pulsing vein as described above. Readings from that certain detector or cluster of detectors can be ignored or the detector(s) suspected to be cover a pulsing vein may be deactivated. When two or more physiological parameter measurements, such as oxygen saturation measurements, do not agree among two or more detectors (for example, having a variation exceeding a certain range), the sensor or module processor can use the higher or highest measurement value, or alternatively use a combination of the measurement values from the two or more detectors (for example, using one of the two measurement values at different times or otherwise).

Alternatively or additionally, the mapped measurements can be compared with experimentally determined data at the same detector location or detector cluster location. The experimentally determined data can be obtained using, for example, a conventional reflectance type pulse oximeter taped over the corresponding detector location, or any other suitable known methods for making the same measurements, including the same wrist-based sensor arrangements described herein. The comparison between the mapped measurements and the experimentally determined data can provide indication of whether the device has achieved a desired pressure on the body of the wearer, whether certain detectors and/or clusters of detectors are placed over or near a pulsing vein, which may interfere with the physiological parameter measurements, or otherwise. For example, if the difference between the mapped measurements and the experimental data at a certain location falls outside a predetermined range, the sensor or module processor can determine that pressure is too high or too low at that location, and/or that the pressure distribution over the body is not sufficiently balanced to make accurate measurements, and/or a detector or cluster of detectors is/are placed over the wearer's pulsing vein. The experimental data can be stored in a memory device of the sensor or module processor.

The comparison among the mapped measurements and/or between the mapped measurements and the experimental data can be performed when the wearer first puts on the device and/or at certain time intervals in the duration when the device is worn on the wearer. Additionally, running the comparison-based diagnostics can allow the sensor or module processor to determine, at the start of the measurement and/or dynamically during use of the device, which detector(s) provide the most accurate and/or reliable measurements.

Various Example Components of the Wearable Device

Figure 7A:
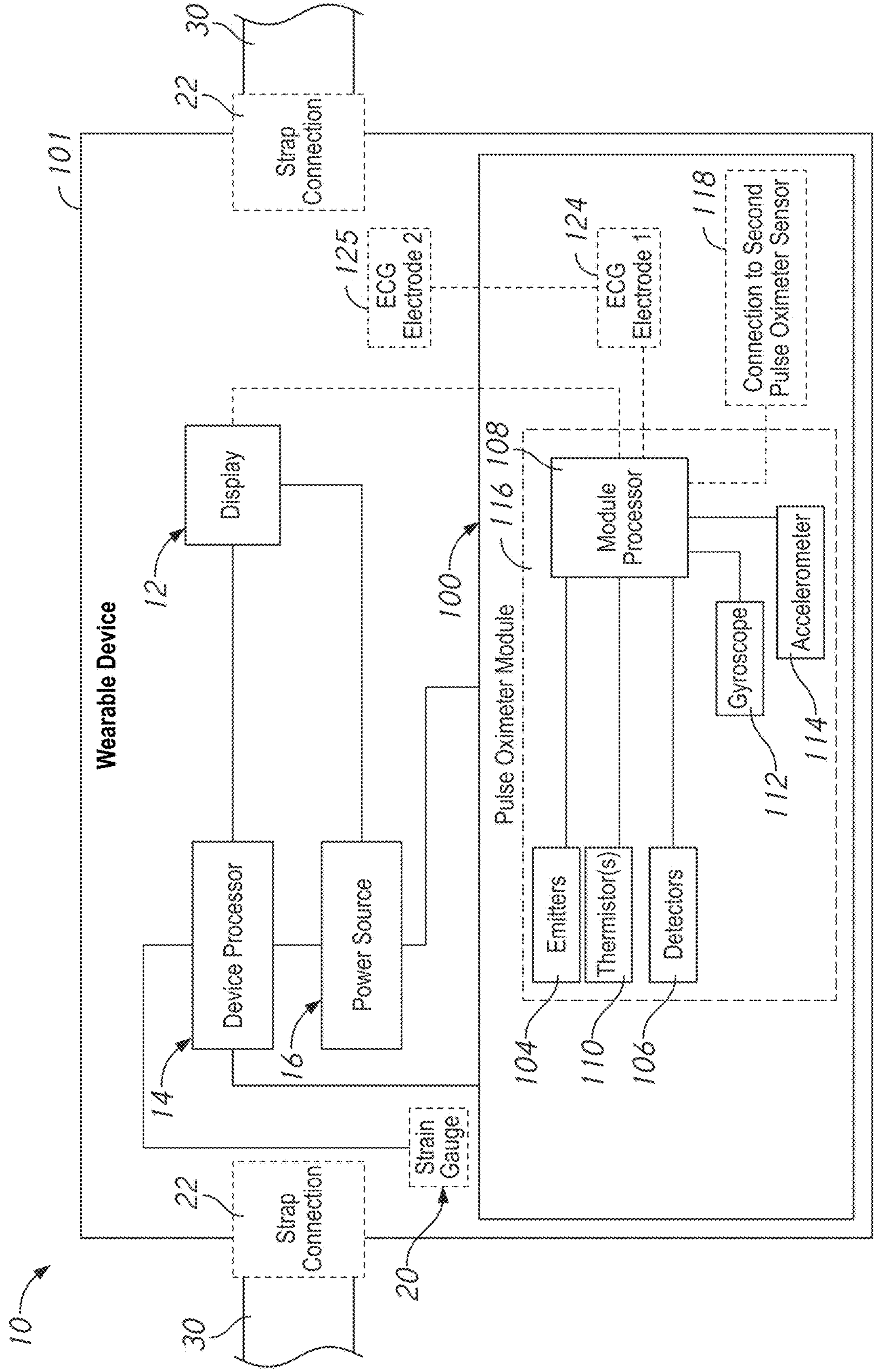
FIG. 7A illustrates a schematic system diagram of a wearable device including a physiological parameter measurement module.
Figure 7B:
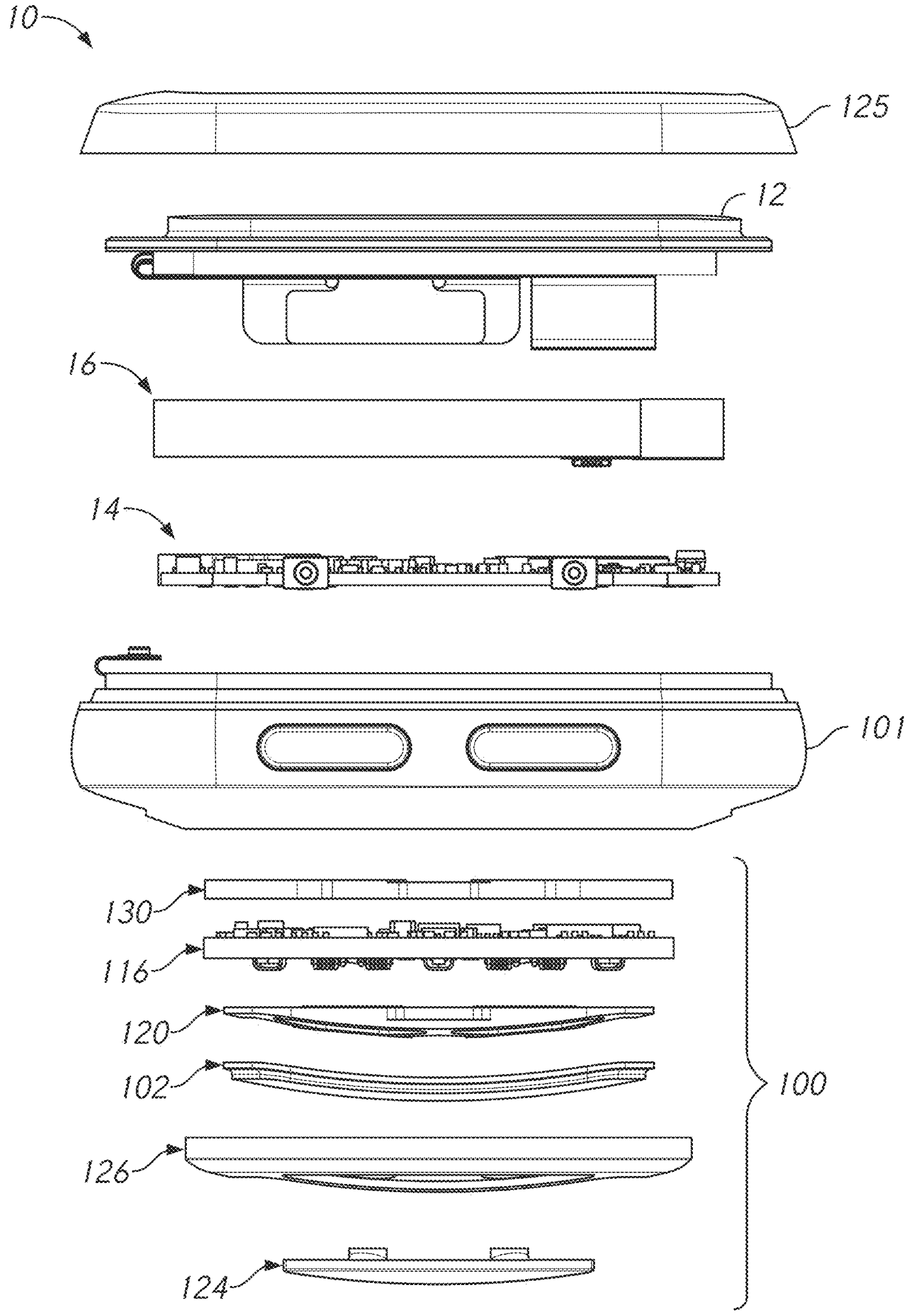
FIG. 7B illustrates a partially exploded view of an example wearable device.
Figure 7E:
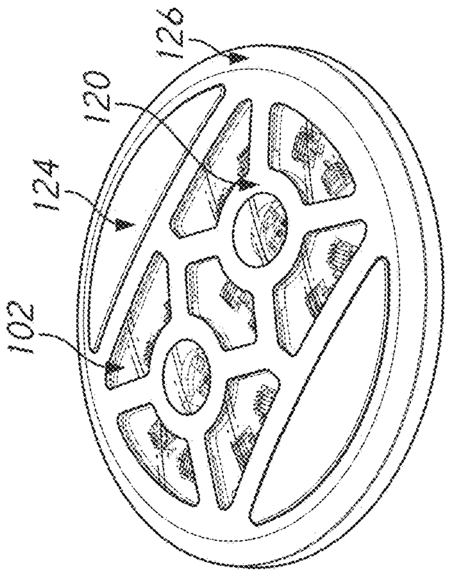
FIG. 7E illustrates a bottom perspective view of a physiological parameter measurement module incorporating the ECG electrodes, light transmissive cover(s), and a opaque frame of FIG. 7C or 7D.
Figure 7F:
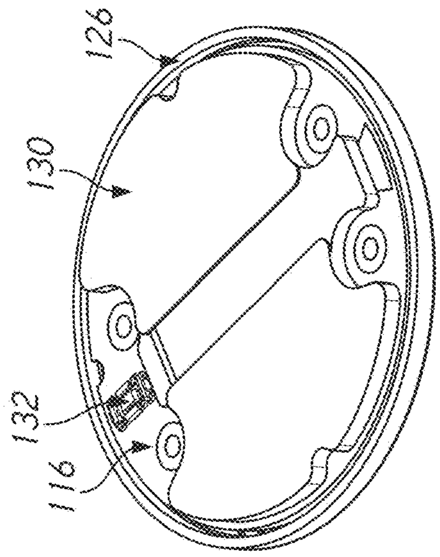
FIG. 7F illustrates a top perspective view of the example physiological parameter measurement module of FIG. 7E.

Components of the wearable device will now be described. As shown in FIGS. 7A and 7B, the device 10 can include its own device processor 14, which can be a digital/analog chip or other processor(s), such as a digital watch processor or a smartwatch processor. As shown in FIGS. 7B, 7G, and 7H, the device processor 14 can be located on a PCB. FIGS. 7G and 7H illustrate example layouts of the PCB for the device processor 14. As shown in FIGS. 7A and 7B, the device 10 can include a power source 16, which can be a battery, for powering the device processor 14, the display screen 12, and/or the physiological parameter measurement sensor or module 100. The power source 16 can last at least 10 hours, or at least 12 hours, or at least 14 hours, or at least about 16 hours after each charge, with continuous measurements and/or displaying of certain physiological parameters, such as SpO2 and pulse rate.

The device 10 can be configured to display time after the power source 16 has been depleted, even if other features (for example, measuring physiological parameters using the module) may not be available when the power source 16 has been depleted. Additionally, when the device 10 is used clinically, the display screen 12 can also continue displaying critical patient information (for example, the patient's name, date of admission, etc.) after the power source 16 has been depleted. The device 10 may include nonvolatile memory to store the critical patient information. The device 10 can include a dual-battery configuration with a main battery and a backup battery. Power management of the device 10 may switch automatically for the device 10 to be powered by the backup battery when the main battery has been depleted. The device can additionally or alternatively be configured to be solar-powered, for example, by including a solar panel on the dial or elsewhere of the wearable device 10. The display screen 12 of the device 10 can use e-ink or ULP (ultra low power screen) technology, which draws little amount of current for displaying information. The display screen 12 may automatically adjust the brightness, being brighter when outdoors and dimmer when indoors to further prolong battery life.

Figure 11A:
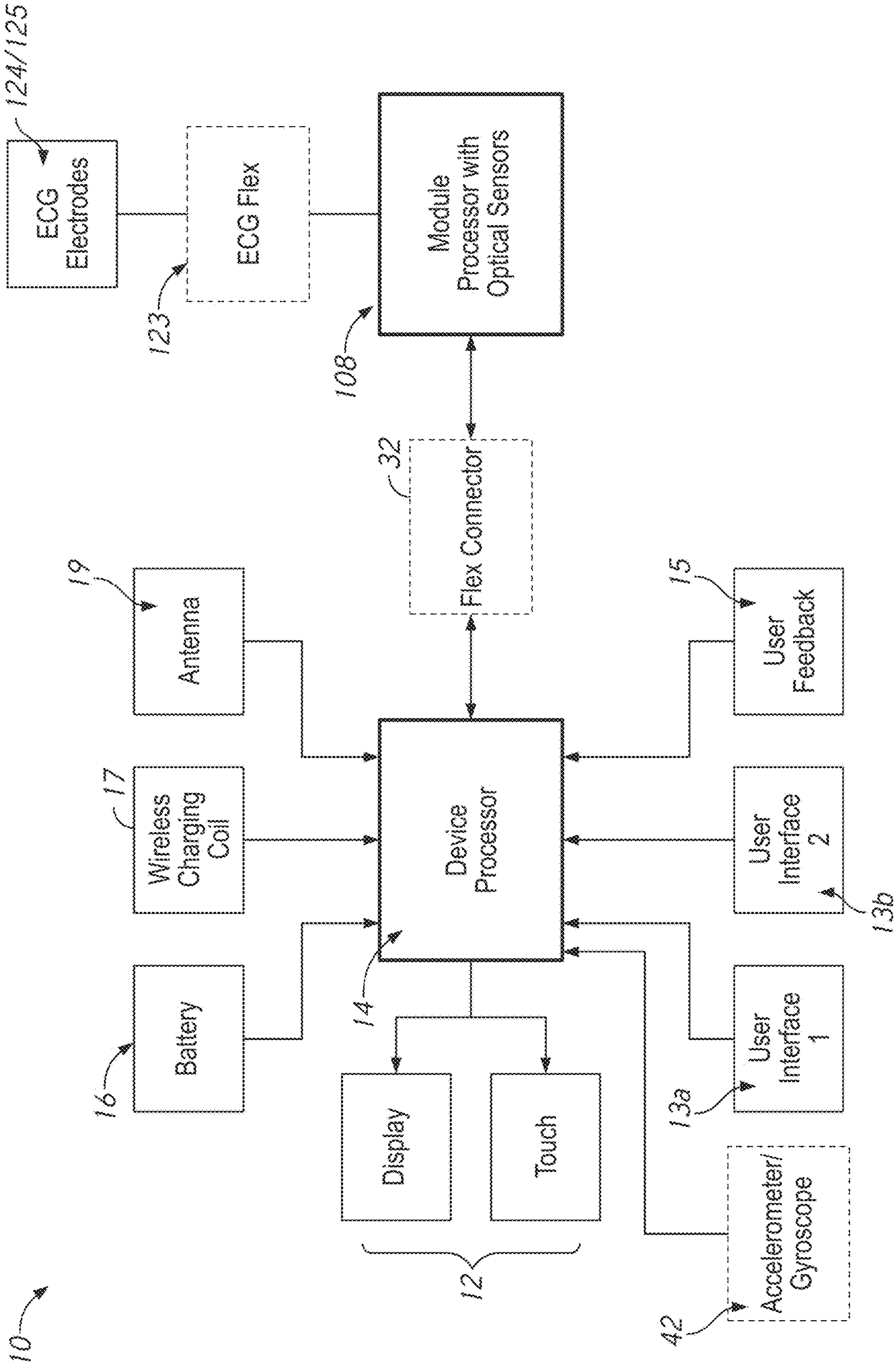
FIG. 11A illustrates a schematic system diagram of an example wearable device including a physiological parameter measurement module.
Figure 11B:
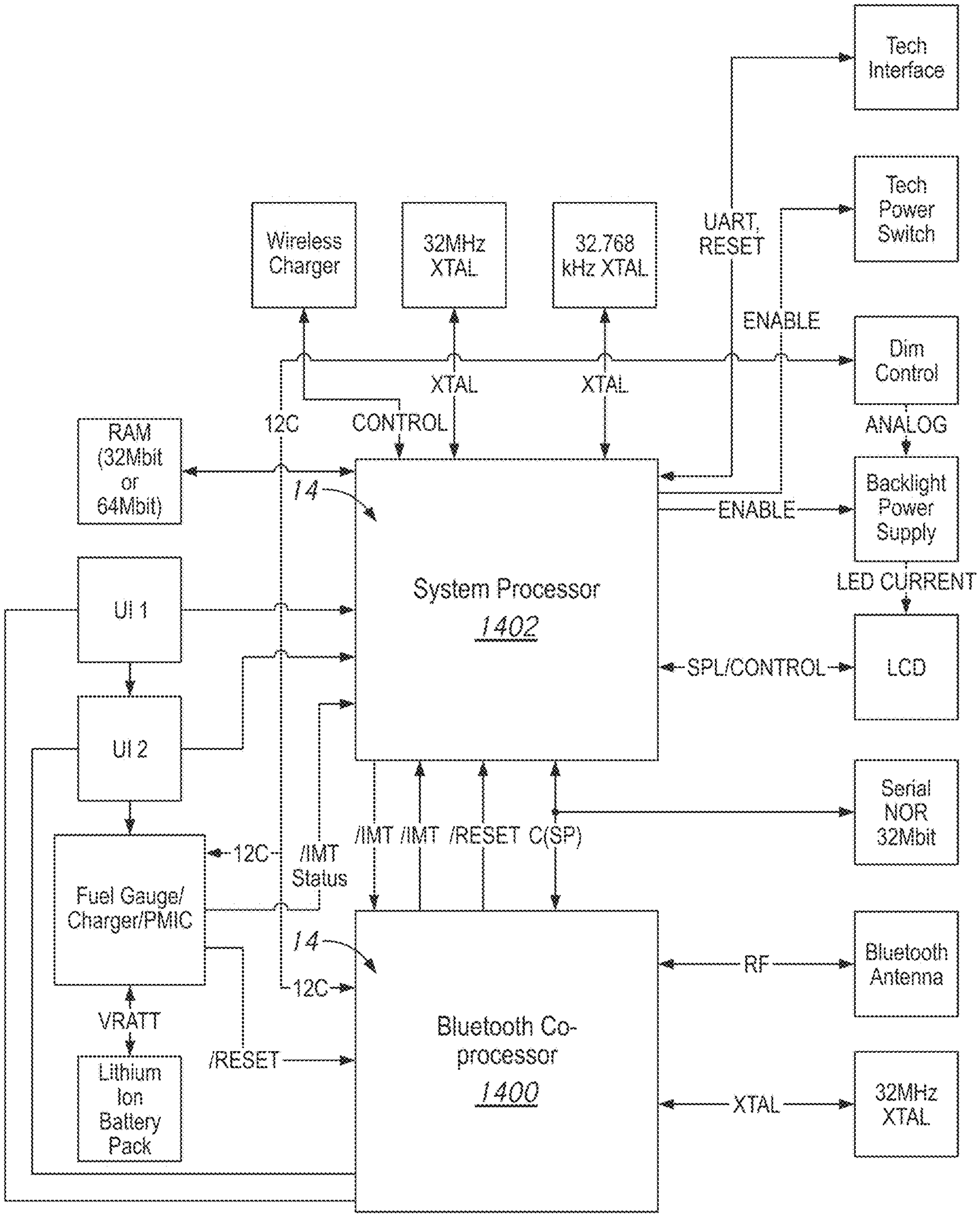
FIG. 11B illustrate a schematic diagram of an example device processor shown in FIG. 11A.
Figure 11C:
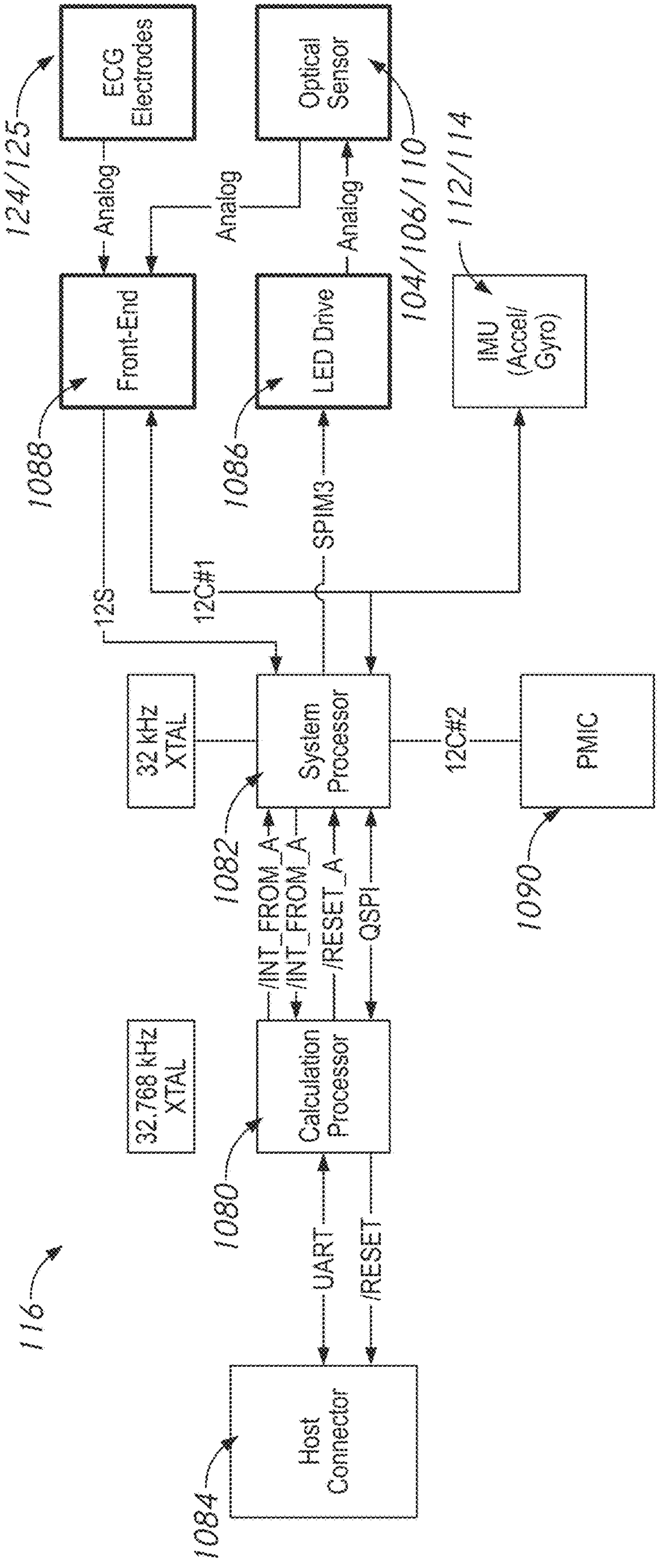
FIG. 11C illustrates a schematic system diagram of an example sensor or module processor shown in FIG. 11A.

As shown in FIGS. 7A and 7B, the sensor or module 100 of the wearable device 10 can include a sensor or module processor 108 (which can include a memory and/or other electronics, such as shown in FIG. 11C). The sensor or module processor 108 can process signals from one or more of the sensors in the sensor or module 100 (or optionally other sensors in communication with the device 10) to determine a plurality of physiological parameters. All the processing of the raw sensor data of the sensors in communication (via a wired and/or wireless connection) with the sensor or module processor 108 is performed by the sensor or module processor 108. The sensor or module processor 108 can be configured to drive the emitters 104 to emit light of different wavelengths and/or to process signals of attenuated light after absorption by the body tissue of the wearer from the detectors 106. The sensor or module processor 108 can determine and output for display on the device display screen 12 the physiological parameters based on the detected signals. Optionally, the sensor or module 100 can send the signals from the detectors 106 (for example, preprocessed signals) to the device processor 14, which can determine and output for display the physiological parameters based on the detected signals. The absorption of light can be via transreflectance by the wearer's body tissue, for example, by the pulsatile arterial blood flowing through the capillaries (and optionally also the arteries) within a tissue site where the device 10 is worn (for example, the wrist). The sensor or module processor 108 can be located on a PCB 116, such as shown in FIG. 7B.

The sensor or module 100 can include more than one group or cluster of light emitters (such as LEDs) 104 and more than one group of photodetectors (also referred to as "detectors") 106. Each group of emitters 104 can be configured to emit four (or three) different wavelengths described herein. The sensor or module 100 can include one or more thermistors 110 or other types of temperature sensors. The thermistor(s) 110 can be placed near one or more groups of emitters 104. There can be at least one thermistor 110 near each group of emitters 104. The thermistor(s) 110 can provide for wavelength correction of the light emitted by the emitters 104. Optionally, the thermistor(s) 110 can additionally measure a temperature of the wearer of the device 10. Optionally there can be one or more thermistors 110 located at other places of the sensor or module 100. The emitters 104, the thermistor(s) 110, and/or the detectors 106 can be positioned on the PCB 116.

As shown in FIG. 7A, the device 10 can include a gyroscope 112, an accelerometer 114, and/or other position and/or posture detection sensor(s). The gyroscope 112 and/ or the accelerometer 114 can be in electrical communication with the sensor or module processor 108. The sensor or module processor 108 can determine motion information from signals from the gyroscope 112 and/or the accelerometer 114. The motion information can provide noise reference for analysis of the pleth information and other signal processing (for example, processing of ECG signals) performed by the sensor or module processor 108. The gyroscope 112 and/or the accelerometer 114 can be located on the PCB 116.

Figure 8B:
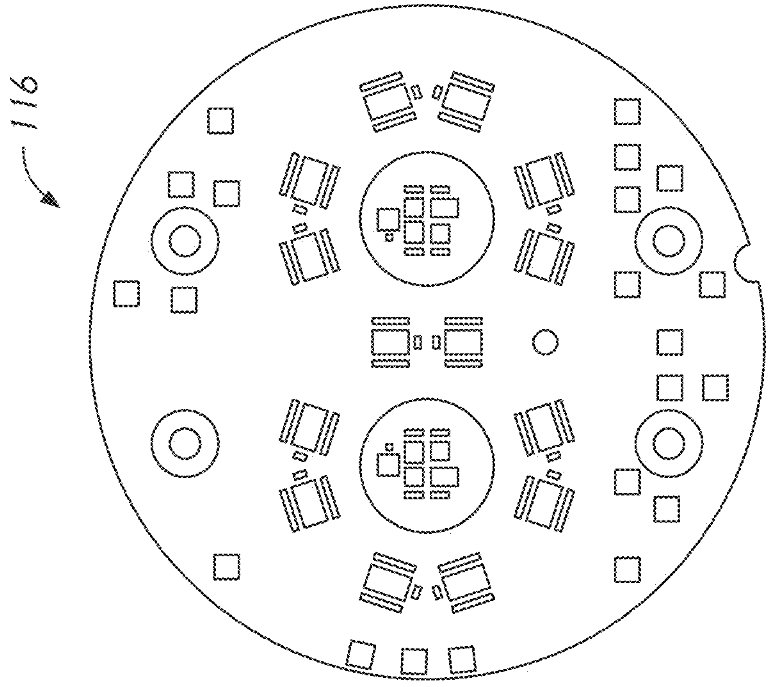
FIGS. 8A and 8B illustrate schematically top and bottom views of an example sensor or module processor board of an example physiological parameter measurement module.
Figure 8A:
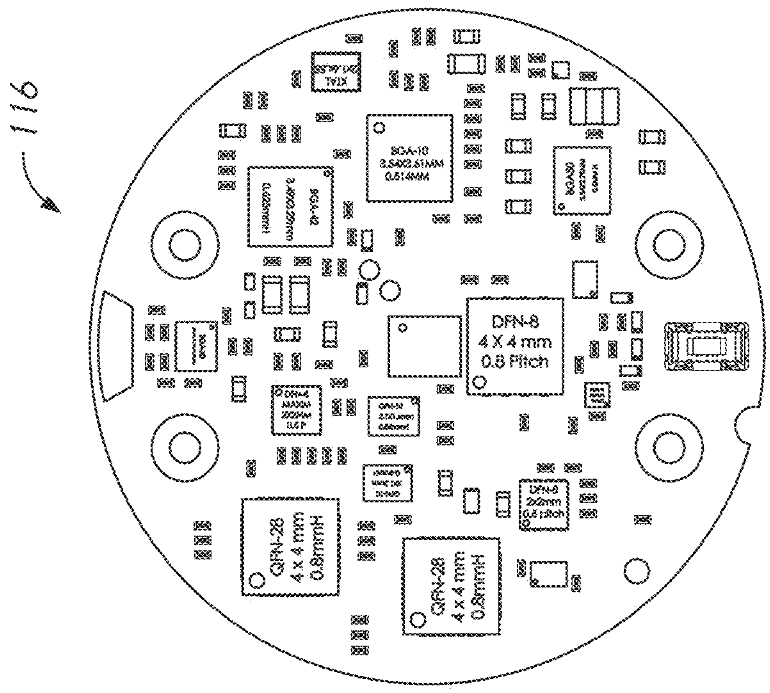
Figure 8C:
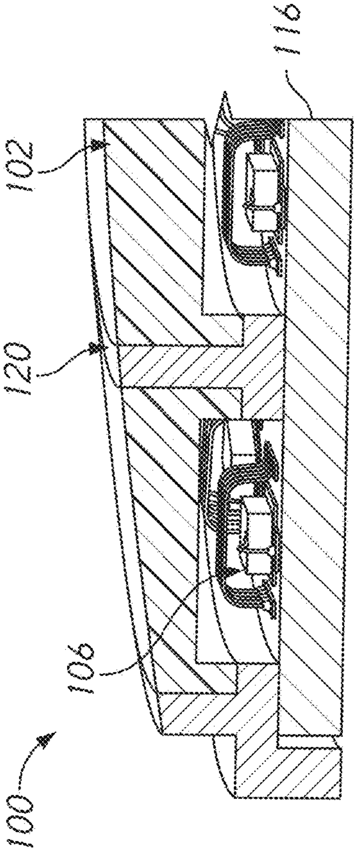
FIGS. 8C-8E illustrate various view of bonding of detectors to a PCB substrate of a physiological parameter measurement module.
Figure 8D:
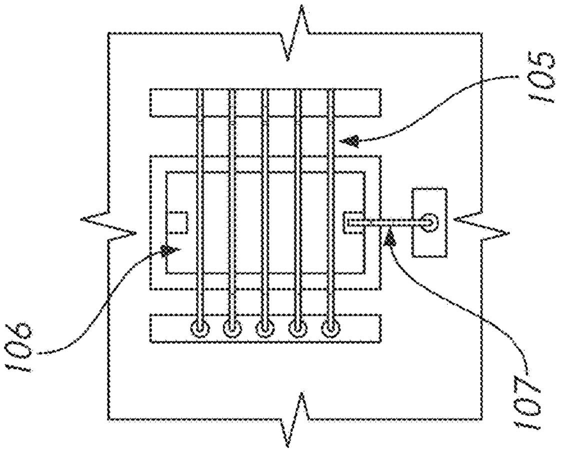
Figure 8E:
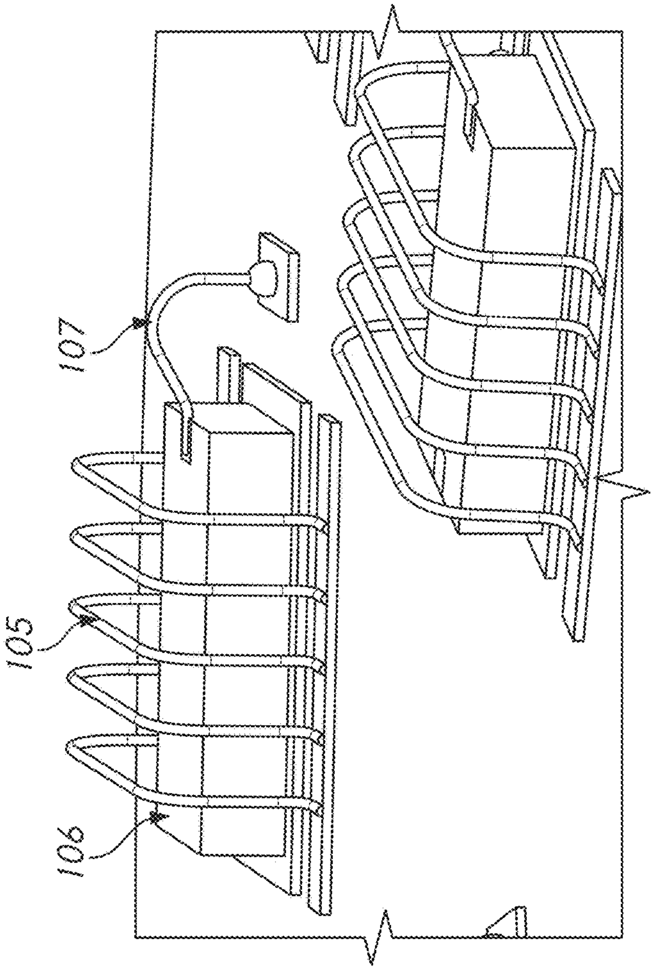
Figure 8F:
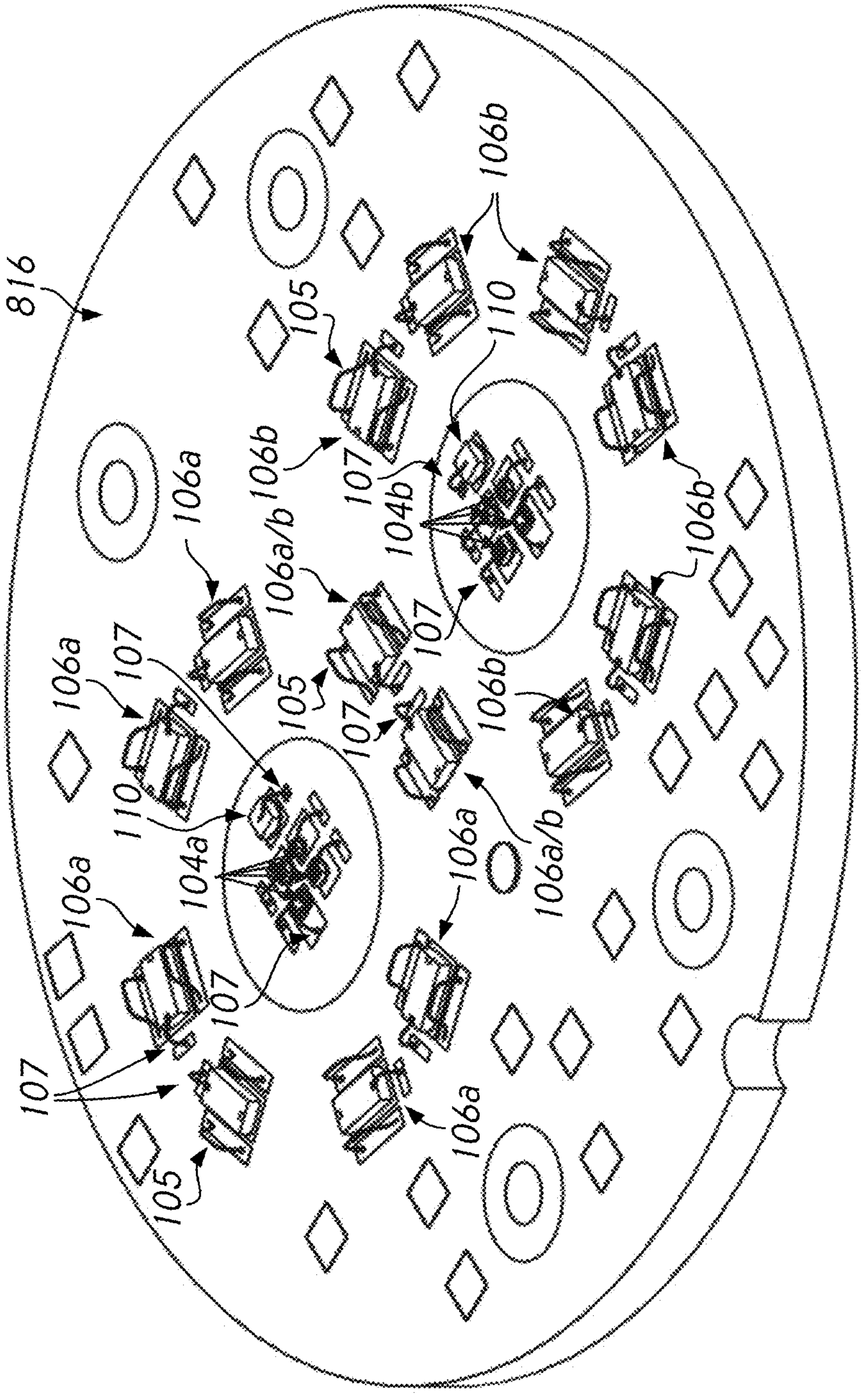
FIG. 8F illustrates a perspective view of a PCB substrate of a physiological parameter measurement module with different wire bonding arrangements than shown in FIGS. 8C-8E.

FIG. 8A illustrates example layouts of a top side of the PCB 116. FIG. 8B illustrates example layouts of a bottom side of the PCB 116. The first or bottom side of the PCB 116 can include the emitters 104, the detectors 106, the thermistor(s) 110, and any other sensors, for example, the gyroscope, the accelerometer, and/or the like. FIGS. 8C-8E illustrate the detectors 106 being connected electrically to the PCB 116 via wire bonds 107. The module can include wires 105 extending over the detector 106 for shielding purposes. The number of wires 105 extending over the detector 106 may vary. The manner in which the wires 105 extend over the detector 106 may vary. The wires 105 may not extend all the way over the detectors 106 across the detector's width or length. For example, as shown in FIG. 8F, the detectors of detector groups 106*a*, 106*b*, 106*a/b* can each be connected electrically to the first side of the PCB 816 via wire bonds 107. A wire 105 can extend along each side of the detector for noise shielding. In the illustrated example, the wire 105 can extend along each long side of the detector. The wire 105 may extend parallel with the length of the detector. The wire 105 may not extend over the body of the detector 106*a*, 106*b*, 106*a/b*. The emitters in the emitter groups 104*a*, 104*b* can each be electrically connected to the first side of the PCB 816 via wire bonds 107. The thermistors 110 at each of the emitter groups 104*a*, 104*b* can be electrically connected to the first side of the PCB 816 via wire bonds 107. The detectors, emitters, and/or thermistor can alternatively be electrically connected to the PCB 116 via other suitable types of electrical connectors.

The second or top side of the PCB 116 can include the sensor or module processor 108 and other circuit hardware. The second side of the PCB 116 can be electrically noisy and is isolated from the sensors on the first side of the PCB 116 by the board. Electronics on the same side of the PCB 116 can be substantially entirely overmoulded to reduce or avoid components shifting in place or being damaged during use. On the second side of the PCB 116, which faces away from the light transmissive cover 102, the PCB 116 can be covered by melt plastic or other suitable electronics protective material 130, such as shown in FIGS. 7B and 7F. As shown in FIG. 7F, the electronic components on the second side of the PCB 116 can be generally sealed by the protective material 130 except that a connector 132 can extend from the second side of the PCB 116 and be exposed. The connector 132 can electronically connect the sensor or module 100 to circuitry of the wearable device 10.

Figure 7D:
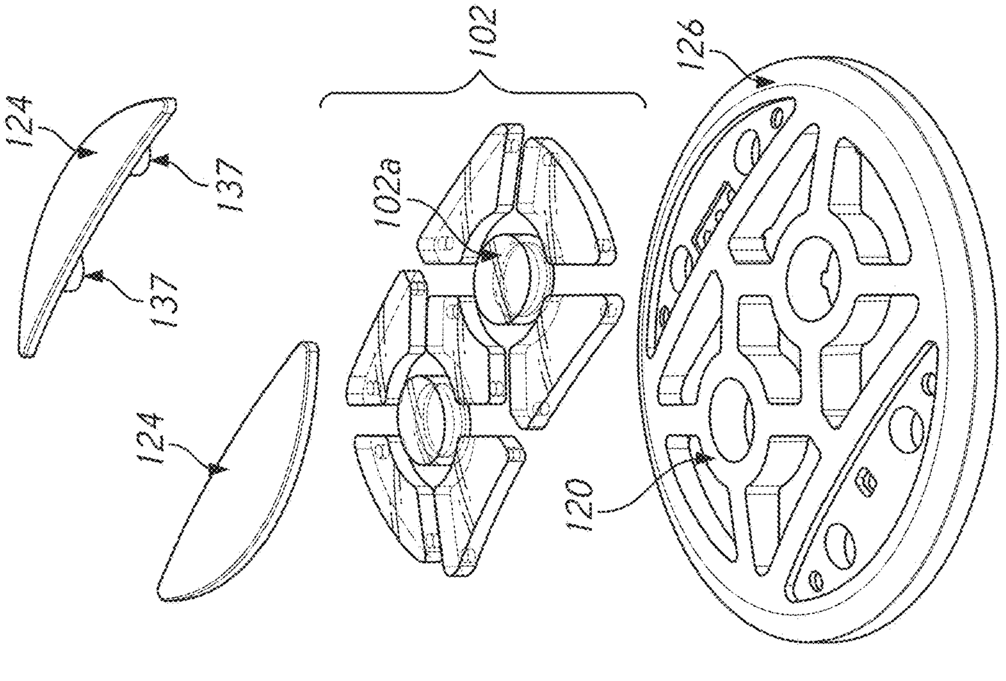
FIG. 7D illustrate an exploded view of ECG electrodes, light transmissive cover(s), and a opaque frame of the physiological parameter measurement module of FIG. 7B.

Optionally, as shown in FIGS. 7A, 7B, and 7D, the device 10 can include an electrocardiogram (ECG) sensor including a plurality of electrodes 124, 125 configured to make contact with the wearer's skin. One or more ECG electrodes 124 may be located on the sensor or module 100 (such as shown in FIGS. 7B and 7E). One or more ECG electrodes 125 may be located elsewhere on the device (for example, an ECG electrode 125 can form a part of the housing of the wearable device 10 as shown in FIG. 7B). The ECG sensor can be in electrical communication with the sensor or module processor 108 via an ECG connector.

Figure 7C:
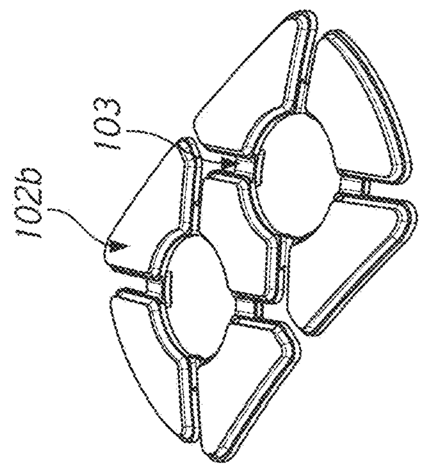
FIG. 7C illustrates an example light transmissive cover of the physiological parameter measurement module of FIG. 7B.
Figure 7H:
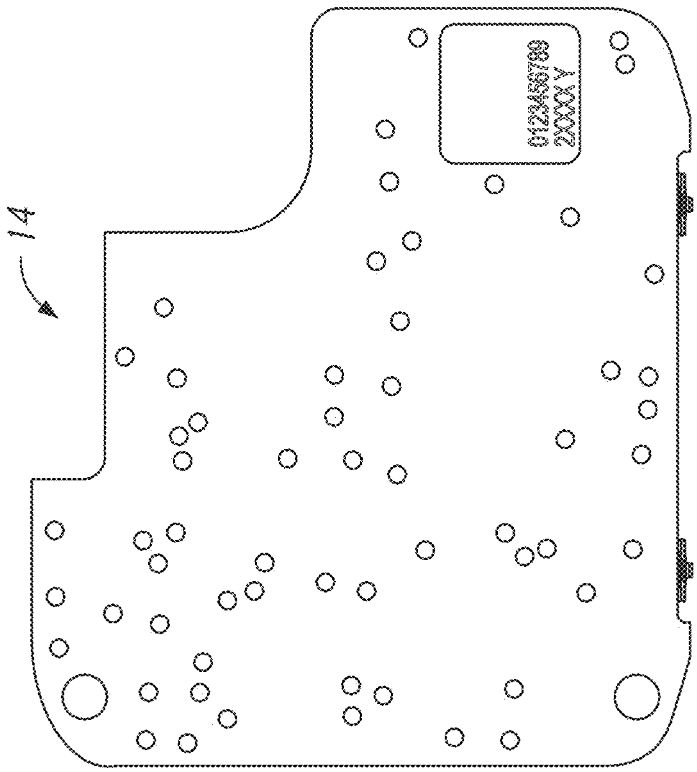
FIGS. 7G and 7H illustrate schematically top and bottom views of an example device processor board of the wearable device disclosed herein.
Figure 7G:
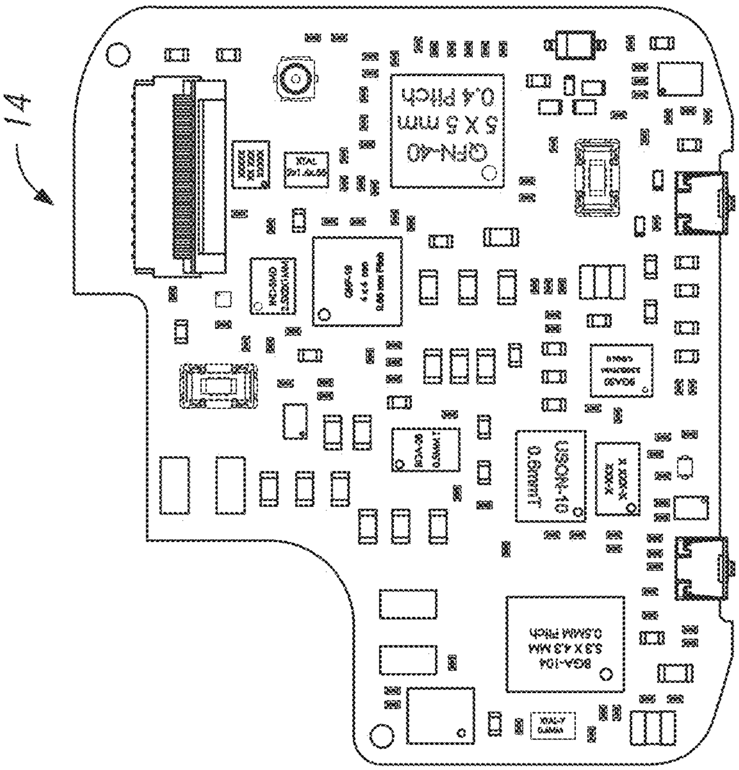
Figure 17B:
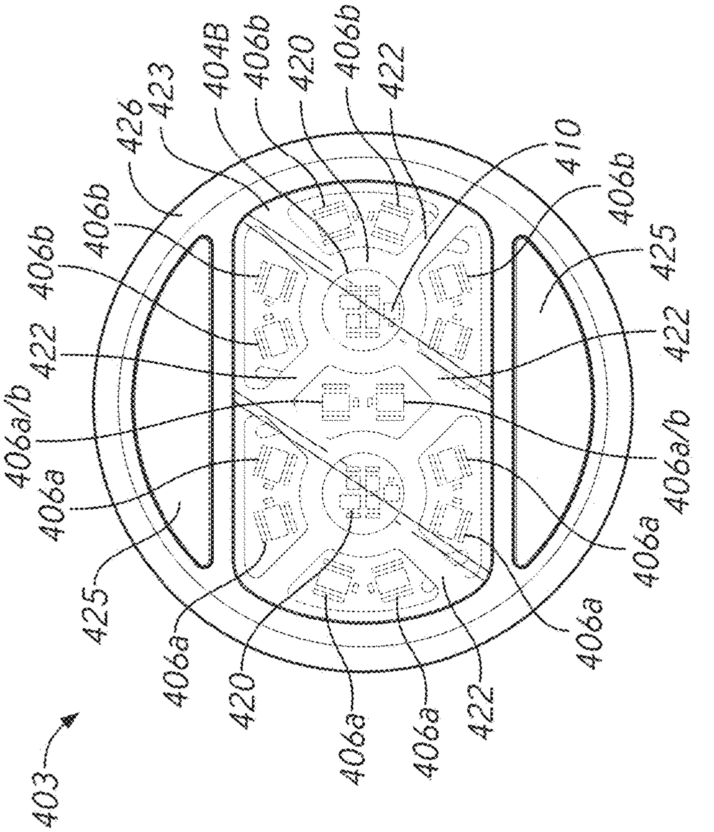
FIG. 17B illustrates a bottom view of the example physiological parameter measurement module of FIG. 17A.
Figure 17C:
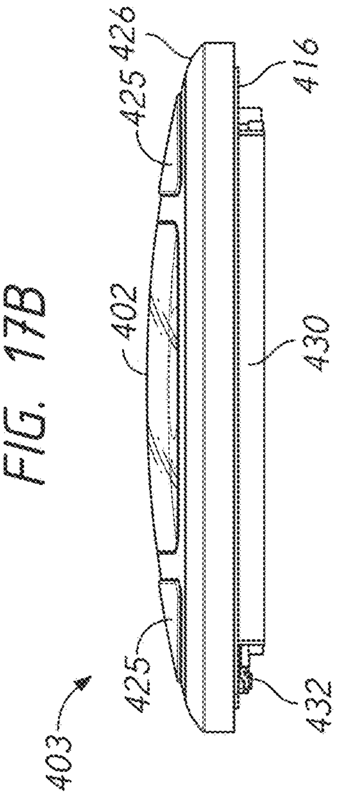
FIG. 17C illustrates a side view of the example physiological parameter measurement module of FIG. 17A.
Figure 17A:
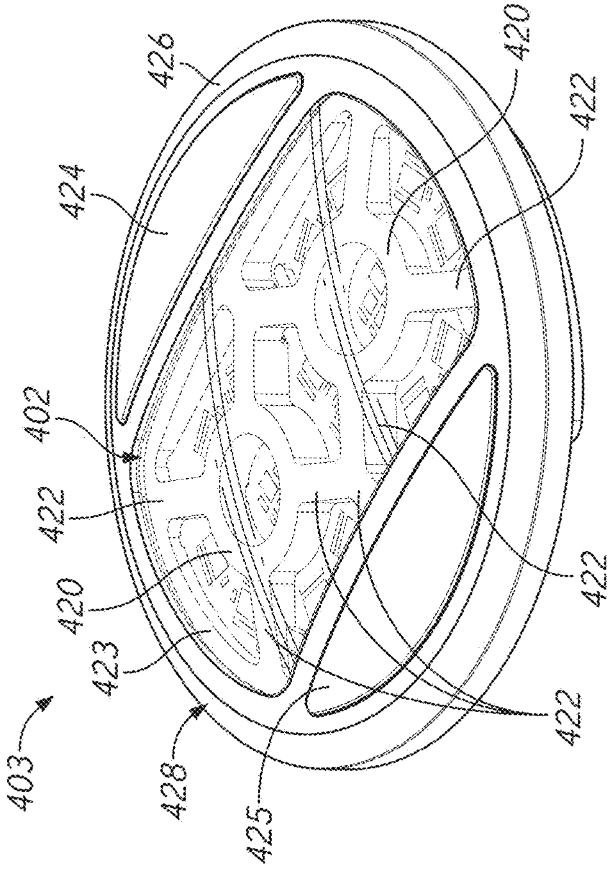
FIG. 17A illustrates a bottom perspective view of an example physiological parameter measurement module incorporating the plethysmograph sensor arrangement of FIG. 16A.

As shown in FIGS. 7B-7E, the physiological parameter measurement sensor or module 100 can include a skin-interfacing light transmissive cover 102 that encloses the first side of the PCB 116, which positions the plurality of light emitters 104 and detectors 106. The sensor or module 100 can include a light barrier construct 120 that is configured to divide the emitters 104 and the detectors 106 into different chambers such that light cannot travel or substantially cannot travel between the chambers. The light transmissive cover 102 can extend over the various emitter and detector chambers formed by the light barrier construct 120 and the PCB 116. The light transmissive cover 102 can include individual lenses or covers such as shown in FIG. 7D, a single lens or cover such as shown in FIGS. 17A-17C, or a combination of individual emitter chamber covering lenses or covers and a single lens or cover covering a plurality of detector chambers, such as shown in FIG. 7C. In the example lens or cover 102*b* shown in FIG. 7C, the individual lenses or covers that are configured to cover the detector chambers such as shown in FIG. 7D can be interconnected with bridging portions 103 between the detector chambers, forming a single piece of lens or cover. The lens or cover 102*b* can be combined with the lenses or covers 102*a* covering the emitter chambers to cover all the openings in the light barrier construct 120 for forming sealed emitter and detector chambers. The light barrier construct 120 can be overmoulded to the lens or cover 102*b* and the lenses or covers 120*a*. The lens or cover 102*b* may not be configured to cover the emitter chambers, which can be covered by individual lenses, so as to avoid any light traveling between an emitter chamber and a detector chamber.

As shown in FIG. 7B, the physiological parameter measurement sensor or module 100 can include a opaque frame 126. The opaque frame 126 can accommodate the light barrier construct 120. Alternatively, the opaque frame 126 and the light barrier construct 120 can form an integral piece, such as shown in FIG. 7D. The opaque frame 126 can include indentations having the shape and size to accommodate the ECG electrodes 124 or other components with a suitable shape and size. A front side of the electrodes 124 can have one or more posts 137 extending past openings in the opaque frame 126 into corresponding openings on the PCB 116. The posts 137 of the electrodes 124 can establish an electrical connection with the corresponding openings of the PCB 116. A plurality of screws (or other types of fasteners) can extend into the corresponding openings of the PCB 116 from the front side of the PCB 116 to secure the electrodes 124 to the sensor or module 100 by threadedly mating or otherwise with the posts 137. When a wearer puts the wearable device incorporating the sensor or module 100 onto the wearer's wrist, the electrodes 124 can made contact with the wearer's skin.

The physiological parameter measurement sensor or module 100 can include diffusing materials or encapsulant, which can include, for example, microspheres or glass microspheres. As described above, the encapsulant can eliminate air gaps between the surface of the light transmissive cover 102 and the emitters 104 and/or the detectors 106. The encapsulant can be included around the emitters 104 to more evenly spread the emitted light, which appears to be emitted from an entire emitter chamber rather than from a point source (that is, a single LED emitter) if the encapsulant is absent. The encapsulant can allow the emitted light to travel through a greater volume of the tissue at the tissue site. The diffusing material can act as a beam shaper that can homogenize the input light beam from the emitter, shape the output intensity profile of the received light, and define the way (for example, the shape or pattern) the emitted light is distributed to a tissue measurement site. Such diffuser materials can, for example, deliver substantially uniform illumination over a specified target area in an energy-efficient manner. According to the Beer-Lambert law, the amount of light absorbed by a substance is proportional to the concentration of the light-absorbing substance in the irradiated solution (for example, the arterial blood). Therefore, by irradiating a larger volume of tissue and/or by increasing the amount of detected light, a larger sample size of light attenuated by the wearer's tissue can be measured. The larger sample size provides a data set that can be more representative of the complete interaction of the emitted light as it passes through the patient's blood as compared to a smaller sample size.

The diffusing materials can be any suitable materials, for example, glass, ground glass, glass beads, opal glass, greyed glass, polytetrafluoroethylene, or a microlens-based, band-limited, engineered diffuser that can deliver efficient and uniform illumination UV-cured flow glass microspheres injected into one or more openings on the sensor or module 100 (for example, after the sensor or module 100 has been assembled). Examples of engineered diffusers can include molded plastics with specific shapes, patterns, and/or textures designed to diffuse the emitter light across the entirety of a tissue surface. The diffusing material can be made of ground glass, which spreads the emitted light with a Gausian intensity profile. The diffusing material can include glass beads. The diffusing material can be constructed so as to diffuse the emitted light in a Lambertian pattern. A Lambertian pattern is one in which the radiation intensity is substantially constant throughout the area of dispersion. One such diffusing material can be made from opal glass. Opal glass is similar to ground glass, but has one surface coated with a milky white coating to diffuse light evenly. The diffusing material can be capable of distributing the emitted light on the surface of a plane (for example, the surface of the tissue measurement site) in a predefined geometry (for example, a rectangle, square, circle, or otherwise), and with a substantially uniform intensity profile and energy distribution. The efficiency, or the amount of light transmitted by the diffusing material, can be greater than 70% of the light emitted by the emitter. The efficiency can be greater than 90% of the emitted light. Additional examples of the diffusing material are described in U.S. Pat. No. 10,448,871, the entirety of which is hereby incorporated herein by reference and should be considered part of the disclosure.

Additionally or alternatively, the physiological parameter measurement sensor or module 100 can include encapsulant or light diffusing materials in the detector chambers to more evenly spread the reflected light to so as to increase the amount of the reflected light reaching the detectors. The module can include light diffusing materials positioned around the detectors to scatter and/or deflect the reflected light so that more reflected light can be detected by the detectors. For example, the reflected light can keep bouncing off the diffusing materials until the reflected light reaches the detector. Accordingly, the light detecting surface area in the module can be greater than the surface area of the detectors. Having the light diffusing materials can reduce the power needed to drive the LEDs of the emitters and/or the number of detectors at a particular location of the module, which can reduce the power consumption of the module.

Figure 9B:
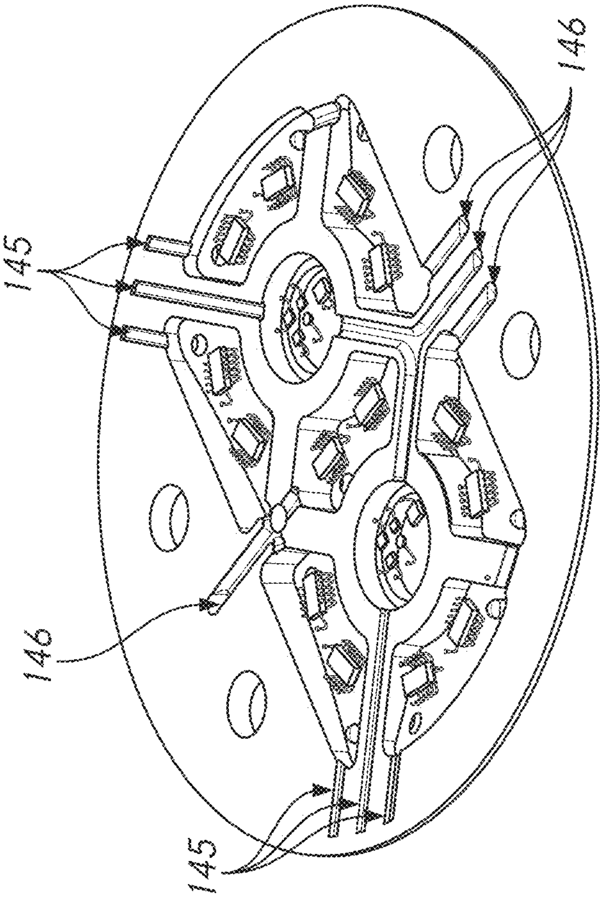
FIGS. 9A and 9B illustrate light diffusing material fill channels and air venting channels in a opaque frame of an example physiological parameter measurement module.
Figure 9A:
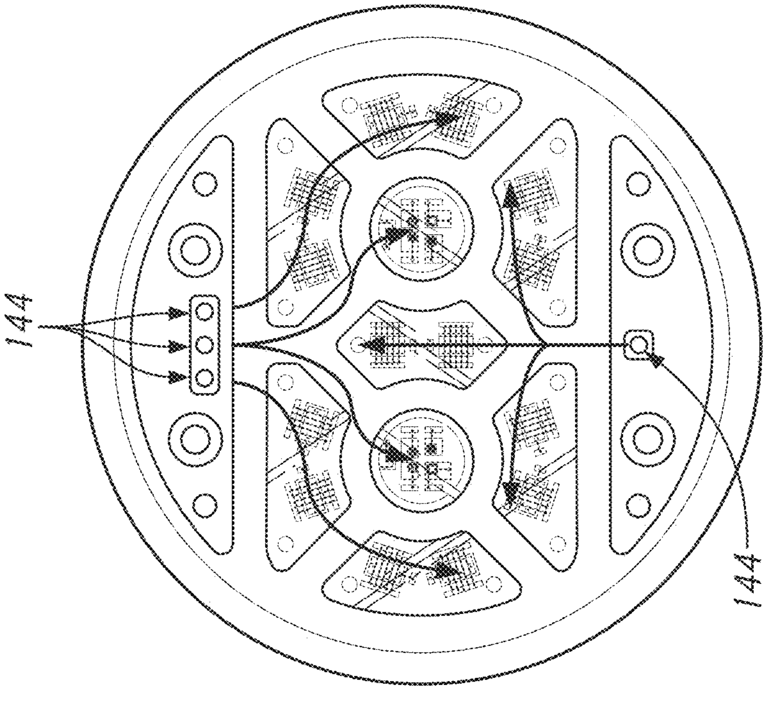

As shown in FIG. 9A, the opaque frame 126 of the sensor or module 100 can include a plurality of light diffusing material(s) (or encapsulant) fill holes 144. Light diffusing material(s) or encapsulant (for example, a flow of glass microspheres) can be injected into the plurality of chambers via the fill holes 144, and be directed to the respective emitter or detector chambers as illustrated by the arrows in FIG. 9A along a plurality of the fill channels 446 (see FIG. 9B) which are interconnected with the fill holes 144. The fill channels 146 can be located at a side of the opaque frame 126 facing away from the tissue of the wearer. As shown in FIG. 9B, the side of the opaque frame 126 facing away from the tissue of the wearer can further include a plurality of air vent channels 145. Air can escape into the vent channels 145 as the diffusing material solution or encapsulant is injected into the respective chambers via the fill holes 144, making it easier for the injected solution to flow into the respective chamber. As shown in FIG. 9B, the module 401 may not have air vent channels or fill channels between emitter and detector chambers to avoid light piping along such a channel. The encapsulant can be UV-cured after being injected into the respective chambers.

The opaque frame 126 may be configured such that the fill holes 144 and channels 146 allow the light diffusing materials to fill only the emitter chambers, or only the detector chambers, or both the emitter and detector chambers. Optionally, in addition or alternative to the light diffusing materials, the detector chamber can include light transmissive lens(es) or covers on the surface of the PCB that is not occupied by the detectors. The light transmissive lens(es) or covers inside the detector chamber can help in focusing the reflected light onto the detectors inside the detector chamber.

Figure 10:
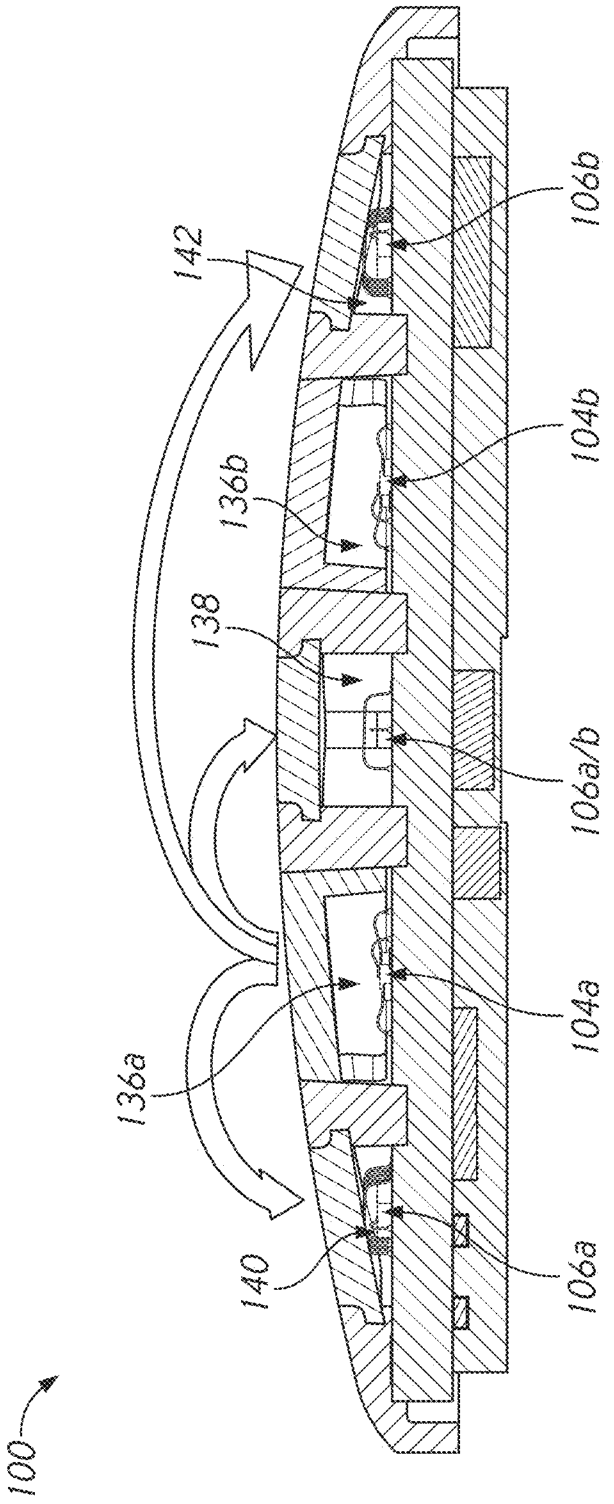
FIG. 10 illustrates a longitudinal cross-sectional view of an example physiological parameter measurement module and example light paths between emitters and detectors of the module.

In FIG. 10, a cross-sectional view of the sensor or module 100 illustrates some of the emitter and detector chambers. The chambers illustrated in FIG. 10 include a first emitter chamber **136*a* enclosing a first emitter group 104*a*, a second emitter chamber 136*b* enclosing a second emitter group 104*b*, a first detector chamber 140 enclosing one of first groups of detectors 106*a* that surround the first emitter group 104*a*, a second detector chamber 142 enclosing one of second groups of detectors 106*b* that surround the second emitter group 104*b*, and a third detector chamber 138 enclosing one of shared groups of detectors 106*a/b* that surround both the first and second emitter groups 104*a*, 104*b* on opposite sides of the third detector chamber 138**.

As shown in FIG. 10, light from the first emitter group **104*a* can travel a shorter path, as indicated by the shorter arrows, to the first group of detectors 106*a* or the shared group of detectors 106*a/b*; and light from the first emitter group 104*a* can travel a longer path, as indicated by the longer arrows, to the second group of detectors 106*b*. The reverse is true for light from the second emitter group 104*b*, which can travel a shorter path to the second group of detectors 106*b* or the shared group of detectors 106*a/b* and a longer path to the first group of detectors 106*a*. As described herein, the different groups of emitters 104*a*, 104*b* and/or detectors 106*a*, 106*b*, 106*a/b* can be run independently and/or simultaneously. Signals outputted by the different groups of detectors 106*a*, 106*b*, 106*a/b* based on light emitted from the first emitter group 104*a* and/or the second emitter group 104*b* can provide different information due to the different light paths, which can travel through different areas of the tissue. The longer path penetrates deeper into the tissue and through a greater volume of the tissue to reach the "far" groups of detectors than the shorter path, which penetrates less deep into the tissue and travels through a smaller volume of tissue to reach the "near" group of detectors. The different information can be separated and/or combined to calculate a plurality of physiological parameters of the wearer of the sensor or module 100**, for example, an indication of the wearer's hydration status, which will be described in greater detail below.

FIG. 11A illustrates schematically an example wearable device 10 disclosed herein. As described above, the device processor 14 can be connected to the sensor or module processor 108 of the physiological parameter measurement sensor or module 100, which includes the emitters, the detectors, the thermistors, and other sensors disclosed herein. The electrical connection between the device processor 14 and the sensor or module processor 108 can be establish optionally via a flex connector 32. The sensor or module processor 108 can be coupled to the ECG electrodes 124, 125, optionally via an ECG flex connector 123.

The device processor 14 can be connected to a display screen 12, which can include the display screen 12 and touch input from the wearer. The device processor 14 can include a power source 16, and optionally one or more wireless charging coils 17 to enable wireless charging of the power source 16. The device processor 14 can be connected to an antenna 19 for extending signals transmitted wirelessly, for example, to an external device as described with reference to FIG. 2. The device processor 14 can include connection to a first user interface (UI 1) 13*a* and a second user interface (UI 2) 13*b* on the device 10 to receive input from the wearer. As shown in FIG. 1F, example first and second user interface 13*a*, 13*b* can be in the form of buttons 13. Additionally or alternatively, the device 10 can include a microphone. The device 10 can receive user inputs via the user interfaces, which can be the buttons, the microphone, and/or the touchscreen. The user inputs can command the device 10 to turn on and/or off certain measurements, and/or to control externally connected devices, such as an insulin pump, a therapeutics delivery device, or otherwise. The device processor 14 can be connected to a user feedback output 15 to provide feedback to the wearer, for example, in the form of vibration, an audio signal, and/or otherwise. The device processor 14 can optionally be connected to an accelerometer and/or a gyroscope 41 located on the device 10 that is different from the accelerometer 114 and gyroscope 112 on the physiological parameter measurement sensor or module 100. The accelerometer and/or gyroscope 41 can measure position and/or orientation of the wearer for non-physiological parameter measurement functions, for example, for sensing that the wearer has woken up, rotating the display screen 12, and/or the like.

FIG. 11B illustrates example components of the device processor 14 PCB board. As shown in FIG. 11B, the device processor 14 can include a Bluetooth co-processor 1400 and a system processor 1402. The system processor 1402 can run the peripheral functions of the device 10, receive user (that is, the wearer) input and communicate to the sensor or module processor 108. The Bluetooth co-processor 1400 can focus on managing Bluetooth communication so as to allow the system processor 1402 to focus on the high memory utilization tasks, such as managing the display screen 12. The Bluetooth co-processor 1400 can be activated when there is incoming and/or outgoing Bluetooth communication. Alternatively, the Bluetooth co-processor 1400 can be replaced by a different wireless co-processor configured to manage wireless communication using a different wireless communication protocol.

FIG. 11C illustrates example components of the module processor PCB board 116. As shown in FIG. 11C, the sensor or module processor 108 can include a calculation processor 1080 and a system processor 1082. The calculation processor 1080 can manage host communication with the device processor 14 via a host connector 1084. The calculation processor 1080 can perform algorithm computations to calculate the physiological parameters based on the signals received from the ECG electrodes 124/125 and the optical sensor including the emitters 104, the detectors 106, and the thermistor(s) 110, and optionally from other sensors in communication with the sensor or module processor 108. The calculation processor 1080 can have relatively large memory suitable for running algorithm computations. The system processor 1082 can be in communication with a power management integrated circuit (PMIC) 1090. The system processor 1082 can run the physical system of the sensor or module 100 (for example, including turning on and off the emitter LEDs, changing gain, setting current, reading the accelerometer 114 and/or the gyroscope 112, and the like) and decimate data to a lower sampling rate. The system processor 1082 can focus on data processing, taking measurements and diagnostics, and basic functions of the sensor or module processor 108. The system processor 1082 can allow the calculation processor 1080 to sleep (being inactive) most of the time, and only wake up when there is enough measurement data to perform calculations.

Figure 11D:
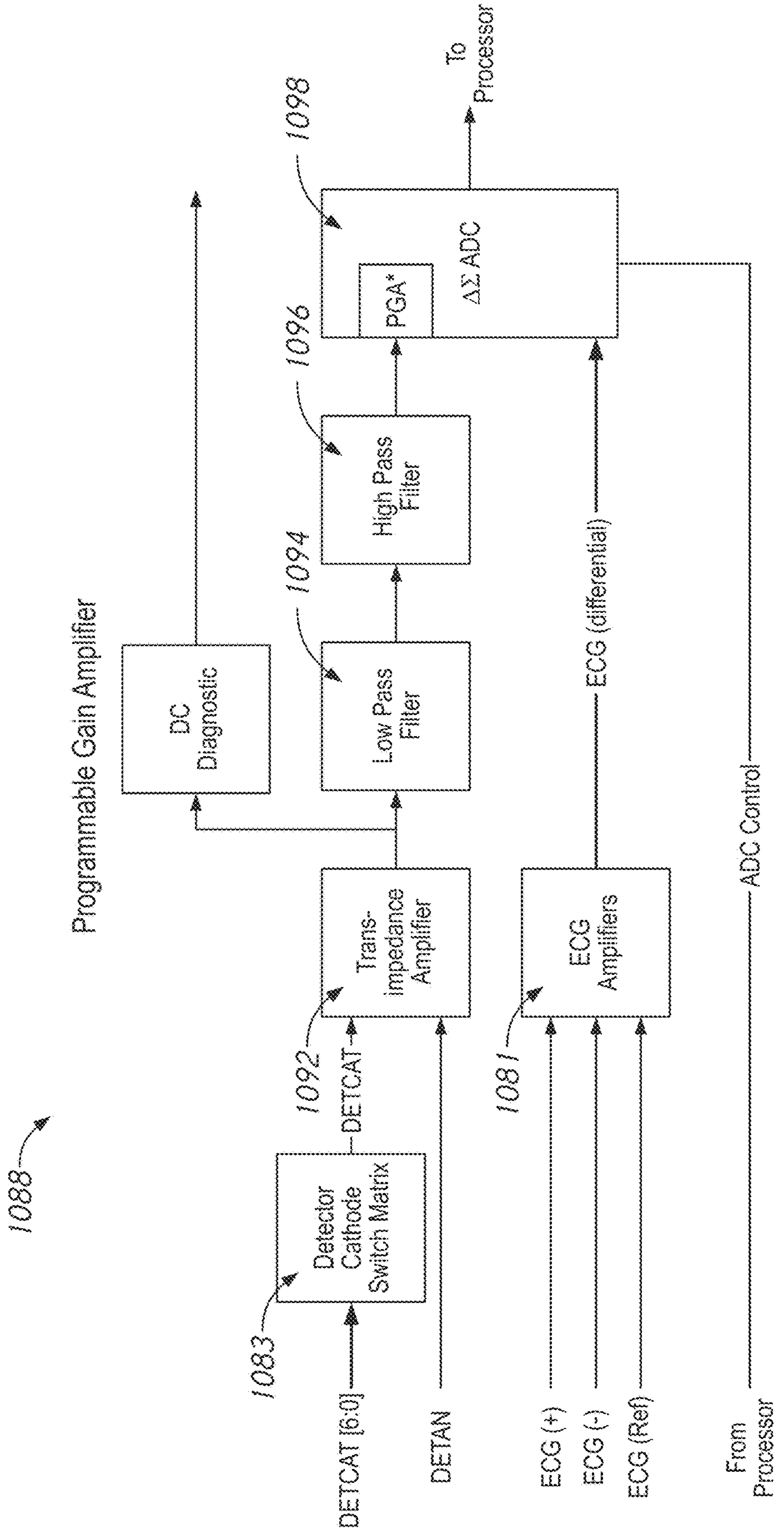
FIG. 11D illustrates a block diagram of an example front end circuitry of the sensor or module processor of FIG. 11C.

FIG. 11D illustrates an example front-end analog signal conditioning circuitry 1088 of the module PCB 116 shown in FIG. 11C. The entire front end circuitry 1088 can be located on a single application-specific integrated circuit (ASIC).

The front-end circuitry 1088 can include a transimpedance amplifier 1092 configured to receive analog signals from the optical sensor including the emitters 104, the detectors 106, and the thermistor(s) 110, which can be preprocessed (for example, via a low pass filter 1094 and a high pass filter 1096) before being sent to an analog-digital converter 1098. The analog-digital converter 1098 can output a digital signal based on the analog signals from the optical sensor including the emitters 104, the detectors 106, and the thermistor(s) 110 to the system processor 1082 and the calculation processor 1080. The front end circuitry 1088 can include a detector cathode switch matrix 1083 configured to activate the cathode of the detectors that are selected to be activated. The matrix 1083 can be further configured to deactivate (for example, by short-circuiting) anodes of the detectors that are selected to be deactivated in configurations in which the detectors share a common cathode and have different cathodes.

The front-end circuitry 1088 can include an ECG amplifier 1091 configured to receive analog signals from the ECG electrodes 124/125, which can output the amplified analog signals to the analog-digital converter 1098. The amplified analog signals can include an ECG differential between the positive and negative electrodes. The analog-digital converter 1098 can output a digital signal based on the analog signals from the ECG electrodes 124/125 to the system processor 1082 and the calculation processor 1080.

Figure 12B:
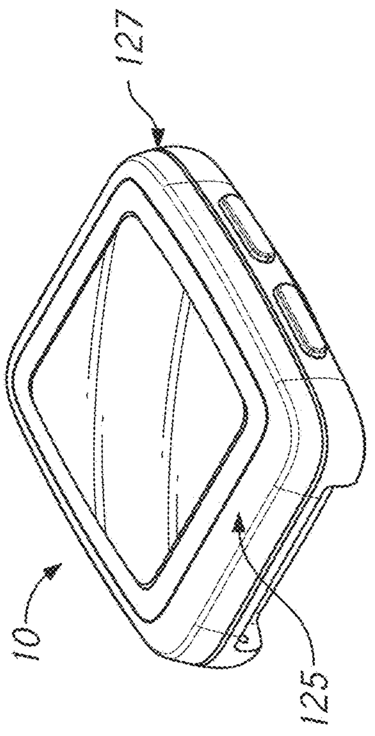
FIG. 12B illustrates a top perspective view of the example wearable device including a third ECG electrode.
Figure 12C:
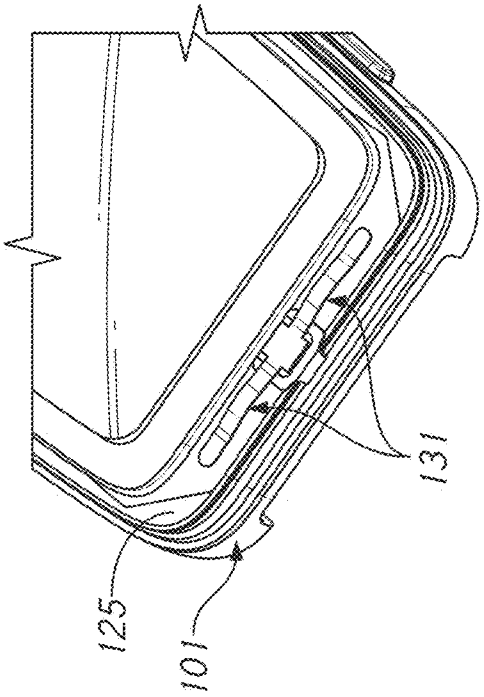
FIG. 12C illustrates a partial top perspective view of the example wearable device of FIG. 12B with the third ECG electrode shown as transparent to illustrate contact springs underneath the third ECG electrode.
Figure 12A:
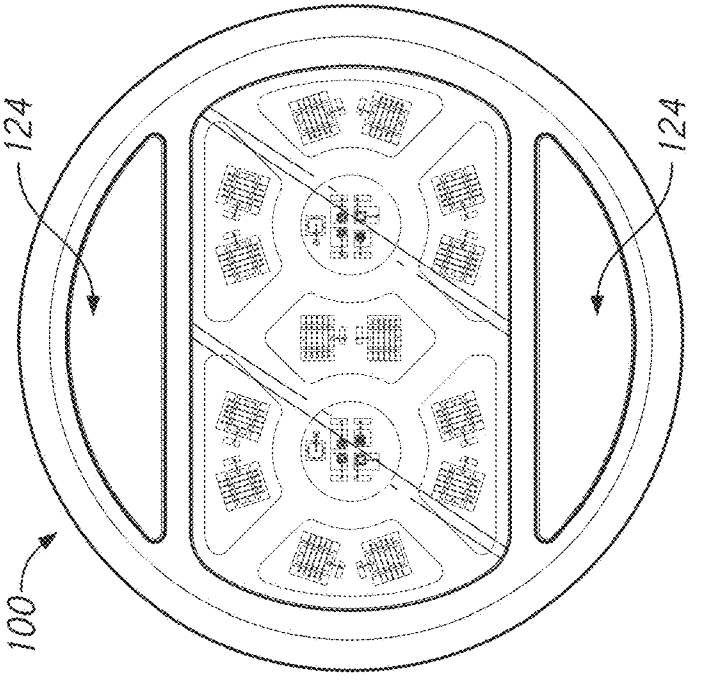
FIG. 12A illustrates a bottom view of an example physiological parameter measurement module with first and second ECG electrodes.

The ECG electrodes 124 can include a negative electrode, a positive electrode, and a reference electrode. As shown in FIG. 12A, the two electrodes 124 located on the sensor or module 100 can act as a reference electrode and a negative (or positive) electrode respectively. As shown in FIGS. 12B and 12C, a portion of the device housing 101 that surrounds the display screen 12 can function as another ECG electrode 125. An electrically insulating material 127 can separate the ECG electrode 125 from the remainder of the housing 101 so that an electrical current between the ECG electrode 125 and the ECG electrodes 124 would travel through the wearer's body. When the wearer wants to make a measurement using the ECG sensor that includes the ECG electrodes 124, 125, the wearer can press on or touch the electrode 125 using the wearer's finger or another part of the wearer's body such that the wearer's skin makes contact with the electrode 125.

In the illustrated examples, the ECG electrode 125 can be positive (or negative if one of the electrodes 124 servers as a positive electrode) electrode. As shown in FIG. 12C, the electrode 125 is illustrated as being transparent to show one or more spring contacts 131 located underneath the electrode 125. The shape, size, and/or number of the spring contacts 131 can vary from the example shown in FIG. 12C. The spring contacts 131 can establish an electrical connection between the electrode 125 and the electrode 125 and the sensor or module processor 108 of the sensor or module 100. For example, the spring contacts 131 can establish an electrical connection between the electrode 125 and the connector 132. The spring contacts 131 can be biased toward the electrode 525 to ensure a firm electrical connection between the spring contacts 131 and the electrode 125. Readings from the electrodes 124, 125 can allow the sensor or module processor 108 to obtain the wearer's ECG signal and optionally to make physiological measurements based on the obtained ECG, for example, the heart rate, the respiratory rate, and/or otherwise. The sensor or module processor 108 can communicate the ECG signals and/or ECG-related measurements to the wearable device processor 14. The wearer's ECG waveform and/or the measurements made from the ECG can be displayed on the display screen 12.

Figure 13A:
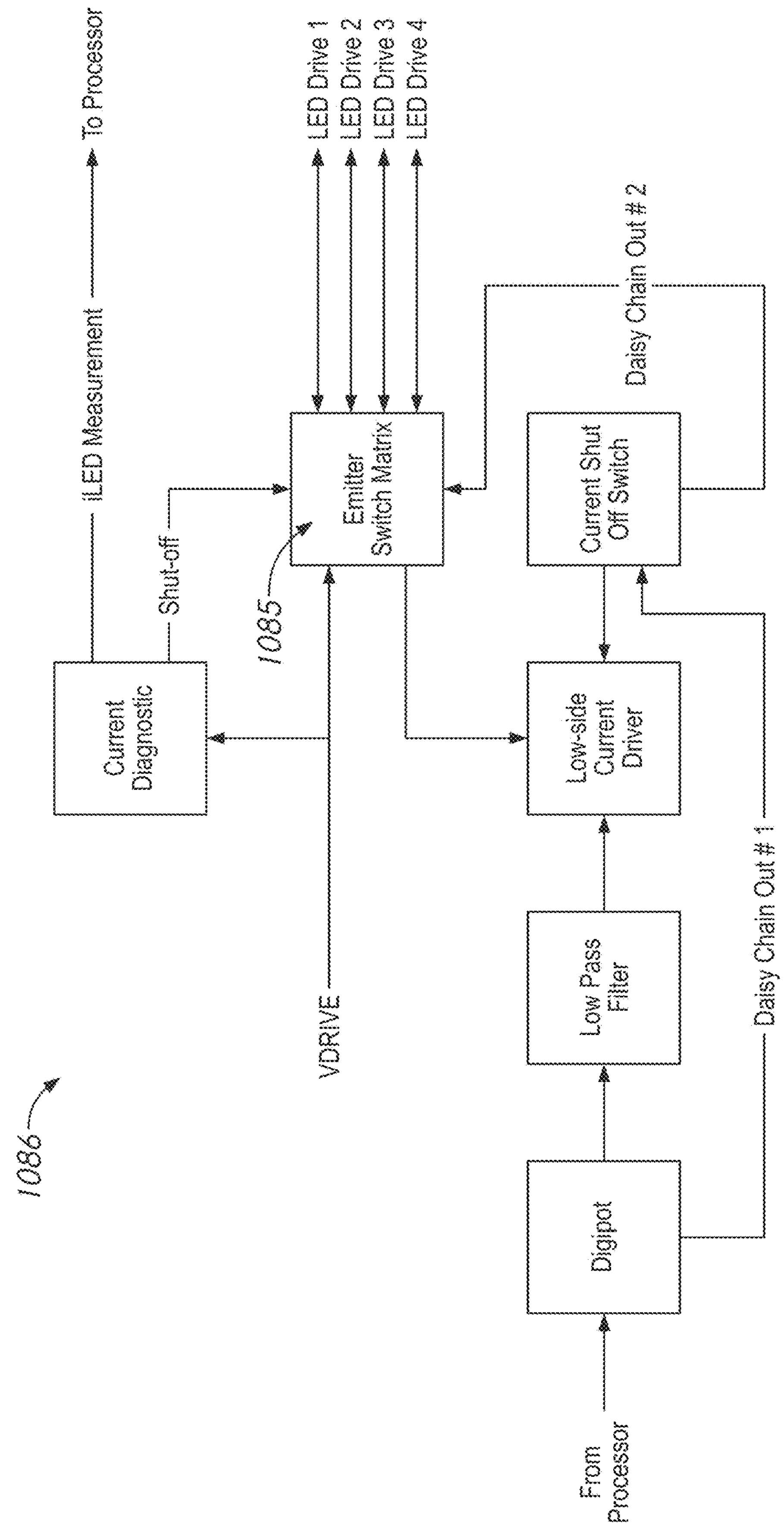
FIG. 13A illustrates an example block diagram of LED drive circuitry of the physiological parameter measurement module disclosed herein.

FIG. 13A illustrates an example LED driver circuitry 1086 of the module PCB 116 shown in FIG. 11C. The entire LED driver circuitry 1086 can be located on the single ASIC with the front end circuitry 1088. As described above, the system processor 1802 can output a control signal to turn on and off the emitter LEDs. As shown in FIG. 13A, the LED driver circuitry 1086 can include an emitter switch matrix 1085 configured to drive any of the emitters (or emitter groups) that are selected to be turned on or turn off any of the emitters (or emitter groups) that are selected to be turned off.

Figure 13C:
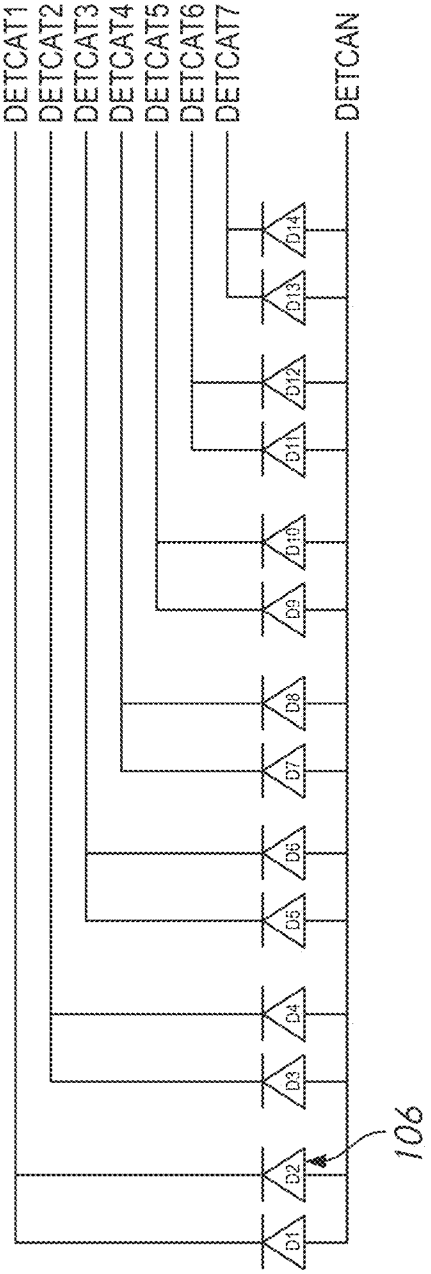
FIG. 13C illustrates an example block diagram of detectors circuitry of the physiological parameter measurement module disclosed herein.
Figure 13D:
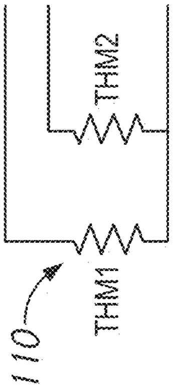
FIG. 13D illustrates an example block diagram of temperature sensors circuitry of the physiological parameter measurement module disclosed herein.
Figure 13B:
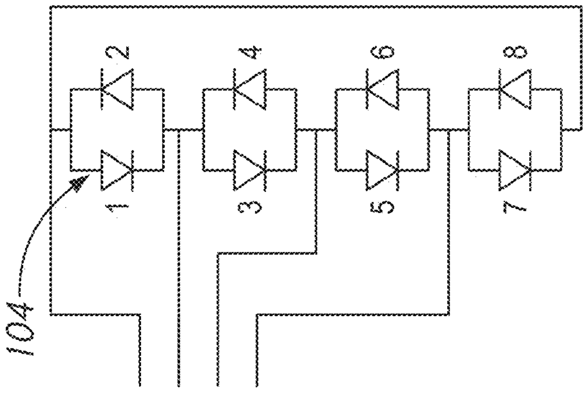
FIG. 13B illustrates an example block diagram of emitters circuitry of the physiological parameter measurement module disclosed herein.

FIG. 13B illustrates an example emitter circuitry including eight different emitter LEDs 104. The number of LEDs may vary and be greater than eight. The emitters of the physiological parameter measurement module can be configured to emit a plurality of (for example, three, four, or more) wavelengths. Each of the emitters can be configured to emit light of a different wavelength than the other emitters. Alternatively, one or more of the emitters can emit light of more than one wavelength. In the illustrated example, the emitter circuitry can include four drivers to drive the eight emitter LEDs. Alternatively, the module can include more than four LEDs per emitter group. Each LED Drive can drive an LED to emit light of a different wavelength. The device or the module can grant access of some of the LEDs to a third party device, for example, for measurement purposes. The LED drivers can selectively drive some but not all the LEDs.

The emitters can be configured to emit light of a first wavelength providing an intensity signal that can act as a reference signal. The first wavelength can be more absorbent by the human body than light of other wavelengths emitted by the emitters. The reference signal can be stronger and less likely to be affected by noise than the signals from other wavelengths emitted by the emitters. The reference signal can be used by the physiological parameter measurement sensor or module processor to extract information from the other signals, for example, information relevant to and/or indicative of the pulsing rate, harmonics, or otherwise. The physiological parameter measurement sensor or module processor can focus the analysis on the extracted information for calculating physiological parameters of the wearer. Including the reference signal can reduce power consumption and saving the battery life of the device. The first wavelength can be from about 525 nm to about 650 nm, or from about 580 nm to about 585 nm, or from about 645 nm to about 650 nm, or about 525 nm, or about 580 nm, or about 645 nm. The light providing the reference signal can have an orange or yellow color. Alternatively, the light providing the reference signal can have a green color.

The emitters can be configured to emit light having a second wavelength having a red color. The second wavelength can be from about 620 nm to about 660 nm. Light of the second wavelength can be more sensitive to changes in oxygen saturation (SpO2) than light of other wavelengths emitted by the emitters. The second wavelength is preferably closer to 620 nm (for example, about 625 nm), which results in greater absorption by the body tissue of the wearer, and therefore a stronger signal and/or a steeper curve in the signal, than a wavelength that is closer to 660 nm. The physiological parameter measurement sensor or module processor 108 can extract information such as the pleth waveform from signals of the second wavelength.

The emitters can be configured to emit light having a third wavelength of about 900 nm to about 910 nm, or about 905 nm, or about 907 nm. The third wavelength can be in the infrared range. The sensor or module processor can use the third wavelength as a normalizing wavelength when calculating ratios of the intensity signals of the other wavelengths, for example, a ratio of the intensity signals of the second wavelength (red) to the third wavelength (infrared).

Additionally or optionally, the emitters can be configured to emit light having a fourth wavelength that is more sensitive to changes in water than the rest of the emitted wavelengths. The fourth wavelength can be in the infrared range and about 970 nm. The physiological parameter measurement sensor or module processor can determine physiological parameters such as a hydration status of the wearer based at least in part on a comparison of the intensity signals of the fourth wavelength and a different wavelength detected by certain detectors. The detectors used for hydration monitoring can be located a predetermined distance away from the emitters (that is, being a "far" detector disclosed herein) so that light travels through a certain depth of the tissue before being detected by those detectors.

The emitters in the physiological parameter measurement sensor or module can be placed in two emitter groups. Each emitter group can include four emitter LEDs configured to emitter the first, second, third, and fourth wavelengths described above. The emitters in the same emitter group can be located in the same emitter chamber disclosed herein. Each of the four drivers are configured to drive the emitters to emit one of the four wavelengths described above.

FIG. 13C illustrates an example detector circuitry including fourteen detectors 106. The total number of detectors on a module can vary. The fourteen detectors can form seven detector groups, each group including two detectors. The number of detectors in each group may vary. Detectors of the same detector group can be located in the same detector chamber disclosed herein. Each detector group can output one signal, which can be a combined signal of the two detectors in the same group. As shown in FIG. 13C, the detectors can share a common anode but have seven different cathodes, corresponding to the seven detector groups.

FIG. 13D illustrates an example thermistor circuitry. In the illustrated example, the physiological parameter measurement module can include two thermistors 110. The two thermistors can be located in the two emitter chambers near the two emitter groups respectively.

Example Signal Processing of the Physiological Parameter Measurement Module

Figure 14A:
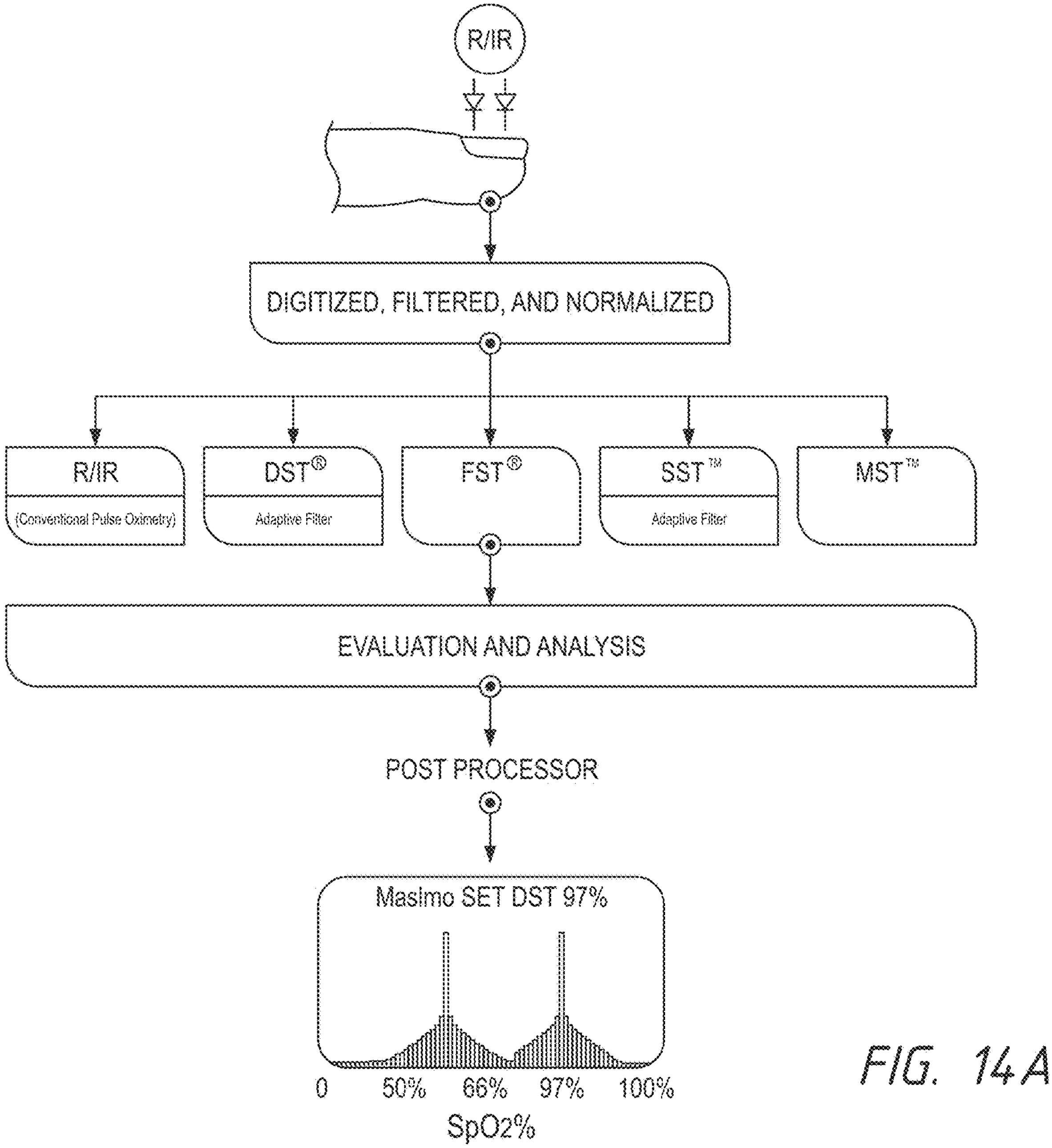
FIGS. 14A and 14B are example block diagrams illustrating signal processing of a conventional plethysmograph sensor.
Figure 14B:
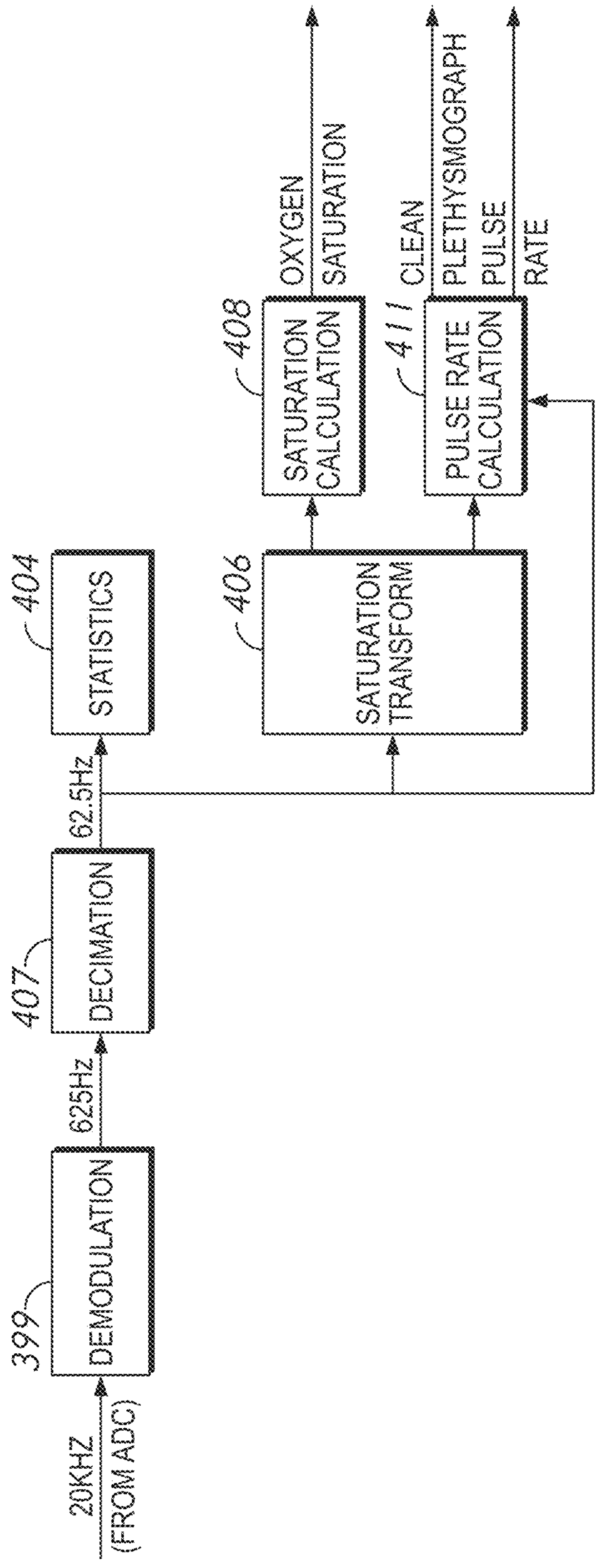

FIGS. 14A and 14B depict functional block diagrams of the operations of a conventional pulse oximeter carried out by the digital signal processing system. The signal processing functions described below are carried out by a digital signal processor (DSP) with a microcontroller providing system management. As shown in FIG. 14A, an analog signal from the detector(s) of the conventional pulse oximeter is digitized, filtered and normalized, and further processed using conventional pulse oximetry signal processing algorithms. Parallel signal processing engines—DST®, FST®, SST™, and MST™ are used to separate the arterial signal from sources of noise (including the venous signal) to measure SpO2 and pulse rate accurately, even during motion. FIG. 14B depicts a generalized functional block diagram for the operations performed on the 20 Khz sample data entering the digital signal processing system from an analog to digital converter (ADC). As illustrated in FIG. 14B, the DSP first performs a demodulation, as represented in a demodulation module 399. The processor performs decimation, as represented in a decimation module 407 on the resulting data from the demodulation. The processor calculates certain statistics, as represented in a statistics module 404, and performs a saturation transform, as represented in a saturation transform module 406, on the data resulting from the decimation operation. The processor forwards data subjected to the statistics operations and the data subjected to the saturation transform operations to saturation operations, as represented by a saturation calculation module 408 to output an oxygen saturation measurement and pulse rate operations, as represented in a pulse rate calculation module 411 to output a pulse rate value.

Figure 15A:
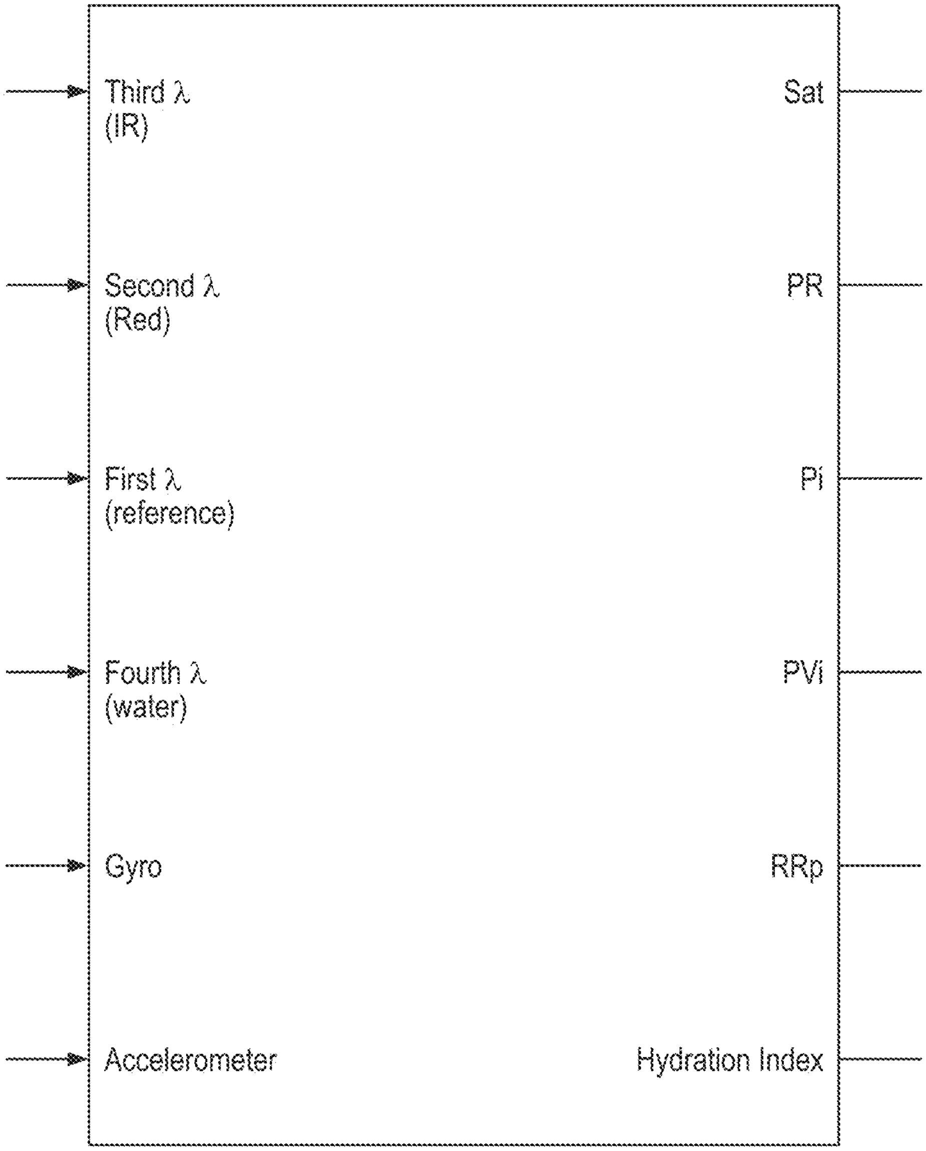
FIGS. 15A and 15B illustrate example schematic input and output flow diagrams of a physiological parameter measurement module disclosed herein.

FIGS. 15A-15G illustrate example signal processing of the physiological parameter measurement sensor or module disclosed herein. As shown in FIG. 15A, the sensor or module processor can receive intensity signals from the detectors in response to detected reflected light of the first (reference signal or signal of green or yellow light), second (signal of red light), third (signal of infrared light), and fourth (signal of infrared light with a wavelength of 970 nm) wavelengths described above, and signals from the gyroscope and accelerometer. The sensor or module processor can output a plurality of physiological parameters based on the input signals from the sensors described above. The plurality of physiological parameters can include, for example, SpO2 (Sat), pulse rate (PR), perfusion index (PI), pleth variability index (PVI), respiration rate from the pleth (RRp), and a hydration index.

Figure 15B:
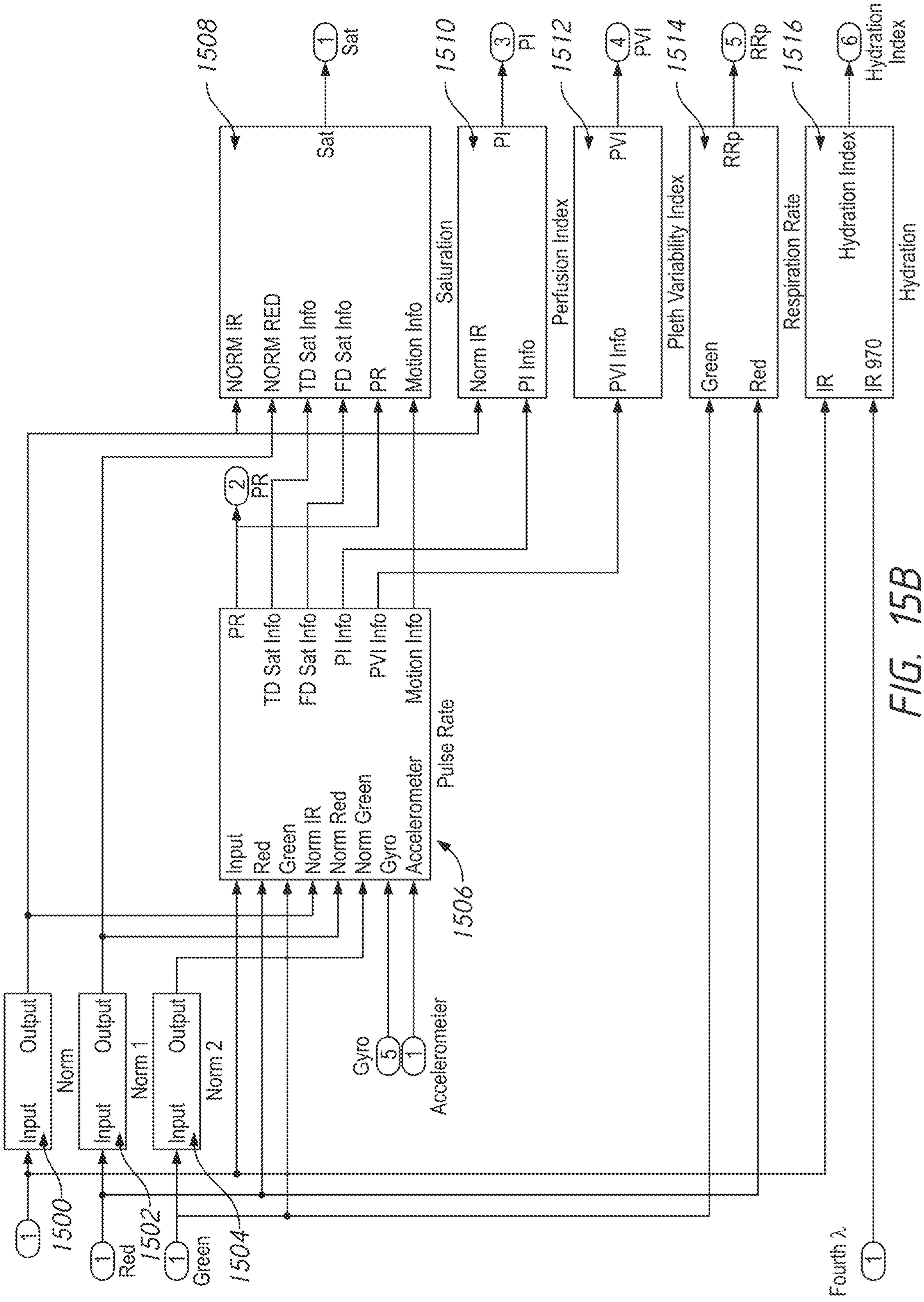

As shown in greater detail in FIG. 15B, the sensor or module processor can process the intensity signal in response to detected light of the first, second, and third wavelengths in the unnormalized form and a normalized form (in normalization modules "Norm" 1500, "Norm 1" 1502, and "Norm 2" 1504). As described above, the signal of the third wavelength can be used as the normalizing signal. The sensor or module processor can extract various information from the intensity signals in response to detected light of the first, second, and third wavelengths and signals from the accelerometer and the gyroscope, such as the PR (which can be output as the PR measurement), time domain (TD) saturation information, frequency domain (FD) saturation information, PI information, and PVI information, in a pulse rate determination module 1506.

Figure 15C:
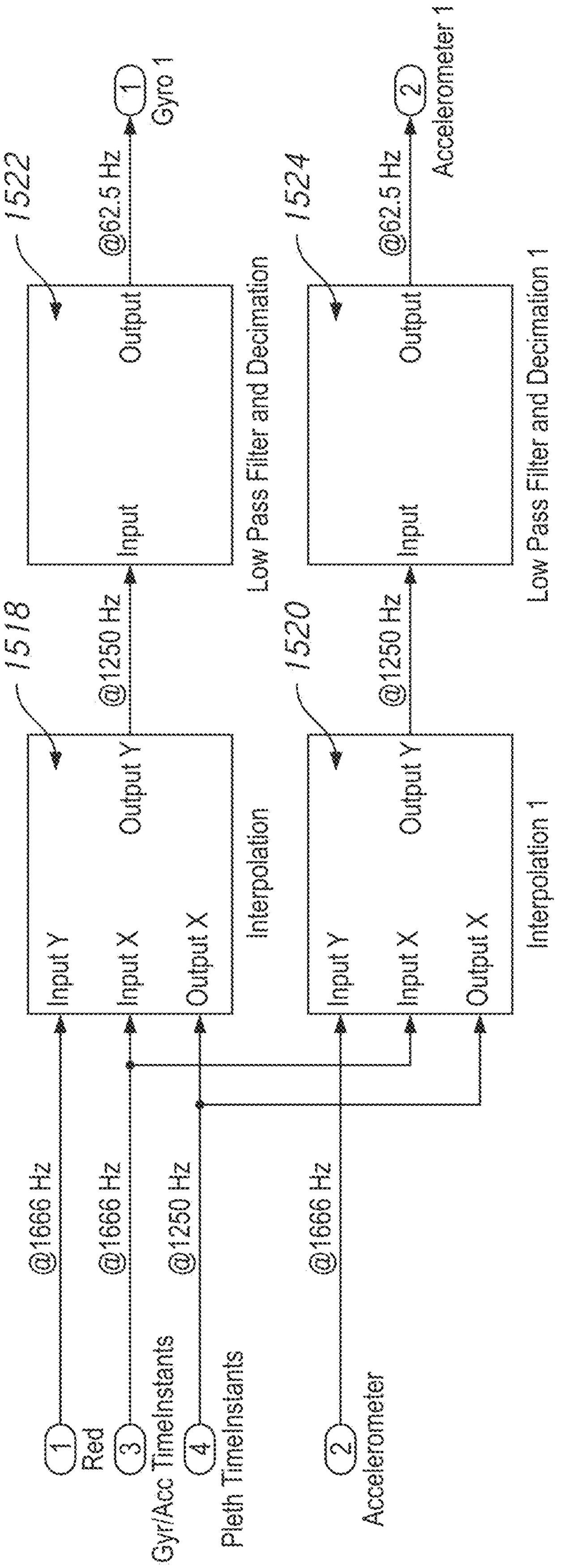
FIG. 15C illustrates an example schematic input and output flow diagram of the gyroscope and accelerometer of a physiological parameter measurement module disclosed herein.

FIG. 15C illustrates example processing of the raw signals from the accelerometer and the gyroscope to output the gyroscope and accelerometer signals. The sensor or module processor can combine each of the raw gyroscope and accelerometer signals (which can be raw signals from any axis of the gyroscope and/or accelerometer) with gyroscope/accelerometer time instants and pleth time instants signals in an interpolation module 1518 or interpolation 1 module 1520 respectively. The sensor or module processor can further process the outputs from the interpolation module 1518 or interpolation 1 module 1520 in a low pass filter and decimation module 1522 or low pass filter and decimation 1 module 1524 respectively to output a gyrol signal and an accelerometer 1 signal. The output gyre 1 and accelerometer 1 signals can be sent to the ASIC described above.

Figure 15D:
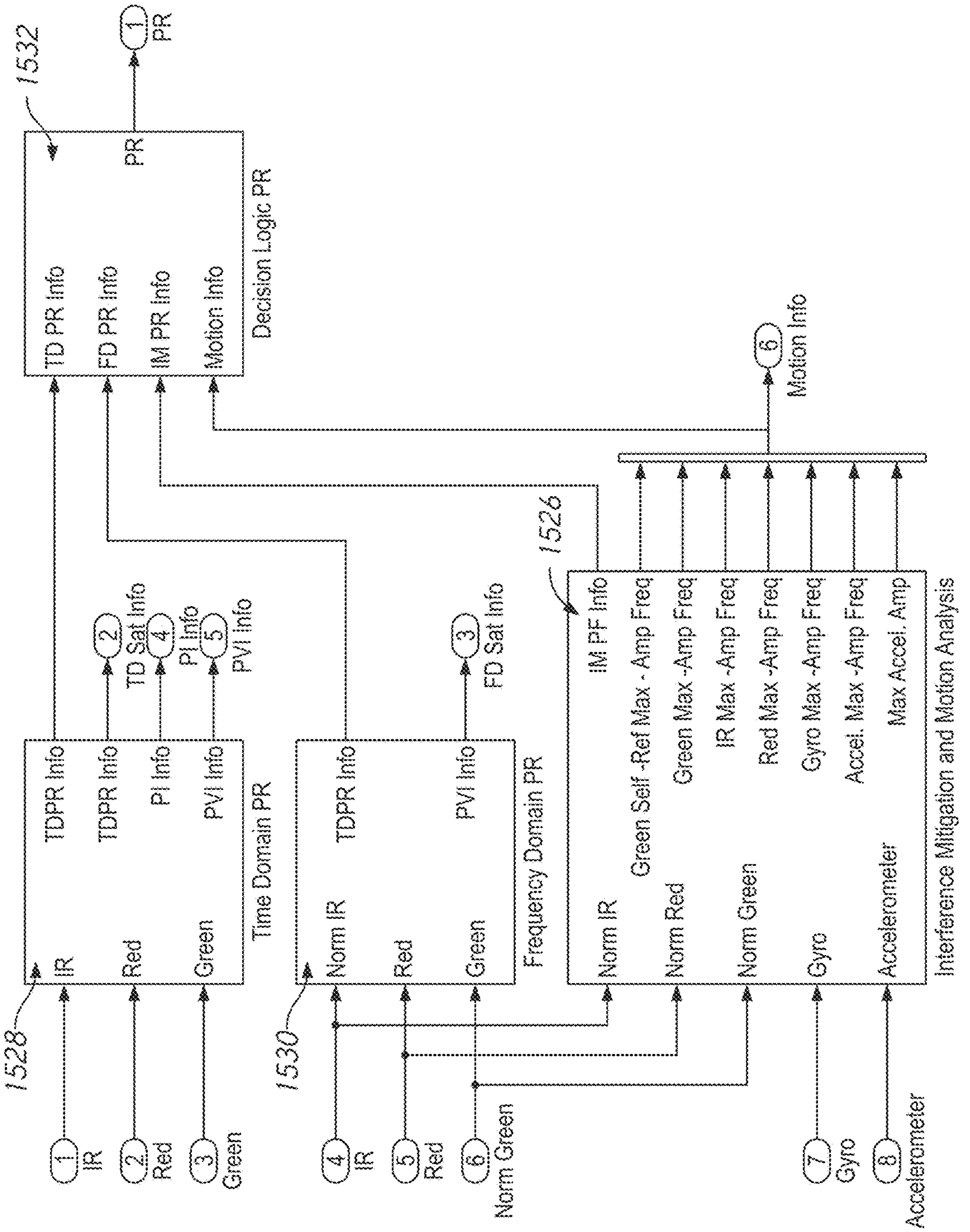
FIG. 15D illustrates an example schematic block diagram for determining pulse rate using a physiological parameter measurement module disclosed herein.

As shown in FIG. 15D, the sensor or module processor can extract motion information from the gyroscope and accelerometer input and the normalized signals of the first, second, and third wavelengths in an interference mitigation (IM) and motion analysis module 1526. As also shown in FIG. 15D, the sensor or module processor can obtain time domain pulse rate (TDPR) information, TD saturation information, PI information, and PVI information in a time domain pulse rate determination module 1528 from the intensity signals of the first, second, and third wavelengths. The sensor or module processor can obtain frequency domain pulse rate (FDPR) information and FD saturation information in a frequency domain pulse rate determination module 1530 based on normalized signals of the first, second, and third wavelengths. The sensor or module processor can determine and output a pulse rate in a pulse rate decision logic 1532 based on the TDPR information, FDPR information, interference mitigation (IM) PR information (output by the interference mitigation and motion analysis module 1526), and motion information.

Figure 15E:
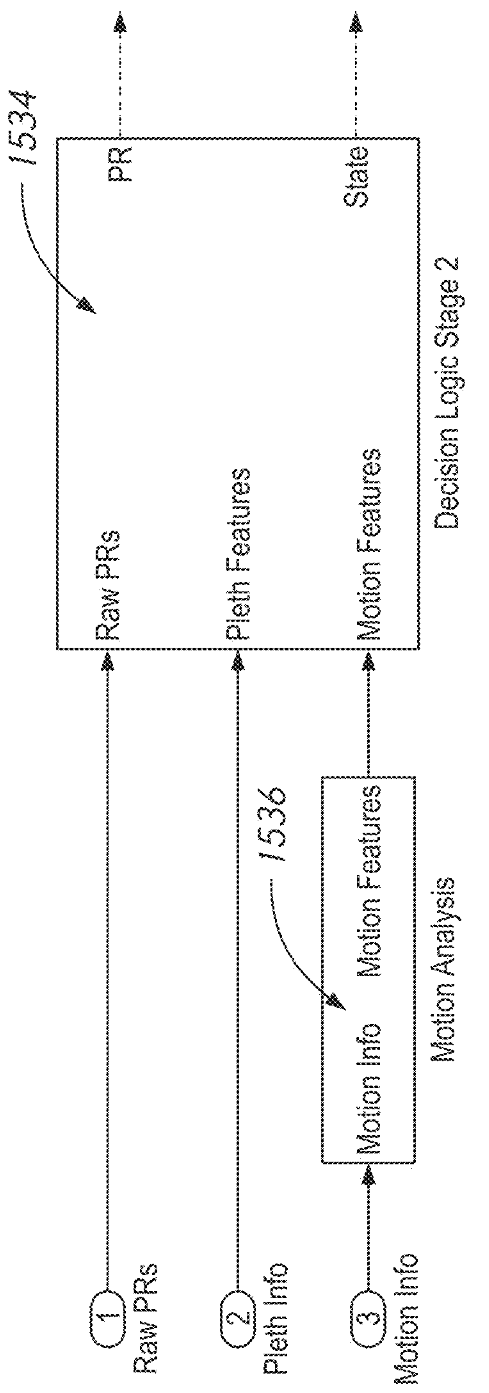
FIG. 15E illustrates an example decision logic for determining pulse rate using a physiological parameter measurement module disclosed herein.

FIG. 15E illustrates an example pulse rate determination decision logic. In this example, a decision logic stage 2 module 1534 can receive as input raw pulse rate calculations from individual pulse rate determination engines (for example, the time domain pulse rate determination module 1528, the frequency domain pulse rate determination module 1530 and the interference mitigation and motion analysis module 1526 as shown in FIG. 15D), pleth features including time domain and frequency domains from N channels (for example, N=4 or more) of pleth signals, and motion features obtained from a motion analysis module 1536. The motion analysis module 1536 can assess the amount of motion, define the type of motion, and calculate a motion rate (for example, per minute) if the motion is determined to be periodic, and/or the like based on motion information from a 6DOF (degree-of-freedom) inertia measurement unit (IMU). The IMU can include the accelerometer and the gyroscope on the physiological parameter measurement module.

Figure 15F:
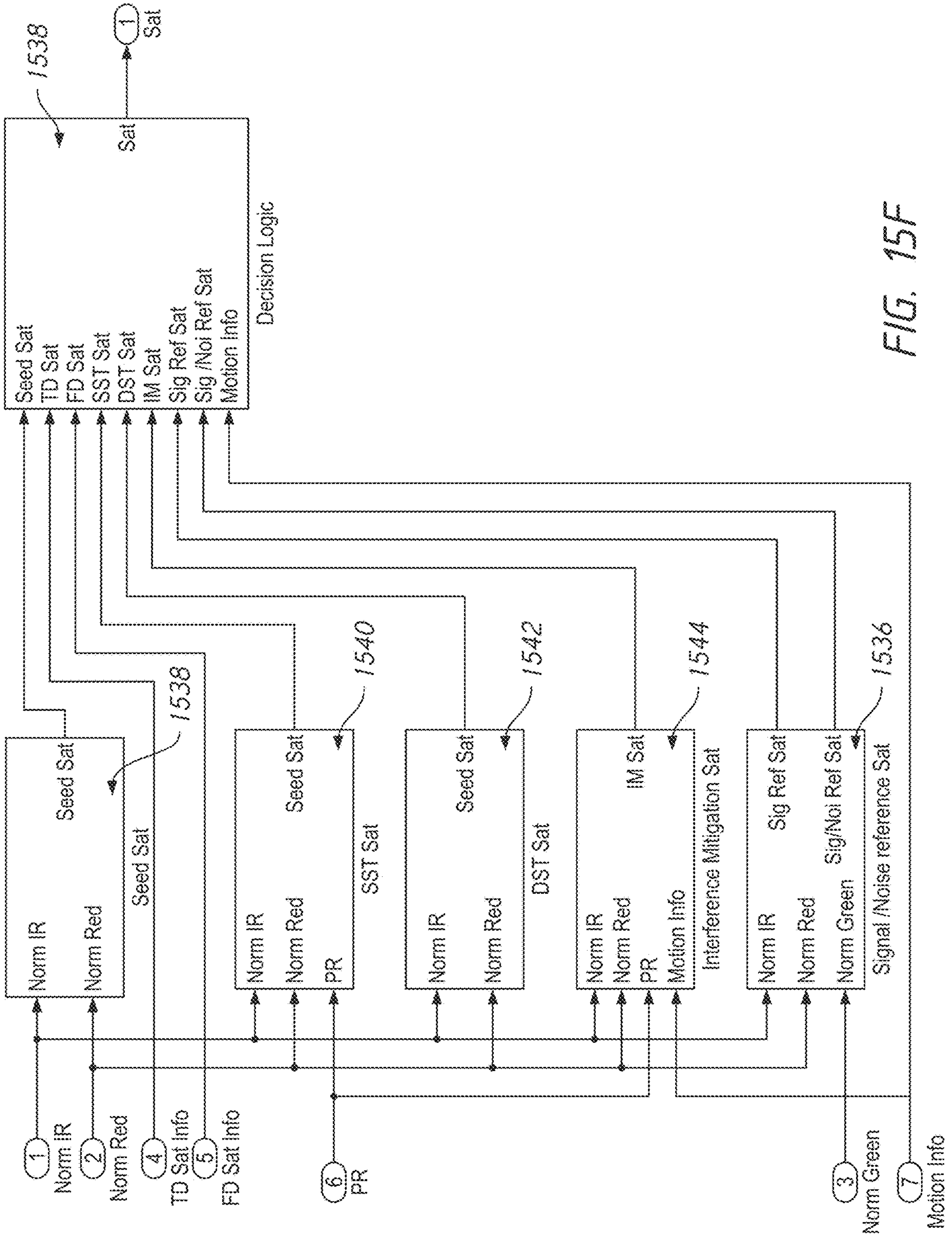
FIG. 15F illustrates an example schematic input and output flow diagram for determining oxygen saturation using a physiological parameter measurement module disclosed herein.
Figure 15G:
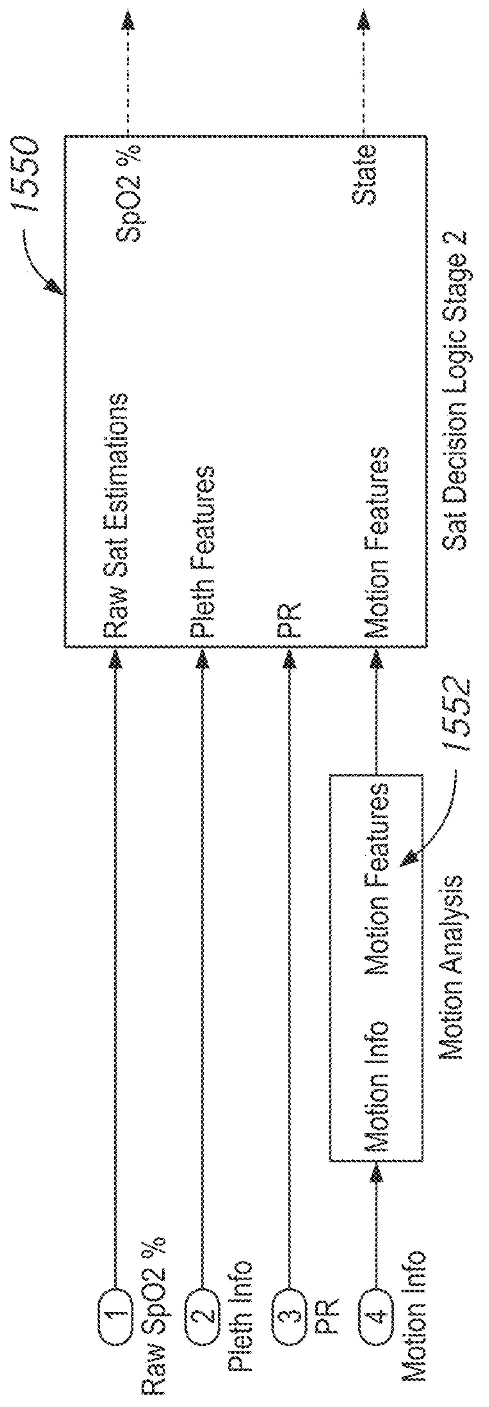
FIG. 15G illustrates an example decision logic for determining oxygen saturation using a physiological parameter measurement module disclosed herein.

With continued reference to FIG. 15B, the sensor or module processor can determine the oxygen saturation measurement based on the normalized signal of the third wavelength, the normalized signal of the second wavelength, the TD saturation information, the FD saturation information, the PR, and the motion information in an oxygen saturation determination module 1508. FIG. 15F illustrates an oxygen saturation determination module including a plurality of parallel signal processing engines, such as a Seed saturation module 1538, an SST saturation module 1540, a DST saturation module 1542, an interference mitigation (IM) saturation module 1544, and a signal/noise reference saturation module 1546, configured to feed individual raw oxygen saturation (SpO2) values to a decision logic 1548. The decision logic 1548 can further receive as input the motion information and output a final oxygen saturation measurement based on the motion information and the raw oxygen saturation values determined by the parallel engines.

FIG. 15E illustrates an example oxygen saturation determination decision logic. In this example, a saturation decision logic stage 2 module 1550 can receive as input raw oxygen saturation calculations from the parallel engines described above, pleth features, pulse rate, and motion features obtained from a motion analysis module 1552. The pleth features received by the module 1550 can include the features in the pulse rate decision logic shown in FIG. 15E. Additionally, the pleth features received by the module 1550 can include features related to saturation, for example, the DC ratio of the second and third wavelengths. The motion analysis module 1552 can receive the same features as the pulse rate decision logic shown in FIG. 15E.

With continued reference to FIG. 15B, the sensor or module processor can determine the PI measurement based on the normalized signal of the third wavelength and the PI information in a perfusion index determination module 1510. The sensor or module processor can determine the PVI measurement based on the PVI information in a pleth variability index determination module 1512. The sensor or module processor can determine the RRp measurement based on the intensity signals of the first and second wavelength in a respiration rate determination module 1514. The sensor or module processor can determine the hydration index in a hydration determination module 1516 based on the intensity signals (for example, from the "far detectors" disclosed herein) of the fourth wavelength, which is more sensitive to changes in water in the measurement site and another wavelength (for example, the third wavelength or about 905 nm) that is less sensitive to changes in water. The sensor or module processor can focus on the DC component of the signals for hydration status monitoring.

Various example physiological parameter measurement modules and wearable devices incorporating the same will be described below. Each of the example modules and devices can incorporate any of the features of the physiological parameter measurement sensor or module 100 and the device 10 described above, all of which are not repeated for brevity. Features of the example modules and devices disclosed herein can be incorporated into one another.

Figure 16B:
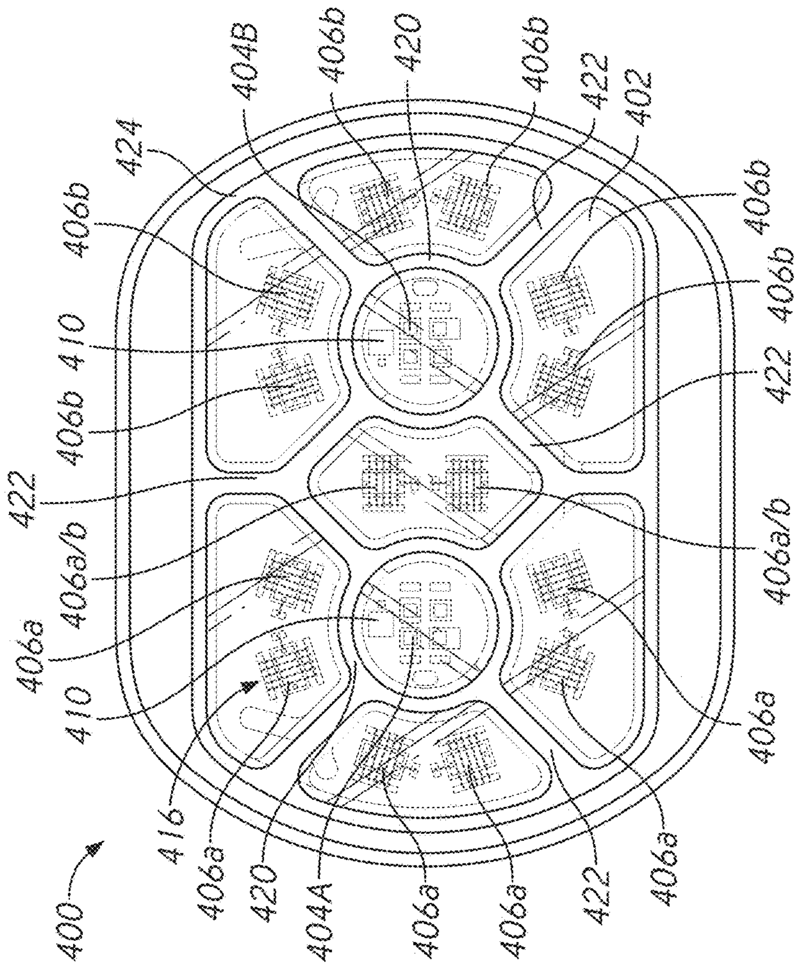
FIG. 16B illustrates a bottom view of an example physiological parameter measurement module incorporating the plethysmograph sensor arrangement of FIG. 16A.
Figure 16A:
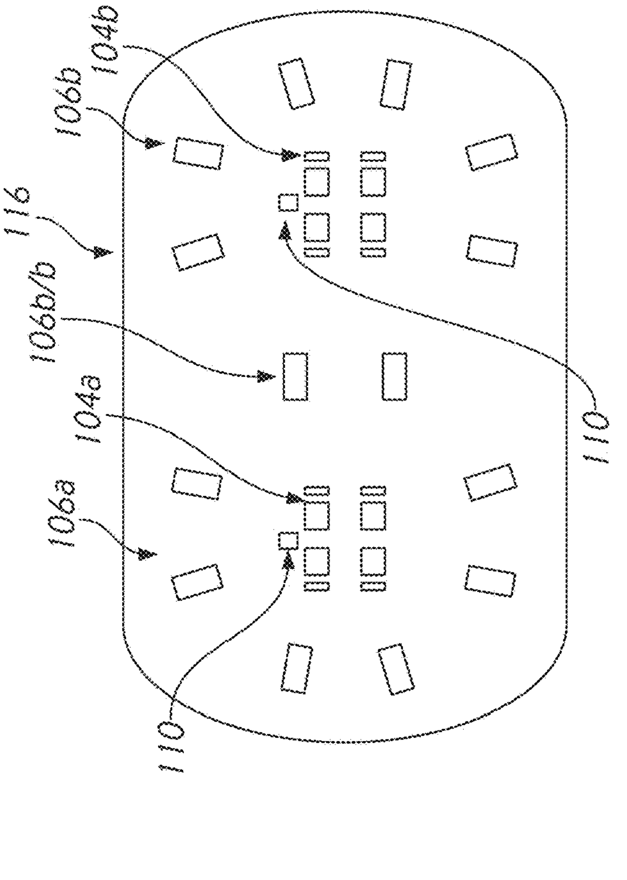
FIG. 16A illustrates schematically an example plethysmograph sensor arrangement on a sensor or module processor board of a physiological parameter measurement module of a wearable device.

Examples of Physiological Parameter Measurement Modules with Double Emitter Groups FIG. 16A illustrates schematically an example arrangement of an optical sensor, including emitters, detectors, and thermistors, on a sensor or module processor PCB 116. As shown in FIG. 16A, the PCB 116 can include a first group of emitters 104*a* and a second group of emitters 104*b*. Each group of emitters can include four emitters. The emitters in each group 404A,404B can emit at least the first, second, third, and fourth wavelengths as described above. The first and second groups of emitters 404A,404B can be located a distance from each other on a first side of a PCB 116. The PCB 116 can include a temperature sensor (such as a thermistor) 110 as described above located on the first side of the PCB 416. One thermistor 110 can be near the first group of emitters 404A. Another thermistor 110 can be near the second group of emitters 404B.

The PCB 116 can be elliptical in shape, although the shape of the PCB is not limiting. The two groups of the emitters 104*a*, 104*b* can be located on different parts of the first side of the PCB 116 divided along the minor diameter of the ellipse. Each of the two groups of the emitters 104*a*, 104*b* can be surrounded by a first light barrier and form an emitter chamber.

The first and second groups of emitters 104*a*, 104*b* can be surrounded by two rings of detectors 106*a*, 106*b* that are separated from the first and second groups of emitters 104*a*, 104*b* respectively by a distance. The two rings of detectors 106*a*, 106*b* can share a plurality of (for example, two or more) detectors 106*a/b* common to both rings. The detectors 106*a/b* common to both rings can be located along the minor axis of the ellipse. In the illustrated example, the PCB 116 can include fourteen detectors coupled to the PCB 116, but the total number of detectors can vary.

The detectors 106*b* can be the far detectors for the first group of emitters 104*a* and the detectors 106*a*, 106*a/b* can be the near detectors for the first group of emitters 104*a*. The detectors 106*a* can be the far detectors for the second group of emitters 104*b* and the detectors 106*b*, 106*a/b* can be the near detectors for the second group of emitters 104*b*. Accordingly, each detector 106*a*, 106*b*, 106*a/b* can receive two signals for each wavelength emitted by the first and second groups of emitters 104*a*, 104*b* respectively. As described above, signals outputted by the far and near detectors can provide different information due to the different light paths, which can travel through different areas of the tissue. In addition, the far detectors for each group of emitters 104*a*, 104*b* can detect the light emitted by the respective group of emitters 104*a*, 104*b*, for example, light of the fourth wavelength and another wavelength, and attenuated by tissue to provide an indication of the wearer's hydration status as described herein.

The detectors 106*a*, 106*b*, 106*a/b* can be separated or partitioned into seven detector regions. Each detector region can include two detectors, or any other number of detectors. Each detector region can form a detector chamber surrounded by light barriers. As described above, the sensor or module processor can process signals from a particular emitter and received at the detectors within the same detector region as one signal source. Accordingly, for each wavelength, the sensor or module processor can receive data from a total of fourteen signal sources, two from each detector region acting as the far and near detectors for the different groups of emitters respectively.

Figure 16D:
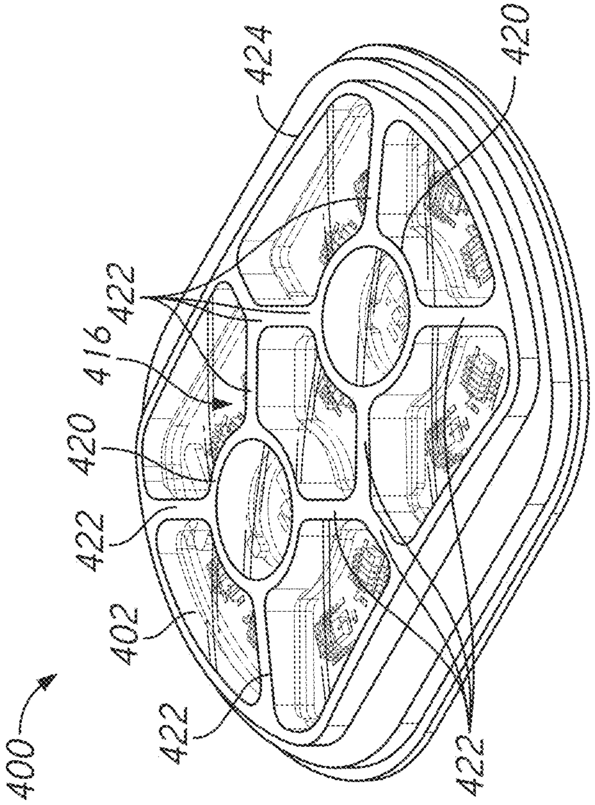
FIG. 16D illustrates a bottom perspective view of the example physiological parameter measurement module of FIG. 16B.
Figure 16C:
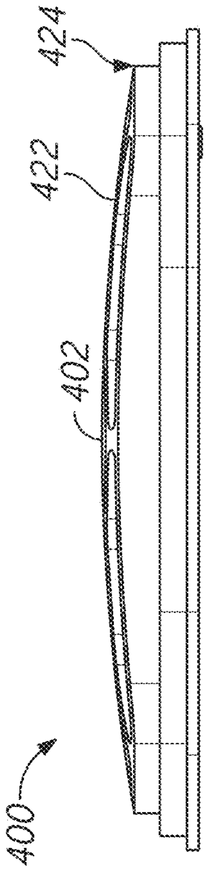
FIG. 16C illustrates a side view of the example physiological parameter measurement module of FIG. 16B.

FIGS. 16B-16D illustrate an example physiological parameter measurement module 400 of a wearable device. The module 400 can incorporate any of the features of the module examples described herein.

As shown in FIG. 16B, the physiological parameter measurement module 400 can include a first group of emitters 404A and a second group of emitters 404B incorporating the arrangement shown in FIG. 16A. Each group of emitters can include four emitters (or optionally a different number of emitters, such as six or eight emitters). The emitters in each group 404A,404B can emit at least the first, second, third, and fourth wavelengths as described above. Each of the two groups of the emitters 404A,404B can be surrounded by a first light barrier 420 and form an emitter chamber.

The first and second groups of emitters 404A,404B in the module 400 can be surrounded by two rings of detectors 406*a*, 406*b* that are separated from the first and second groups of emitters 404A,404B by the first light barrier 420. The two rings of detectors 406*a*, 406*b* can share a plurality of (for example, two or more) detectors 406*a/b* common to both rings. The detectors 406*a*, 406*b*, 406*a/b* can have the same arrangement as the detectors shown in FIG. 16A. In the illustrated example, the module 400 can include fourteen detectors, but the module 400 can also include a different total number of detectors.

As shown in FIGS. 16B and 16D, the detectors 406*a*, 406*b*, 406*a/b* can be separated or partitioned into seven detector chambers by a portion of the first light barrier 420 and second light barriers 422. Each detector region can include two detectors, or any other number of detectors. Along an outer perimeter of the module 400, the detectors 406*a*, 406*b*, 406*a/b* can be enclosed within a module side wall 424. A sensor or module processor of the module 400 can process signals from a particular emitter and received at the detectors within the same detector region as one signal source as described above. The arrangement of emitters 104*a*, 104*b* and detectors 106*a*, 106*b*, 106*a/b* and the light diffusing materials encapsulating the emitters 104*a*, 104*b* and/or detectors 106*a*, 106*b*, 106*a/b* can improve the sensing coverage on the wearer's wrist, which has fewer capillaries per volume than the fingertip as described above. The aggregate light detecting area of the 106*a*, 106*b*, 106*a/b* in FIG. 16B, that is, the aggregate surface area of all the detector chambers, can occupy about 50% or more of the tissue-facing surface of the physiological parameter measurement module. The aggregate light detecting area in FIG. 16B can be, for example, greater than about 100 $mm^2$, or greater than about 125 $mm^2$, or about 150 $mm^2$, or about 165 $mm^2$. The aggregate light emitting area in FIG. 16B, that is, the aggregate surface area of both emitters chambers, can be, for example, greater than about 25 $mm^2$, or about 30 $mm^2$, or about 35 $mm^2$. Any other physiological parameter measurement module examples disclosed herein can have the same or substantially similar aggregate light detecting area and/or light emitting area as the module 400 shown in FIG. 16B.

On the first side of the PCB 416, the module 400 can be enclosed by a curved light transmissive cover 402 with a convex protrusion. As shown in FIG. 16C, the cover 402 can have a continuous curvature. The first and second light barriers 420, 422 are configured to be in contact with the first side of the PCB 416 at one end. At the other end, the height of the first and second light barriers 420, 422, and of the side wall 424 can generally follow the curvature of the cover 402. The side wall 424 can be shorter than the second light barrier 422. The height of the second light barrier 422 can increase from the perimeter of the module 400 toward a center of the module 400 until the second light barrier 422 merges with the first light barrier 420, which is the highest among the light barriers. The first and second light barriers 420, 422 can extend to the tissue-facing surface of the cover 402 so that when the module 400 is pressed into the skin of the wearer of a device incorporating the module 400, the tissue-facing surfaces of the first and second light barriers 420, 422, and of the side wall 424 can be configured to contact the skin of the wearer. The cover 402 can include individual lenses or covers such as shown in FIG. 7D or a combination of individual emitter chamber covering lenses or covers and a lens or cover covering a plurality of detector chambers, such as shown in FIG. 7C. The tissue-facing surface of the module 400 can include a continuous convex curvature.

The first and second light barriers 420, 422 and the side wall 424 can optionally form a single light barrier construct. The single light barrier construct can be formed by any suitable manufacturing techniques and any suitable materials, for example, plastic, colored, or opaque sapphire glass, or others. The single light barrier construct can include at one end a recess that is shaped and sized to receive the PCB 416, including the electronics on the PCB 416. The first side of the PCB 416 can include the emitters 404A,404B, detectors 406*a*, 406*b*, 406*a/b*, temperature sensor 410, and any other sensors, for example, the gyroscope, the accelerometer, and/or the like. The second side of the PCB 416 can include the sensor or module processor and other circuit hardware.

As described above, the module 400 can include a plurality of chambers such that light cannot travel between the chambers because of the various light barriers extending from the PCB 416 to the tissue-facing surface of the cover 402 as described herein. The light diffusing materials described above can be added above (for example, via the fill holes described herein) and around the emitters 404A, 404B, and/or optionally above and around the detectors 406*a*, 406*b*, 406*a/b*, to improve distribution of emitted lighted and/or detected light after attenuation by the tissue. The light diffusing materials can include a flow of glass microsphere solution, which can be injected into the chambers after the module 400 has been assembled. After being injected into the respective chamber, the solution can be UV-cured. Air can escape via the vent openings disclosed herein as the diffusing material solution is injected into the respective chambers via the injection openings, making it easier for the glass microsphere solution to flow into the respective chamber. The cover 402 can also include glass microspheres. The light diffusing materials in the cover 402 and inside the emitter chambers and/or the first light barrier 420 can make the emitted light leave the emitter chambers enclosing the emitters 404A,404B in a direction generally parallel to the height of the first light barrier 420. The light diffusing materials in the cover 402 and the detector chambers can increase the amount of reflected light being directed to and detected by the detectors 406*a*, 406*b*, 406*a/b*.

Figure 16G:
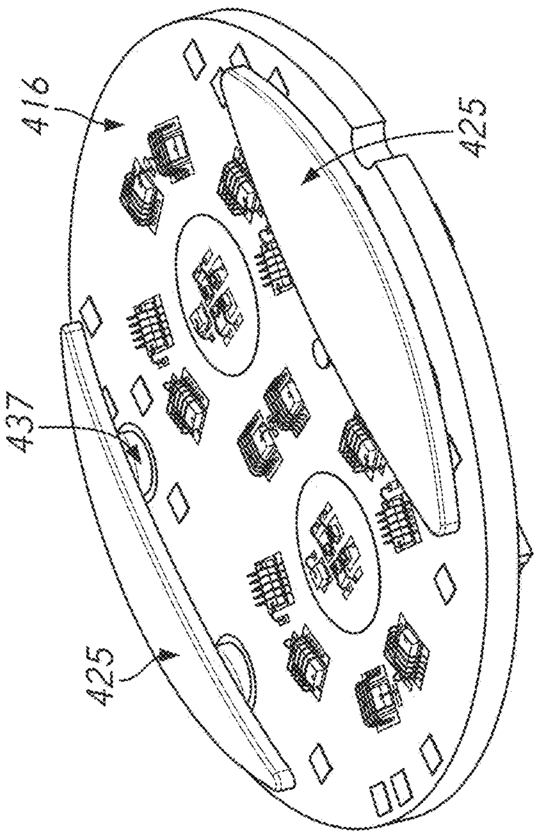
FIG. 16G illustrates a bottom perspective view of the example physiological parameter measurement module of FIG. 16E with the opaque frame and light transmissive cover hidden to show ECG electrodes assembled with the sensor or module processor board.
Figure 16E:
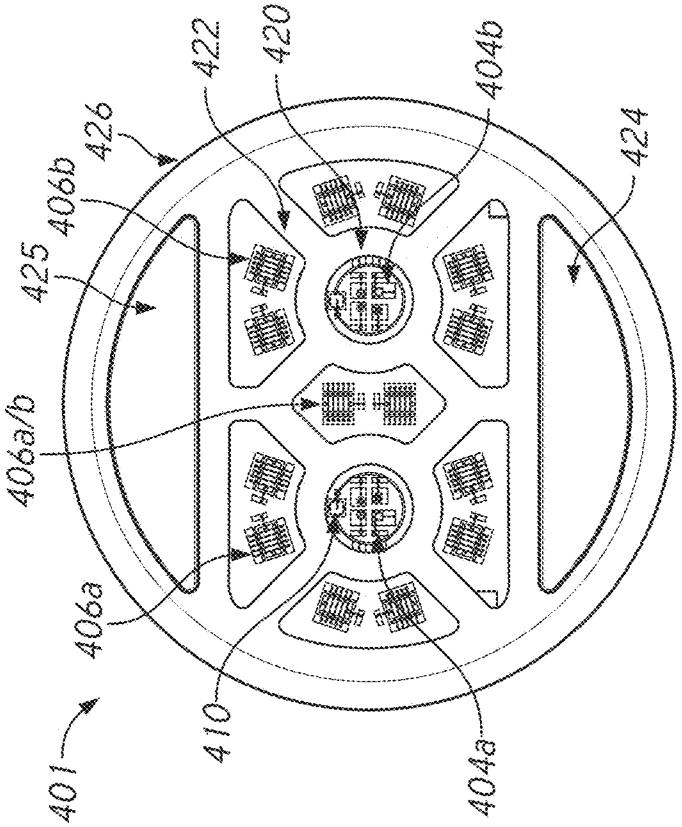
FIG. 16E illustrates a bottom view of a variation of the example physiological parameter measurement module of FIG. 16B including ECG electrodes.
Figure 16F:
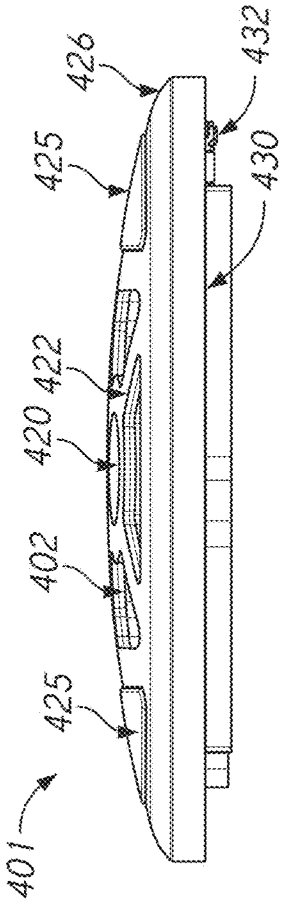
FIG. 16F illustrates a side view of the example physiological parameter measurement module of FIG. 16E.

FIGS. 16E-16G illustrate an example physiological parameter measurement modules 401 of a wearable device. The module 401 can include the same optical sensor arrangements as shown in FIGS. 16A-16D and have any of the features of the module 400 in FIGS. 16B-16D with the differences noted in the description of FIGS. 16E-16G. The module 401 can have any of the features of the other physiological parameter measurement module examples described herein.

The module 401 can include a generally circular outer shape. The generally circular outer shape can be defined by an opaque frame 426 extending over of the PCB 416 from a first side of the PCB 416. The opaque frame 426 can have a height such that a top side of the opaque frame 426 can be generally level with (or receding or protruding slightly from) a second side of the PCB 416. As shown in FIG. 16G, the PCB 416 can be generally circular in shape. The opaque frame 426 can be generally concentric with the PCB 416. The opaque frame 426 and the PCB 416 are not transmissive to light. The opaque frame 426 in FIGS. 16E and 16F can include the first light barrier 420 and second light barriers 422 as an integral piece.

The module 401 can include one or more (for example, two or otherwise) ECG electrodes 425. In the illustrated examples of FIGS. 16E-16G, one of the ECG electrodes 425 can be a reference electrode and the other one of the ECG electrode 425 can be a negative or positive electrode. The opaque frame 426 can have indentations having the shape and size to accommodate the electrodes 425, similar to the indentations on the opaque frame 126 shown in FIG. 7D. As shown in FIG. 16F, a bottom surface of the electrodes 425 can have a curvature that is generally continuous with the curvature of the opaque frame 426 and the light-transmissive cover 402. As shown in FIG. 16G, a top side of the electrodes 425 can have one or more posts 437 extending past openings in the opaque frame 426 into corresponding openings on the PCB 416. The posts 437 of the electrodes 425 can establish an electrical connection with the corresponding openings of the PCB 416. A plurality of screws (or other types of fasteners) can extend into the corresponding openings of the PCB 416 from the front side of the PCB 416 to secure the electrodes 425 to the module 401 by threadedly mating with the posts. When a wearer puts the wearable device incorporating the module 401 onto the wearer's wrist, the electrodes 425 can make contact with the wearer's skin. The electrodes 425 can have the same polarity as the electrodes 124 disclosed herein. As disclosed herein, the wearable device incorporating the module 401 can include another ECG electrode 125 located on the housing of the wearable device configured to make contact with the wearer's skin.

On the second side of the PCB 416, which faces away from the cover 402, the PCB 416 can be covered by melt plastic or other suitable electronics protective material 430 (similar to the protective material 130 disclosed herein) except that a flex connector 432 can remain exposed. The flex connector 432 can be configured to connect the module 401 electrically to the wearable device incorporating the module 401.

FIGS. 17A-17C illustrate an example physiological parameter measurement modules 403 of a wearable device. The module 403 can include the same optical sensor arrangements as shown in FIGS. 16A-16G and have any of the features of the module 400 in FIGS. 16B-16D and any of the features of the module 401 in FIGS. 16E-16G with the differences noted in the description of FIGS. 17A-17C. The module 401 can have any of the features of the other physiological parameter measurement module examples described herein.

As shown in FIGS. 17A-17C, the opaque frame 426 can include an opening fitted with the light transmissive cover 402. The cover 402 extending over emitter chambers or detector chambers formed by the light barriers 420, 422, 423 and the PCB 415 can include a single lens or cover. The cover 402 can be elliptical in shape. The cover 402 can have a continuous convex curvature. As shown in FIG. 17C, the light barriers 420, 422, 423 may not extend to the tissue-facing surface of the cover 402 and can extend to below the cover 402 such that when a wearer puts on a wearable device incorporating the module 400, the wearer's tissue comes into contact with the cover 402 and the electrodes 425, but not with any of the light barriers 420, 422, 423.

FIGS. 18A-19C illustrate other non-limiting examples of a physiological parameter measurement module with two emitter groups in two separate emitter chambers formed by a light barrier. In those configurations, the perimeter of the module can have a different shape. For example, FIG. 19A illustrates schematically a module 300 having an outer shape of two circles partially overlapped with each other. The circle in the module 300 can have a radius, for example, between about 6 mm and about 12 mm, or between about 8 mm and about 10 mm. The module 300 can have any of the features of the other modules disclosed herein. The module 300 can include the substantially the same arrangement of emitters 300*a*, 300*b* and detectors 306*a*, 306*b*, 306*a/b* as the module 400, 401, 403 described above except that each emitter group 304*a*, 304*b* includes three emitters. The module 300 can include a thermistor near each emitter group 304*a*, 304*b*. The module 300 can have a length of, for example, between about 22 mm and about 28 mm, or between about 24 mm and about 26 mm.

Figure 18B:
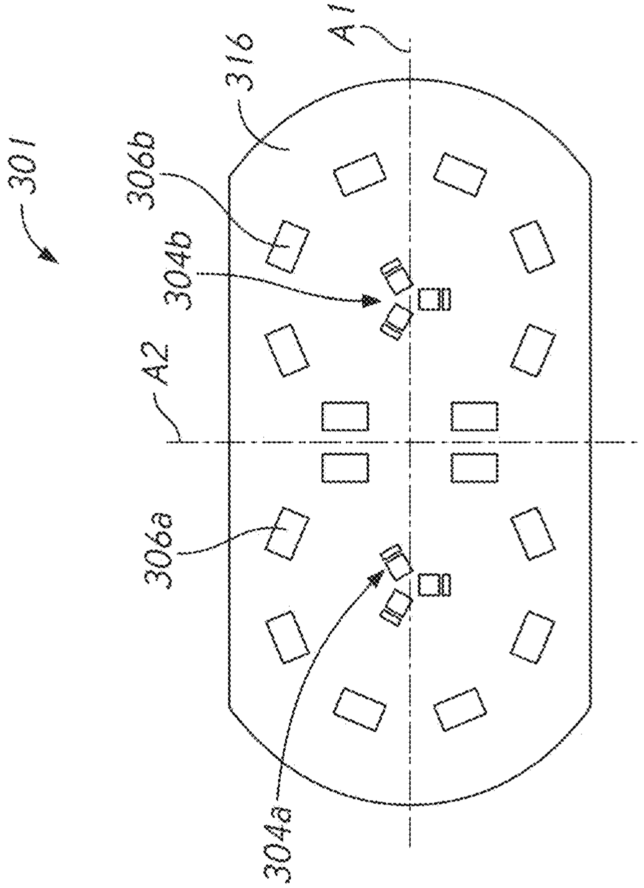
FIG. 18B illustrate schematically an example plethysmograph sensor arrangement on a sensor or module processor board of a physiological parameter measurement module of a wearable device.
Figure 18A:
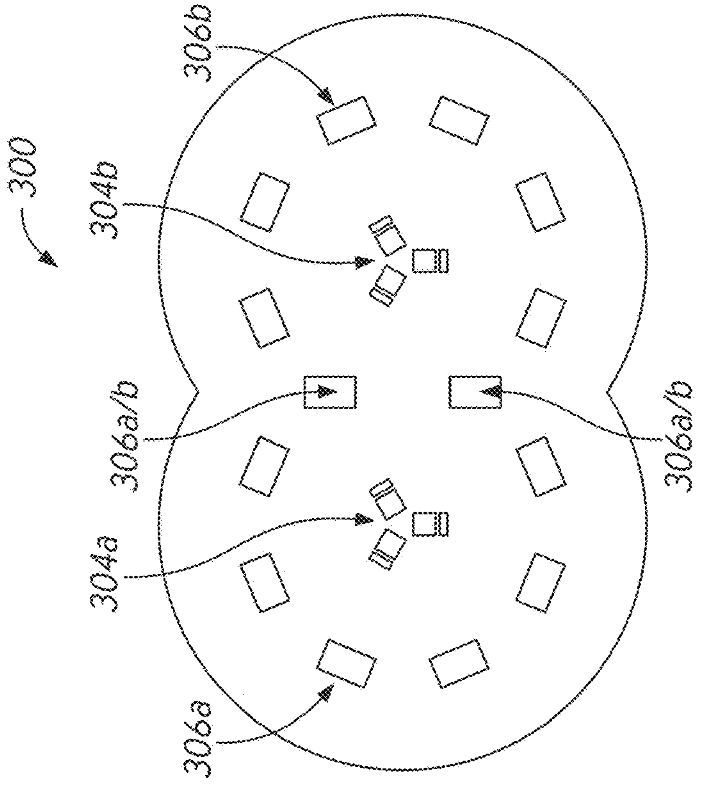
FIG. 18A illustrates schematically an example plethysmograph sensor arrangement on a sensor or module processor board of a physiological parameter measurement module of a wearable device.

FIG. 18B illustrates a physiological parameter measurement module 301 including a variation of the arrangement of emitters and detectors of the module 300 in FIG. 18A, and can include any of the features of the module 300 except for the differences described herein. The module 301 differs from the module 300 by not sharing detectors located between the two groups of emitters 304*a*, 304*b*. The first group of emitters 304*a* can be surrounded by a first ring of detectors 306*a* on a first side of the minor axis A2 and the second group of emitters 304*b* can be surrounded by a second ring of detectors 306*b* that are on a second side of the minor axis A2.

Figure 19A:
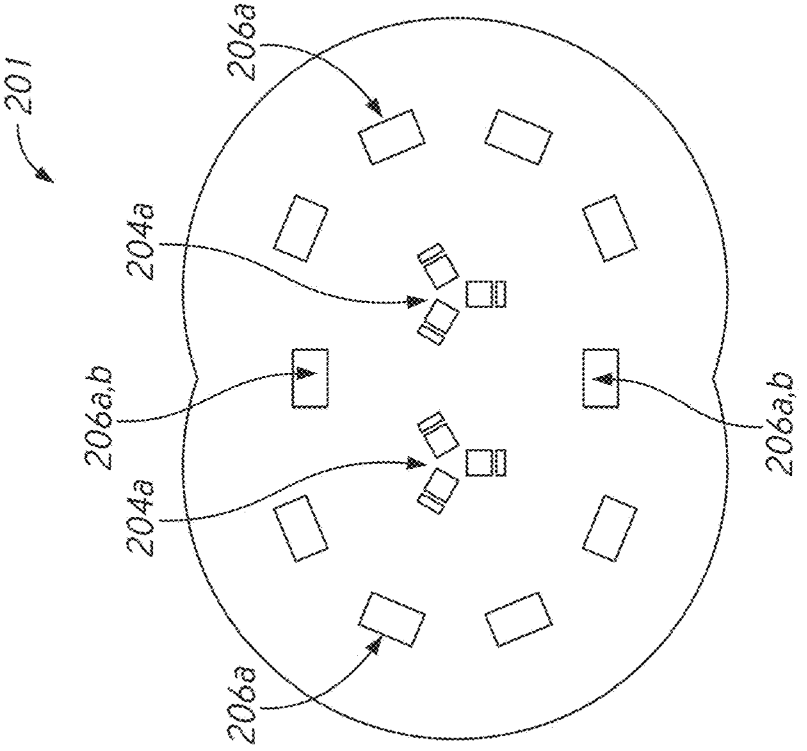
FIG. 19A illustrate schematically an example plethysmograph sensor arrangement on a sensor or module processor board of a physiological parameter measurement module of a wearable device.

FIG. 19A illustrates a physiological parameter measurement module 201 including a variation of the arrangement of emitters and detectors of the module 300 in FIG. 18A. The physiological parameter measurement module 201 can have any of the features of the modules 300, with the differences noted in the description of FIG. 19A. The module 201 can have any of the features of the other modules disclosed herein. In the module 201, the two overlapping circles of detectors 206*a*, 206*b* are closer to each other than in the module 300. The detectors 206*a/b* can be further away from each other than in the module 300 and may not be located between or separating the two emitter groups 204*a*, 204*b*. The module 201 can include two groups of emitters that are separated from each other by one light barrier. Each of the detectors in the module 201 can form its own detector chamber with one or more light barriers. The circle can have a radius, for example, between about 6 mm and about 12 mm, or between about 8 mm and about 10 mm. The module 300 can have a length of, for example, between about 18 mm and about 24 mm, or between about 20 mm and about 22 mm.

Figure 19B:
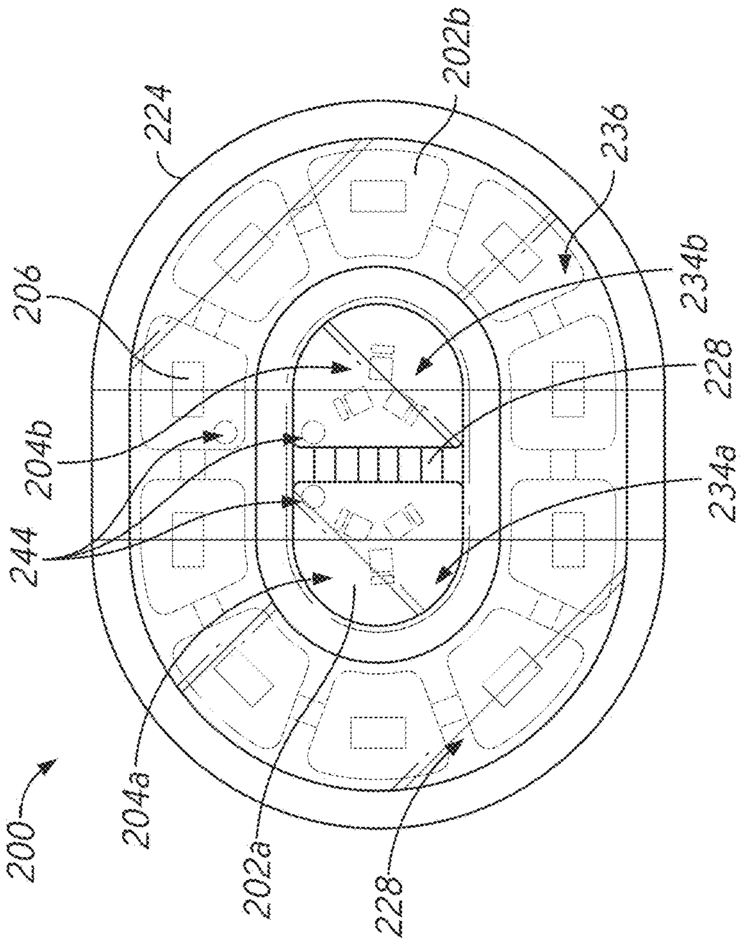
FIG. 19B illustrates a bottom view of an example physiological parameter measurement module incorporating the plethysmograph sensor arrangement of FIG. 19A.
Figure 19C:
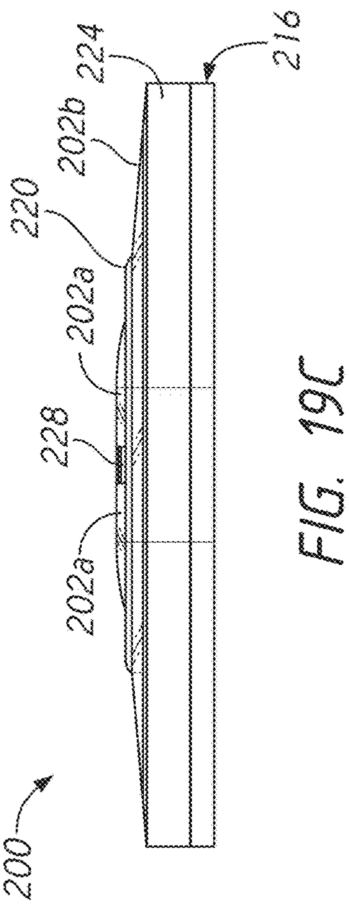
FIG. 19C illustrates a side view of the physiological parameter measurement module of FIG. 19B.

FIGS. 19B and 19C illustrate a variation of the module 201 in FIG. 19A with the differences noted in the description of FIGS. 19B and 19C. The module 200 in FIGS. 19B and 19C can have any of the features of the module examples described herein. In FIGS. 19B and 19C, a physiological parameter measurement module 200 can include two groups of emitters 204*a*, 204*b* surrounded by one ring of detectors 206. The module 200 can have a width, for example, between about 16 mm and about 22 mm, or between about 18 mm and about 20 mm. The module 200 can have a length, for example, between about 20 mm and about 28 mm, or between about 22 mm and about 25 mm.

Each group of the emitters 204*a*, 204*b* can include three of emitters. Each group of the emitters 204*a*, 204*b* can emit at least the first, second, and third wavelength described above. Optionally, each emitter group 204*a*, 204*b* can include a fourth emitter configured to emit the fourth wavelength that is more sensitive to water. The emitters can be located at or near a center portion of a PCB 216 of the module 200. The module 200 can include a temperature sensor located on the PCB 216 near each group of the emitters 204*a*, 204*b*.

The emitters can be covered by an inner lens or cover 202*a*. In the illustrated example, the inner lens or cover 202*a* can be generally elliptical. In other examples, the inner lens or cover may have any other shapes. The two groups of the emitters 204*a*, 204*b* can be located on two parts of the central portion of the PCB divided along the minor diameter of the ellipse. The two groups of the emitters 204*a*, 204*b* can be divided by an opaque divider barrier 228, which can reduce mixing of light emitted by the two groups of the emitters 204*a*, 204*b*. As shown in FIG. 19C, the opaque divider barrier 228 can have a same or substantially the same height as the highest point of the inner lens or cover 202*a* when assembled in the module 200. The inner lens or cover 202*a* can include two components divided by the opaque divider barrier 228.

The module 200 can include a plurality of detectors 206 (for example, about six, eight, ten, or more) that can be arranged on the PCB so that the detectors 206 are spaced apart around the emitters 204*a*, 204*b*. The emitters groups 204*a*, 204*b* and the detectors 206 can be separated by a first light barrier 220. The first light barrier 220 can extend along and surround the inner lens or cover 202*a*. The opaque divider barrier 228 and the first light barrier 220 can form two emitter chambers 234*a*, 234*b*, each enclosing one of the two emitter groups 204*a*, 204*b*. The first light barrier 220 and the opaque divider barrier 228 can also suppress light emitted by the emitters 204*a*, 204*b* at an angle so the light emitted by each group of emitters 204*a*, 204*b* can exit the inner lens or cover 202*a* in a direction generally parallel to the height of the first light barrier 220. The detectors 206 can be enclosed within a module side wall 224. The module side wall 224 can define a perimeter of the module 200. As shown in FIG. 19B, the perimeter of the module 200 can have a generally elliptical outer shape. The detectors 206 can be further separated from one another by a plurality of divider barriers 226, forming detector chambers 236, each containing one detector 206.

As shown in FIG. 19C, the first light barrier 220 can protrude slightly from, that is, proud of the edge of the inner lens or cover 202*a* and the other lenses or covers that will be described below. The detectors 206 can be covered by an outer lens or cover 202*b*. The outer lens or cover 202*b* can be generally concentric with the inner lens or cover 202*a*. In the illustrated examples, the outer lens or cover 202*b* can be an elliptical disc as shown in FIG. 19B. In other examples such as those disclosed herein, the outer lens or cover can have other shapes. As shown in FIG. 19C, the outer lens or cover 202*b* can have a smaller curvature than the inner lens or cover 202*a* such that the inner lens or cover 202*a* protrudes more than if the inner lens or cover had the same curvature as the outer lens or cover 202*b*.

As shown in FIG. 19C, the side wall 224 can be shorter than the first light barrier 220. The height of the side wall 224 can be configured such that the tissue-facing end of the side wall 224 is generally continuous with the curvature of outer lenses or covers 202*b*. The divider barriers 226 can have a height lower than the first light barrier 220. The height of the divider barriers 226 can be configured to accommodate the outer lens or cover 202*b* such that when assembled, the outer lens or cover 202*b* forms a substantially smooth surface with the module side wall 224. The tissue-facing ends of the first light barrier 220 and the side wall 224, and the tissue-facing surfaces of the inner lens or cover 202*a* and the outer lens or cover 202*b* can form the tissue-facing surface of the module 200. The slightly protruding first light barrier 220 and/or inner lens or cover 202*a* can be pressed into the wearer's skin at a higher pressure than the remainder of the lens or cover or light barriers.

The light diffusing materials described above can be included in one or more of the chambers 234*a*, 234*b*, 236 of the module 200 to improve distribution of emitted lighted and/or detected light. As shown in FIG. 19B, one or more of the lenses or covers 202*a*, 202*b* can include an injection opening 244 so that the light diffusing materials, which can include a flow of glass microsphere solution, can be injected into the respective chambers 234*a*, 234*b*, 236 after the module 200 has been assembled. After the injection, the solution can be UV-cured. The lenses or covers 202*a*, 202*b* can include one or more venting openings that are smaller than the injection openings 244. Air can optionally escape via separate vent openings as the diffusing material solution is injected into the respective chambers 234*a*, 234*b*, 236 via the injection openings 244. The inner lens or cover 202*a* and the outer lens or cover 202*b* can also include glass microspheres so as to act as light diffusers.

Figure 20A:
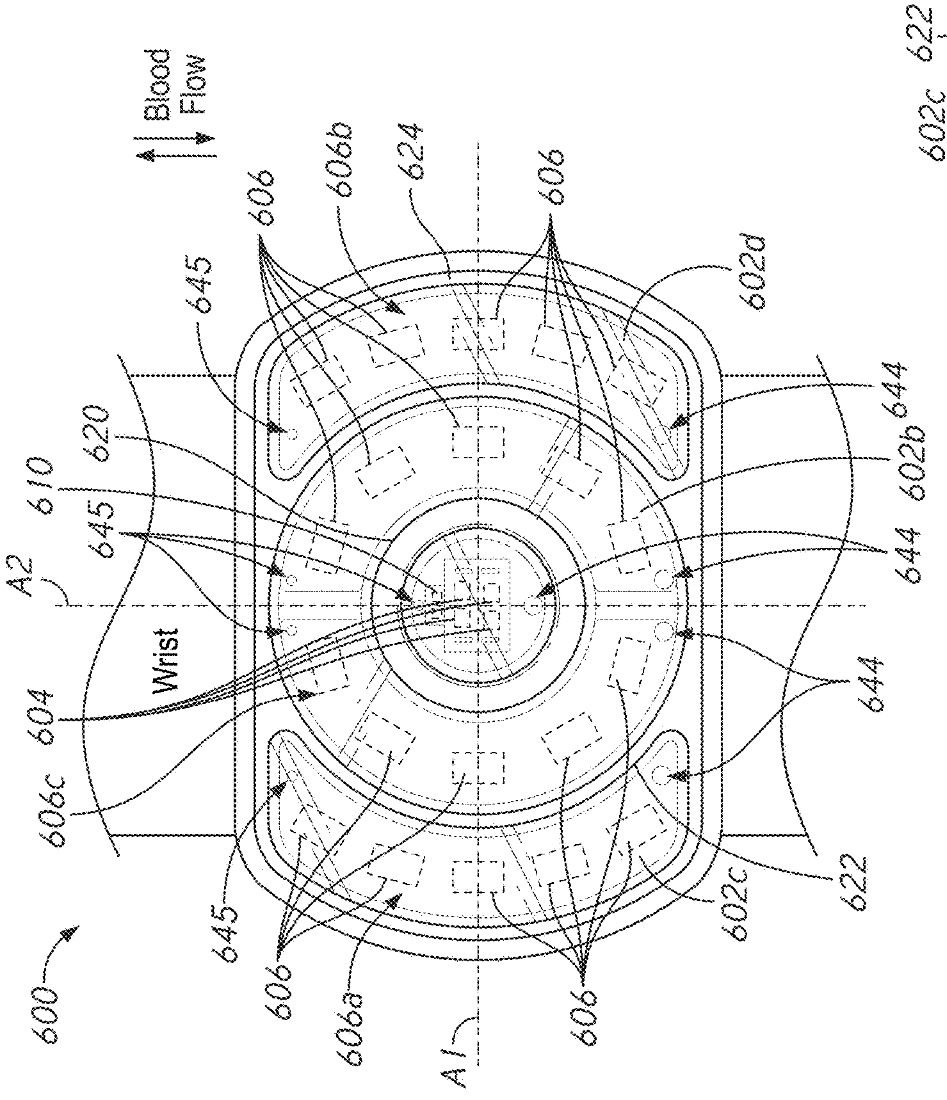
FIG. 20A illustrates a bottom view of an example physiological parameter measurement module of a wearable device as worn on a schematic representation of a wearer's wrist.

Examples of Physiological Parameter Measurement Modules with Inner and Outer Detector Groups and Examples of Wearable Devices Incorporating the Same FIGS. 20A-20D illustrate an example physiological parameter measurement module 600 of a wearable device. The module 600 can have any of the features of the module examples described herein, with the differences noted in the description of FIGS. 20A-20D. The physiological parameter measurement module 600 can include a single emitter group having a plurality of emitters 604, such as four emitters as shown in FIG. 20A, six emitters, or eight emitters. The emitters 604 of the module 600 can emit at least the first, second, third, and fourth wavelengths as described above. The emitters 604 can be located at or near a center portion of a PCB 616 of the module 600. The module 600 can include a temperature sensor 610 located on the PCB 616 near the emitters 604.

The module 600 can include a plurality of detectors 606 that can be arranged on the PCB 616 as an inner group of detectors 606 and an outer group of detectors 606. The inner group 606*c* of detectors 606, which can include, for example, about ten (or a different number of) detectors 606, can surround the emitters 604 and be spaced apart from one another.

The outer group of detectors 606 can be located further away from the emitters 604 than the inner group of detectors 606. The outer group of detectors 606 can be separated into a first outer group 606*a* and a second outer group 606*b* of detectors 606. As shown in FIG. 20A, the module 600 can have a first axis A1 and a second axis A2. The outer groups 606*a*, 606*b* of detectors 606 can be located further away from the emitters 604 than the inner group of detectors 606 generally along the first axis A1. The two outer groups 606*a*, 606*b* of detectors 606 are on opposite sides of the inner group of detectors along the first axis A1. The first and second outer groups 606*a*, 606*b* of detectors 606 can be generally symmetrical about the first axis A2 and the second axis A2. Each of the first or second outer groups 606*a*, 606*b* of detectors 606 can include about five (or a different number) of detectors 606 that are spaced apart from one another generally along the second axis A2. The outer groups 606*a*, 606*b* of detectors 606 can be arranged to be generally concentric with the inner group 606*c* of detectors 606.

The module 600 can be longer in the first axis A1 than in the second axis A2. The module 600 can have a dimension of about 25.4 mm (1 inch) along the first axis A1. The module can have a dimension of about 19.1 mm (0.75 inch) along the second axis A2. As shown in FIG. 20A, when a watch incorporating the module 600 is worn on the wrist of a wearer, the first axis A1 can be generally parallel to the width of the wrist and generally perpendicular to the direction of blood flow along the wrist (that is, along a direction between the hand and the forearm) and the second axis A2 can be generally perpendicular to the width of the wrist and generally parallel to the direction of blood flow along the wrist. The distribution of the detectors 606 along the first axis A1 can improve detection of the light attenuated by the pulsing arterial blood in the capillaries as the detectors 606 are arranged to cover a greater cross-section of the blood flow through the wrist. Similarly, in the other example modules described herein, such as the sensor or module 100, 400, 401, 403, 300, 301, 200, 201, the physiological parameter measurement module is incorporated in the wearable device such that the longer side of the module is generally perpendicular to the direction of the blood flow along the wrist (see, for example, FIG. 1B) when the wearable device is worn on the wrist.

Figure 20B:
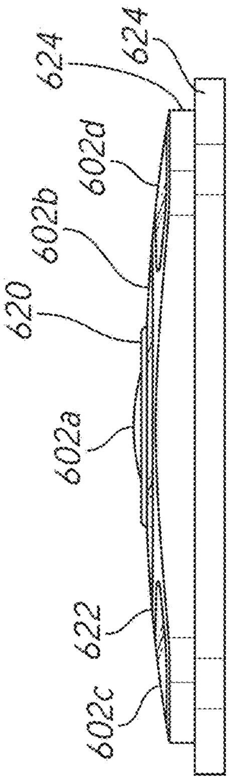
FIG. 20B illustrates a side view of the physiological parameter measurement module of FIG. 20A.

As shown in FIG. 20A, the emitters 604 can be covered by an inner lens or cover 602*a*. In the illustrated example, the inner lens or cover 602*a* can be generally circular. In other examples such as disclosed herein, the inner lens or cover may not be generally circular, but can have other shapes, for example, elliptical, rectangular, square, diamond, or otherwise. The inner group 606*c* of detectors 606 can be covered by a first outer lens or cover 602*b*. The first outer lens or cover 602*b* can be generally concentric with the inner lens or cover 602*a*. In the illustrated example, the first outer lens or cover 602*b* can be disc shaped. The first and second outer groups 606*a*, 606*b* of detectors 606 can be covered by a second outer lens or cover 602*c* and a third outer lens or cover 602*d* respectively. The second and third outer lenses or covers 602*c*, 602*d* can be symmetrical about the second axis A2. As shown in FIG. 20B, the first, second, and third outer lenses or covers 602*b*, 602*c*, 602*d* can have substantially the same curvature. The inner lens or cover 602*a* can be more curved than the outer lenses or covers 602*b*, 602*c*, 602*d* such that the inner lens or cover 602*a* protrudes more than if the inner lens or cover 602*a* had same curvature as the outer lenses or covers 602*b*, 602*c*, 602*d*.

The inner group 606*c* of detectors 606 and the emitters 604 can be separate by a first light barrier 620. The first light barrier 620 can extend along and surround the inner lens or cover 602*a*, forming an emitter chamber. The first and second outer groups 606*a*, 606*b* of detectors 606 can be separated from the inner group 606*c* of detectors 606 by a second light barrier 622. The second light barrier 622 can be shorter than the first light barrier 620. The first and second outer groups 606*a*, 606*b* of detectors 606 can be enclosed within a module side wall 624 enclosing a perimeter of the module 600. The perimeter of the module 600 can be elliptical or any other shape. The side wall 624 can be shorter than the second light barrier 622. The height of the first and second light barriers 620, 622, and of the side wall 624 can generally follow or be substantially continuous with the curvature of the first, second, and third outer lenses or covers 602*b*, 602*c*, 602*d*. The first and second light barriers 620, 622, and of the side wall 624 can have a height so as to be configured to contact the skin of the wearer. Accordingly, the tissue-facing surface of the module 600 can be defined by the tissue-facing side of the first and second light barriers 620, 622, and of the side wall 624 and tissue-facing surfaces of the inner lens or cover 602*a* and the first, second, and third outer lenses or covers 602*b*, 602*c*, 602*d*.

Figure 20C:
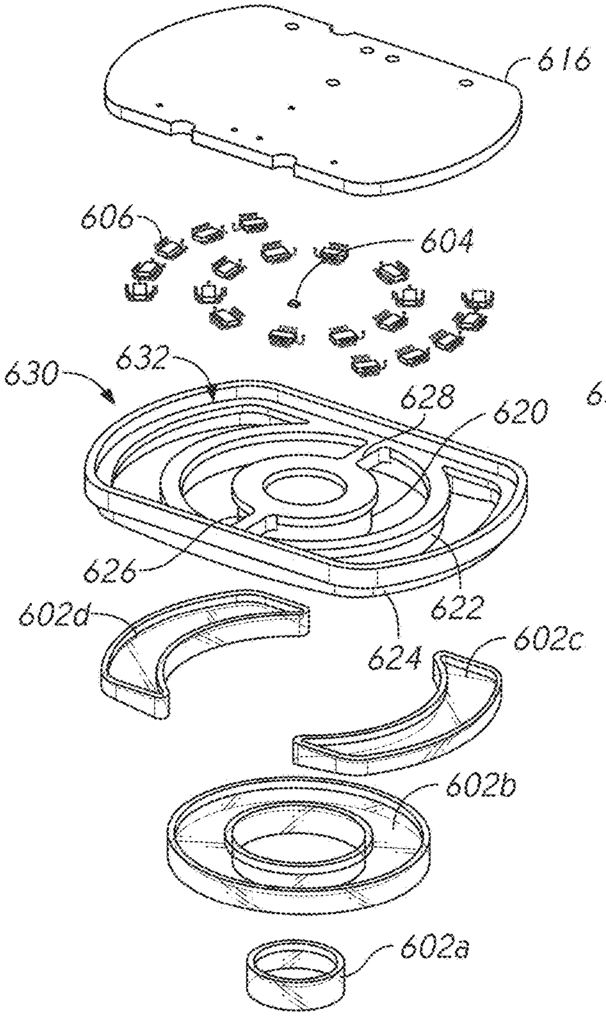
FIGS. 20C and 20D illustrate exploded views of the physiological parameter measurement module of FIG. 20A.
Figure 20D:
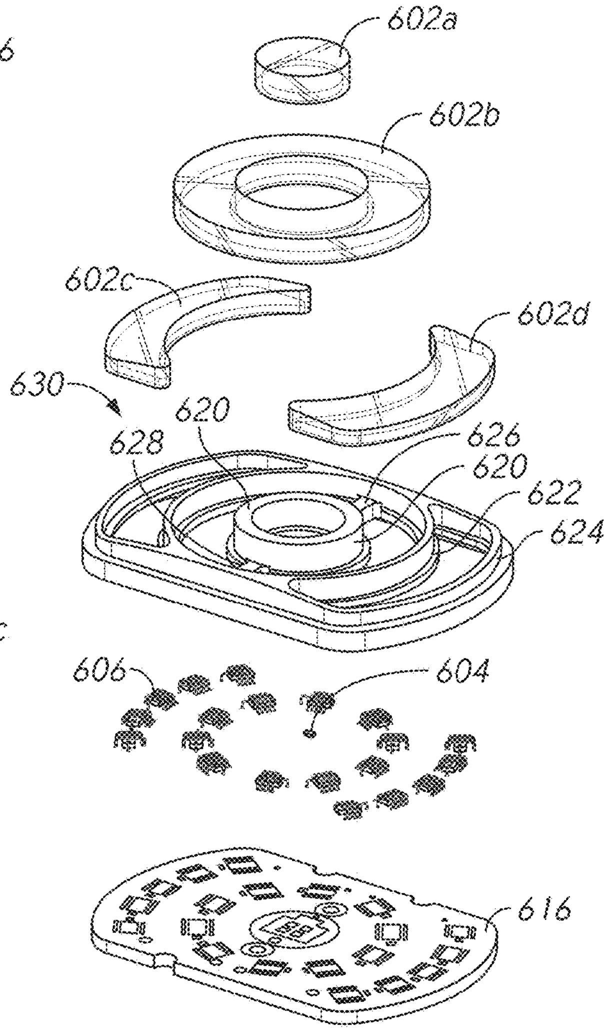
Figure 20G:
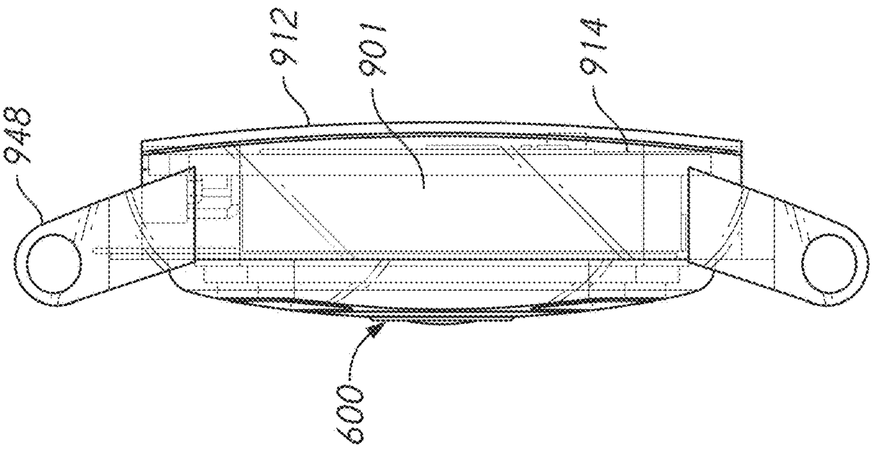
FIG. 20G illustrates a second side view of the wearable device of FIG. 20E.

In the illustrated example, the inner group 606*c* of detectors 606 can be separated by a third light barrier 626 and a fourth light barrier 628 (see FIGS. 20C and 20D). The third and fourth light barriers 626, 628 can have a height lower than the first light barrier 620 or the second light barrier 622. The height of the third and fourth light barriers 626, 628 can be configured to accommodate the first outer lens or cover 602*b* such that when assembled, the first outer lens or cover 602*b* forms a substantially smooth surface with the second and third outer lenses or covers 602*c*, 602*d*. The first outer lens or cover 602*b* can sit on top of the third and fourth light barriers 626, 628.

The first light barrier 620 can protrude slightly from, that is, sit proud of the edge of the inner lens or cover 602*a* and the outer lenses or covers 602*b*, 602*c*, 602*d*. The slightly protruding first light barrier 620 and/or inner lens or cover 602*a* can be pressed into the wearer's skin at a higher pressure than the remainder of the lenses or covers or light barriers. The first light barrier 620 can also reduce mixing of the emitted and reflected light and/or suppress light emitted by the emitters 604 at an angle so that the emitted light exits the inner lens or cover 602*a* generally in a direction parallel to the height of the first light barrier 620.

As shown in FIGS. 20C and 20D, the first, second, third, and fourth light barriers 620, 622, 626, 628 and the side wall 624 can optionally form a single light barrier construct 630. The single light barrier construct 630 can be formed by any suitable manufacturing techniques. The single light barrier construct 630 can include at one end a recess 632 (see FIG. 20C) that is configured to receive the PCB 616 (and the emitters 604, detectors 606, temperature sensor 610, and any other sensors, for example, the gyroscope, the accelerometer, and/or the like, and the sensor or module processor, which are located on the PCB 616). The single light barrier construct 630 can receive the lenses, including the inner lens or cover 602*a*, the first, second, and third outer lenses or covers 602*b*, 602*c*, 602*d* at another end that is opposite to the end including the recess 632.

The module housing can include a plurality of chambers such that light cannot travel between the chambers because of the various light barriers described herein. As described above, the first chamber can be enclosed by the inner lens or cover 602*a*, the first light battier 620, and a portion of the PCB 616. The first chamber 634 enclose the emitters 604. A second chamber and a third chamber can be enclosed by the first outer lens or cover 602*b*, the first light barrier 620, the second light barrier 622, the third light barrier 626, the fourth light barrier 628, and a portion of the PCB 616. The second and third chambers can enclose the inner group 606*c* of detectors 606, with half of the inner group 606*c* of detectors enclosed by each of the second and third chambers. A fourth chamber can be closed by the second outer lens or cover 602*c*, the second light barrier 622, the side wall 624, and part of the PCB 616. A fifth chamber can be enclosed by the third outer lens or cover 602*d*, the second light barrier 622, the side wall 624, and part of the PCB 616. The fourth and fifth chambers can enclose the first and second outer groups 606*a*, 606*b* of detectors 606 respectively.

Light from the emitters 604 can travel a shorter path to the inner group 606*c* of detectors 606 and a longer path to the first and second outer groups 606*a*, 606*b* of detectors 606. The inner group 606*c* of detectors 606 and the first and second outer groups 606*a*, 606*b* of detectors 606 can be run independently and/or simultaneously. Signals outputted by the inner and outer groups 606*a*, 606*b* of detectors 606 can provide different information due to the different light paths, which can travel through different areas of the tissue. The longer path penetrates deeper into the tissue and through a greater volume of the tissue to reach one of the outer groups 606*a*, 606*b* of detectors 606 than the short path, which penetrates less deep into the tissue and travels through a smaller volume of tissue to reach one of the inner group 606*c* of detectors 606. The different information can be separated and/or combined to calculate a plurality of physiological parameters of the wearer of the module 600, for example, an indication of the wearer's hydration status, which will be described in greater detail below.

The light diffusing materials described above can be included in one or more chambers of the module 600 to improve distribution of emitted lighted and/or detected light after attenuation by the tissue. As shown in FIG. 20A, one or more of the lenses or covers 602*a*, 602*b*, 602*c*, 602*d* can include an injection opening 644 so that the light diffusing materials, which can include a flow of glass microsphere solution, can be injected into the respective chambers after the module 600 has been assembled. After being injected into the respective chamber, the solution can be UV-cured. The lenses or covers 602*a*, 602*b*, 602*c*, 602*d* can include one or more venting openings 645 that are smaller than the injection openings 644. Each of the lenses or covers can include at least one venting opening 645. Air can escape via the vent openings 645 as the diffusing material solution is injected into the respective chambers via the injection openings 644, making it easier for the glass microsphere solution to flow into the respective chamber. The inner lens or cover 602*a* and/or the outer lenses or covers 602*b*, 602*c*, 602*d* can also include glass microspheres. The light diffusing materials in the inner lens or cover 602*a* and the UV-cured material in the first chamber 634 and/or the first light barrier 620 can make the emitted light leave the first chamber 634 in a direction generally parallel to the height of the first light barrier 620. The light diffusing materials in the outer lenses or covers 602*b*, 602*c*, 602*d* and the UV-cured material in the other chambers 636, 638, 640, 642 can increase the amount of reflected light being directed to the detectors 606.

Figure 20F:
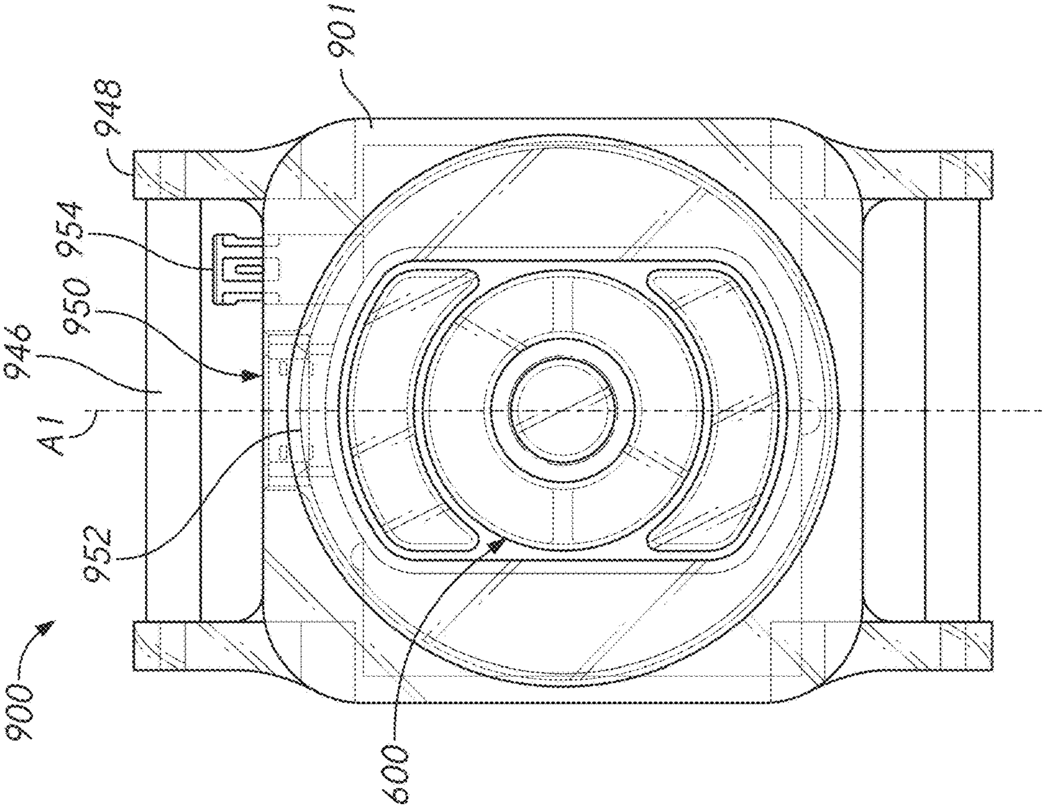
FIG. 20F illustrates a bottom view of the wearable device of FIG. 20E.
Figure 20E:
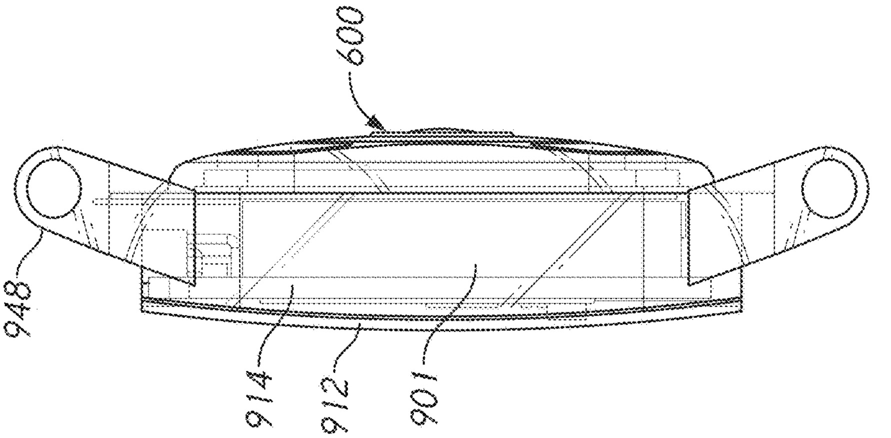
FIG. 20E illustrates a first side view of an example wearable device incorporating the physiological parameter measurement module of FIGS. 20A-20D.
Figure 20J:
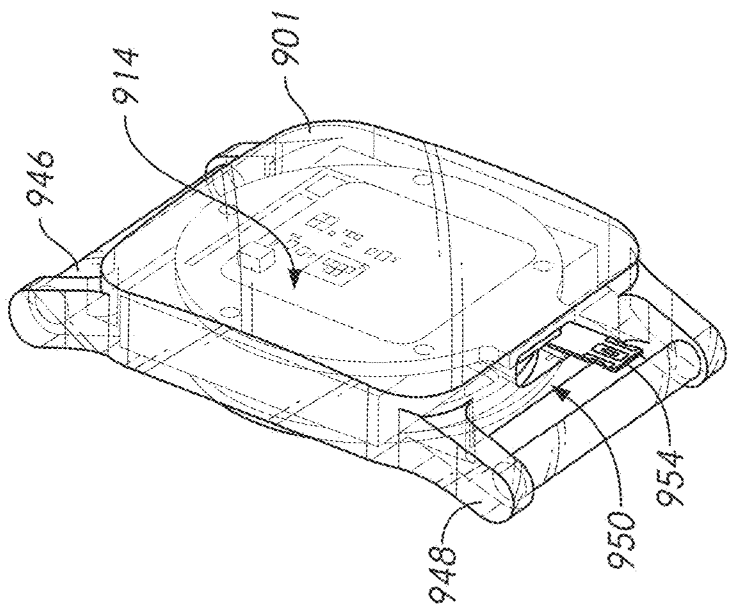
FIG. 20J illustrates a top perspective view of the wearable device of FIG. 20E.
Figure 20H:
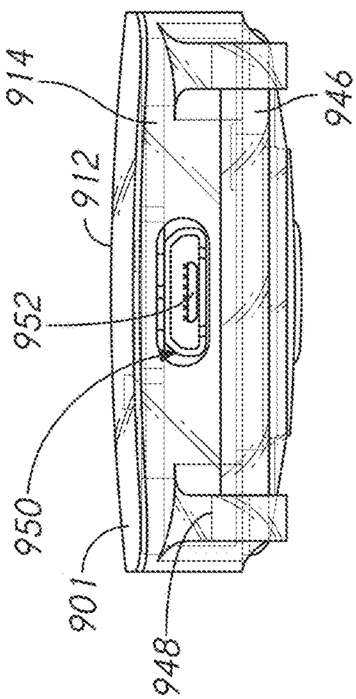
FIG. 20H illustrates a third side view of the wearable device of FIG. 20E.
Figure 20I:
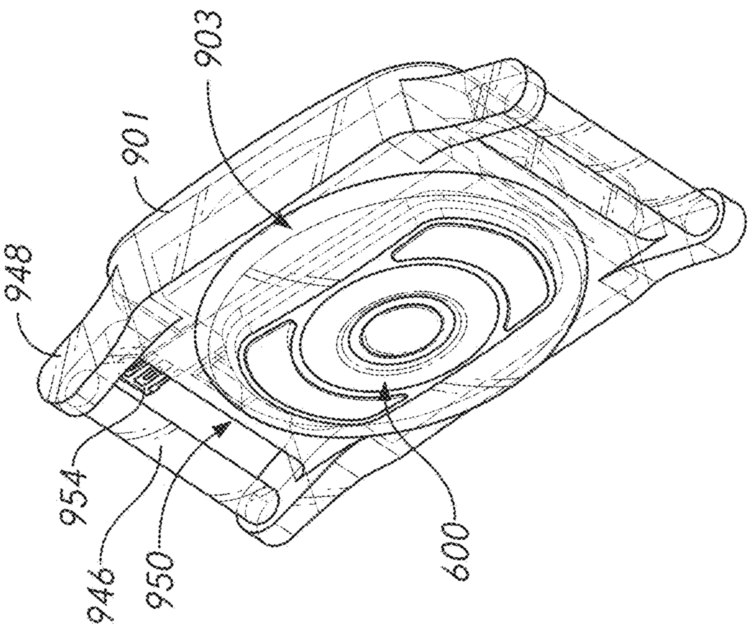
FIG. 20I illustrates a bottom perspective view of the wearable device of FIG. 20E.
Figure 22A:
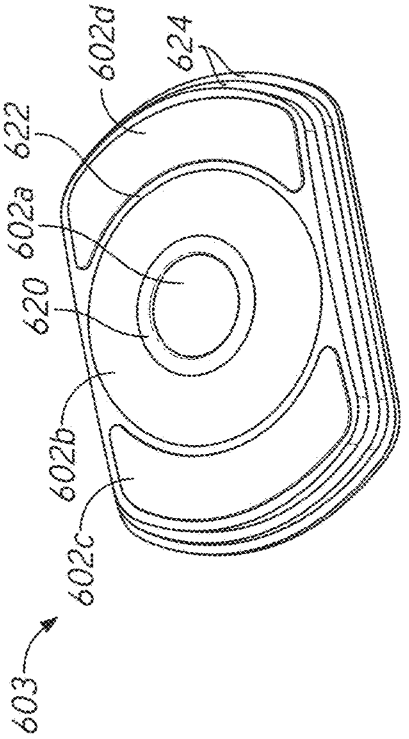
FIGS. 22A and 22B illustrate perspective views of an example physiological parameter measurement module with another alternative light transmissive cover curvatures from the module in FIG. 20A.
Figure 22B:
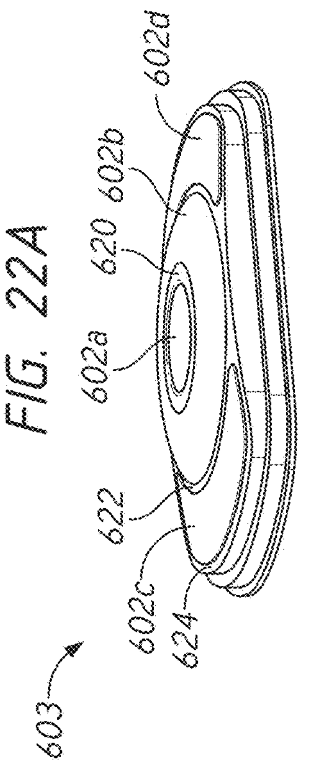
Figure 22C:
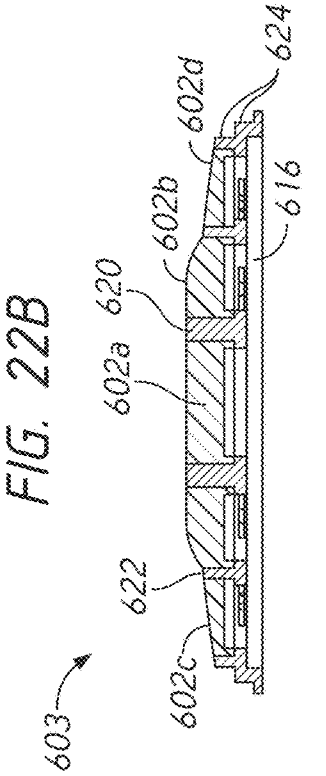
FIG. 22C illustrates a longitudinal cross-sectional view of the physiological parameter measurement module of FIGS. 22A and 22B.

The module 600 shown in FIGS. 20A-20D can be incorporated in a wearable device disclosed herein, such as a watch 900 shown in FIGS. 20E-20J. The watch processor 914 and power source can be enclosed within the watch housing 901. The watch housing 901 can include a connection port opening 950 configured to allow access to a connection port 952 that is in electrical communication with the watch processor 914 and/or the power source. The connection port opening 950 can be located at one end of the watch housing 901 transverse to the first axis A1 of the module 600. The connection port 952 can allow for charging of the power source and/or data transfer to and from the watch processor 914. Optionally, as shown in FIGS. 20F and 20I, the watch 900 can include a cable connector 945 extending outward from the watch housing 901. The cable connector 945 can be located adjacent to or near the connection port opening 950.

The watch 900 can include a display screen 912 positioned at a first side of the watch housing 901. The watch housing 901 has a second side that is opposite the first side. The second side of the watch housing 901 can include an opening sized to retain the physiological parameter measurement module 600 while still allowing the tissue-facing surface of the module 600 to be exposed. The second side of the watch housing 901 can be removably attached to the first side of the watch housing 901 without using external fasteners or alternatively via one or more fasteners. An electrical connection can be established between the physiological parameter measurement module PCB and the watch circuit, for example, using a flex connector as disclosed herein.

The watch housing 901 can include strap coupling extensions 948 on opposing sides of the watch 900 along the length of the watch housing 901 (that is, along the first axis A1 of the module 600). The strap coupling extensions 948 can include a bar 946 for coupling to any suitable watch straps.

Figure 21A:
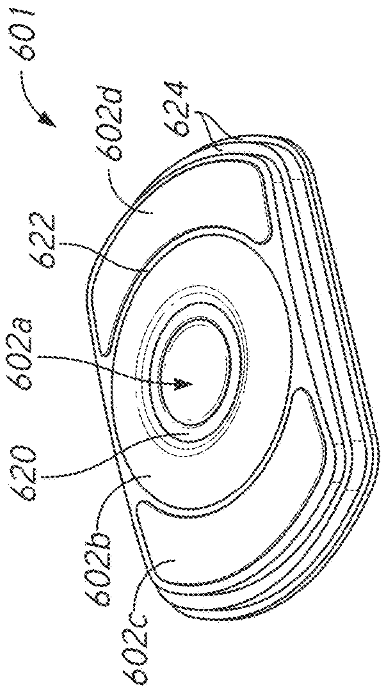
FIGS. 21A and 21B illustrate perspective views of an example physiological parameter measurement module with alternative light transmissive cover curvatures from the module in FIG. 20A.
Figure 21B:
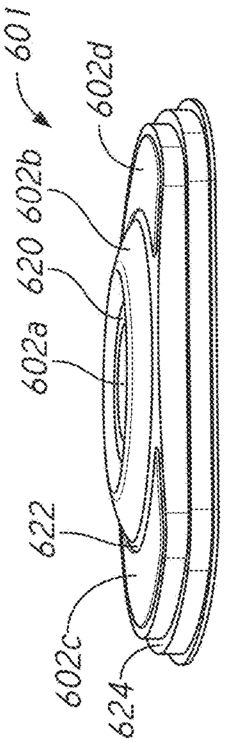
Figure 21C:
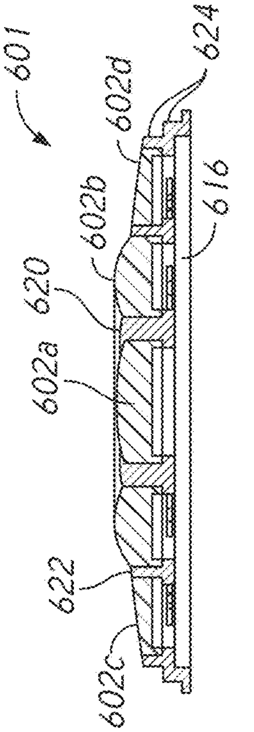
FIG. 21C illustrates a longitudinal cross-sectional view of the physiological parameter measurement module of FIGS. 21A and 21B.

FIGS. 21A-21C and 22A-22C illustrate alternative lens or cover curvatures of the physiological parameter measurement module 600 of FIGS. 20A-20D and can incorporate any of the features of the module 600 of FIGS. 20A-20D except the differences described below. As shown in FIGS. 21A-21C, the first outer lens or cover 602*b* of the module 601 can be more convex (that is, protrude more) than the inner lens or cover 602*a* the second and third outer lenses or covers 602*c*, 602*d*. The curvatures of the tissue-facing side of the second light barrier 622 and of the side wall 624 can be substantially continuous with the curvature of the second and third outer lenses or covers 602*c*, 602*d*. The second light barrier 622 can be shorter than the first light barrier 620. The first light barrier 620 can be higher than an outer edge of the inner lens or cover 602*a*, which can facilitate separation of light emitted by the emitters 604 and light being detected by the detectors 606 before the light is attenuated by the wearer's body tissue. In the FIGS. 22A-22C, the module 603 can be different from the module 601 in FIGS. 21A-21C in that the inner lens or cover 602*a* can have the same height as the first light barrier 620 and the first outer lens or cover 602*b*. The inner lens or cover 602*a* can have a generally flat surface or a slight curvature that can be substantially continuous from the curvature of the first outer lens or cover 602*b*. The module 601, 603 in FIGS. 21A-22C can facilitate pressing the first outer lens or cover 602*b* or the first outer lens or cover 602*b* and the inner lens or cover 602*a* into the skin of the wearer more than the remainder of the tissue-facing surface of the module 600.

FIGS. 23A-23E illustrate a watch 700 that can incorporate the physiological parameter measurement module 600. The watch 700 can have any of the features of the watch 900 with the differences noted in the description of FIGS. 23A-23E. As shown in FIGS. 23A-23E, the watch housing 701 of the watch 700 can include a flap 750 on a side of the housing 701 along a length of the watch housing 701, which is along the first axis A1 of the physiological parameter measurement module (see FIG. 23E). The flap 750 can be opened to give access to a connection port (such as the connection port in the watch 900) in electrical communication with the watch processor 714 and/or the power source 716. The connection port can allow for charging of the power source 716 and/or data transfer to and from the watch processor 714. The flap 750 can be closed when the connection port 752 is not in use.

The watch 700 can include a display screen positioned at a first side of the watch housing 701. The watch housing 701 has a second side that is opposite the first side. The second side of the watch housing 701 can include an opening sized to retain the physiological parameter measurement module 600 while still allowing the tissue-facing surface of the module 600 to be exposed. The second side of the watch housing 701 can be removably attached to the first side of the watch housing 701 via one or more screws 718 or other fasteners. When fully assembled, the watch 700 can have a thickness or height, for example, between 10 mm to about 15 mm, or between 12 mm to about 14 mm.

The watch housing 701 can include suitable strap connections configured to couple to watch strap(s). The strap connections in the watch housing 701 can be different from the strap connections shown in the watch 900. In an example, a plurality of strap openings can be at opposite ends of the watch and the watch housing can additionally and/or alternatively include strap slots on the same opposite ends of the watch as the strap openings. In this example, the strap slots can be configured to slidably receive ends of watch straps that include a shape corresponding to the shape of the strap slots. The strap openings can be configured to receive spring-biased buttons near the ends of the watch straps to releasably retain the straps after the ends of the watch straps are received into the strap slots. Alternatively, the watch may not include strap openings. The strap(s) coupled to the watch examples disclosed herein can be configured to allow adjusting of tightness around the wearer's wrist, for example, using a buckle connector, a Velcro connector, and/or the like.

Hydration Monitoring by Wearable Devices Incorporating Examples Physiological Parameter Measurement Modules with "Near" and "Far" Detectors or Detector Groups The physiological parameter measurement module examples disclosed herein can monitor a hydration status of the wearer. This is because water in the body tissue can allow a greater portion of the light of the third (or first or second) wavelength disclosed herein to go through (that is, acting as a light pipe), but can bulk absorb the light of the fourth wavelength disclosed herein. The physiological parameter measurement processor can compare intensity signals of the fourth wavelength and another wavelength that is less sensitive to changes in water from the same detector(s). When the wearer's hydration status is in a normal range such that the wearer is not considered dehydrated in a medical sense, the signals of the fourth wavelength and the other wavelength can show opposite trends, that is, one is increasing when the other one is decreasing. When the wearer becomes dehydrated in a medical sense, the opposite trends can become less distinct, for example, by falling below a threshold.

Hydration monitoring can be performed when the physiological parameter measurement module, such as the sensor or module 100, is configured such that at least some of the detectors 106 are located further away (far detector) from one of the emitters 104 (or emitter groups than the other detectors 106 (near detector), such as illustrated in FIG. 10. In configurations where there are two emitter groups, each detector 106 or detector region (which can include more than one detector 106 placed enclosed in the same detector chamber) can act as a near (or shallow) detector or detector region for the group of emitters that are closer to that detector 106 or detector region and as a far (or deeper) detector or detector region for the group of emitters that are further away from that detector 106 or detector region.

The physiological parameter measurement module 400, 401, 403 illustrates an example configuration for hydration monitoring of the wearer. The detectors **406*a* can be the far detectors for the second group of emitters 404B and the detectors 406*b*, 406*a/b* can be the near detectors for the second group of emitters 404B. The detectors 406*b* can be the far detectors for the first group of emitters 404A and the detectors 406*a*, 406*a/b* can be the near detectors for the first group of emitters 404A. The physiological parameter measurement modules 300, 301 illustrate similar detector arrangements in configurations (except that in the module 301, there are no shared detectors between the two groups of emitters 304*a*, 304*b*) where the modules 300, 301** include a fourth emitter in at least one of the emitter groups configured to emit light of the four wavelength.

The physiological parameter measurement modules 200, 201 illustrate additional example detectors configurations that can include "near" detectors for one emitter group and "far" detectors for another emitter group, in configurations where the modules 200, 201 include a fourth emitter configured to emit light of the fourth wavelength. For example, the detectors 206 on the far side of each group of emitters **204*a*, 204*b* can act as "far" detectors for detecting the light emitted by the respective group of emitters 204*a*, 204*b***, for example, light of the fourth wavelength and another wavelength, and attenuated by tissue to provide an indication of the wearer's hydration status.

The physiological parameter measurement module 600 illustrates an example configuration for hydration monitoring of the wearer, with the inner group **606*c* of detectors 606 acting as the "near" detectors and the outer groups 606*a*, 606*b*** of the detectors acting as the "far" detectors.

In the above-described configurations, each detector or detector region can provide two measurements calculated from the signals received from the closer emitter group and the signals from the further emitter group respectively. Signals detected at the far detectors can provide indication of the hydration status of the wearer as light travels through a deeper portion of the tissue of the wearer to reach the far detectors than to reach the near detectors). Signals detected at the near detectors can optionally be used as reference or for comparison with the signals detected at the far detectors when the physiological parameter measurement sensor or module processor determines the wearer's hydration status. The sensor or module processor of the physiological parameter measurement module disclosed herein can compare intensity signals of the fourth wavelength and another wavelength (for example, the third wavelength or about 905 nm) that is less sensitive to changes in water from one of the "far" detectors. The module processor can focus on the DC component, or the DC bulk absorption measurement of the signals detected by the "far" detectors for hydration status monitoring. At the DC level, water can act as a light block (that is, less transmissive of light) for the fourth wavelength and as a lens or cover (that is, more transmissive of light) for the other wavelength.

Additionally and/or alternatively, any of the modules disclosed herein can monitor the wearer's hydration status by monitoring the wearer's PVI values. The module can determine a baseline PVI value of the wearer, and can output a notification that the wearer is dehydrated or hydrated based on fluctuations in the PVI value from the baseline.

The module can further combine the hydration status monitoring by the optical detectors and other sensors (such as a sweat sensor or a skin impedance sensors) in outputting a final hydration status indication of the wearer. The module can calculate an average, a weight average or otherwise of raw hydration index values calculated based on signals from the different sensors, and/or rely on the different hydration monitoring sensors for redundancy.

As a person's hydration status is not expected to change rapidly, the physiological parameter measurement module can optionally make a measurement of the hydration status less frequently than making measurements related to the wearer's pulse rate or SpO2 or other parameters. For example, the physiological parameter measurement sensor or module processor can make a measurement of hydration status every 5 minutes, or longer, and/or upon (for example, only upon) a request by the wearer, such as when the wearer presses a button (a physical button and/or a touch button on the display) on the device or otherwise instructs the device using voice commands, hand gestures, and/or the like.

Examples of Generally Circular Physiological Parameter Measurement Modules and Examples of Wearable Devices Incorporating the Same A physiological parameter measurement module can alternatively include an inner portion of emitters and an outer ring of detectors as shown in FIGS. 24A-24B and FIGS. 25A-25B. The sensor or module 1000 in FIGS. 24A-24B and the module 1100 in FIGS. 25A-25B can have any of the features of the module examples described herein, with the differences noted in the description of FIGS. 24A-24B and 25A-25B. Such a physiological parameter measurement module can have a generally circular outer shape. The sensor or module 1000 in FIGS. 24A-24B can be smaller than the module 1100 in FIGS. 25A-25B. For example, the sensor or module 1000 can have an outer diameter between about 12 mm and about 16 mm, or between about 14 mm and about 15 mm. For example, the module 1100 can have an outer diameter between about 16 mm and about 22 mm, or between about 18 mm and about 20 mm.

The physiological parameter measurement module 1000, 1100 can each include a single emitter group having a plurality of emitters 1004, 1104, such as three emitters. The emitters 1004, 1104 of the sensor or module 1000, 1100 can emit at least the first, second, and third wavelengths as described above. The emitters 1004, 1104 can be located at or near a center portion of a PCB of the sensor or module 1000, 1100. The sensor or module 1000, 1100 can include a temperature sensor located on the PCB near the emitters 1004, 1104.

The sensor or module 1000, 1100 can include a plurality of detectors 1006, 1106 (for example, about six, eight, or more) that can be arranged on the PCB so that the detectors 1006, 1106 are spaced apart around the emitters 1004, 1104. The emitters 1004, 1104 and the detectors 1006, 1106 can be separated by a first light barrier 1020, 1120. The first light barrier 1020, 1120 can surround the emitters 1004, 1104. The first light barrier 1020, 1120 can also suppress light emitted by the emitters 1004, 1104 at an angle so that the emitted light exits the inner lens or cover 1002*a*, 1102*a* in a direction generally parallel to the height of the first light barrier 1020, 1120.

Figure 25A:
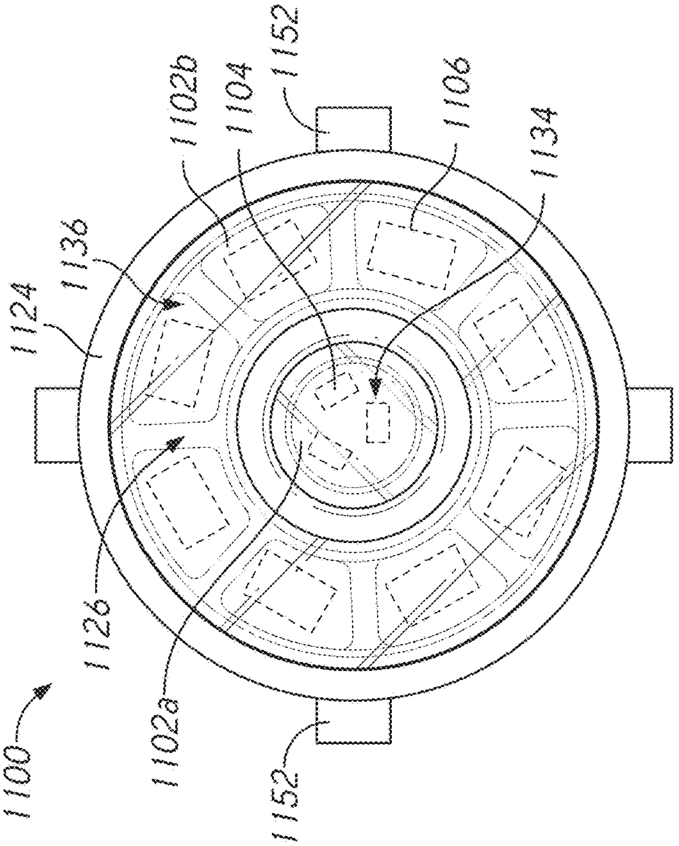
FIG. 25A illustrates a bottom view of another example physiological parameter measurement module of a wearable device.
Figure 25B:
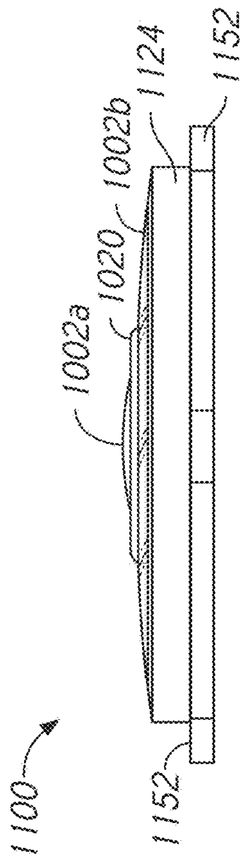
FIG. 25B illustrates a side view of the physiological parameter measurement module of FIG. 25A.
Figure 24A:
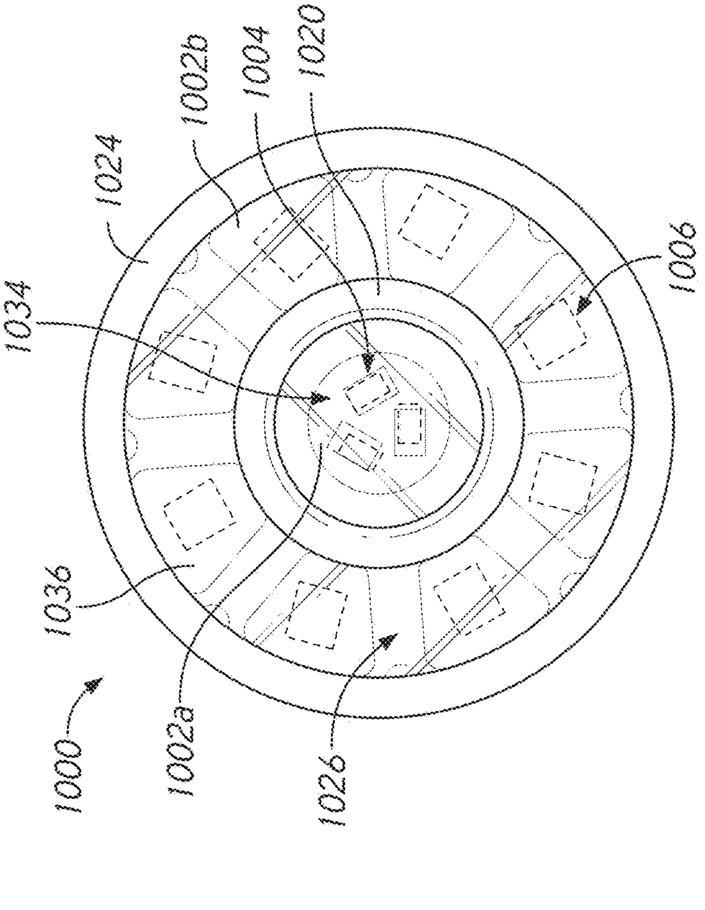
FIG. 24A illustrates a bottom view of another example physiological parameter measurement module of a wearable device.
Figure 24B:
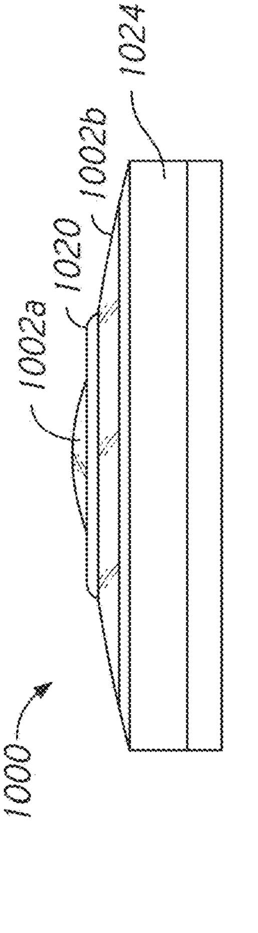
FIG. 24B illustrates a side view of the physiological parameter measurement module of FIG. 24A.

The emitters 1004, 1104 can be covered by an inner lens or cover 1002*a*, 1102*a*. In the illustrated example, the inner lens or cover 1002*a*, 1102*a* can be generally circular. The detectors 1006, 1106 can be covered by an outer lens or cover 1002*b*, 1102*b*. The outer lens or cover 1002*b*, 1102*b* can be generally concentric with the inner lens or cover 1002*a*, 1102*a*. In the illustrated examples, the outer lens or cover 1002*b*, 1102*b* can be a disc when viewed directly above from the sensor or module 1000, 1100. In other examples such as those disclosed herein, the outer lens or cover can have other shapes, for example, being elliptical or otherwise. The outer lens or cover 1002*b*, 1102*b* can have a smaller curvature than the inner lens or cover 1002*a*, 1102*a* such that the inner lens or cover 1002*a*, 1102*a* protrudes more than if the inner lens or cover had the same curvature as the outer lens or cover 1002*b*, 1102*b*. As shown in FIGS. 24B and 25B, the first light barrier 1020, 1120 can protrude slightly from, that is, proud of the outer edge of the inner lens or cover 1002*a*, 1102*a*. The slightly protruding first light barrier 1020, 1120 and/or inner lens or cover 1002*a*, 1102*a* can be pressed into the wearer's skin at a higher pressure than the remainder of the light barriers or lenses or covers of the sensor or module 1000, 1100.

The detectors 1006, 1106 can be enclosed within a module side wall 1024, 1124 that defines a perimeter of the sensor or module 1000, 1100. The perimeter can be generally circular or of any other shape. The side wall 1024, 1124 can be shorter than the first light barrier 1020, 1120. The height of the side wall 1024, 1124 can be such that the tissue-facing end of the side wall 1024, 1124 is generally continuous with the curvature of outer lenses or covers 1002*b*, 1102*b*. In the illustrated example, the detectors 1006, 1106 can be separated from one another by a plurality of generally opaque divider barriers 1026, 1126. The divider barriers 1026, 1126 can have a height lower than the first light barrier 1020, 1120. The height of the divider barriers 1026, 1126 can be configured to accommodate the outer lens or cover 1002*b*, 1102*b* such that when assembled, the outer lens or cover 1002*b*, 1102*b* forms a substantially smooth surface with the module side wall 1024, 1124. The outer lens or cover 1002*b*, 1102*b* can sit on top of the divider barriers 1026, 1126. The tissue-facing end of the first light barrier 1020, 1120 and the side wall 1024, 1124, and the tissue-facing surfaces of the inner lens or cover 1002*a*, 1102*a* and the outer lens or cover 1002*b*, 1102*b* can be configured to contact the skin of the wearer and form the tissue-facing surface of the sensor module 1000, 1100.

The first light barrier 1020, 1120, the side wall 1024, 1124, and the divider barriers 1026, 1126 can optionally form a single light barrier construct. The single light barrier construct can receive the PCB of the sensor or module 1000, 1100, and the emitters 1004, 1104, detectors 1006, 1106, temperature sensor, and any other sensors, for example, the gyroscope, the accelerometer, and/or the like, and the sensor or module processor that are located on the PCB. The single light barrier construct can receive the lenses, including the inner lens or cover 1002*a*, 1102*a* and the outer lens or cover 1002*b*, 1102*b* on another end that is opposite the end receiving the PCB. As shown in FIGS. 25A and 25B, the light barrier construct of the module 1100 or the PCB can additionally include a plurality of (for example, four or otherwise) extension prongs 1152. The plurality of extension prongs 1152 can be generally equally spaced around the side wall 1124.

The sensor or module 1000, 1100 can include a plurality of chambers such that light cannot travel between the chambers because of the various light barriers described herein. A first chamber 1034, 1134 can be enclosed by the inner lens or cover 1002*a*, 1102*a*, the first light barrier 1020, 1120, and a portion of the PCB. The first chamber 1034, 1134 can enclose the emitters 1004, 1104. A plurality of second chambers 1036, 1136 can be enclosed by the outer lens or cover 1002*b*, 1102*b*, the first light barrier 1020, 1120, the divider barriers 1026, 1126, the side wall 1024, 1124, and part of the PCB. Each of the second chambers 1036, 1136 can enclose one detector 1006, 1106.

The light diffusing materials described above can be included in one or more of the chambers 1034, 1134, 1036, 1136 of the module housing to improve distribution of emitted lighted and/or detected light. The inner lens or cover 1002*a*, 1102*a* and the outer lens or cover 1002*b*, 1102*b* can also include glass microspheres as described above.

Figure 25E:
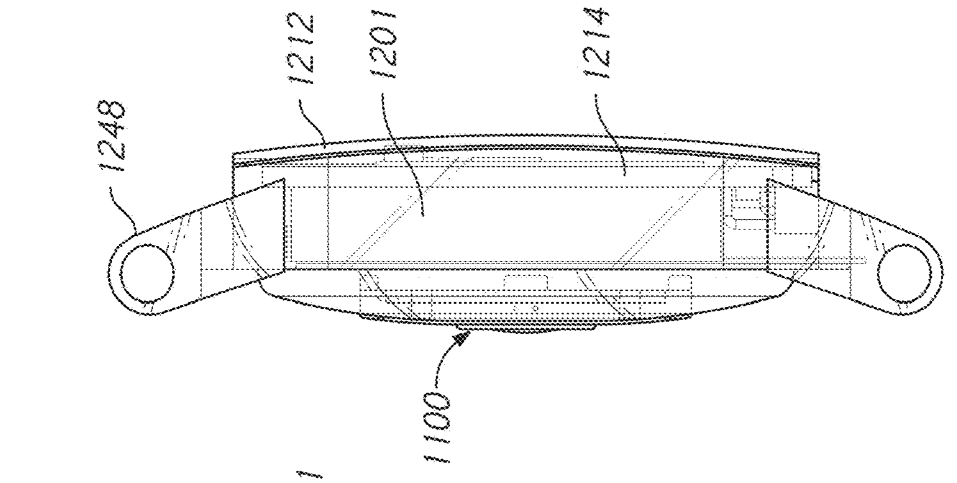
FIG. 25E illustrates a second side view of the wearable device of FIG. 25C.
Figure 25D:
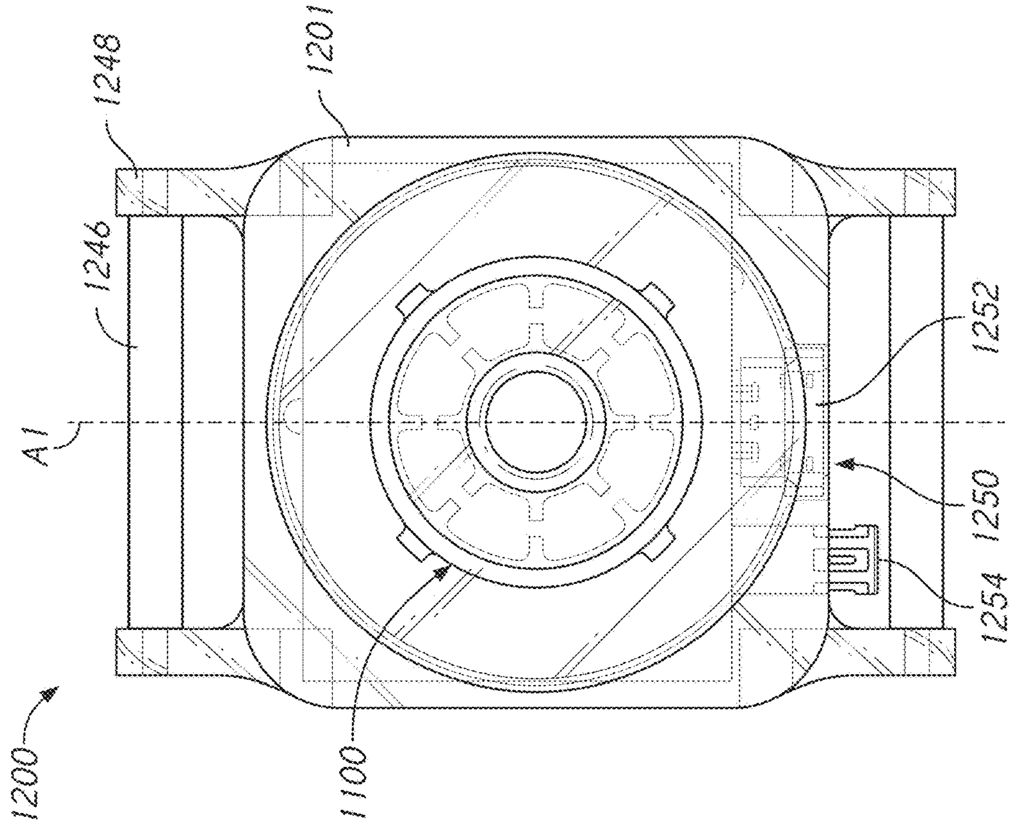
FIG. 25D illustrates a bottom view of the wearable device of FIG. 25C.
Figure 25C:
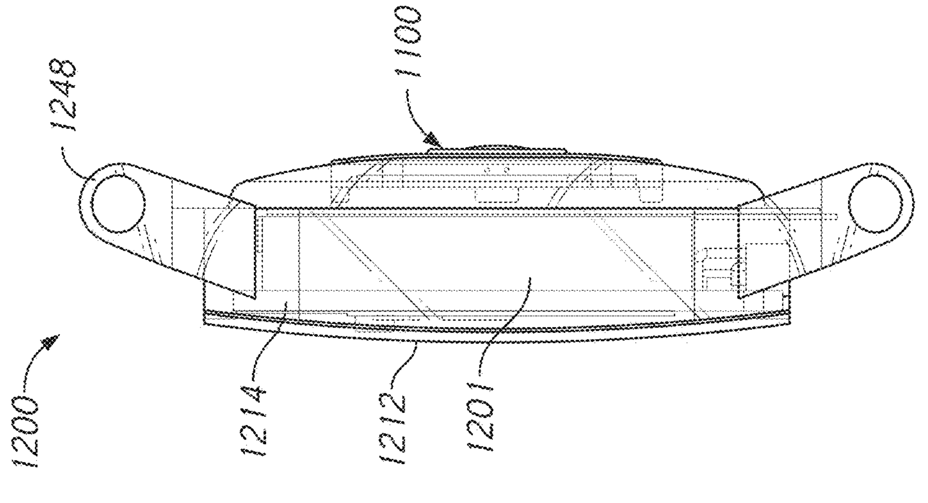
FIG. 25C illustrates a first side view of another example wearable device incorporating the physiological parameter measurement module of FIGS. 25A-25B.
Figure 25F:
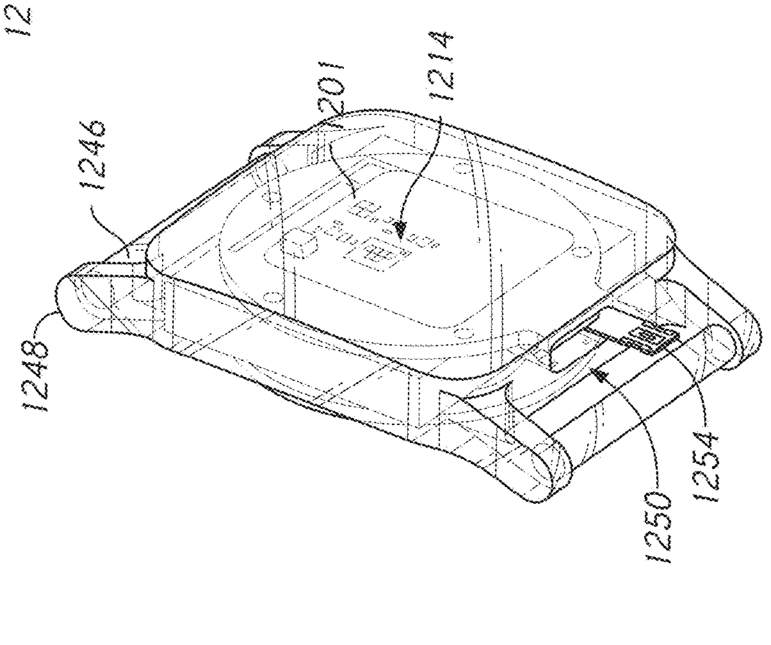
FIG. 25F illustrates a top perspective view of the wearable device of FIG. 25C.
Figure 25G:
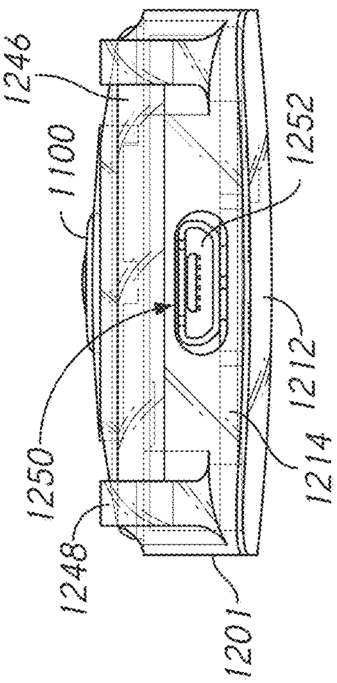
FIG. 25G illustrates a third side view of the wearable device of FIG. 25C.
Figure 25H:
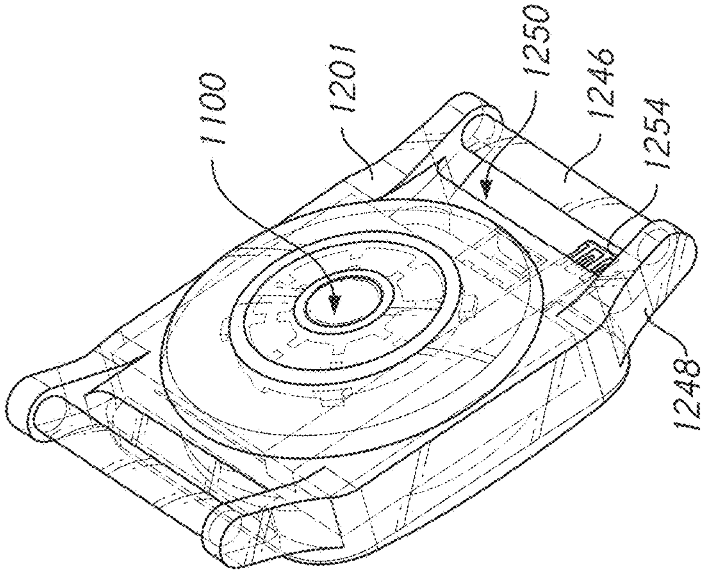
FIG. 25H illustrates a bottom perspective view of the wearable device of FIG. 25C.

The watch 1200 in FIGS. 25C-25H is illustrated as incorporating the module 1100 shown in FIGS. 25A-25B. However, any of the example watches disclosed herein can incorporate the physiological parameter measurement module 1000, 1100 shown in FIGS. 24A-24B or FIGS. 25A-25B. The watch 1200 can have any of the features of the wearable devices disclosed herein, such as the watch 700, 900, all of which are not repeated for brevity. The watch processor 1214 and power source can be enclosed within the watch housing 1201. The watch housing 1201 can include a connection port opening 1250 configured to allow access to a connection port 1252 in electrical communication with the watch processor 1214 and/or the power source. The opening 1250 can be on one side of the watch 1200 perpendicular to the first axis A1 of the module 1100, closer to the strap coupling mechanisms. The connection port 1252 can allow for charging of the power source and/or data transfer to and from the watch processor 1214. Optionally, as shown in FIGS. 25D, 25F, and 25H, the watch 1200 can include a cable connector 845 extending outward from the watch housing 1201. The cable connector 1245 can be located adjacent to or near the connection port opening 1250.

The watch 1200 can include a display screen 1212 positioned at a first side of the watch housing 1201. The watch housing 1201 has a second side that is opposite the first side. The second side of the watch housing 1201 can include an opening sized to retain the physiological parameter measurement module 1100 while still allowing the tissue-facing surface of the module 1100 to be exposed. The extension prongs 1152 of the module 1100 can be received into corresponding structures, for example, recesses, on the second side of the watch housing 1201, which can prevent rotation of the module 1100 when being installed in the watch 1200. The second side of the watch housing 1201 can be removably attached to the first side of the watch housing 1201 without using external fasteners or via one or more fasteners as described above. An electrical connection can be established between the physiological parameter measurement module circuit and the watch circuit. Optionally, the electrical connection can include a flex circuit.

The watch housing 1201 can include strap coupling extensions 1248 on opposite sides of the watch 1200 along the first axis A1 of the module 1100. The extensions 1248 can include a bar 1246 for coupling to any suitable watch straps.

Example Second Sensor Connection on Physiological Parameter Measurement Modules for Preventing Opioid Overdose The physiological parameter measurement module examples disclosed herein can include an optional connector 118 (see FIG. 7A) for receiving a second sensor, which can be a plethysmograph sensor or other suitable sensors. The connector 118 can be oriented such that the second sensor can extend from a housing of the device 10 with reduced or no impingement of the tissue at the device/tissue interface, resulting in less or no effect of the connection of a second sensor to the connector 118 on the blood flow through the device measurement site. The second plethysmograph sensor can include any suitable plethysmograph sensors, for example, a fingertip sensor configured to monitor opioid overdose as described in U.S. Pub. No. 20190374173, the entirety of which is incorporated herein by reference and should be considered part of the disclosure. FIG. 1C illustrates a non-limiting example of the second sensor 119 that is a fingertip sensor. The second sensor 119 can extend from a wearable device as shown in FIG. 1C or any of the wearable device examples disclosed herein.

Figure 23C:
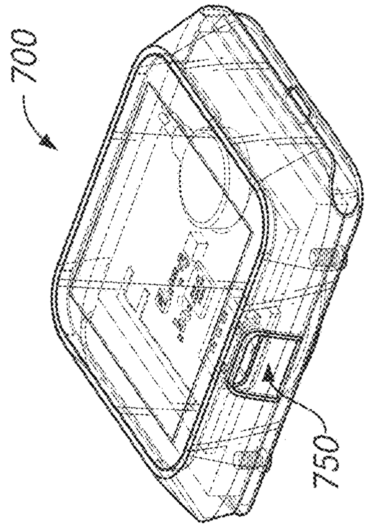
FIG. 23C illustrates a top perspective view of the wearable device of FIG. 23A.
Figure 23B:
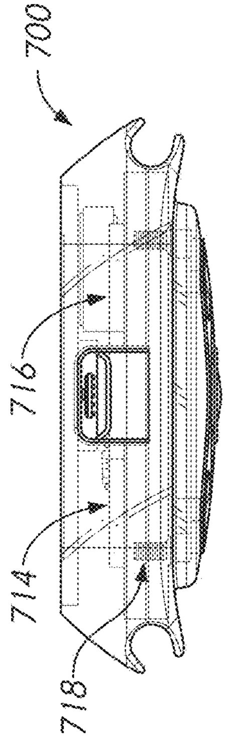
FIG. 23B illustrates a side view of the wearable device of FIG. 23A.
Figure 23A:
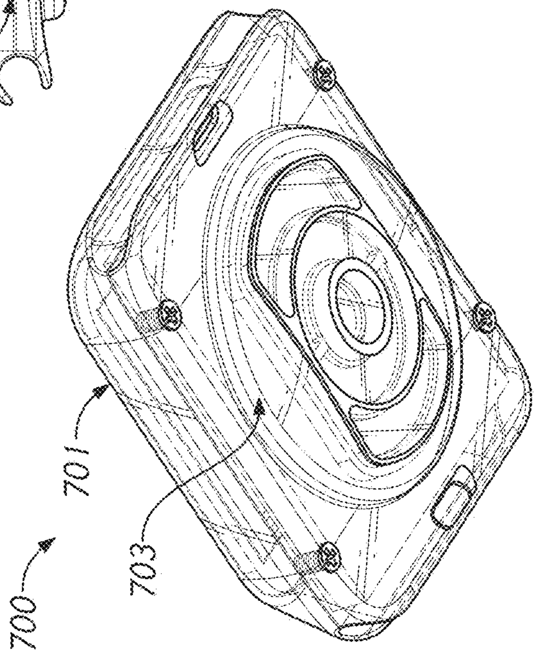
FIG. 23A illustrates a bottom perspective view of an example wearable device incorporating the physiological parameter measurement module of FIGS. 20A-20D.
Figure 23E:
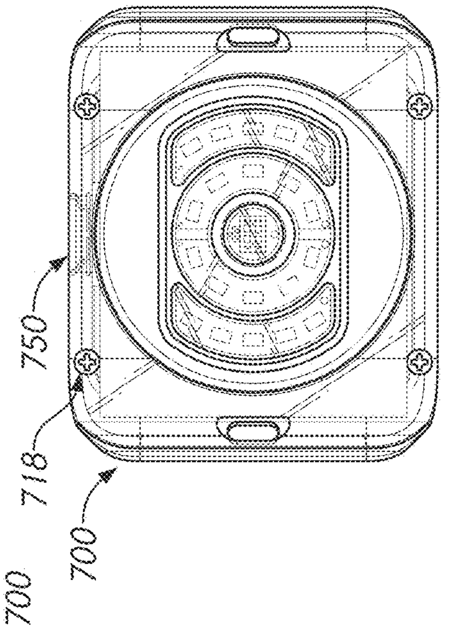
FIG. 23E illustrates a bottom view of the wearable device of FIG. 23A.
Figure 23D:
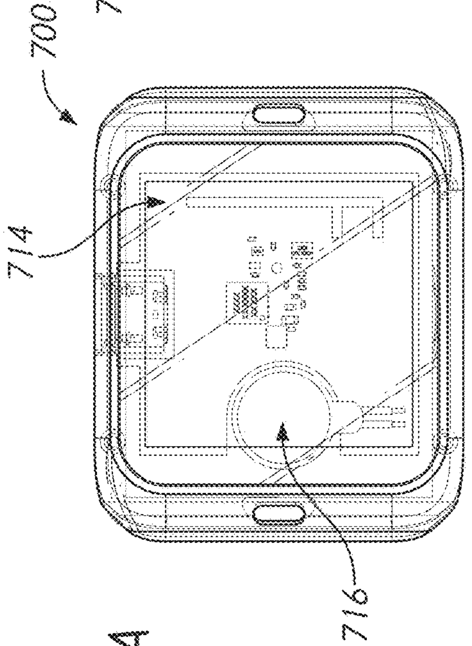
FIG. 23D illustrates a top view of the wearable device of FIG. 23A.

Alternative to the connection to a wearable device as shown in FIG. 1C, the connector from the watch disclosed herein can extend from an opening on a tissue-facing side of the device housing, for example, on a raised platform 703, 903 (FIGS. 201 and 23A). The connector can be coupled to the PCB 616 via a cable, which can optionally have a length configured to extend around the raised platform 703, 903, for example, in a groove of the raised platform 703, 903, or otherwise. Having the cable extending around the raised platform 703, 903 can allow adjustment of the slack of the cable when the connector connects to the second sensor. Having the connector extending from an opening on the raised platform 703, 903 can also avoid the connector and/or the cable impinging on the tissue at the watch/tissue interface as described above. The connector can alternatively be located at other suitable locations on the watch 700, 900.

The second plethysmograph sensor can have a higher measurements accuracy than the physiological parameter measurement module disclosed herein. The wearer can disconnect and/or deactivate the second sensor while the wearer is awake and/or moving about. The wearer can connect and activate the second sensor, for example, when going to sleep or resting. The sensor or module processor can ignore signals from the detectors of the module when the second sensor is activated so that the sensor or module processor can output physiological parameters based on the readings from the second sensor. Alternatively, the sensor or module processor can output physiological parameters based on a combination of the readings from the second sensor and the detectors of the module. The wearer can have the flexibility of choosing to use the physiological parameter measurement module and/or the second sensor, depending on the wearer's need.

The second plethysmograph sensor can aid in detection of opioid overdose in a wearer who uses opioid (for example, for medical reasons), in particular, by detecting low saturation of oxygen in the blood of the wearer. Depressed breathing is the most dangerous side effect of opioid overdose. Lack of oxygen to the brain can not only result in permanent neurologic damage, but may also be accompanied by the widespread failure of other organ systems, including the heart and kidneys. If a person experiencing an opioid overdose is left alone and asleep, the person could easily die as the respiratory depression worsens. The second plethysmograph sensor can be configured to detect depressed breathing by detecting decreased oxygen saturation in the blood of the wearer. The wearable device can be configured to automatically notify a first responder and/or the wearer's family or guardian in response to detecting opioid overdose of the wearer.

Optionally, the device processor of the wearable device can be in communication (for example, via Bluetooth or NFC communication, or via the network) with a processor of a drug delivery apparatus that is wearable by the wearer and configured to deliver one or more doses of a therapeutic drug, such as opioid. The drug delivery apparatus can include a delivery device that includes a dose of a therapeutic drug stored in a reservoir, a drug delivery channel, a dispensing device to dispense the therapeutic drug from the reservoir through the drug delivery channel, and activation circuitry to activate the dispensing device. The processor of the drug delivery apparatus can receive the parameters measured by the second plethysmograph sensor of the wearable device disclosed herein. The processor of the drug delivery apparatus can store memory-storing instructions and be configured to execute the instructions to at least compare the received parameters from the wearable device to a threshold that is indicative of opioid overdose. The processor of the drug delivery apparatus can determine whether an overdose event is occurring or likely to occur based on the comparison and send at least one activation signal to the drug delivery apparatus to dispense at least one dose of the therapeutic drug based on the determination.

Alternatively, the sensor or module processor of the physiological parameter measurement module can perform the comparison of the parameters measured by the second plethysmograph sensor to the predetermined opioid overdose threshold. Optionally, a microneedle patch may be used for providing a medication that can counteract opioid overdose. The wearer can apply the microneedle patch containing the medication to the skin when the wearable device outputs an alert that the wearer's physiological parameters (for example, SpO2) has exceeded a threshold (which may be indicative of opioid overdose).

Alternatively or additionally, the second sensor can be any other suitable noninvasive sensor disclosed herein. Alternatively or additionally, the physiological parameter measurement module examples disclosed herein can connect to a second sensor via wireless connection, for example, using Bluetooth technology. The module can receive measured parameters from the connected second sensor and/or process the sensor data received from the second sensor to calculate additional physiological parameters.

Example Microneedle Patch

In addition and/or alternative to delivering medication to prevent opioid overdose as described herein, a microneedles patch can be used for other purposes in combination with the wearable device. Microneedles have been used in recent years as a painless alternative to hypodermic needles to deliver drugs to the body. Microneedles on a patch can be placed on an arm or leg, or other parts of the body, which then create small holes in the skin's outermost layer, allowing the drugs coated on each needle to diffuse into the body. Microneedles can be made from silicon, metals, synthetic polymers, or natural, biodegradable materials such as silk and chitin.

Because of the small size, microneedles are minimally invasive and cause less pain compared to larger needles (for example, hypodermic needles). Additionally, the microneedle patch are easier to apply by the wearer than a hypothermal needle. In comparison, larger needles may require correct injection depth and injection angle to ensure that the drugs are injected at a right location.

Figure 26A:
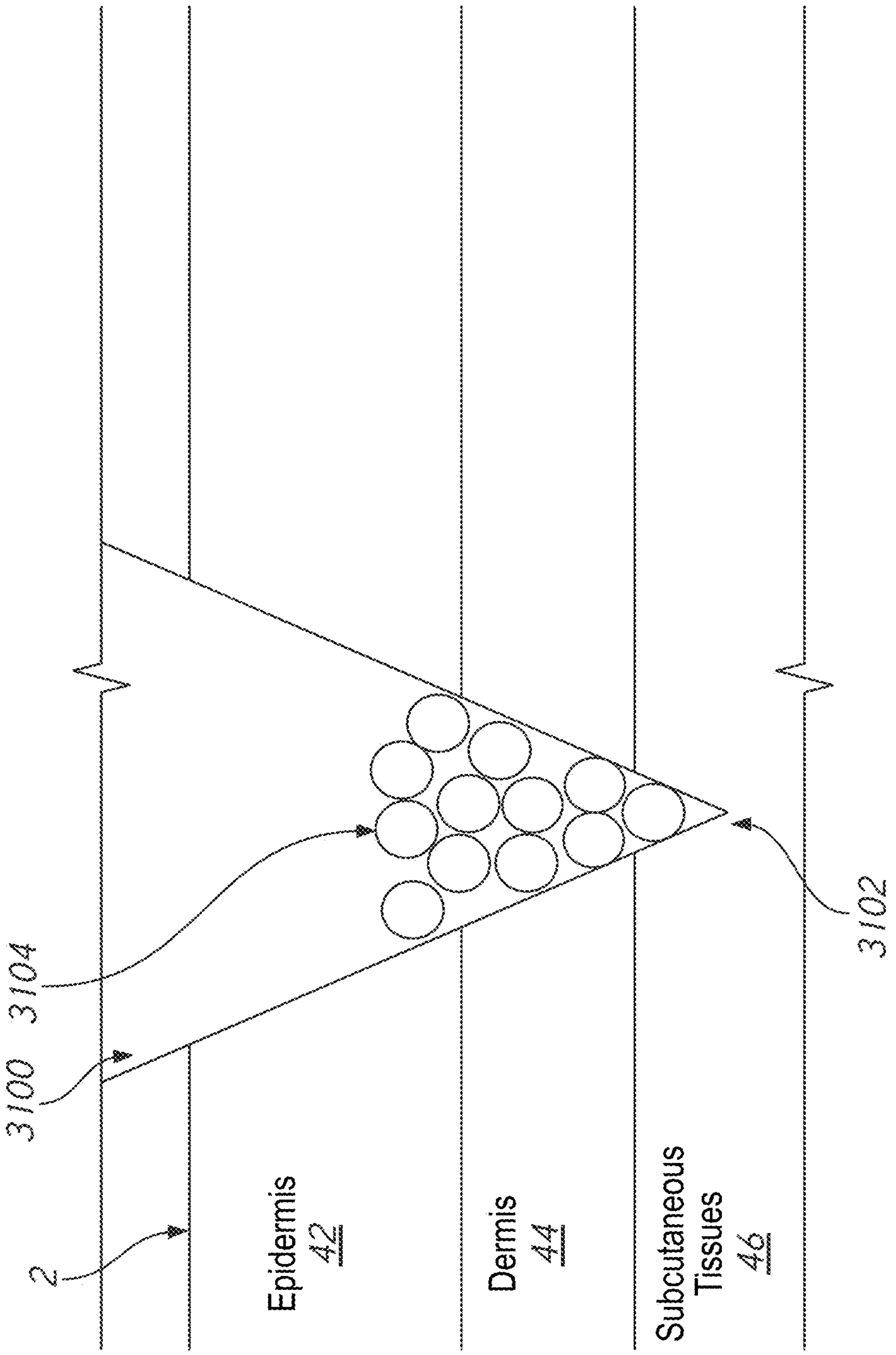
FIG. 26A illustrates schematically a microneedle inserted into skin of a wearer.

FIG. 26A illustrates schematically a microneedle 3100 of a microneedle patch that has penetrated the tissue surface 2 of the wearer. Depending on its height, the microneedle 3100 may have varying injection depths. For example, the microneedle 3100 may puncture just the epidermis (including the stratum corneum, which is the outer layer of the epidermis) 42. In other examples, the microneedle 102 may puncture the epidermis 42 and dermis 44, with a tip of the microneedle 3102 terminating in the dermis 44. In other examples such as shown in FIG. 26A, the microneedle 3100 may puncture the epidermis 42 and dermis 44, with the tip 3102 end in the subcutaneous tissues 46.

Depending on the use, the microneedles 3100 with different heights may be used for delivery of medication and/or irrigation fluid 3104 into different parts of the wearer's tissue. The microneedles 3100 can be used to deliver a broad range of drugs, biotherapeutics, and vaccines. The microneedles 3100 can be hollow with internal reservoirs to store and deliver medication and/or irrigation fluid 3104. Alternatively, the microneedles 3100 can be solid and coated with medication 3104, and optionally other surfactant/thickening agents. Optionally, the microneedle 3100 can be dissolvable and encapsulate the drug in a nontoxic polymer that can dissolve once inside the skin.

Alternatively or additionally, the microneedles 3100 can be used to extract a irrigation fluid 3104 (for example, the interstitial fluid of the wearer) for detection and/or analysis of analytes in the irrigation fluid 3104. Optionally, the microneedle 3100 can irrigate the tissue of the wearer with a fluid before extracting the fluid (which, for example, may have equilibrated with the chemical composition of the wearer's bodily fluid sample) back into the microneedles 3100. The microneedles 3100 can be hollow and can extract a fluid sample via surface tension. The analyte detection and/or analysis can provide information such as the hydration status, glucose concentration, hemoglobin concentration, and/or orthogonal information about the fluid. The analyte detection and/or analysis can provide additional information related to, for example, sodium, potassium, glucose, chloride, bicarbonate, blood urea nitrogen, magnesium, creatinine, LDL cholesterol, HDL cholesterol, triglyceride, pH, and the like.

Figure 26B:
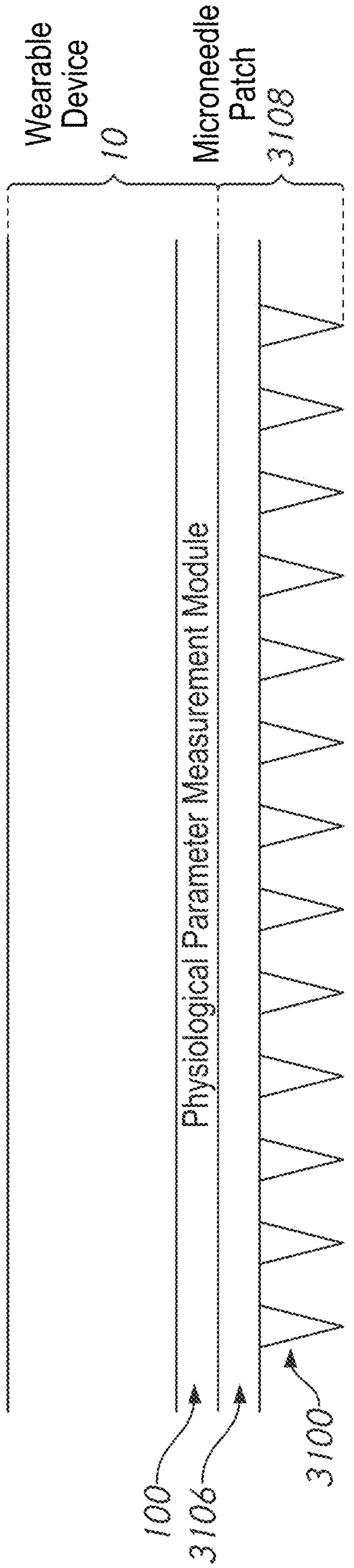
FIG. 26B illustrates schematically a microneedle patch coupled to a body of the wearable device disclosed herein.
Figure 26C:
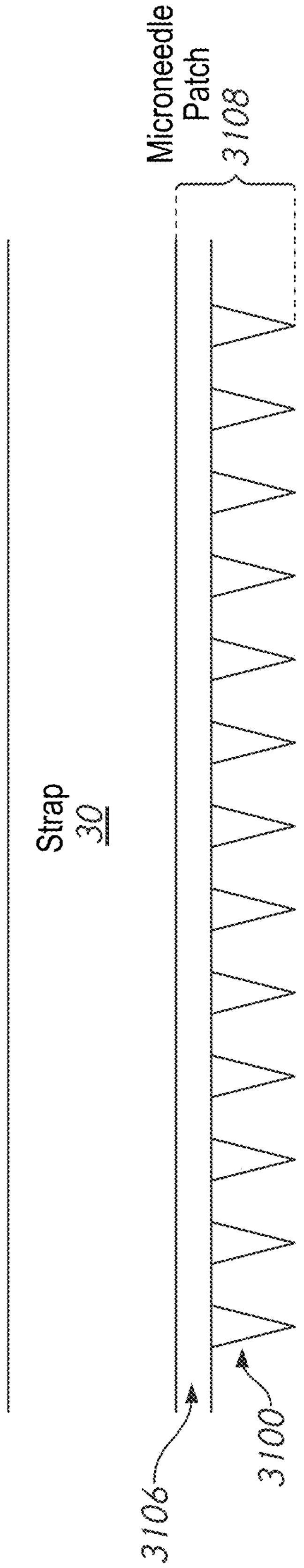
FIG. 26C illustrates schematically a microneedle patch coupled to a strap of the wearable device disclosed herein.

A microneedle patch may be located under one of the straps or the body of the wearable device, or be applied remotely (anywhere else on the wearer's body) from the wearable device without contacting the device. A plurality of microneedle patches can be applied to the wearer at different locations on the wearer's body. As shown in FIGS. 26B and 26C, the microneedles 3100 may be connected to a patch body 3106, forming a microneedle patch 3108. The patch body 3106 may be circular, oval, rectangular, square, triangular, tear-drop shaped, or of any other shape. The size of the patch body 3106 is not limiting. A surface of the patch body 3106 that is not connected to the microneedles 3100 can include an adhesive layer for releasably attach the patch 3108 to the wearable device. The adhesive layer may be covered by a back layer, which can be peeled off before applying the patch 3108 to the wearable device.

As shown in FIG. 26B, the microneedle patch 3108 can be placed on the body of the device 10. The patch 3108 can be applied under the skin-facing surface of the physiological parameter measurement sensor or module 100. The microneedles 3100 of the microneedle patch 3108 can face the skin of the wearer of the device 10 when the device 10 is worn. Accordingly, when the device 10 is worn, for example, on the wrist of the wearer with the straps wrapped around the wearer's wrist, the microneedles 3100 can puncture the skin on the wrist.

Additionally or alternatively, the microneedle patch 3108 may be integrated or releasably secured to an inner side of the adjustable strap 30 of the wearable device 10, such as shown in FIG. 26C. The microneedles 3100 can be pointing toward the skin around the wrist of the wearer when the device 10 is worn. When the strap 30 is wrapped around the wrist of the wearer, the microneedle patch 3108 may come in contact with the skin around the wrist of the wearer and the microneedles 3100 can penetrate the skin of the wearer.

Figure 26D:
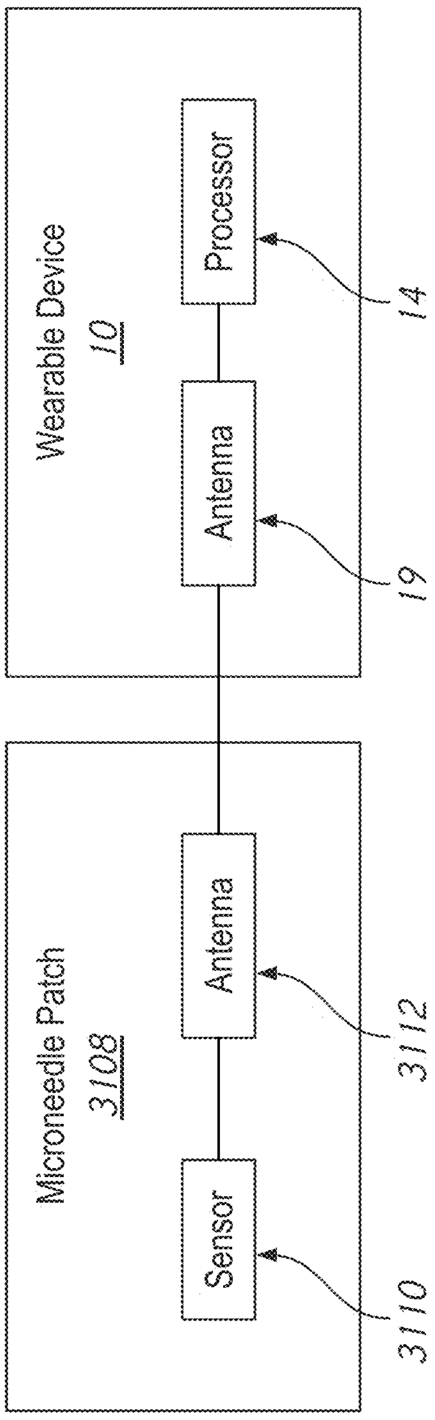
FIG. 26D illustrates schematically a simplified system diagram of the microneedle patch and the wearable device.

As shown in FIG. 26D, the microneedle patch 3108 can communicate with the wearable device 10, using the wearable device 10 as a platform or hub to detect and/or analyze analytes in the fluid sample collected in the microneedles patch 3108. The patch 3108 can optionally include a sensor 3110, for example, an electrochemical sensor (with electrodes built into the microneedles), a colorimetric sensor, or otherwise. Alternatively, the patch 3108 can be brought to an external sensor for analyte detection and analysis. The patch 3108 can include an antenna 3112, which may be an NFC antenna or otherwise. The sensor 3110 can output a signal via the antenna 3112. The wearable device can receive the signal from the sensor 3110 via the antenna 19. The device processor 14 (or optionally the sensor or module processor of the physiological parameter measurement sensor or module on the device 10) can process the signal from the sensor 3110 to determine the presence and/or concentration of certain analyte(s) in the fluid sample.

Examples Device Tightness Monitoring Systems and Methods

A desired tightness and/or pressure of the device on the body can be indicated by the skin interfacing with the wearable device moving with the device when the device is moved. If there is insufficient tightness and/or pressure of the device on the body of the wearer, ambient light entering the device-skin interface can result in noises in the signals detected by the detectors, and therefore inaccurate measurements made by the device. If the device is worn too tight (and/or the pressure exerted by the device on the body is too high), blood pulsation and circulation at the wrist can be restricted, which can lead to a decrease in oxygen saturation readings of the wearer of the device. Optionally, the device can output a warning that the device is worn too tight (which can include a message displayed on the device to the wearer to loosen the straps) when the device has determined that the wearer's oxygen saturation readings are decreasing by a certain percentage, at a certain rate, and/or at a certain rate within a predetermined amount of time.

The device 10 can include an optional strain gauge 20 (see FIG. 7A) to measure a pressure of the device 10 on the wearer. The strain gauge 20 can be located in a device housing 101 between the physiological parameter measurement sensor or module 100 and other components of the device 10, for example, the power source 16, the device processor 14, or otherwise. For example, the strain gauge 20 can be flanged between the physiological parameter measurement sensor or module 100 and the device processor 14. When the device 10 is worn on the wearer, for example, on the wrist, the pressure exerted by the module, particularly by the convex protrusion of the cover 102 against the tissue can be transmitted to and measured by the strain gauge 20. The strain gauge 20 can also be incorporated in the other wearable device examples disclosed herein.

Readings from the strain gauge 20 can be communicated to the device processor 14, which can process the readings and output an indication of the pressure asserted by the device 10 on the wearer to be displayed on the display screen 12. The indication can be in a variety of suitable forms, for example, using different colors to indicate whether the pressure is too low, appropriate, or too high for obtaining accurate or reliable measurements using the physiological parameter measurement sensor or module 100. In one example, the device 10 can display a green light when the pressure on the wearer is suitable for using the physiological parameter measurement sensor or module 100 and display a red or other colored light for a pressure that is too high or too low than the desired pressure or pressure range. The physiological parameter measurement sensor or module 100 may not be activated unless the readings from the strain gauge 20 indicate that the desired pressure or pressure range has been achieved. Optionally, the device processor can also deactivate the physiological parameter measurement sensor or module 100, and/or any other sensors on or attached to the device 10, in response to not detecting any readings from the strain gauge 20, indicating that the device 10 is not worn on the wearer. Automatically turning on and/or off the sensors on or attached to the device 10 can reduce power consumption and increase battery life of the device 10.

Optionally, the wearable device 10 can include a motor to adjust tightness of the straps based on a monitored tightness of the straps and/or pressure exerted by the sensor or module 100 on the wearer's skin.

Figure 27:
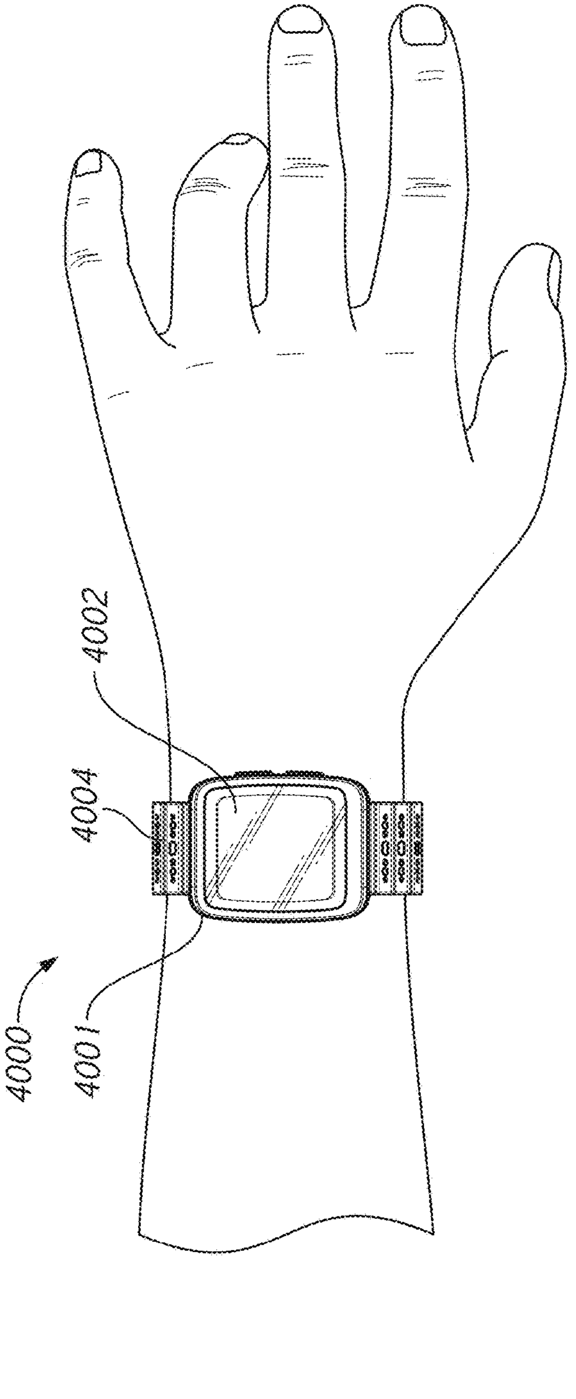
FIG. 27 is a top view of an example of a wearable device including a physiological parameter measurement sensor or module worn on a wrist using a strap or straps.
Figure 28:
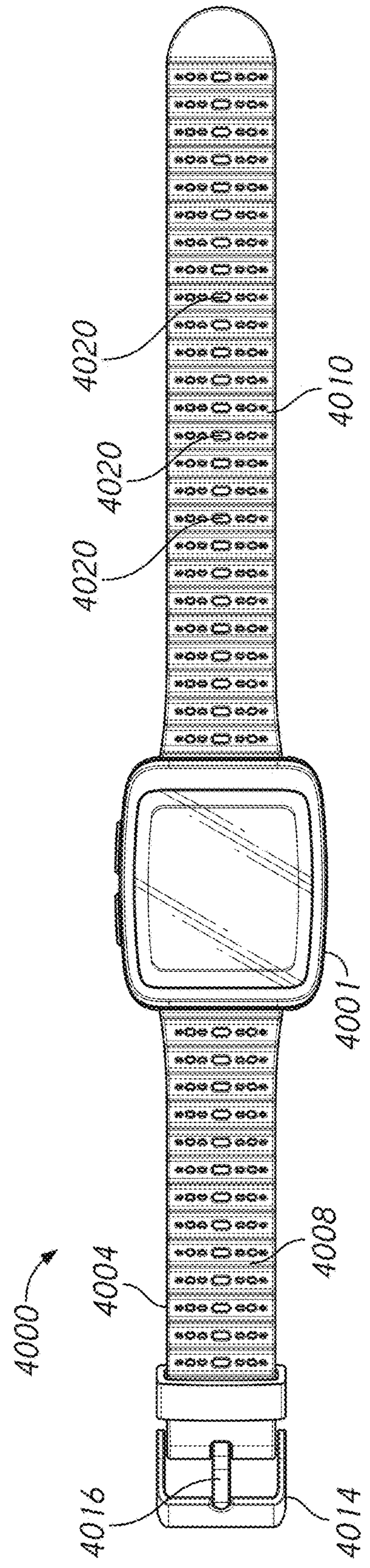
FIG. 28 is a top view of the example of a wearable device shown in FIG. 27.

FIGS. 27-28 show another example of wearable device 4000 that can be configured to be secured to a wrist of a user. In some examples, the wearable device 4000 can have a body portion 4001 having a graphical interface or display screen 4002. The body portion 4001 can, in some examples, have a case or housing that houses or supports the electronic components of the wearable device 4000, including one or more sensors, a processor, a power supply, and the display screen 4002. The wearable device 4000 can also have a strap 4004 (also referred to as a band) that can be used to secure the body portion 4001 of the wearable device 4000 to a wrist of the user. For example and without limitation, some examples of the wearable device 4000 can look or be similar to a wrist watch.

In any examples disclosed herein, the wearable device 4000 can have any of the components, features, or other details of any other examples of wearable devices disclosed herein, including without limitation any of the examples of the wearable device 10 shown in FIG. 1A-1H or in other FIGS., in any combination with any of the components, features, or details described below. For example and without limitation, any examples of the wearable device can 4000 disclosed herein can include any of the examples of the optical physiological sensors (also referred to as physiological parameter measurement sensors or merely sensors) and/or components or features thereof, any examples of the processors disclosed herein, and/or any examples of the displays and/or components or features thereof in combination with any of the other components and/or features described or shown herein. Similarly, any examples of wearable devices disclosed herein can have any of the components, features, or other details of any examples of the wearable device 4000 disclosed herein in any combination with any of the components, features, or details of the other wearable devices.

The strap 4004 of any examples of the wearable device 4000 disclosed herein can be adjustable. In some examples, the strap 4004 can include a first strap portion 4008 and a second strap portion 4010. The first strap portion 4008 can include a buckle 4014 and a buckle pin 4016 (also referred to as a buckle tongue) that can be configured to be advanced into any of a plurality of notches 4020 formed in the second strap portion 4010 so that a user can adjust a size or tightness of the strap 4004 around the user's wrist. The buckle components are also referred to herein as a buckle unit. In some examples, the notches can be numbered or uniquely identified so that a user can easily record and/or recall a tightness setting of the strap 4004. The numbers or unique identifiers can be in several forms including visual markers and/or protrusions and/or indentations. As will be discussed, in some examples, optimizing a tightness of the strap 4004 around the user's wrist and, hence, the contact pressure between the body portion 4001 and the skin of the user can improve the quality and accurateness of the signal(s) from the sensor(s) of the wearable device significantly.

In some examples, the strap can be made without notches so that a user can choose from a greater range of possible sizes or tightness levels. For example and without limitation, the second strap portion can be formed without notches and can be configured to be secured in any desired size or position. For example, the strap 4004 can have a buckle 4014, a buckle pin 4016, and a second strap portion 4010 that can be made from a woven or braided material (such as a synthetic woven, braided, or fiber nylon material) and configured so that the buckle pin 4016 can be advanced through the material of the second strap portion 4010 at nearly any desired position along the length of the second strap portion 4010. For example, the buckle pin 4016 can be configured to pass between the fibers or the clusters of fibers of the second strap portion 4010. This can, in some examples, result in a greater degree of adjustability of the strap 4004.

In some examples, the strap 4004 can be made from metal links, wherein a size of the strap 4004 can be adjusted by reducing or increasing a length of the first and strap portions, such as by adding or removing metal links. Some examples of this type of strap can also have a clasp having a plurality of holes (sometimes called micro holes) or positions that an end portion of the metal links can engage or couple with to provide a greater degree of adjustability of the watch strap. For example and without limitation, a spring bar or other connector can be rotatably coupled with an end portion of the metal band and can be configured to be removably positioned within any of a plurality of different adjustment holes formed in a clasp components of the band, wherein the plurality of different adjustment holes, each provide a different connection point between the strap and the clasp.

Coupling the strap end portion with a more distally positioned adjustment hole can result in the strap providing a smaller overall size and a tighter fit around a user's wrist, and/or can accommodate a smaller wrist size. Coupling the strap end portion with a more proximally positioned adjustment hole can result in the strap providing a larger overall size and a looser fit around a user's wrist, and/or can accommodate a larger wrist size. In any examples disclosed herein, the strap 4004 can be made from metal, rubber, and/or plastic, and can have any of the features of any other suitable watch straps or bands.

In some examples, the strap 4004 can have a first portion 4008 and a second portion 4010 that a clasp that is configured to allow the first portion 4008 slide relative to the second portion 4010 and/or the second portion 4010 to slide relative to the first portion 4008 for adjustment of a size of the strap 4004. For example, and without limitation, the strap can have a clasp coupled with one of the first strap and the second strap, the clasp having a deflectable tab configured to engage with a plurality of detents, depressions, ridges, and/or similar complementary features (complementary to the deflectable tab) arranged along a length of the other of the first strap and the second strap, like a zip-tie strap. The clasp can be configured to allow the user to disengage the deflectable tab from the plurality of complementary features so that the user can increase a size of the strap or remove the strap from her or his wrist.

Figure 29:
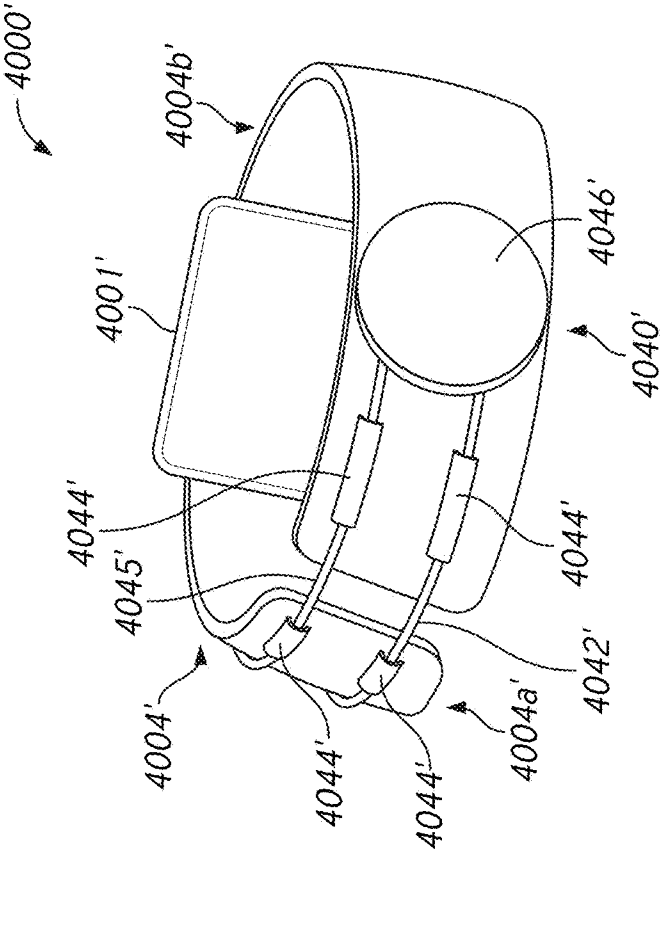
FIG. 29 is a perspective view of another example of a wearable device including a physiological parameter measurement sensor or module to be worn on a wrist using a strap or straps.

In some examples, with reference to FIG. 29, the strap 4004' can have an adjustable reel and cable wire system 4040' like the system developed by Boa Technology™. For example, in some examples, the wrist strap 400'4 can have a cable 404'2 that advances through one or more guides 4044' and is attached to a reel system 4046' (also referred to herein as a reel) that can be used to loosen or tighten the cable, thereby loosening or tightening the wrist strap. The reel system 4046' can be configured to tighten the cable 4042' and, hence, the strap 4004', if the reel system 4046' is rotated in a first direction when the reel system 4046' is in a first state or position. When the reel system 4046' is in the first state or position, the reel system 4046' can be configured to resist (e.g., prevent) rotation of the reel system 4046' in the second direction. The reel system 4046' can also be configured to unwind or loosen the cable (e.g., the reel system 4046' can be configured to be freely rotatable) when the reel system 4046' is moved to a second state or position. In other examples, the reel system 4046' can be configured to be selectively rotatable in either a first or a second direction, to permit a user to tighten or loosen the cable, respectively, without changing the state of the reel system 4046' (e.g., without moving the reel system 4046' between the first and second states). The strap 4004' can have a gap 4045' or space to allow adjustability or tightening of the strap 4004'. In some examples, the strap 4004' can have a strip of a flexible material (not shown) that extends across the gap 4045' to provide additional comfort to the user, and to maintain alignment of the portions of the strap 4004' on both sides of the strap 4004'.

In some examples, as in the example illustrated in FIG. 29, the cable 4042' can form a loop around one side of the strap 4004'. In this configuration, the cable 4042' can extend through guides 4044' formed on a first portion **4004*a*' of the strap 4004'. In this configuration, some examples of the second portion 4004*b*' of the strap 4004' can have a fixed or nonadjustable length. In other examples, a length of the second portion 4004*b*' of the strap 4004' can be adjusted using spring pins and micro adjustment holes in the body portion 4001' or portion of the strap 4004' coupled with the body portion 4001'**.

In other examples, the cable 4042' can extend along a length of both the first and second portions **4004*a*', 4004*b*' of the strap 4004'. For example and without limitation, some examples of the cable wire system 4040' can have a cable 4042' that forms at least one loop around the user's wrist, with the cable 4042' sliding through a plurality of guides 4044' coupled with the strap 4004' or integrally formed with the strap 4004'. In any examples, the cable 4042' can pass through the guides 4044' as the cable 4042' is tightened or loosened. In some examples, the reel system 4046' can have a low profile and be coupled with or positioned on an outside surface of the strap 4004'**.

Figure 30:
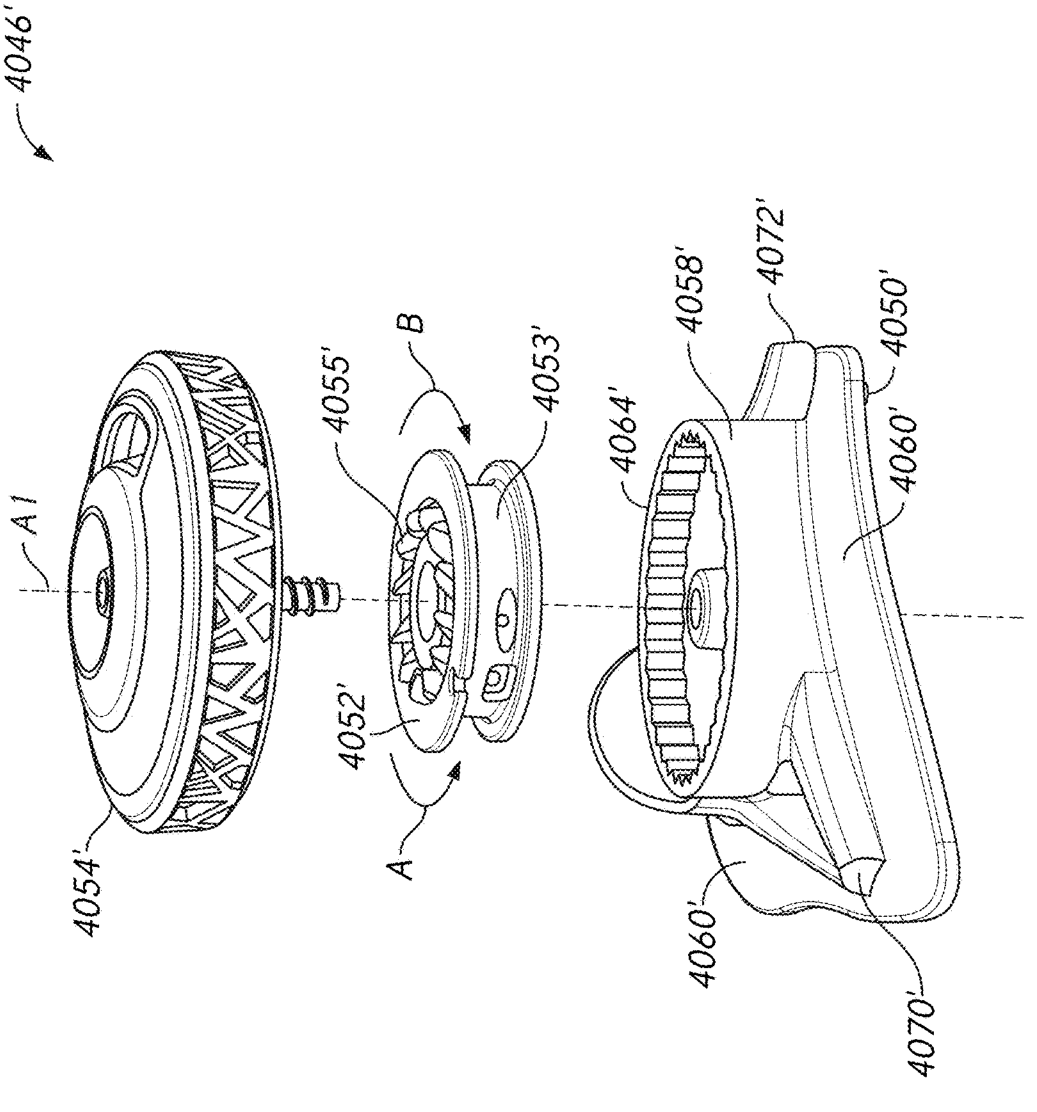
FIG. 30 shows an exploded perspective view of a portion of the reel system of the example of the wearable device shown in FIG. 29.

As shown in FIG. 30, the reel system 4046' can include a base element 4050', a spool member 4052', and a knob 4054'. For example and without limitation, the reel system 4046' shown in FIG. 30 could be configured to tighten a cable 4042' that extends along a length of both the first and second portions **4004*a*', 4004*b*' of a strap 4004' (e.g., forms at least one loop around the user's wrist). The base element 4050' can include a housing 4058' and a flange 4060'. The housing 4058' can include a plurality of radially inwardly extending teeth 4064' and openings or channels 4070', 4072' that proved a channel for the cable 4042' to pass into the housing 4058'. The spool member 4052' can be supported within the housing 4058' such that the spool member 4052' is rotatable about an axis A1 with respect to the housing 4058'. The cable 4042' can be secured to the spool member 4052' such that when the spool member 4052' rotates in a first, tightening direction (represented by arrow A in FIG. 30), the cable 4042' can be withdrawn into the housing 4058' and wrap or wind around the channel 4053' formed in the spool member 4052'. When the spool member 4052' rotates in a second, loosening direction (represented by arrow B in FIG. 30), the cable 4042' can unwind from the channel 4053' of the spool member 4052' and pass through the channels 4070', 4072' in the housing 4058'. The spool member 4052' can also include teeth or projections 4055' formed thereon configured to engage with complementary teeth on an inside, mating surface of the knob 4054' when the knob 4054' is engaged with the spool member 4052' (e.g., when the knob 4054' is in the first state or position). In some examples, the knob 4054' can be raised axially away from the spool member 4052' to move the knob 4054' from the first, engaged state to the second, disengaged or freewheeling state. Again, in the second state, the cable 4042' can be loosened. When the knob is in the first state, the teeth on the knob 4054' can be configured to mate with the spool teeth or projections 4055' to couple the knob 4054' to the spool member 4052' such that rotation of the knob 4054' in the first direction causes the spool member 4052' to simultaneously rotate in the first direction. In any examples, the components of the reel system 4046'** can be modified to reverse the tightening and loosening rotational directions.

Figure 31:
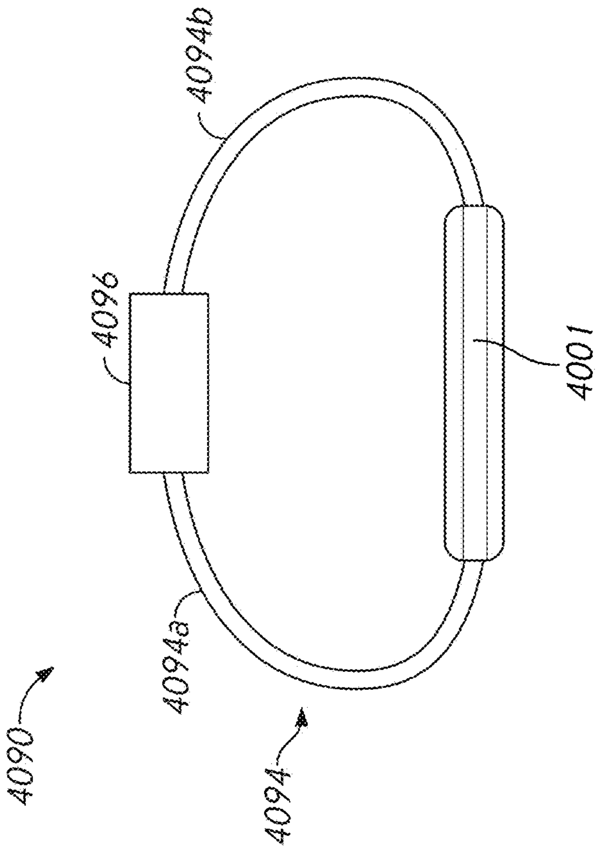
FIG. 31 is a side view of another example of a wearable device including a physiological parameter measurement sensor or module to be worn on a wrist using a strap or straps having a constant tension mechanism.

FIG. 31 shows another example of a wearable device 4090 having a body portion 4001, a strap 4094 having a first strap portion **4094*a* and a second strap portion 4094*b*, and a constant tension mechanism 4096 shown schematically therein. In some examples, the first strap portion 4094*a* and/or the second strap portion 4094*b* can be coupled with the constant tension mechanism 4096. The constant tension mechanism 4096 can be configured to provide a constant tension to the wrist of the user. For example and without limitation, some examples of the constant tension mechanism 4096 can have a wound spring therein that can be coupled with the end of the first strap portion 4094***a* and/or the second strap portion 4094*b* such that, as the spring is wound up, the first and/or second strap portions 4094*a*, 4094*b* can decrease in length and, as the spring is unwound, the first and/or second strap portions 4094*a*, 4094*b* can increase in length. In other examples, the wound spring can extend into the first strap portion 4094*a* and/or the second strap portion 4094*b* so that the size or length of the strap can be decreased as the spring of the constant tension mechanism 4096 is wound up and can be increased as the spring of the constant tension mechanism 4096 is unwound.

In some examples, when the strap 4094 is in a relaxed state, the strap 4094 can be increased in size by pulling the first and/or second strap portions 4094*a*, 4094*b* away from the constant tension mechanism 4096 with a force that is greater than the spring force of the wound spring so that the strap 4094 can be passed over the hand of the user. This can cause the wound spring of the constant tension mechanism 4096 to unwind and gain potential energy. When the strap 4094 has been passed over the user's wrist and the tension applied to the strap 4094 is released, the spring can return to the relaxed state, thereby causing the end portions of the first and/or second strap portions 4094*a*, 4094*b* to be withdrawn toward the constant tension mechanism 4096 to thereby decrease the size of the strap.

In any examples disclosed herein, the wearable device 4090 can have any of the components, features, or other details of any other examples of wearable devices disclosed herein, including without limitation any of the examples of the wearable device 4090 described herein or the wearable device 10 shown in FIG. 1A-1H or in other FIGS., in any combination with any of the components, features, or details described below. For example and without limitation, any examples of the wearable device 4090 disclosed herein can include any of the examples of the optical physiological sensors (also referred to as physiological parameter measurement sensors or merely sensors) and/or components or features thereof, any examples of the processors disclosed herein, and/or any examples of the displays and/or components or features thereof in combination with any of the other components and/or features described or shown herein. Similarly, any examples of wearable devices disclosed herein can have any of the components, features, or other details of any examples of the wearable device 4090 disclosed herein in any combination with any of the components, features, or details of the other wearable devices.

As another example of a constant tension mechanism, the example of the reel system shown in FIG. 29 or FIG. 30 can be modified such that the reel system can have a wound spring therein that is configured to rotate the reel knob and/or spool, based on the spring tension provided by a wound spring. For example and without limitation, the reel system can have a wound spring therein that is configured to automatically rotate the knob and/or spool of the reel system to cause the cable(s) of the system to be wound around the knob and/or spool of the reel system to tighten the strap. The knob can be configured to be selectively lockable and/or rotatable, in some examples. Any examples of the constant tension strap can be configured such that a user can open or loosen the strap by exerting a force on the strap that is greater than the tension provided by the constant tension mechanism or wound spring. Further, in any examples, the level of the tension can be adjusted by the user, such as by increasing the tension of a wound spring in the constant tension mechanism 4096.

As mentioned, in some examples, optimizing a tightness of the strap 4004' around the user's wrist and, hence, the contact pressure between the body portion 4001' and the skin of the user can improve the quality and accurateness of the signal(s) from the sensor(s) of the wearable device significantly. For example and without limitation, FIG. 32 shows example data from the sensor(s) of an example of a wearable device, wherein each line represents the signal obtained by the sensor for a particular wavelength of optical radiation or light that is transmitted through a user's skin.

Figure 32:
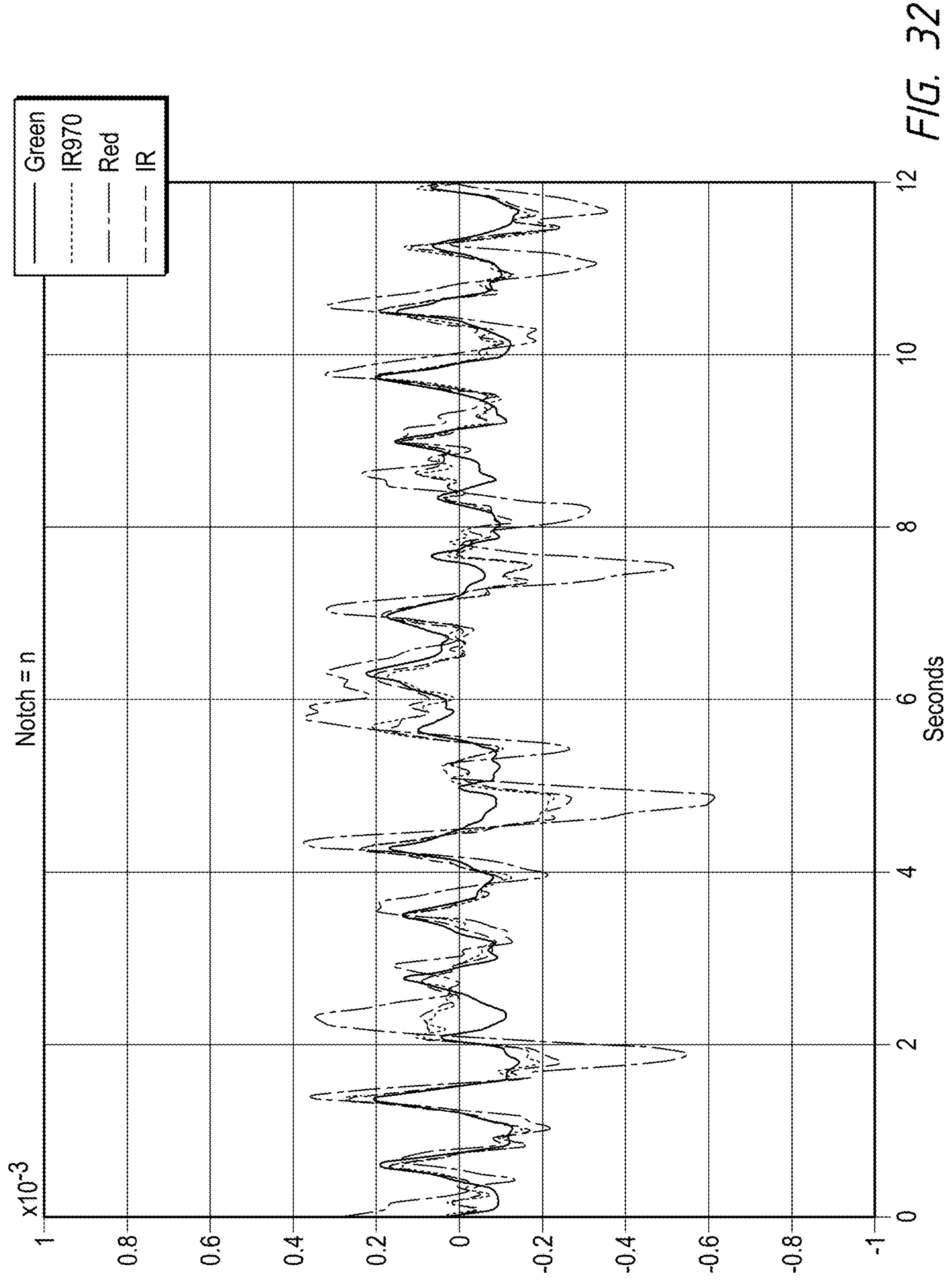
FIG. 32 shows a plot of signal data from a physiological parameter measurement sensor with the strap at a first level of tension.

The signal data from the sensors shown in FIG. 32 was obtained from the device when the strap of the device was in a first position or notch "n". By comparison, the signal data from the sensors shown in FIG. 33 was obtained from the same device and same user when the strap of the device was in a second, improved or more optimal position or notch "n−1". For example, the first position or notch "n" could be notch 9 and the second position or notch "n−1" could be notch 8 in the strap, where 8 is one notch or position tighter than notch 9. In some cases, the device can be configured to analyze the quality of the signal data to determine if the strap is too tight or too loose, both of which can, in some examples, degrade the quality of the signal data. For example and without limitation, some examples of the device can be configured to analyze phase as an indicator of the level of quality of the signal data, wherein a phase alignment can improve as you tighten the strap but can also start to degrade as you overtighten the strap. In some examples, the device can be configured to instruct a user to increase or decrease the level of tightness of the strap and then determine if the quality of the signal data has improved or degraded. If the quality of the signal data has improved and the quality level of signal data meets or exceeds the threshold or desired value, then no further adjustments may be needed. If the quality of the signal data has improved but the quality level of signal data is below the threshold or desired value, then the device can be configured to instruct the user to continue tightening the strap if the strap was tightened in the previous step or continue loosening the strap if the strap was loosened in the previous step. In some examples, without limitation, the device can be configured to instruct a user to tighten the strap until the body portion does not slide or move around with respect to skin, and then to tighten the strap one notch further.

Figure 33:
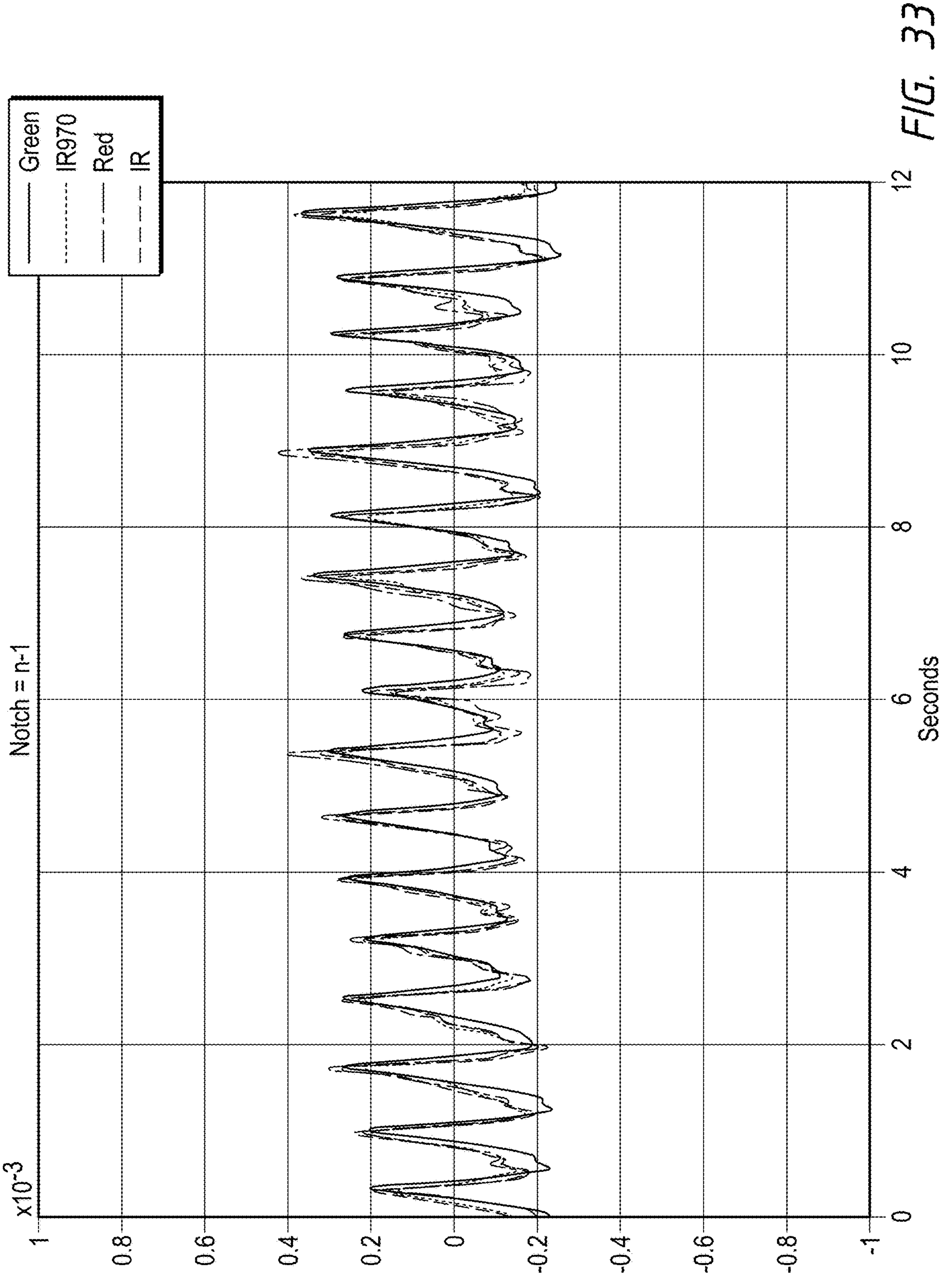
FIG. 33 shows a plot of signal data from the same physiological parameter measurement sensor with the strap at a second level of tension that is tighter than the first level of tension.

As can be seen, the quality of the signal data shown in FIG. 33 is significantly better than the quality of the signal data shown in FIG. 32, wherein the only difference is the level of tightness of the strap and, accordingly, the level of contact pressure between the body portion 4001' and the user's skin. In this example, the contact pressure between the body portion 4001' and the user's skin is greater in the second position, resulting in higher quality signal data from the sensor(s). In some examples, the quality of the signal data, can be improved by increasing the level of tightness of the strap and, accordingly, the contact pressure between the body portion 4001' of the device 4000' and the user's skin. For example and without limitation, better alignment of phases between data signals of different wavelengths of light, more consistent waveforms and amplitudes of the waveforms, feature extraction, and other parameters related to the signal data can be measured and analyzed to assess the quality of the signal data. Note that, in some examples, the strap should not be tightened to the point of restricting capillaries or otherwise impeding or affecting blood flow through the wrist of the user. Overtightening the strap can also degrade the signal quality by introducing noise and, if too tight, can make the signal data unusable. As an additional example, without limitation, better alignment of phases between data signals of different wavelengths of light can be achieved by loosening the strap, if the strap has been overtightened. Hence, in some examples, there may be an upper limit to the level of tightness of the strap of the device, at which the tightness of the strap is not physiologically optimal.

Figure 34:
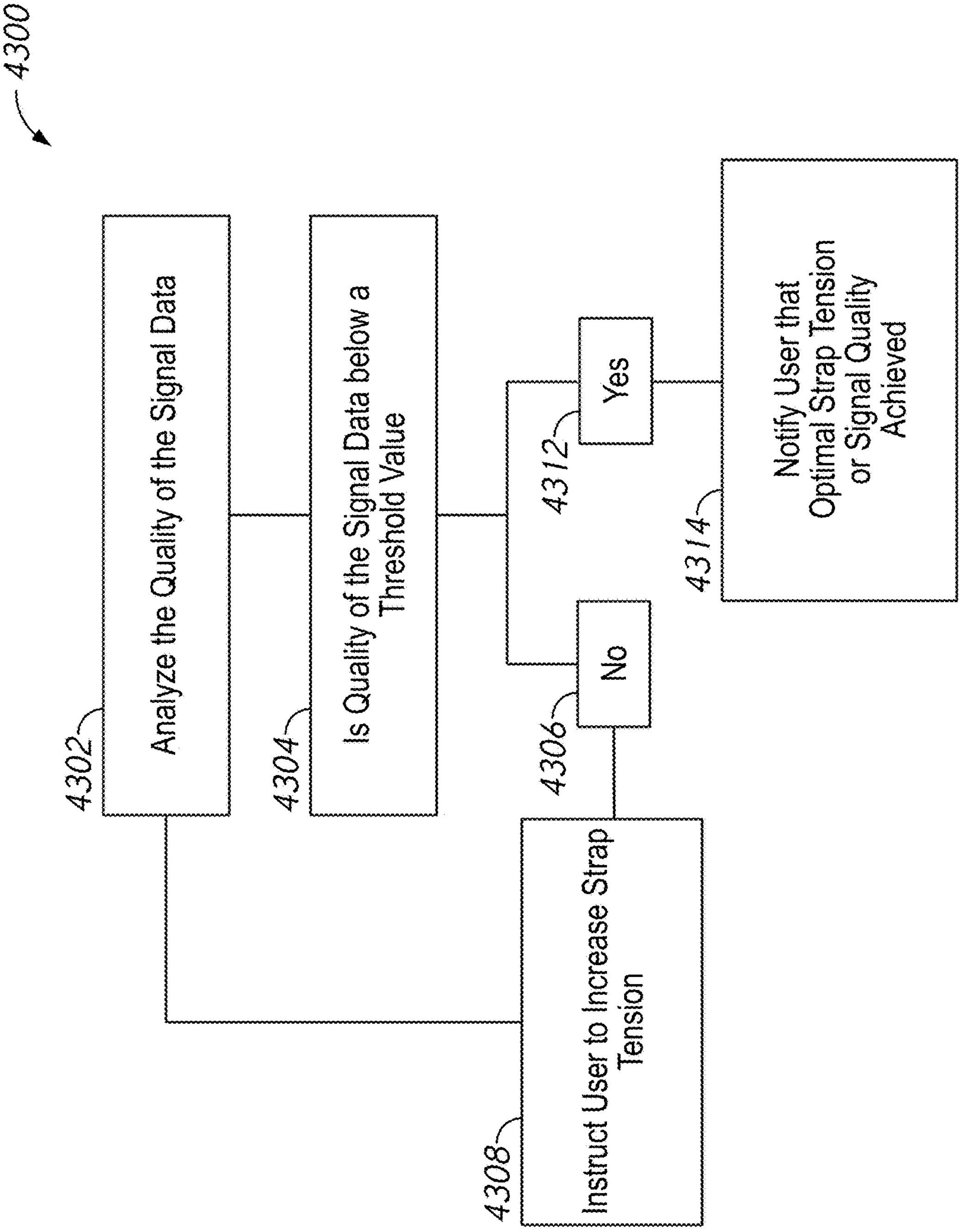
FIG. 34 is a flow chart showing an example of a process for analyzing a quality of the signal data from physiological parameter measurement sensor by a processor of an example of a wearable device.
Figure 36:
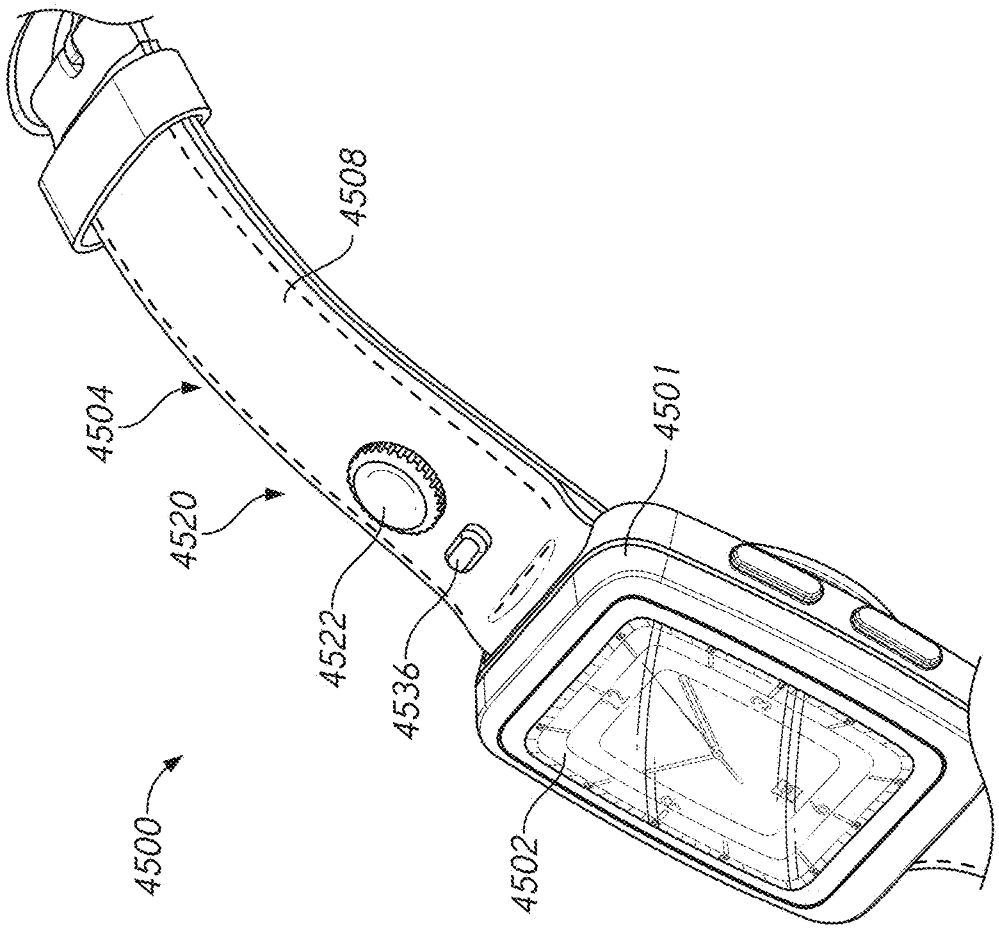
FIGS. 35-39 show another example of wearable device that can be configured to be secured to a wrist of a user.

FIG. 34 is a flow chart showing an example of a process 4300 for analyzing a quality of the signal data from a physiological parameter measurement sensor by a processor of an example of a wearable device. In some examples, with reference to FIG. 34, the device 4000' or 4090 can be configured to analyze the quality of the signal data from a physiological parameter measurement sensor 4302 and provide feedback to a user regarding the quality of the signal data. For example and without limitation, if the quality of the signal data is determined by the processor to be below a predefined threshold or desired value (collectively, threshold value), as shown at step 4306 in FIG. 34, or, in some examples, at a predefined threshold value, the device can be configured to, at step 4308 in FIG. 34, output an appropriate warning to the user and/or provide an instruction to the user to increase the tightness of the strap or decrease the size of the strap to increase the contact pressure between the body portion 4001 and 4001' of the device and the user's skin. The process 4300 can then, after instructing the user to increase the strap tension, to analyze the quality of the signal data from a physiological parameter measurement sensor 4032 and provide feedback to a user regarding the quality of the signal data.

This process can be repeated until the quality of the signal data is determined by the processor to be above a predefined threshold value, as shown at step 4312 in FIG. 34, or, in some examples, at a predefined threshold value. Additionally, if the quality of the signal data is above a predefined threshold value or, in some examples, at a predefined threshold value, the device can be configured to, at step 4314 in FIG. 34, output an appropriate message to the user to indicate to the user that an appropriate or optimal strap tension has been achieved and/or prompt the user to record or remember the wrist strap notch position or setting, as appropriate.

In some examples, the device can be configured with an automatic tightening system, wherein the system processor can also control one or more powered tightening mechanisms of the strap. For example and without limitation, some examples of the device can be configured such that, if the quality of the signal data is determined by the processor to be below a predefined threshold value or, in some examples, at a predefined threshold value, the device can automatically tighten the strap to a second level of tightness and then analyze the quality of the signal data at the second level of tightness to determine if the quality of the signal data is at, below, or above a predefined threshold value. If the quality of the signal data at the second level of tightness is determined by the processor to be below a predefined threshold value or, in some examples, at a predefined threshold value, the device can automatically tighten the strap to a third level of tightness and then analyze the quality of the signal data at the third level of tightness to determine if the quality of the signal data is at, below, or above a predefined threshold value. This can be repeated until the quality of the signal data is determined by the processor to be at or above a predefined threshold value.

FIGS. 35-39 show another example of wearable device 4500 that can be configured to be secured to a wrist of a user. The wearable device 4500 can have a body portion 4501 having a graphical interface or display screen 4502. The body portion 4501 can, in some examples, have a case or housing that houses or supports the electronic components of the wearable device 4500, including one or more sensors, a processor, a power supply, and the display screen 4502. The wearable device 4500 can also have a strap 4504 (also referred to as a band) that can be used to secure the body portion 4501 of the wearable device 4500 to a wrist of the user. For example and without limitation, some examples of the wearable device 4500 can look or be similar to a wrist watch.

In any examples disclosed herein, the wearable device 4500 can have any of the components, features, or other details of any other examples of wearable devices disclosed herein, including without limitation any of the examples of the wearable device 10 shown in FIGS. 1A-1H, in any combination with any of the components, features, or details described below. For example and without limitation, any examples of the wearable device 4500 disclosed herein can include any of the examples of the optical physiological sensors (also referred to as physiological parameter measurement sensors or merely sensors) and/or components or features thereof, any examples of the processors disclosed herein, and/or any examples of the displays and/or components or features thereof in combination with any of the other components and/or features described or shown herein. Similarly, any examples of wearable devices disclosed herein can have any of the components, features, or other details of any examples of the wearable device 4500 disclosed herein in any combination with any of the components, features, or details of the other wearable devices.

The strap 4504 of any examples of the wearable device 4500 disclosed herein can be adjustable. In some examples, the strap 4504 can include a first strap portion 4508 and a second strap portion 4510. The first strap portion 4508 can include a buckle 4514 and a buckle pin 4516 (also referred to as a buckle tongue) that can be configured to be advanced into any of a plurality of notches (not shown) formed in the second strap portion 4510 so that a user can adjust a size or tightness of the strap 4504 around the user's wrist. In some examples, the notches can be numbered or uniquely identified so that a user can easily record and/or recall a tightness setting of the strap 4504. The numbers or unique identifiers can be in several forms including visual markers and/or protrusions and/or indentations. As discussed, in some examples, optimizing a tightness of the strap 4504 around the user's wrist and, hence, the contact pressure between the body portion 4501 and the skin of the user can improve the quality and accurateness of the signal(s) from the sensor(s) of the wearable device significantly.

Any examples of the wearable devices disclosed herein, including any examples of the wearable device 4500, can have a mechanical adjustment mechanism 4520 (also referred to herein as a mechanical adjustment unit) that can be used to increase and/or decrease a level of tightness of the strap 4504. At least some of the components of the mechanical adjustment mechanism 4520 can be coupled with or integrated into the strap 4504, such as the first strap portion 4508.

Figure 37:
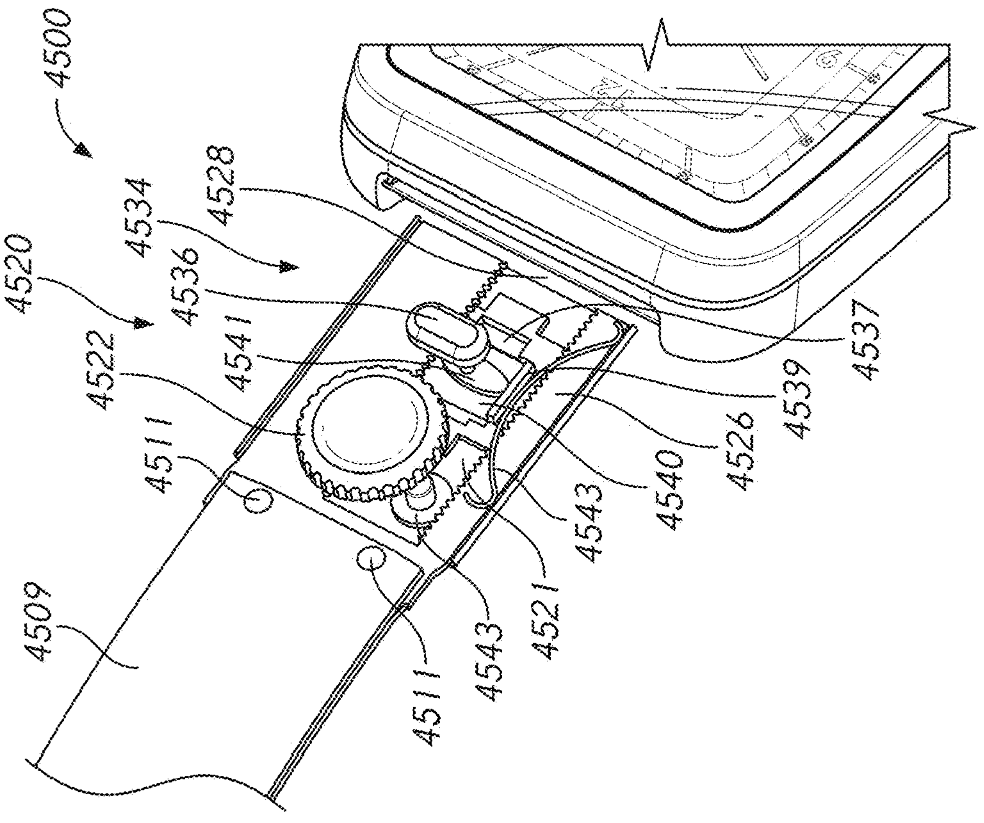
Figure 39:
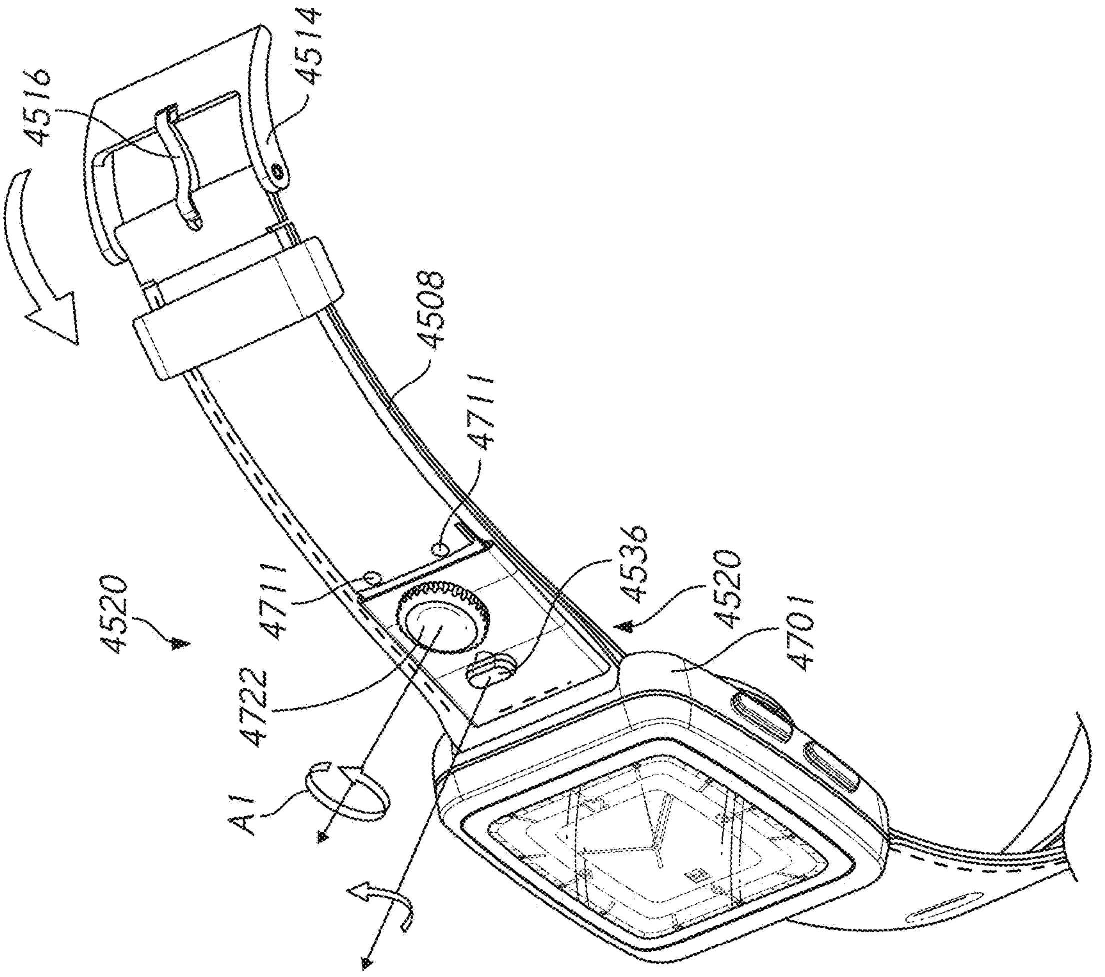
Figure 41:
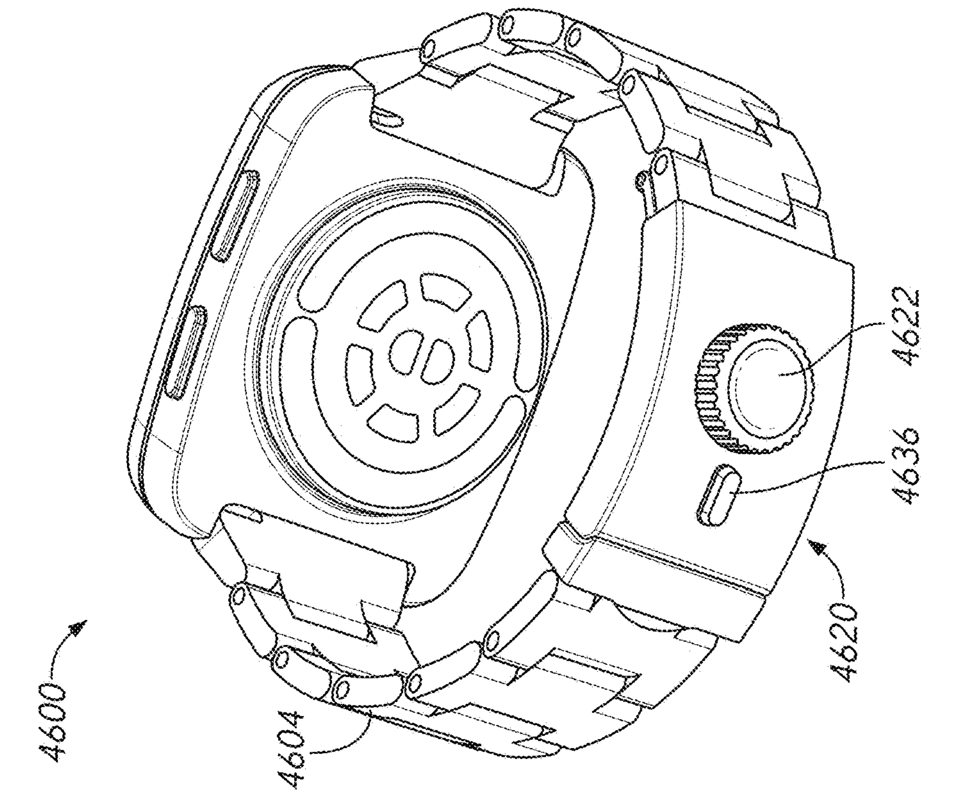
FIGS. 40-45 show another example of wearable device that can be configured to be secured to a wrist of a user.
Figure 40:
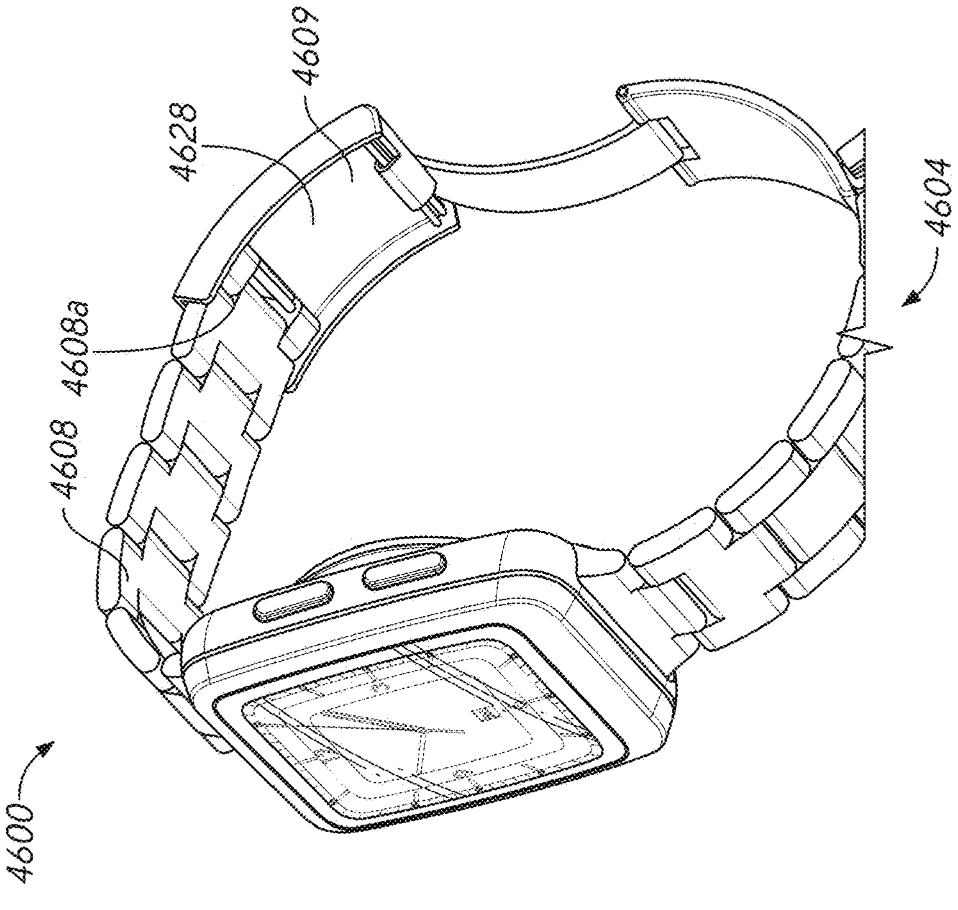
Figure 43:
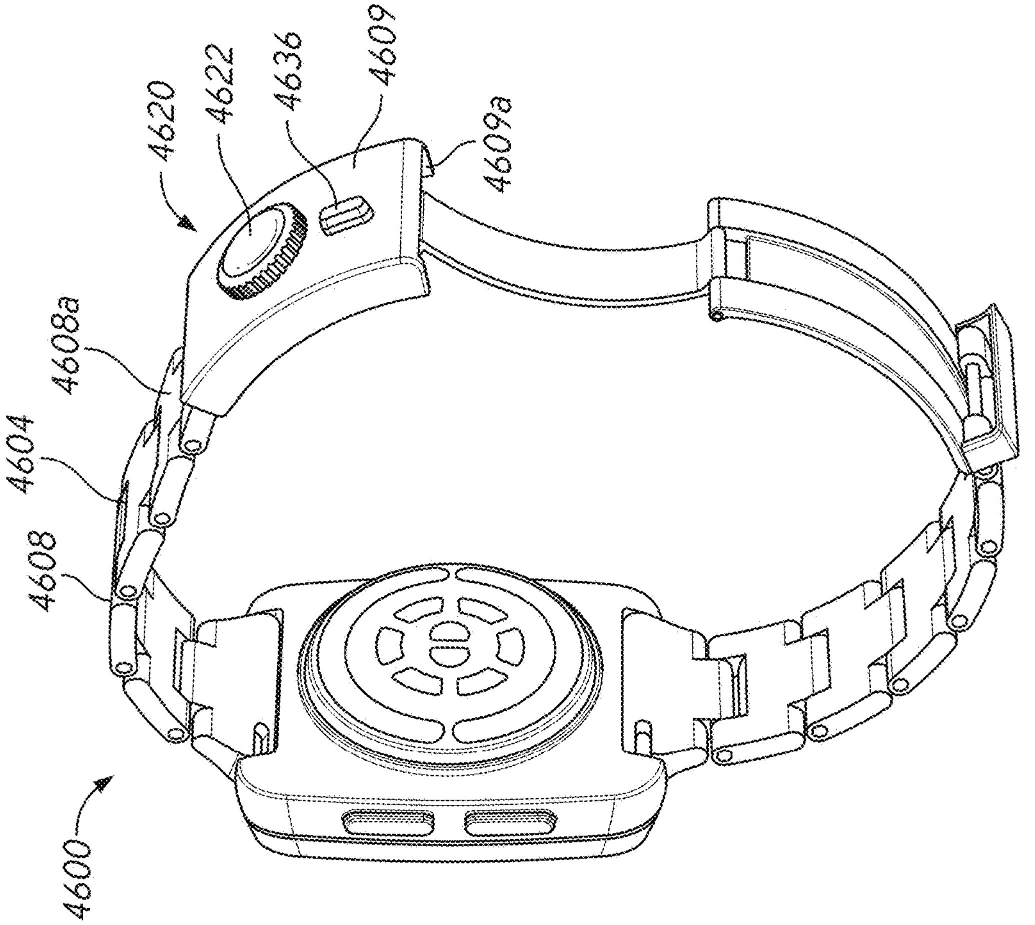
Figure 42:
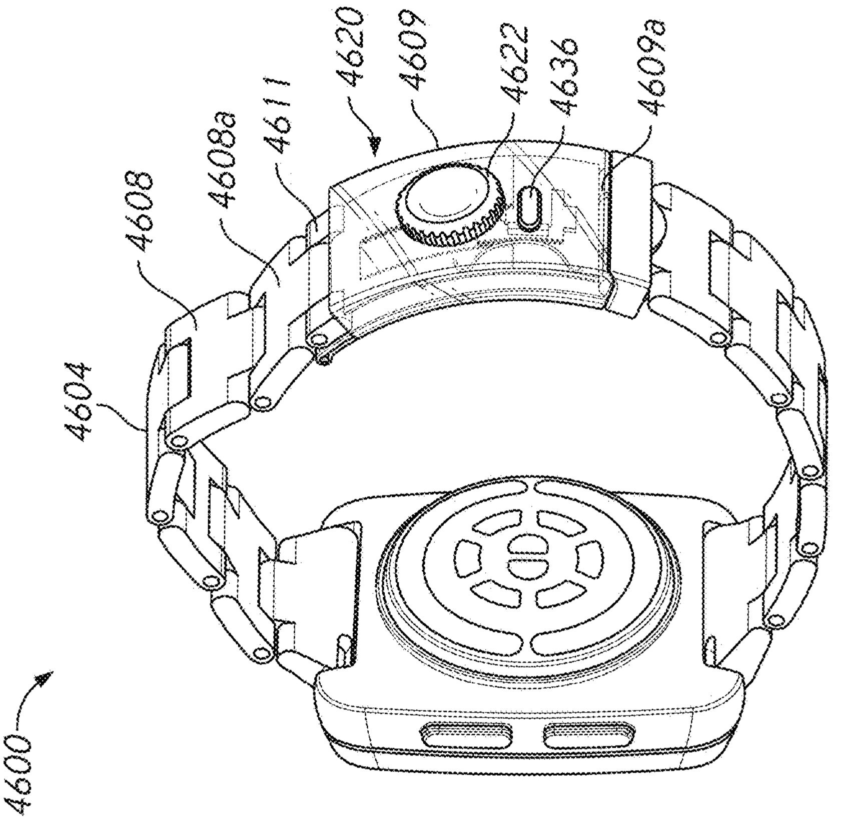
Figure 44:
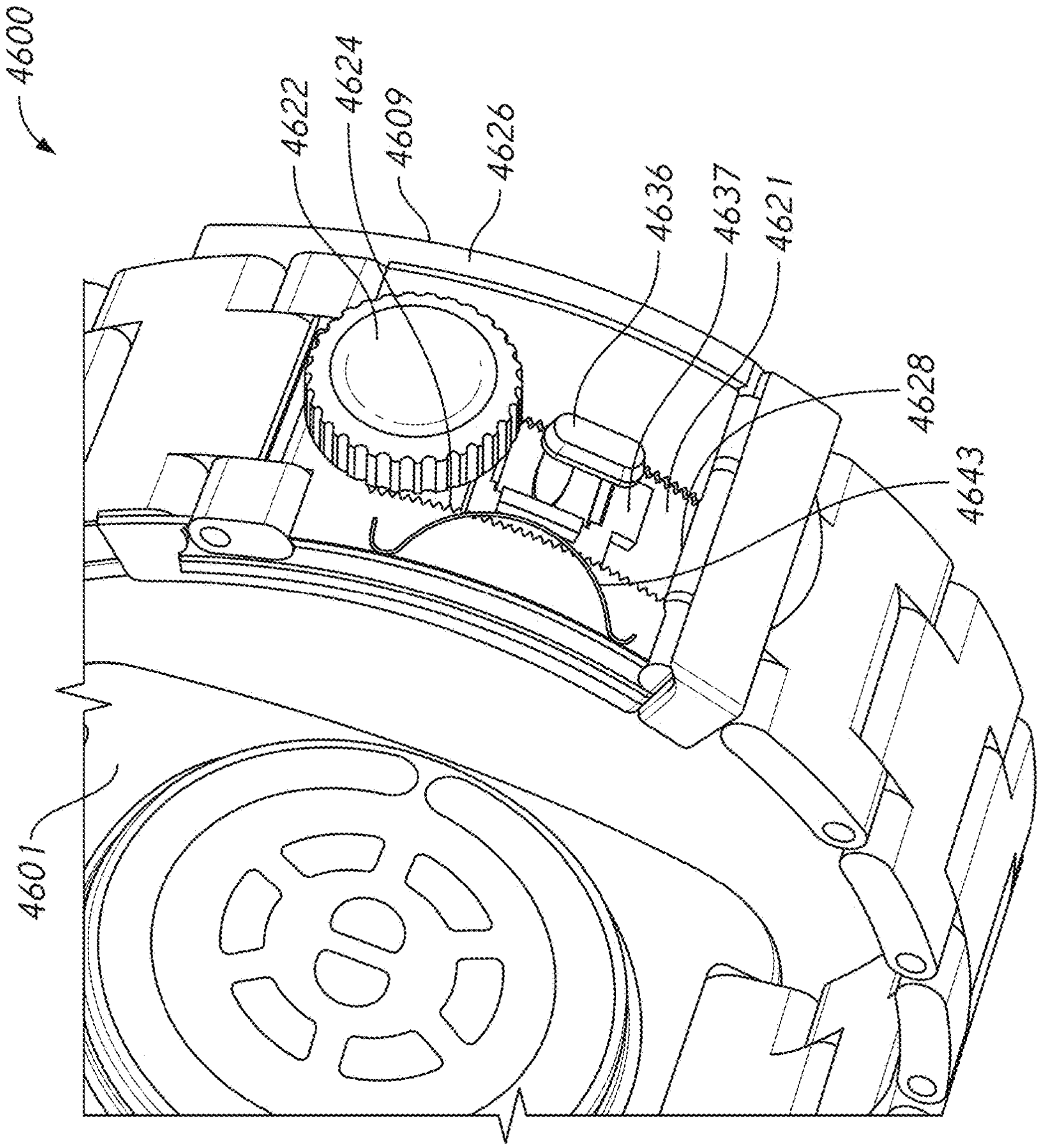

In some examples, the mechanical adjustment mechanism 4520 can include a rack and pinion system including at least a support body 4521, a dial 4522, a gear 4524 (e.g., a pinion gear) rotationally coupled or locked to the dial 4522, and a rack 4526. With reference to FIG. 37, the support body 4521 can be configured to support some of the other components of the mechanical adjustment mechanism 4520, including for example and without limitation, the dial 4522 and gear 4524. In some examples, the support body 4521 can be coupled with the body portion 4501 of the device so that the dial 4522 and gear 4524 can be held in a fixed position relative to the body portion 4501 of the wearable device 4500. The dial 4522 and gear 4524 can be configured to freely rotate relative to the support body 4521. In some examples, the gear 4524 can be integrally formed with the dial 4522.

In some examples, an end portion of the rack 4526 can be coupled with an end portion of the strap core layer 4509 using pins or other fasteners 4511, and/or using adhesive, stitching, a clamp mechanism, or any other suitable fastening components or means. The rack 4526 can be configured to translate relative to the support body 4521 by the action of the mechanical adjustment mechanism 4520, as will be described in greater detail below. Because the support body 4521 can be rigidly coupled with the body portion 4501 of the wearable device 4500, translational movement of the rack 4526 relative to the support body 4521 can cause the simultaneous and equal translational movement of the strap core layer 4509 that can be coupled with the rack 4526. This can be achieved through adjustment of the mechanical adjustment mechanism 4520, as described herein.

The dial 4522 can be configured to be rotated by a user in either direction, thereby rotating the gear 4524 in either direction, to either tighten or loosen the mechanical adjustment mechanism 4520. For example and without limitation, in any examples, the gear 4524 can be configured to engage or mesh with the rack 4526, which can have a linear arrangement of teeth thereon that are configured to engage with or mesh with the plurality of teeth on the gear 4524. In this arrangement, the rotational movement of the gear 4524 can translate into and/or can cause a linear movement of the rack 4526 relative to the support body 4521. For example and without limitation, a rotation of the gear 4524 in a first direction (such as, without limitation, a clockwise direction) can cause the rack 4526 to move in a first linear direction relative to the support body 4521 (such as, without limitation, in a direction away from the body portion 4501 of the wearable device 4500) to thereby increase a length of the strap 4504. In some examples, the rack 4526 can be configured to translate out of and into of a space 4528 formed in the body portion 4501 as the dial 4522 and the gear 4524 are rotated in the first and second directions, respectively.

The mechanical adjustment mechanism 4520 can be configured such that, as the rack 4526 is translated in either direction relative to the support body 4521 by the rotation of the dial 4522, the strap core layer 4509 and/or first strap portion 4508 that can be coupled with the rack 4526 can be equally and simultaneously translated either direction. In this arrangement, the strap 4504 can be loosened or tightened by the rotation of the dial 4522 in the first direction or second direction, respectively.

The strap core layer 4509 can include a braided, mesh, or fabric material, or any other suitable material that can resist stretching when under a tensile load. In other examples, the strap core layer 4509 can be a flexible and/or resilient material. A leather layer or layer of other material can surround the strap core layer 4509 to provide a greater level of comfort and aesthetics to the first strap portion 4508 than the strap core layer 4509.

Figure 35:
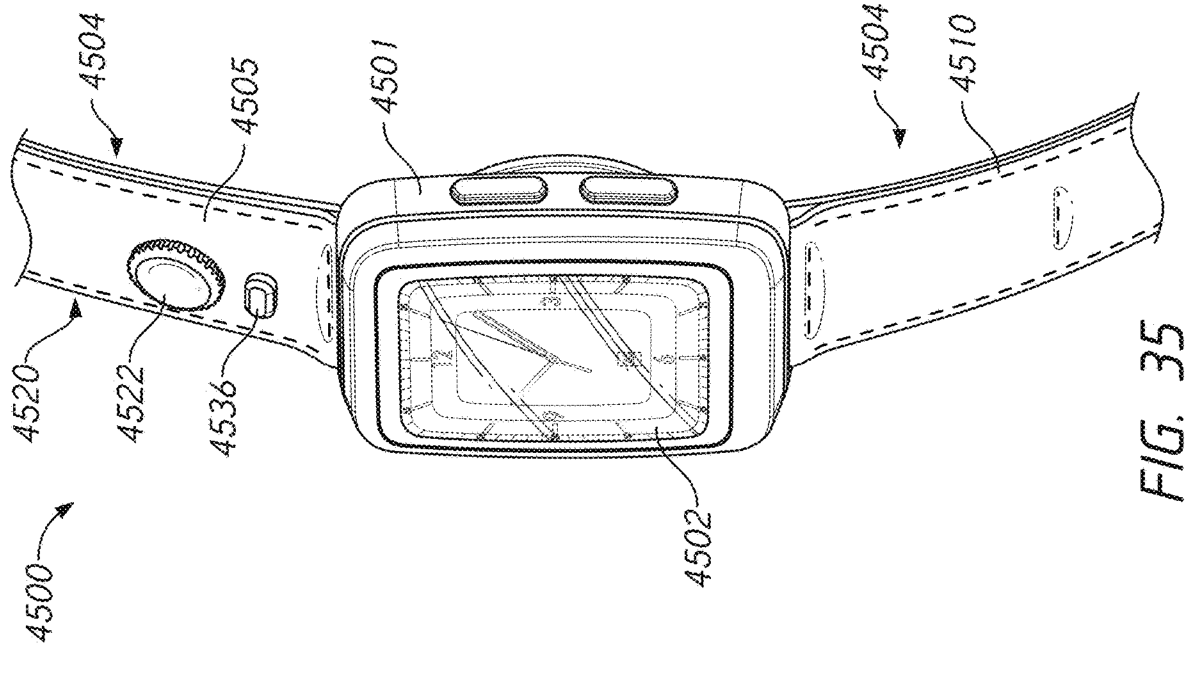
Figure 38:
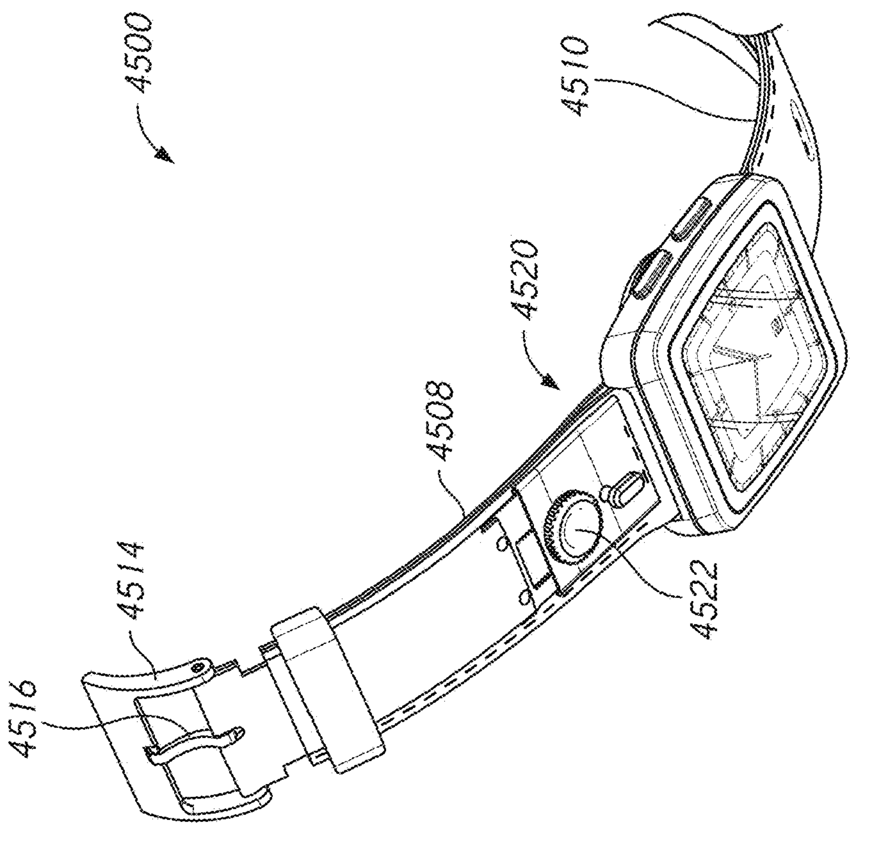

In any examples, the mechanical adjustment mechanism 4520 can include a locking mechanism 4534 configured to selectively inhibit (e.g., prevent) a movement of the mechanical adjustment mechanism 4520 and the first strap portion 4508 relative to the body portion 4501. For example and without limitation, the locking mechanism 4534 can be selectively engaged to inhibit (e.g., prevent) a movement of the mechanical adjustment mechanism 4520 and the first strap portion 4508 relative to the body portion 4501 and disengaged to permit a movement of the mechanical adjustment mechanism 4520 and the first strap portion 4508 relative to the body portion 4501. Some examples of the locking mechanism 4534 be supported by or coupled with the support body 4521. The locking mechanism 4534 can have a lever 4536 configured to rotate between a first position (as shown in FIG. 35) in which the locking mechanism 4534 is engaged and a second position (as shown in FIG. 38) in which the locking mechanism 4534 is disengaged. A cam or projection 4541 that can be rotationally coupled with the lever 4536 can be configured to move a lock body 4537 into engagement with the rack 4526 to prevent the movement of the rack 4526 relative to the support body 4521. The cam or projection can be configured to engage with a flange or tab 4539 formed on or coupled with the lock body 4537 so that, as the cam is rotated into contact with the flange or tab 4539, the cam can force the lock body 4537 to move into engagement with the rack 4526. The lock body 4537 can slide in a lateral direction relative to the support body 4521, but be restrained from any movement in the longitudinal direction relative to the support body 4521. The locking mechanism 4534 can include a spring 4543 configured to bias the lock body 4537 away from the rack 4526 (i.e., toward a disengaged position).

In this arrangement, a user can disengage the locking mechanism 4534 by rotating the lever 4536 to the second position before tightening or loosening the strap 4504 and can, for example and without limitation, engage the locking mechanism 4534 by rotating the lever 4536 to the first position after tightening the strap 4504. The locking mechanism 4534 can have a lock body 4537 that can be slid into and out of engagement with a portion of the rack 4526 to either lock or unlock the mechanical adjustment mechanism 4520.

In any examples, as described above, the strap 4504 of the wearable device 4500 can have a separate clasping mechanism that can include, for example and without limitation, a buckle 4514 and a buckle pin 4516 that can engage with corresponding features on the second strap portion 4510 to secure the wearable device 4500 to the user's wrist and also provide for a separate and additional tightening and loosening mechanism relative to the mechanical adjustment mechanism 4520. The user can also remove the wearable device 4500 from his or her wrist by separating the strap at the clasping mechanism.

In any examples, the 4520 can be positioned in a clasp portion of a metal strap or band. For example and without limitation, with reference to FIGS. 40-45, the example of the wearable device 4600 shown therein can have a metal strap or band 4604 having any of the components, features, or other details of any other examples of wearable devices disclosed herein, including without limitation any of the examples of the device 4000 and/or the wearable device 4500, in any combination with any of the components, features, or details described below. Additionally, as mentioned, the wearable device 4600 can have a metal strap having any of the same components, features, or other details of the strap 4004 having metal links described above.

With reference to FIGS. 40-45, similar to the wearable device 4500, the wearable device 4600 can have a body portion 4601 having a graphical interface or display screen 4602. The body portion 4601 can, in some examples, have a case or housing that houses or supports the electronic components of the wearable device 4600, including one or more sensors, a processor, a power supply, and the display screen 4602.

The metal strap or band 4604 of any examples of the wearable device 4600 disclosed herein can have a mechanical adjustment mechanism 4620 having any of the same components, features, and details of the mechanical adjustment mechanism 4520 described above, to adjust the tension or tightness of the metal strap or band 4604. As discussed, in some examples, optimizing a tightness of the metal strap or band 4604 around the user's wrist and, hence, the contact pressure between the body portion 4601 and the skin of the user can improve the quality and accurateness of the signal (s) from the sensor(s) of the wearable device significantly.

Figure 45:
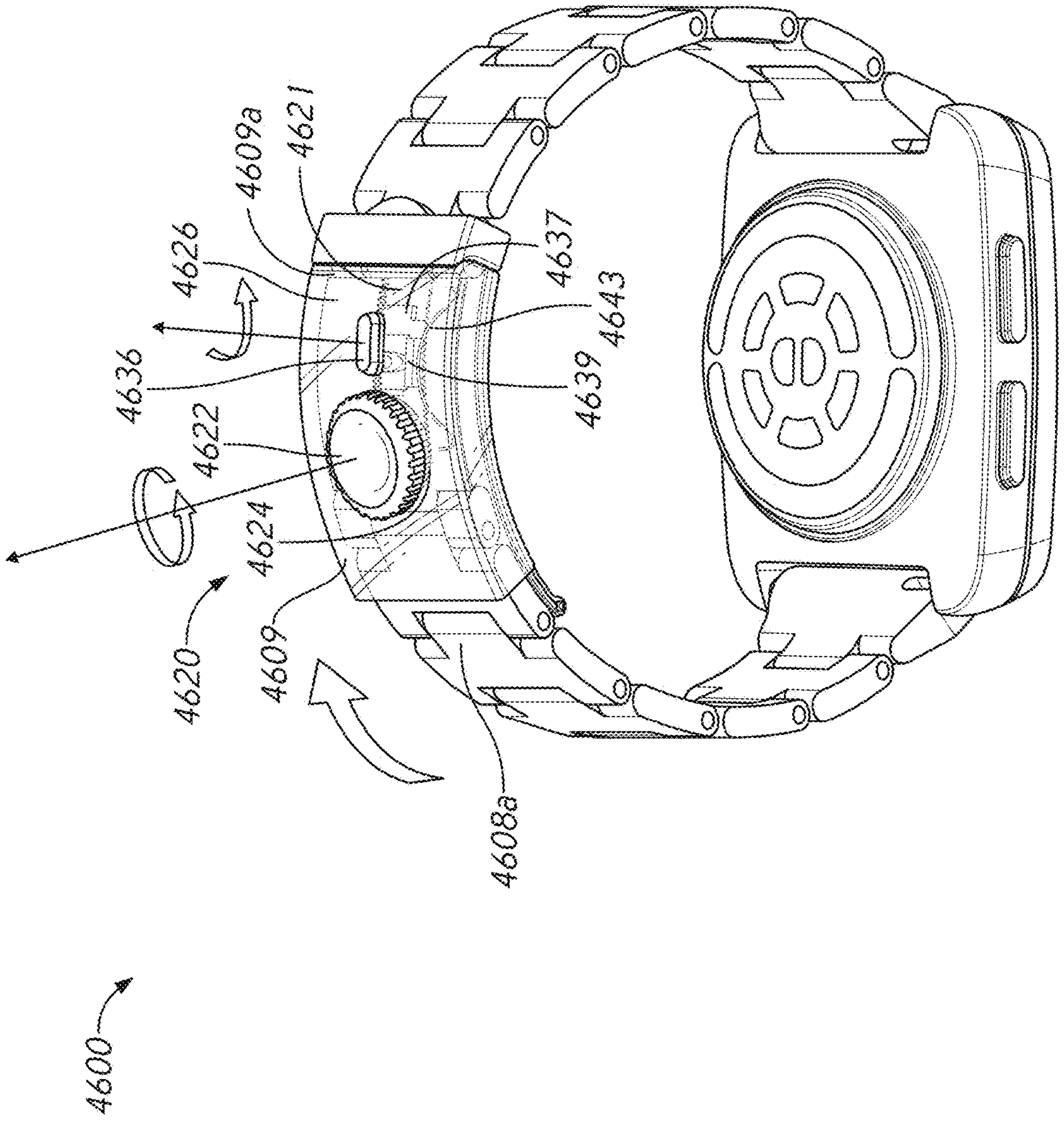
Figure 47:
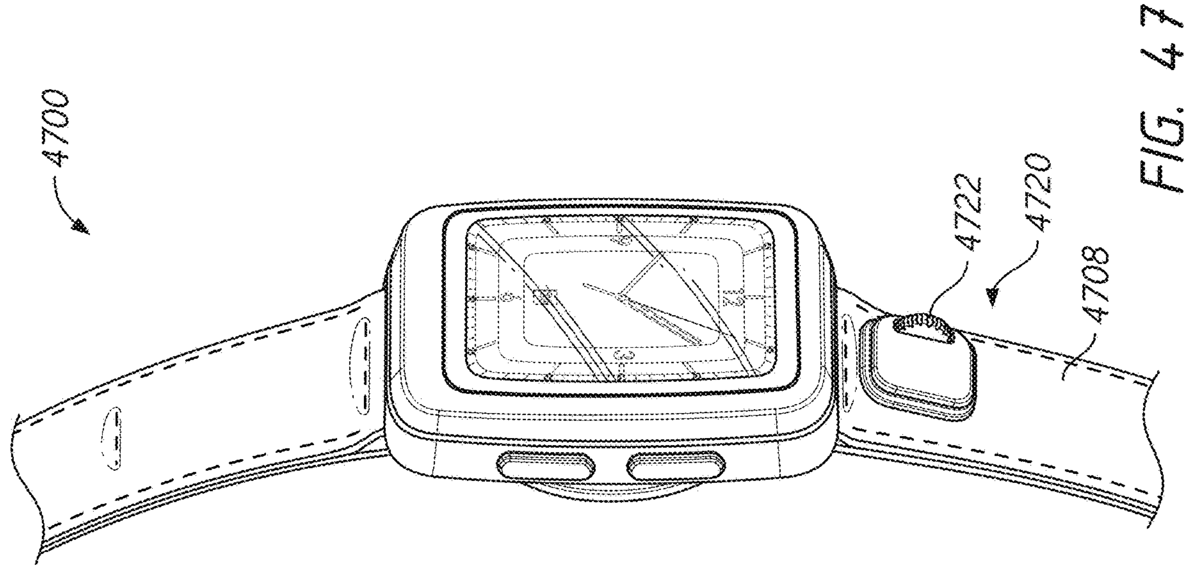
FIGS. 46-50 show another example of wearable device that can be configured to be secured to a wrist of a user.
Figure 46:
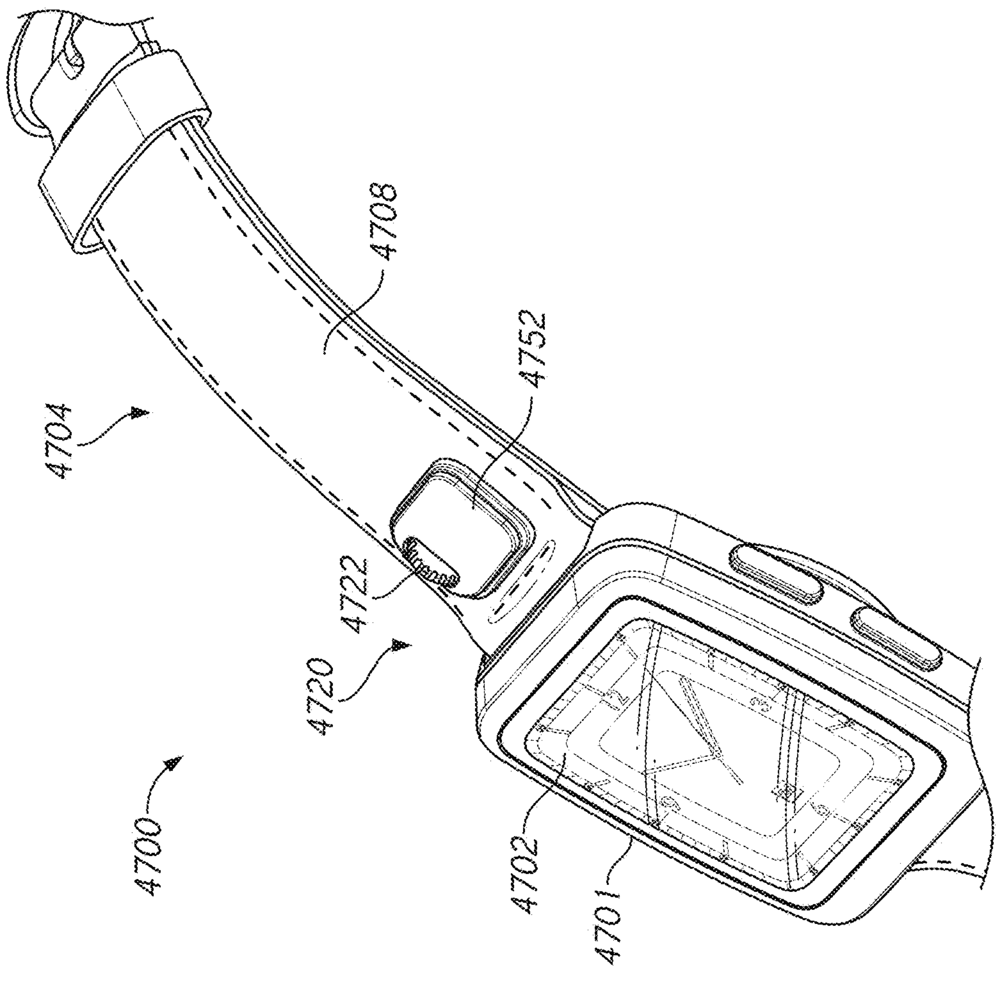

At least some of the components of the mechanical adjustment mechanism 4620 can be coupled with or integrated into the clasp 4609 of the first strap portion 4608 of the metal strap or band 4604. In some examples, the mechanical adjustment mechanism 4620 can include a rack and pinion system including at least a support body 4621, a dial 4622, a gear 4624 (e.g., a pinion gear) rotationally coupled or locked to the dial 4622, and a rack 4626. With reference to FIG. 45, the support body 4621 can be configured to support some of the other components of the mechanical adjustment mechanism 4620, including for example and without limitation, the dial 4622 and gear 4624. In some examples, the support body 4621 can be coupled with the clasp 4609 of the device so that the dial 4622 and gear 4624 can be held in a fixed position relative to the clasp 4609 while the rack 4626 can translate in a lengthwise direction relative to the support body 4621 and the clasp 4609 to tighten and loosen the metal strap or band 4604. The dial 4622 and gear 4624 can be configured to freely rotate relative to the support body 4621. In some examples, the gear 4624 can be integrally formed with the dial 4622.

In some examples, an end portion of the rack 4626 can be coupled with an end portion 4608*a* of the first strap portion 4608. For example, a special link 4611 can be connected with the end portion of the rack 4626 to couple the first strap portion 4608 with the rack 4626. The rack 4626 can be configured to translate relative to the support body 4621 by the action of the mechanical adjustment mechanism 4620. Because the support body 4621 can be rigidly coupled with the clasp 4609, translational movement of the rack 4626 relative to the support body 4621 can cause the simultaneous and equal translational movement of the first strap portion 4608 that can be coupled with the rack 4626. This can be achieved by rotating the dial 4622.

The dial 4622 can be configured to be rotated by a user in either direction, thereby rotating the gear 4624 in either direction, to either tighten or loosen the mechanical adjustment mechanism 4620. For example and without limitation, the gear 4624 can be configured to engage or mesh with the rack 4626, which can have a linear arrangement of teeth thereon that are configured to engage with or mesh with the plurality of teeth on the gear 4624. In this arrangement, the rotational movement of the gear 4624 can translate into and/or can cause a linear movement of the rack 4626 relative to the clasp 4609. For example and without limitation, a rotation of the gear 4624 in a first direction can cause the rack 4626 to move in a first linear direction relative to the clasp 4609 (such as, without limitation, in a direction away from a distal end portion 4609*a* of the clasp 4609) to thereby increase a length of the metal strap or band 4604. In some examples, the rack 4626 can be configured to translate out of and into of a space 4628 formed in the clasp 4609 as the dial 4622 and the gear 4624 are rotated in the first and second directions, respectively.

The mechanical adjustment mechanism 4620 can be configured such that, as the rack 4626 is translated in either direction relative to the support body 4621 by the rotation of the dial 4622, the first strap portion 4608 that can be coupled with the rack 4626 can be equally and simultaneously translated either direction. In this arrangement, the metal strap or band 4604 can be loosened or tightened by the rotation of the dial 4622 in the first direction or second direction, respectively.

In any examples, the mechanical adjustment mechanism 4620 can include a locking mechanism 4634 configured to selectively inhibit (e.g., prevent) a movement of the mechanical adjustment mechanism 4620 and the first strap portion 4608 relative to the body portion 4601. The locking mechanism 4634 can have a lever 4636, a cam or projection 4641 that can be rotationally coupled with the lever 4636, a lock body 4637 having a flange 4639, a spring 4643, and other components and features. In some examples, the locking mechanism 4634 can operate in a manner similar to the locking mechanism 4534 of the examples of the wearable device 4500 described above, and can have any of the same components and features as the locking mechanism 4534.

FIGS. 46-50 show another example of wearable device 4700 that can be configured to be secured to a wrist of a user. The wearable device 4700 can have a body portion 4701 having a graphical interface or display screen 4702. The body portion 4701 can, in some examples, have a case or housing that houses or supports the electronic components of the wearable device 4700, including one or more sensors, a processor, a power supply, and the display screen 4702. The wearable device 4700 can also have a strap 4704 (also referred to as a band) that can be used to secure the body portion 4701 of the wearable device 4700 to a wrist of the user.

In any examples disclosed herein, the wearable device 4700 can have any of the components, features, or other details of any other examples of wearable devices disclosed herein, including without limitation any of the examples of the wearable device 10 shown in FIGS. 1A-1H and/or the examples of the wearable devices 4500, 4600, in any combination with any of the components, features, or details described below. For example and without limitation, any examples of the wearable device 4700 disclosed herein can include any of the examples of the optical physiological sensors (also referred to as physiological parameter measurement sensors or merely sensors) and/or components or features thereof, any examples of the processors disclosed herein, and/or any examples of the displays and/or components or features thereof in combination with any of the other components and/or features described or shown herein. Similarly, any examples of wearable devices disclosed herein can have any of the components, features, or other details of any examples of the wearable device 4700 disclosed herein in any combination with any of the components, features, or details of the other wearable devices.

The strap 4704 of any examples of the wearable device 4700 disclosed herein can be adjustable. In some examples, the strap 4704 can include a first strap portion 4708 and a second strap portion 4710. The first strap portion 4708 can include a buckle 4714 and a buckle pin 4716 (also referred to as a buckle tongue) that can be configured to be advanced into any of a plurality of notches (not shown) formed in the second strap portion 4710 so that a user can adjust a size or tightness of the strap 4704 around the user's wrist. Other examples of the device can have other fastening clasps or mechanisms to selectively connect the first and second strap portions 4708, 4710 together. In some examples that have notches in the second strap portion 4710, the notches can be numbered or uniquely identified so that a user can easily record and/or recall a tightness setting of the strap 4704. As discussed, in some examples, optimizing a tightness of the strap 4704 around the user's wrist and, hence, the contact pressure between the body portion 4701 and the skin of the user can improve the quality and accurateness of the signal (s) from the sensor(s) of the wearable device significantly.

Any examples of the wearable devices disclosed herein, including any examples of the wearable device 4700, can have a mechanical adjustment mechanism 4720 that can be used to increase and/or decrease a level of tightness of the strap 4704. At least some of the components of the mechanical adjustment mechanism 4720 can be coupled with or integrated into the strap 4704, such as the first strap portion 4708 as shown.

Figure 53:
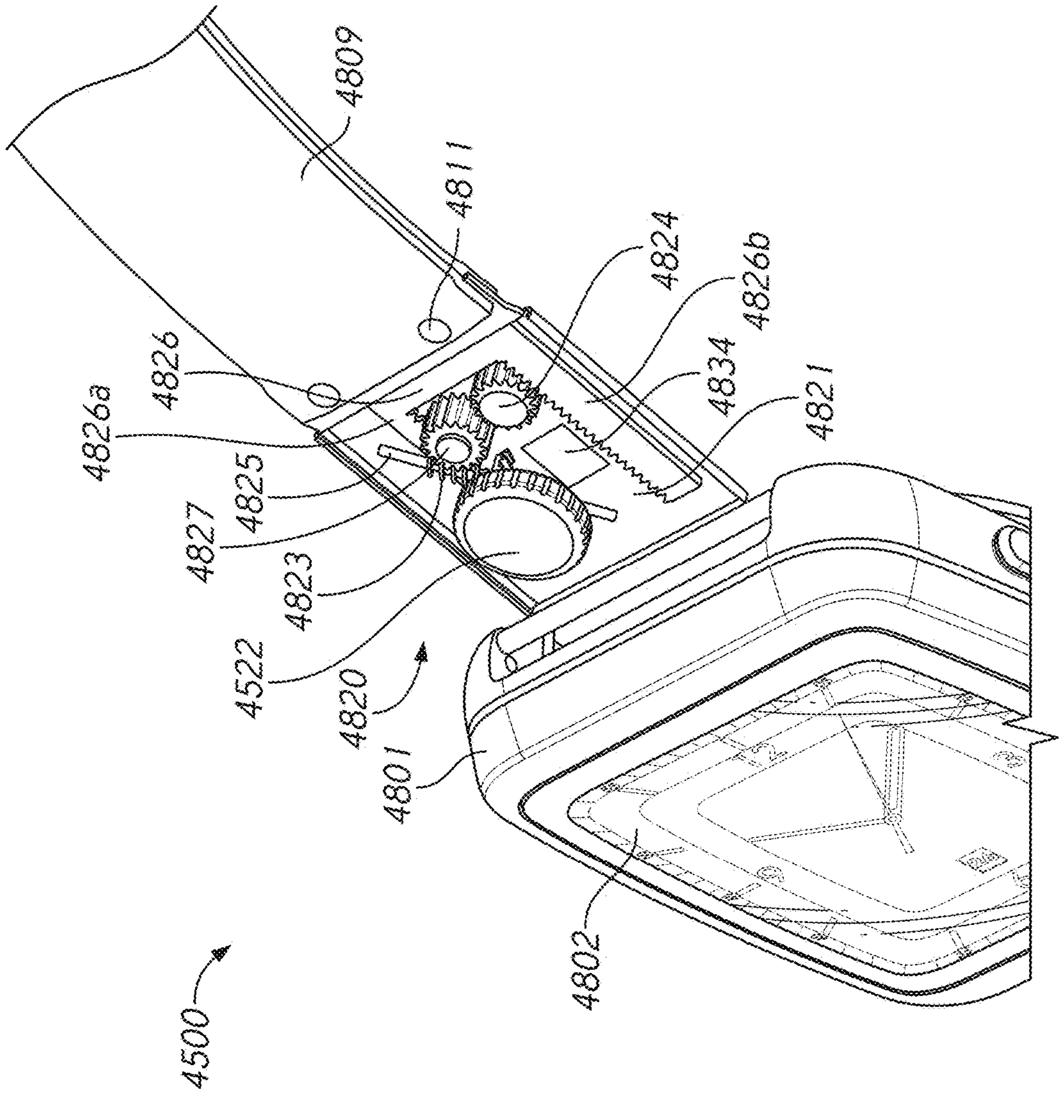
Figure 55:
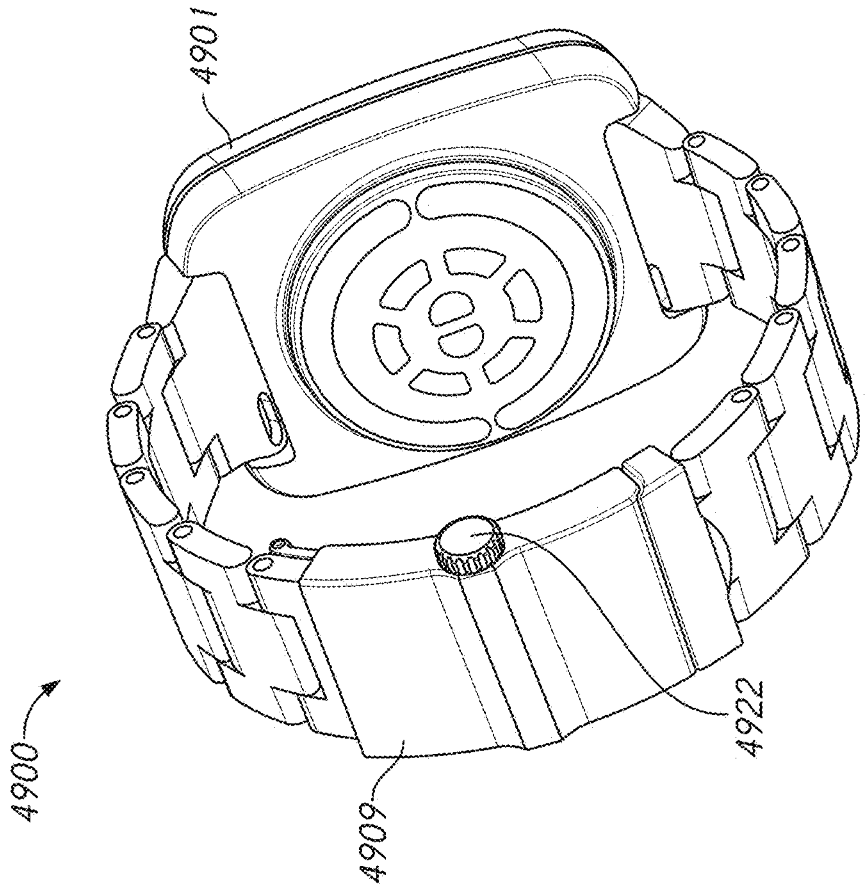
FIGS. 54-59 show another example of wearable device that can be configured to be secured to a wrist of a user.
Figure 54:
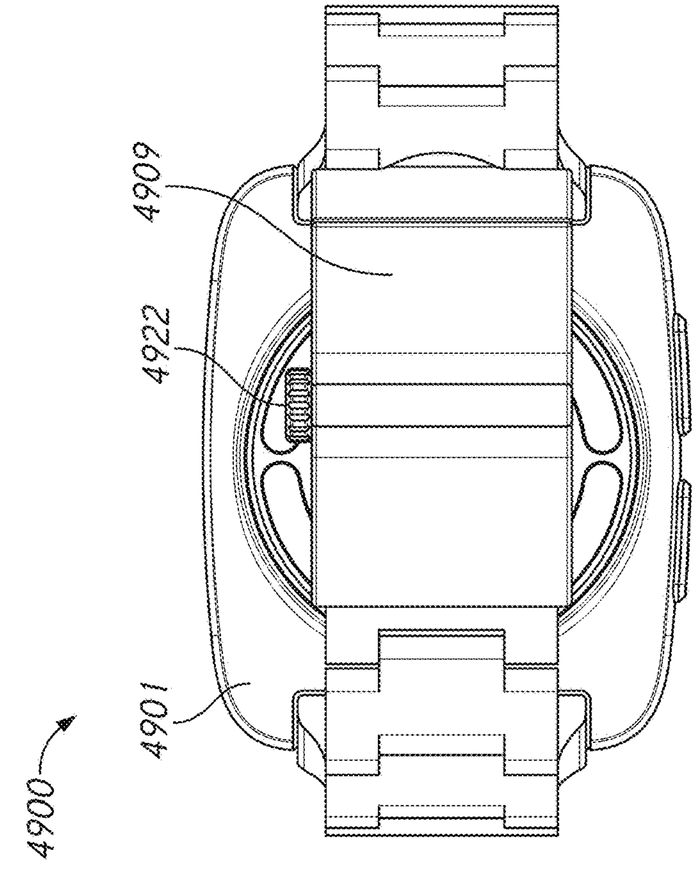

In some examples, the mechanical adjustment mechanism 4720 can include a rack and pinion system including at least a support body 4721, a dial 4722, a first gear 4723 (e.g., a worm gear) rotationally coupled or locked to the dial 4722 or a shaft 4725 coupled with the dial 4722, a second gear (e.g., a worm wheel) 4727 configured to engage with the first gear 4723, a third gear (e.g., a slave gear) 4729 rotationally coupled or locked with the second gear 4727, a pinion gear 4724, and a rack 4726. In some examples, the second gear 4727 and the third gear 4729 can be integrally formed or can be a single gear, such as is shown in FIG. 53.

Figure 48:
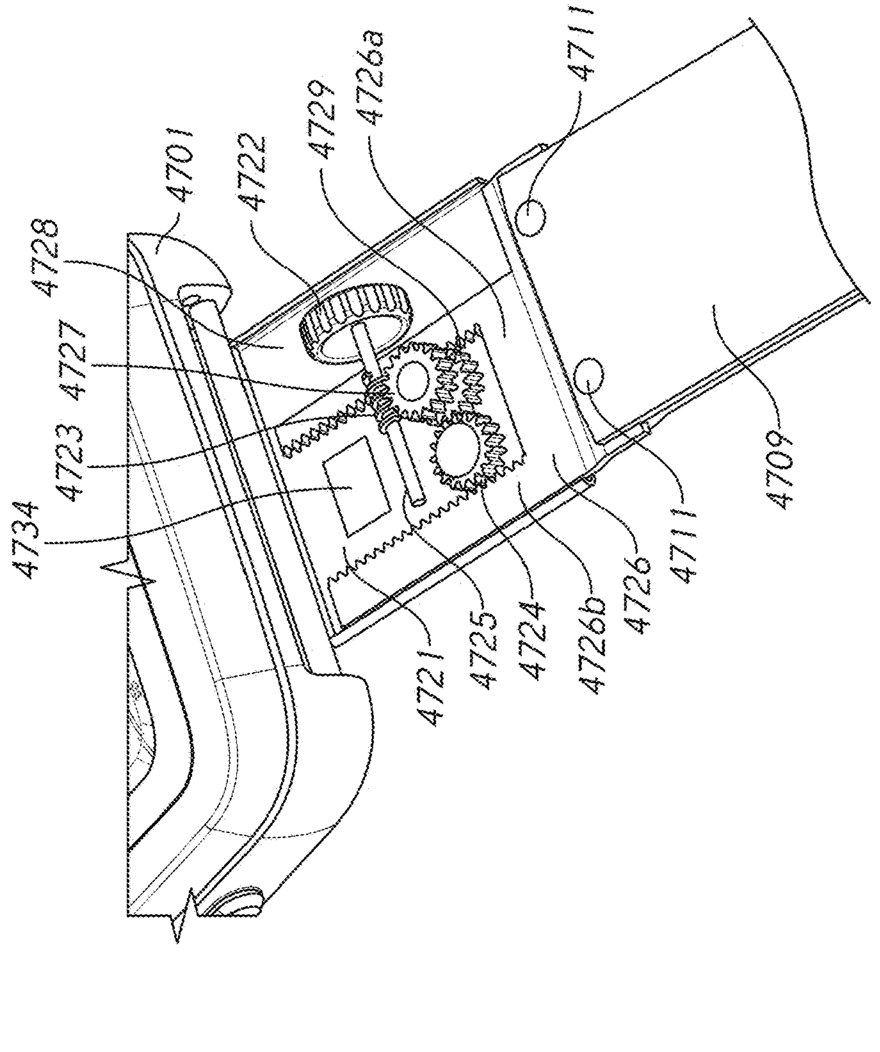
Figure 49:
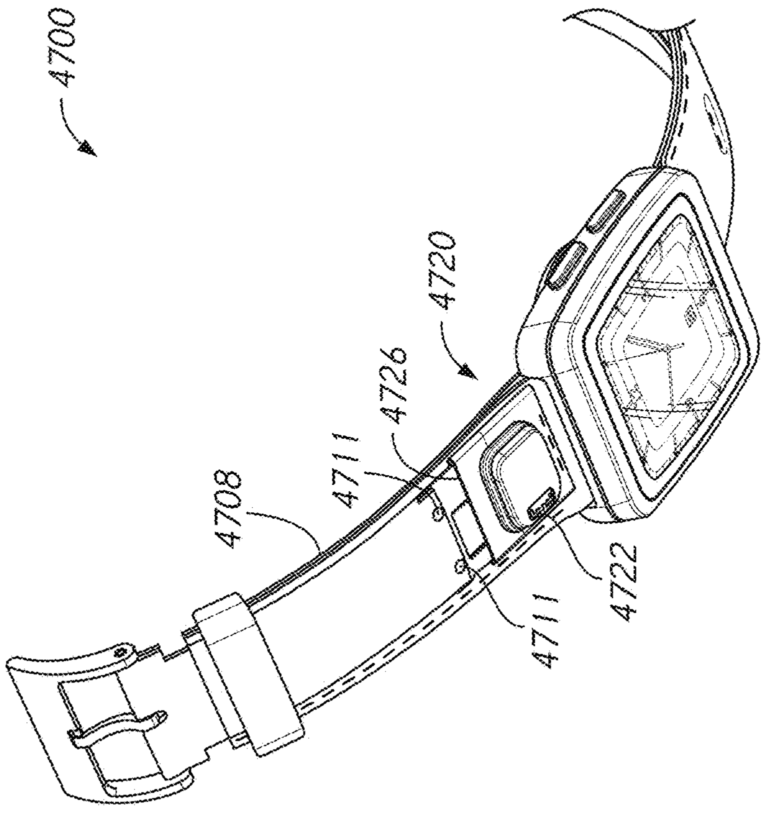

With reference to FIG. 48, the support body 4721 can be configured to support some of the other components of the mechanical adjustment mechanism 4720, including for example and without limitation, the shaft 4725 (such as with a flange coupled with the support body 4721) so that the dial 4722 and first gear 4723 are coupled with and supported by the support body 4721. In some examples, the support body 4721 can be coupled with the body portion 4701 of the device so that the support body 4721, the dial 4722, the shaft 4725, the first gear 4723, the second gear 4727, the third gear 4729, and the pinion gear 4724 can be held in a fixed position relative to the body portion 4701 of the wearable device 4700, even as the length of the strap is adjusted using the mechanical adjustment mechanism 4720.

The dial 4722 and pinion gear 4724 can be configured to freely rotate relative to the support body 4721, but for the interaction of the pinion gear 4724 and/or the third gear 4729 with the rack 4726. In some examples, the pinion gear 4724 can be coupled with and freely rotate about a shaft that can be supported by or coupled with the support body 4721. The second gear 4727 and the third gear 4729 can be coupled together to be rotationally locked together such that a rotation of the second gear 4727 caused by a rotation of the first gear 4723 can cause the simultaneous and equal rotation of the third gear 4729. The second gear 4727 and the third gear 4729 can be coupled with and freely rotate about a shaft that is coupled with or supported by the support body 4721. In this arrangement, a rotation of the dial 4722 in either direction will cause the simultaneous and equal rotation of the first gear 4723, which is engaged with and configured to rotate the second gear 4727. The rotation of the second gear 4727 will cause the simultaneous and equal rotation of the third gear 4729. The third gear 4729 can be configured to engage with a plurality of teeth or protrusions on a first portion 4726*a* of the rack 4726 such that a rotation of the third gear 4729 can move the rack 4726 relative to the support body 4721 and the body portion 4701.

The third gear 4729 can also be engaged with and configured to rotate the pinion gear 4724 such that a rotation of the dial 4722 can cause a rotation of the pinion gear 4724 relative to a second portion 4726*b* of the rack 4726 to thereby move the rack 4726 relative to the support body 4721 and the body portion 4701. The dial 4722 can be configured to be rotated by a user in either direction, thereby rotating the pinion gear 4724 in either direction, to either tighten or loosen the mechanical adjustment mechanism 4720. A cover 4752 can cover and/or enclose one or more of the components of the mechanical adjustment mechanism 4720.

In some examples, an end portion of the rack 4726 can be coupled with an end portion of the strap core layer 4709 using pins or other fasteners 4711, and/or using adhesive, stitching, a clamp mechanism, or any other suitable fastening components or means. The rack 4726 can be configured to translate relative to the support body 4721 by the action of the mechanical adjustment mechanism 4720. Because the support body 4721 can be rigidly coupled with the body portion 4701 of the wearable device 4700, translational movement of the rack 4726 relative to the support body 4721 can cause the simultaneous and equal translational movement of the strap core layer 4709 that can be coupled with the rack 4726 and the first portion 4708 of the strap 4704. This can be achieved through adjustment of the mechanical adjustment mechanism 4720, as described herein.

For example and without limitation, in any examples, the third gear 4729 and the pinion gear 4724 can be configured to engage or mesh with the rack 4726, which can have a linear arrangement of teeth on a first portion 4726*a* and a second portion 4726*b* thereof that are configured to engage with or mesh with the plurality of teeth on the third gear 4729 and the pinion gear 4724. In this arrangement, the rotational movement of the pinion gear 4724 can translate into and/or can cause a linear movement of the rack 4726 relative to the support body 4721. For example and without limitation, a rotation of the pinion gear 4724 in a first direction can cause the rack 4726 to move in a first linear direction relative to the support body 4721 (such as, without limitation, in a direction away from the body portion 4701 of the wearable device 4700) to thereby increase a length of the strap 4704. In some examples, the rack 4726 can be configured to translate out of and into of a space 4728 formed in the support body 4721 as the dial 4722 and the pinion gear 4724 are rotated in the first and second directions, respectively.

The mechanical adjustment mechanism 4720 can be configured such that, as the rack 4726 is translated in either direction relative to the support body 4721 by the rotation of the dial 4722, the strap core layer 4709 and/or first strap portion 4708 that can be coupled with the rack 4726 can be equally and simultaneously translated either direction. In this arrangement, the strap 4704 can be loosened or tightened by the rotation of the dial 4722 in the first direction or second direction, respectively.

The strap core layer 4709 can include a braided, mesh, or fabric material, or any other suitable material that can resist stretching when under a tensile load. In other examples, the strap core layer 4709 can be a flexible and/or resilient material. A leather layer or layer of other material can surround the strap core layer 4709 to provide a greater level of comfort and aesthetics to the first strap portion 4708 than the strap core layer 4709.

In any examples, the mechanical adjustment mechanism 4720 can include a locking mechanism 4734 (shown schematically in FIG. 48) configured to selectively inhibit (e.g., prevent) a movement of the mechanical adjustment mechanism 4720 and the first strap portion 4708 relative to the body portion 4701. For example and without limitation, the locking mechanism 4734 can be selectively engaged to inhibit (e.g., prevent) a movement of the mechanical adjustment mechanism 4720 and the first strap portion 4708 relative to the body portion 4701 and disengaged to permit a movement of the mechanical adjustment mechanism 4720 and the first strap portion 4708 relative to the body portion 4701. Some examples of the locking mechanism 4734 be supported by or coupled with the support body 4721. The locking mechanism can have any of the components, features, and/or details of any of the other examples of the locking mechanisms disclosed herein.

In any examples, as described above, the strap 4704 of the wearable device 4700 can have a separate clasping mechanism that can include, for example and without limitation, a buckle 4714 and a buckle pin 4716 that can engage with corresponding features on the second strap portion 4710 to secure the wearable device 4700 to the user's wrist and also provide for a separate and additional tightening and loosening mechanism relative to the mechanical adjustment mechanism 4720. The user can also remove the wearable device 4700 from his or her wrist by separating the strap at the clasping mechanism.

Figure 51:
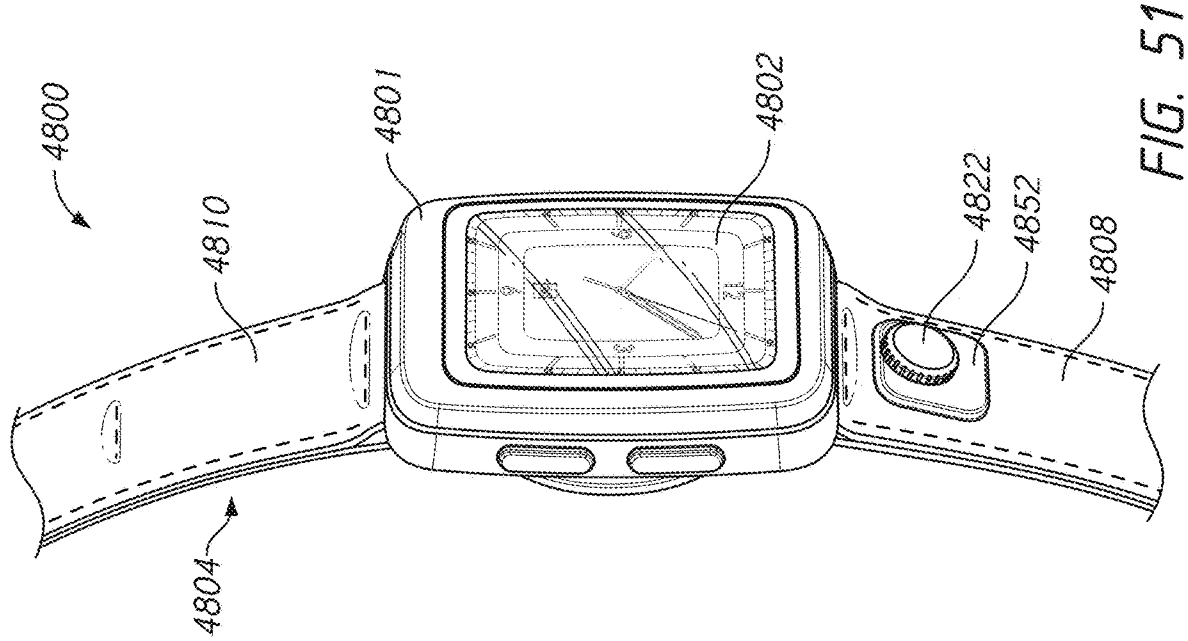
FIGS. 51-53 show another example of wearable device that can be configured to be secured to a wrist of a user.
Figure 50:
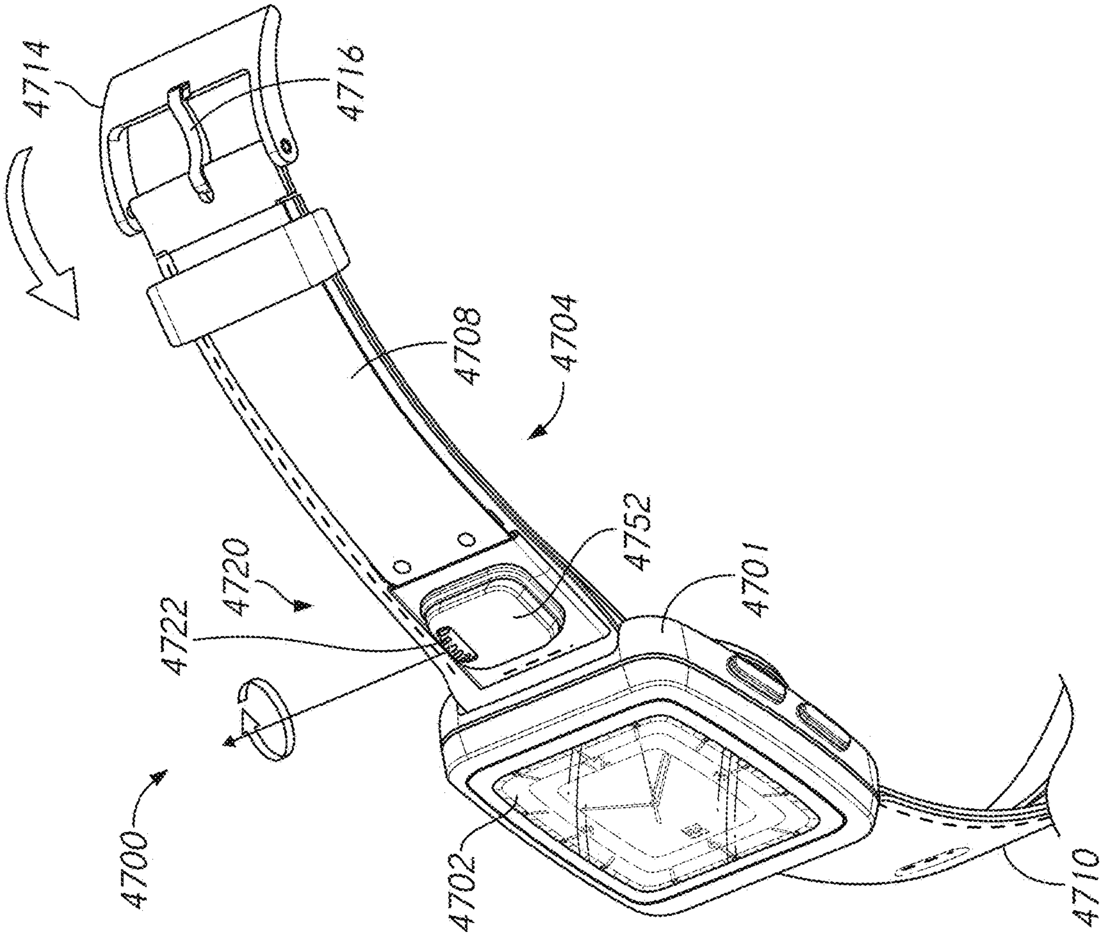
Figure 52:
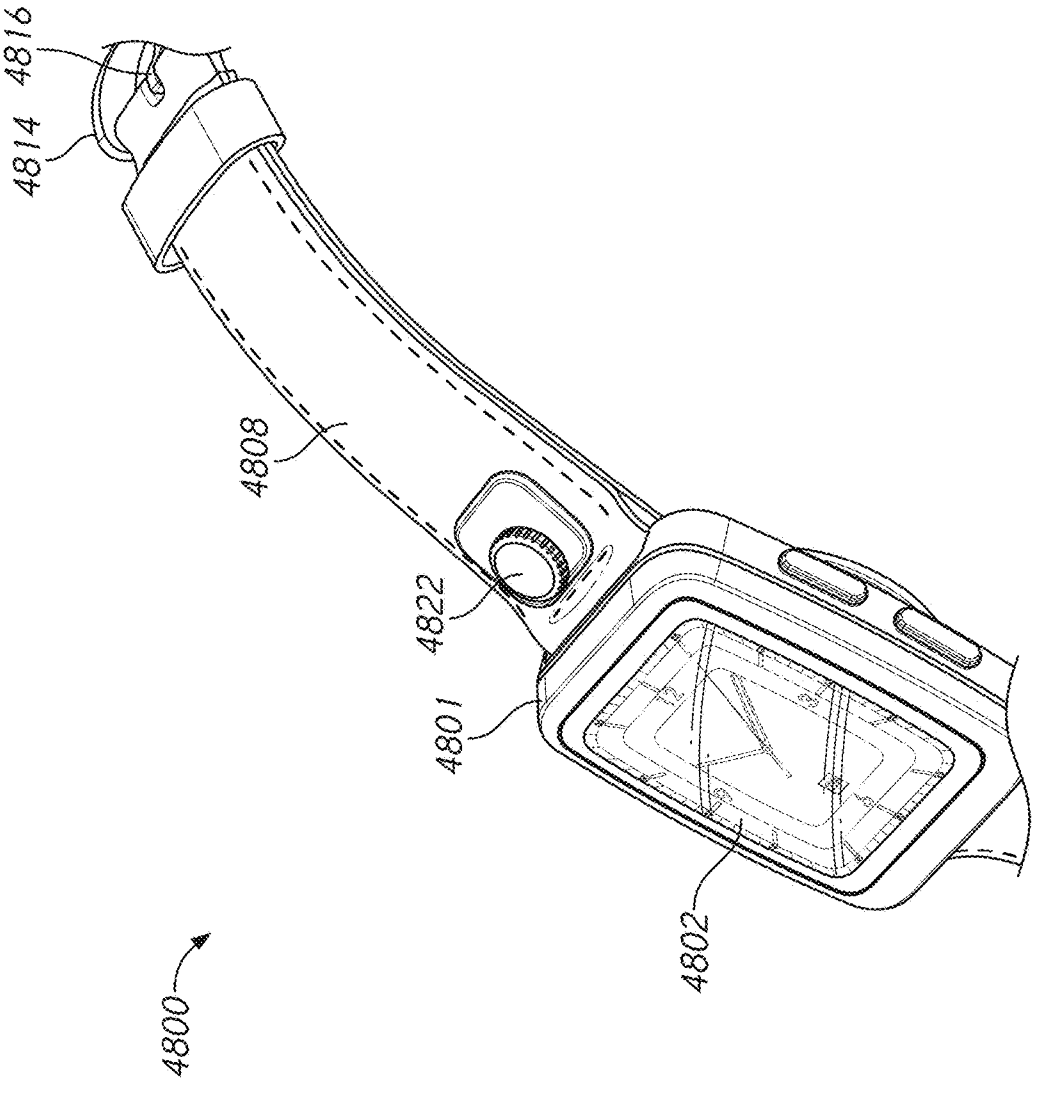

FIGS. 51-53 show another example of wearable device 4800 that can be configured to be secured to a wrist of a user. The wearable device 4800 can have a body portion 4801 having a graphical interface or display screen 4802. The body portion 4801 can, in some examples, have a case or housing that houses or supports the electronic components of the wearable device 4800, including one or more sensors, a processor, a power supply, and the display screen 4802. The wearable device 4800 can also have a strap 4804 (also referred to as a band) that can be used to secure the body portion 4801 of the wearable device 4800 to a wrist of the user.

In any examples disclosed herein, the wearable device 4800 can have any of the components, features, or other details of any other examples of wearable devices disclosed herein, including without limitation any of the examples of the wearable device 10 shown in FIGS. 1A-1H and/or the examples of the wearable devices 4500, 4600, 4700 in any combination with any of the components, features, or details described below. For example and without limitation, any examples of the wearable device 4800 disclosed herein can include any of the examples of the optical physiological sensors (also referred to as physiological parameter measurement sensors or merely sensors) and/or components or features thereof, any examples of the processors disclosed herein, and/or any examples of the displays and/or components or features thereof in combination with any of the other components and/or features described or shown herein. Similarly, any examples of wearable devices disclosed herein can have any of the components, features, or other details of any examples of the wearable device 4800 disclosed herein in any combination with any of the components, features, or details of the other wearable devices.

The strap 4804 of any examples of the wearable device 4800 disclosed herein can be adjustable. In some examples, the strap 4804 can include a first strap portion 4808 and a second strap portion 4810. The first strap portion 4808 can include a buckle 4814 and a buckle pin 4816 (also referred to as a buckle tongue) that can be configured to be advanced into any of a plurality of notches (not shown) formed in the second strap portion 4810 so that a user can adjust a size or tightness of the strap 4804 around the user's wrist. Other examples of the device can have other fastening clasps or mechanisms to selectively connect the first and second strap portions 4808, 4810 together. In some examples that have notches in the second strap portion 4810, the notches can be numbered or uniquely identified so that a user can easily record and/or recall a tightness setting of the strap 4804. As discussed, in some examples, optimizing a tightness of the strap 4804 around the user's wrist and, hence, the contact pressure between the body portion 4801 and the skin of the user can improve the quality and accurateness of the signal(s) from the sensor(s) of the wearable device significantly.

Any examples of the wearable devices disclosed herein, including any examples of the wearable device 4800, can have a mechanical adjustment mechanism 4820 that can be used to increase and/or decrease a level of tightness of the strap 4804. At least some of the components of the mechanical adjustment mechanism 4820 can be coupled with or integrated into the strap 4804, such as the first strap portion 4808 as shown.

In some examples, the mechanical adjustment mechanism 4820 can include a rack and pinion system including at least a support body 4821, a dial 4822, a first gear 4823 (e.g., a worm gear) configured to be rotated by the dial 4822 or a dial gear coupled with the dial 4822 or with a shaft coupled with the dial 4822, a shaft 4825 coupled with the first gear 4823, a second gear (e.g., a worm wheel) 4827 configured to engage with the first gear 4823, a pinion gear 4824, and a rack 4826.

With reference to FIG. 53, the support body 4821 can be configured to support some of the other components of the mechanical adjustment mechanism 4820, including for example and without limitation, the dial 4822, the shaft 4825 (such as with one or more flanges coupled with the support body 4821), the second gear 4827, and/or the pinion gear 4824 so that these components can be coupled with and supported by the support body 4821. In some examples, the support body 4821 can be coupled with the body portion 4801 of the device so that the support body 4821, the dial 4822, the shaft 4825, the first gear 4823, the second gear 4827, and the pinion gear 4824 can be held in a fixed longitudinal position relative to the body portion 4801 of the wearable device 4800, even as the length of the strap is adjusted using the mechanical adjustment mechanism 4820.

The dial 4822 and pinion gear 4824 can be configured to freely rotate relative to the support body 4821, but for the interaction of the pinion gear 4824 and the second gear 4827 with the rack 4826. In some examples, the pinion gear 4824 can be coupled with and freely rotate about a shaft that can be supported by or coupled with the support body 4821. The second gear 4827 can be coupled with and freely rotate about a shaft that is coupled with or supported by the support body 4821. In this arrangement, a rotation of the dial 4822 in either direction will cause the simultaneous and equal rotation of the first gear 4823, which is engaged with and configured to rotate the second gear 4827. The second gear 4827 can be configured to engage with a plurality of teeth or protrusions on a first portion 4826*a* of the rack 4826 such that a rotation of the second gear 4827 can move the rack 4826 relative to the support body 4821 and the body portion 4801.

The second gear 4827 can also be engaged with and configured to rotate the pinion gear 4824 such that a rotation of the dial 4822 can cause a rotation of the pinion gear 4824 relative to a second portion 4826*b* of the rack 4826 to thereby move the rack 4826 relative to the support body 4821 and the body portion 4801. The dial 4822 can be configured to be rotated by a user in either direction, thereby rotating the pinion gear 4824 and the second gear in either direction, to either tighten or loosen the mechanical adjustment mechanism 4820. A cover 4852 can cover and/or enclose one or more of the components of the mechanical adjustment mechanism 4820.

In some examples, an end portion of the rack 4826 can be coupled with an end portion of the strap core layer 4809 using pins or other fasteners 4811, and/or using adhesive, stitching, a clamp mechanism, or any other suitable fastening components or means. The rack 4826 can be configured to translate relative to the support body 4821 by the action of the mechanical adjustment mechanism 4820. Because the support body 4821 can be rigidly coupled with the body portion 4801 of the wearable device 4800, translational movement of the rack 4826 relative to the support body 4821 can cause the simultaneous and equal translational movement of the strap core layer 4809 that can be coupled with the rack 4826 and the first portion 4808 of the strap 4804. This can be achieved through adjustment of the mechanical adjustment mechanism 4820, as described herein.

For example and without limitation, in any examples, the second gear 4827 and the pinion gear 4824 can be configured to engage or mesh with the rack 4826, which can have a linear arrangement of teeth on a first portion 4826*a* and a second portion 4826*b* thereof that are configured to engage with or mesh with the plurality of teeth on the second gear 4827 and the pinion gear 4824. In this arrangement, the rotational movement of the second gear 4827 and the pinion gear 4824 can translate into and/or can cause a linear movement of the rack 4826 relative to the support body 4821. For example and without limitation, a rotation of the pinion gear 4824 in a first direction can cause the rack 4826 to move in a first linear direction relative to the support body 4821 (such as, without limitation, in a direction away from the body portion 4801 of the wearable device 4800) to thereby increase a length of the strap 4804. In some examples, the rack 4826 can be configured to translate out of and into of a space 4828 formed in the support body 4821 as the dial 4822 and the pinion gear 4824 are rotated in the first and second directions, respectively.

The mechanical adjustment mechanism 4820 can be configured such that, as the rack 4826 is translated in either direction relative to the support body 4821 by the rotation of the dial 4822, the strap core layer 4809 and/or first strap portion 4808 that can be coupled with the rack 4826 can be equally and simultaneously translated either direction. In this arrangement, the strap 4804 can be loosened or tightened by the rotation of the dial 4822 in the first direction or second direction, respectively.

The strap core layer 4809 can include a braided, mesh, or fabric material, or any other suitable material that can resist stretching when under a tensile load. In other examples, the strap core layer 4809 can be a flexible and/or resilient material. A leather layer or layer of other material can surround the strap core layer 4809 to provide a greater level of comfort and aesthetics to the first strap portion 4808 than the strap core layer 4809.

In any examples, the mechanical adjustment mechanism 4820 can include a locking mechanism 4834 (shown schematically in FIG. 53) configured to selectively inhibit (e.g., prevent) a movement of the mechanical adjustment mechanism 4820 and the first strap portion 4808 relative to the body portion 4801. For example and without limitation, the locking mechanism 4834 can be selectively engaged to inhibit (e.g., prevent) a movement of the mechanical adjustment mechanism 4820 and the first strap portion 4808 relative to the body portion 4801 and disengaged to permit a movement of the mechanical adjustment mechanism 4820 and the first strap portion 4808 relative to the body portion 4801. Some examples of the locking mechanism 4834 be supported by or coupled with the support body 4821. The locking mechanism can have any of the components, features, and/or details of any of the other examples of the locking mechanisms disclosed herein.

In any examples, as described above, the strap 4804 of the wearable device 4800 can have a separate clasping mechanism that can include, for example and without limitation, a buckle 4814 and a buckle pin 4816 that can engage with corresponding features on the second strap portion 4810 to secure the wearable device 4800 to the user's wrist and also provide for a separate and additional tightening and loosening mechanism relative to the mechanical adjustment mechanism 4820. The user can also remove the wearable device 4800 from his or her wrist by separating the strap at the clasping mechanism.

FIGS. 54-59 show another example of wearable device 4900 that can be configured to be secured to a wrist of a user. The wearable device 4900 can have a body portion 4901 having a graphical interface or display screen 4902. The body portion 4901 can, in some examples, have a case or housing that houses or supports the electronic components of the wearable device 4900, including one or more sensors, a processor, a power supply, and the display screen 4902. The wearable device 4900 can also have a strap 4904 (also referred to as a band) that can be used to secure the body portion 4901 of the wearable device 4900 to a wrist of the user. The strap 4904 of any examples of the wearable device 4900 disclosed herein can have a mechanical adjustment mechanism 4920 to adjust the tension or tightness of the strap 4904. As discussed, in some examples, optimizing a tightness of the strap 4904 around the user's wrist and, hence, the contact pressure between the body portion 4901 and the skin of the user can improve the quality and accurateness of the signal(s) from the sensor(s) of the wearable device significantly.

In any examples disclosed herein, the wearable device 4900 can have any of the components, features, or other details of any other examples of wearable devices disclosed herein, including without limitation any of the examples of the wearable device 10 shown in FIGS. 1A-1H and/or the examples of the wearable devices 4500, 4600, 4700, 4800 in any combination with any of the components, features, or details described below. For example and without limitation, any examples of the wearable device 4900 disclosed herein can include any of the examples of the optical physiological sensors (also referred to as physiological parameter measurement sensors or merely sensors) and/or components or features thereof, any examples of the processors disclosed herein, and/or any examples of the displays and/or components or features thereof in combination with any of the other components and/or features described or shown herein. Similarly, any examples of wearable devices disclosed herein can have any of the components, features, or other details of any examples of the wearable device 4900 disclosed herein in any combination with any of the components, features, or details of the other wearable devices.

At least some of the components of the mechanical adjustment mechanism 4920 can be coupled with or integrated into the clasp 4909 of the first strap portion 4908 of the strap 4904. In some examples, the mechanical adjustment mechanism 4920 can include a rack and pinion system including at least a support body 4921, a dial 4922, a first gear 4923 (e.g., a worm gear), a shaft 4925 coupled with the first gear 4923 or integrally formed with the first gear 4923, a second gear (e.g., a worm wheel) 4927 configured to engage with the first gear 4923, a third gear 4929 rotationally coupled with and/or integrally formed with the second gear 4927, a pinion gear 4924, and a rack 4926. In some examples, the second and third gears 4927, 4929 can be formed as a single, extended or longer gear. The first gear 4923 can be configured to be rotated by the dial 4922 or a shaft 4925 coupled with the dial 4922.

Figure 56:
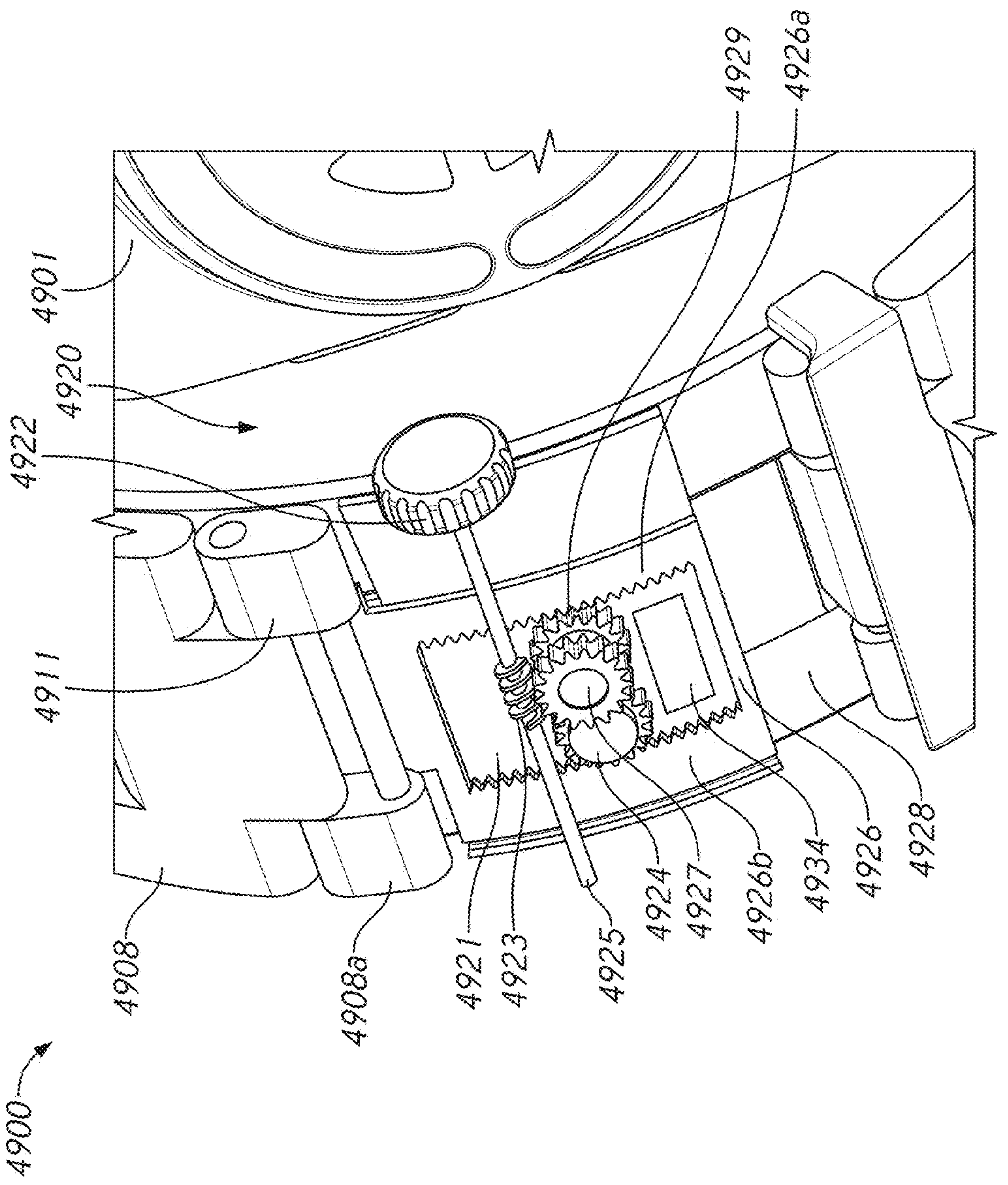
Figure 58:
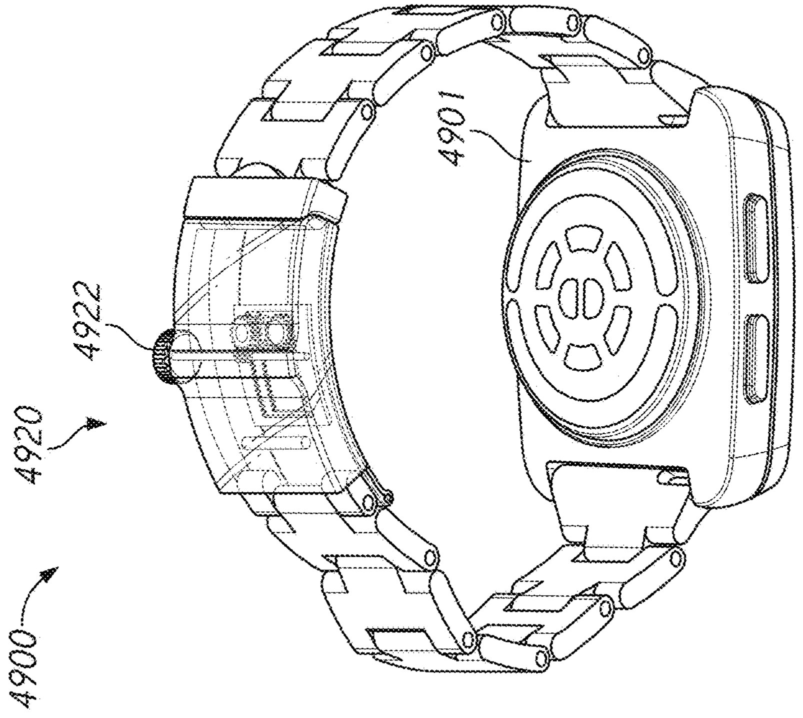
Figure 57:
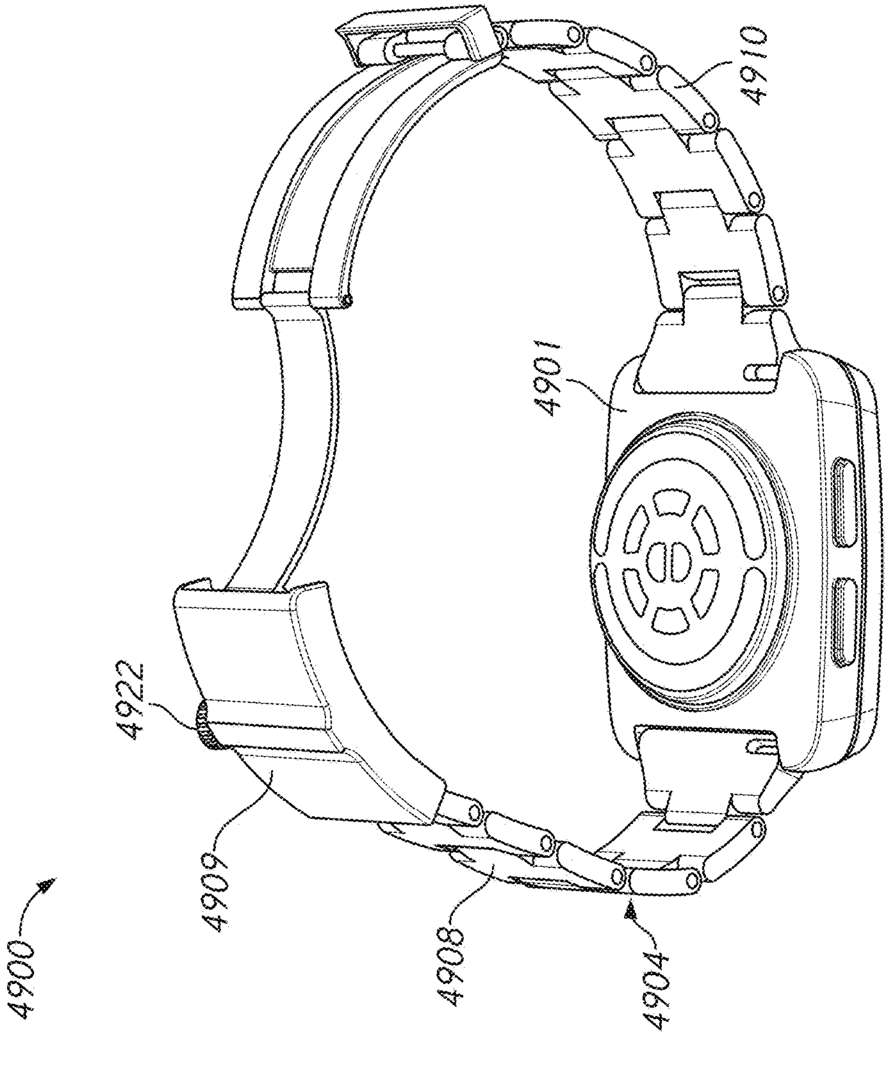
Figure 60:
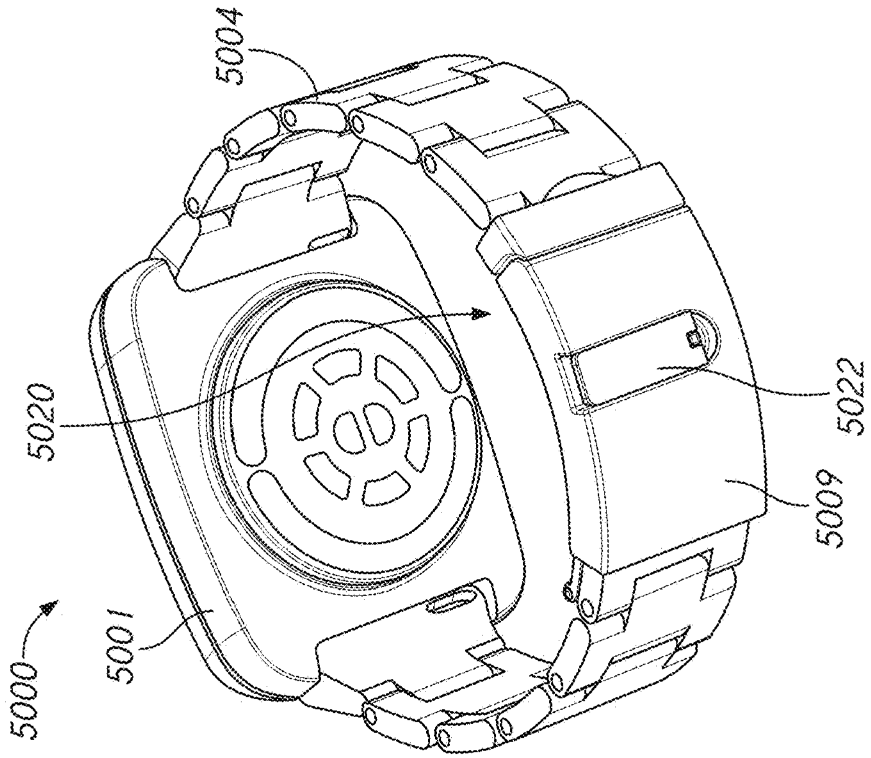
FIGS. 60-65 show another example of wearable device that can be configured to be secured to a wrist of a user.
Figure 59:
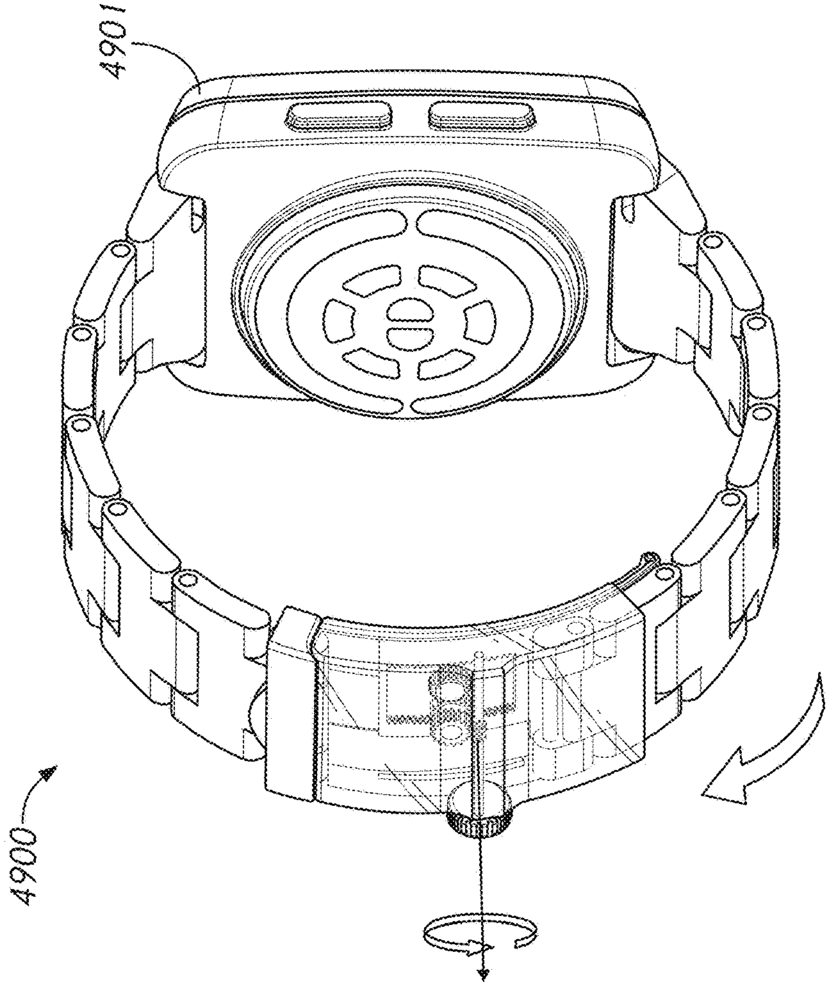

With reference to FIG. 56, the support body 4921 can be configured to support some of the other components of the mechanical adjustment mechanism 4920, including for example and without limitation, the dial 4922, the shaft 4925 (such as with one or more flanges coupled with the support body 4921), the second gear 4927, the third gear 4929, and/or the pinion gear 4924 so that these components can be coupled with and supported by the support body 4921.

The dial 4922 and pinion gear 4924 can be configured to freely rotate relative to the support body 4921, but for the interaction of the pinion gear 4924 and the second gear 4927 with the rack 4926. In some examples, the pinion gear 4924 can be coupled with and freely rotate about a shaft that can be supported by or coupled with the support body 4921. The second gear 4927 can be coupled with and freely rotate about a shaft that is coupled with or supported by the support body 4921. In this arrangement, a rotation of the dial 4922 in either direction will cause the simultaneous and equal rotation of the first gear 4923, which is engaged with and configured to rotate the second gear 4927 and the third gear 4929. The third gear 4929 can be configured to engage with a plurality of teeth or protrusions on a first portion 4926*a* of the rack 4926 such that a rotation of the third gear 4929 can move the rack 4926 relative to the support body 4921 and the body portion 4901.

The third gear 4929 can also be engaged with and configured to rotate the pinion gear 4924 such that a rotation of the dial 4922 can cause a rotation of the pinion gear 4924 relative to a second portion 4926*b* of the rack 4926 to thereby move the rack 4926 relative to the support body 4921 and the body portion 4901. The dial 4922 can be configured to be rotated by a user in either direction, thereby rotating the pinion gear 4924 and the third gear 4929 in either direction, to either tighten or loosen the mechanical adjustment mechanism 4920.

In some examples, an end portion of the rack 4926 can be coupled with an end portion 4908*a* of the first strap portion 4908. For example, a special link 4911 can be connected with the end portion of the rack 4926 to couple the first strap portion 4908 with the rack 4926. The rack 4926 can be configured to translate relative to the support body 4921 by the action of the mechanical adjustment mechanism 4920. Because the support body 4921 can be rigidly coupled with the clasp 4909 or integrally formed with the clasp 4909, translational movement of the rack 4926 relative to the support body 4921 can cause the simultaneous and equal translational movement of the first strap portion 4908 that can be coupled with the rack 4926. This can be achieved by rotating the dial 4922.

The dial 4922 can be configured to be rotated by a user in either direction, thereby rotating the third gear 4929 and the pinion gear 4924 in either direction, to either tighten or loosen the mechanical adjustment mechanism 4920. For example and without limitation, the third gear 4929 and the pinion gear 4924 can be configured to engage or mesh with the rack 4926, which can have a linear arrangement of teeth on a first and a second portion 4926*a*, 4926*b* thereof that are configured to engage with or mesh with the plurality of teeth on the third gear 4929 and the pinion gear 4924. In this arrangement, the rotational movement of the third gear 4929 and the pinion gear 4924 can translate into and/or can cause a linear movement of the rack 4926 relative to the clasp 4909. For example and without limitation, a rotation of the pinion gear 4924 in a first direction can cause the rack 4926 to move in a first linear direction relative to the clasp 4909 (such as, without limitation, in a direction away from a distal end portion 4909*a* of the clasp 4909) to thereby increase a length of the strap 4904, and a rotation of the pinion gear 4924 in a second direction can cause the rack 4926 to move in a second linear direction relative to the clasp 4909 (such as, without limitation, in a direction toward from a distal end portion 4909*a* of the clasp 4909) to thereby decrease a length of the strap 4904 and tighten the strap 4904. In some examples, the rack 4926 can be configured to translate out of and into of a space 4928 formed in the clasp 4909 as the dial 4922 and the pinion gear 4924 are rotated in the first and second directions, respectively. In this arrangement, the strap 4904 can be loosened or tightened by the rotation of the dial 4922 in the first direction or second direction, respectively.

In any examples, the mechanical adjustment mechanism 4920 can include a locking mechanism 4934 configured to selectively inhibit (e.g., prevent) a movement of the mechanical adjustment mechanism 4920 and the first strap portion 4908 relative to the body portion 4901. The locking mechanism 4934 can have a lever 4936, a cam or projection 4941 that can be rotationally coupled with the lever 4936, a lock body 4937 having a flange 4939, a spring 4943, and other components and features. In some examples, the locking mechanism 4934 can operate in a manner similar to the locking mechanism 4534 of the examples of the wearable device 4500 described above, and can have any of the same components and features as the locking mechanism 4534.

FIGS. 60-65 show another example of wearable device 5000 that can be configured to be secured to a wrist of a user. The wearable device 5000 can have a body portion 5001 having a graphical interface or display screen 5002. The body portion 5001 can, in some examples, have a case or housing that houses or supports the electronic components of the wearable device 5000, including one or more sensors, a processor, a power supply, and the display screen 5002. The wearable device 5000 can also have a strap 5004 (also referred to as a band) that can be used to secure the body portion 5001 of the wearable device 5000 to a wrist of the user. The strap 5004 of any examples of the wearable device 5000 disclosed herein can have a mechanical adjustment mechanism 5020 to adjust the tension or tightness of the strap 5004. As discussed, in some examples, optimizing a tightness of the strap 5004 around the user's wrist and, hence, the contact pressure between the body portion 5001 and the skin of the user can improve the quality and accurateness of the signal(s) from the sensor(s) of the wearable device significantly.

In any examples disclosed herein, the wearable device 5000 can have any of the components, features, or other details of any other examples of wearable devices disclosed herein, including without limitation any of the examples of the wearable device 10 shown in FIGS. 1A-1H and/or the examples of the wearable devices 4500, 4600, 4700, 4800, 4900 in any combination with any of the components, features, or details described below. For example and without limitation, any examples of the wearable device 5000 disclosed herein can include any of the examples of the optical physiological sensors (also referred to as physiological parameter measurement sensors or merely sensors) and/or components or features thereof, any examples of the processors disclosed herein, and/or any examples of the displays and/or components or features thereof in combination with any of the other components and/or features described or shown herein. Similarly, any examples of wearable devices disclosed herein can have any of the components, features, or other details of any examples of the wearable device 5000 disclosed herein in any combination with any of the components, features, or details of the other wearable devices.

Figure 63:
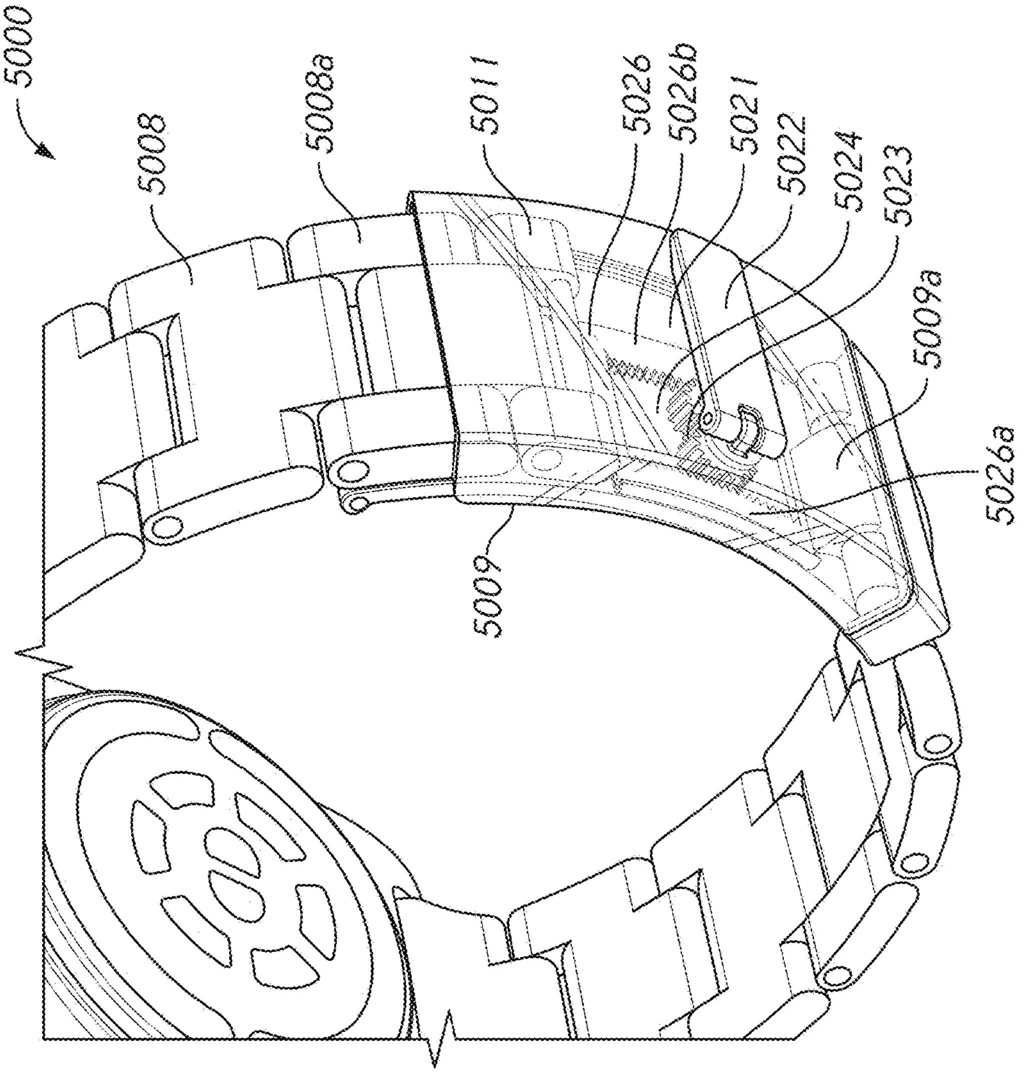
Figure 65:
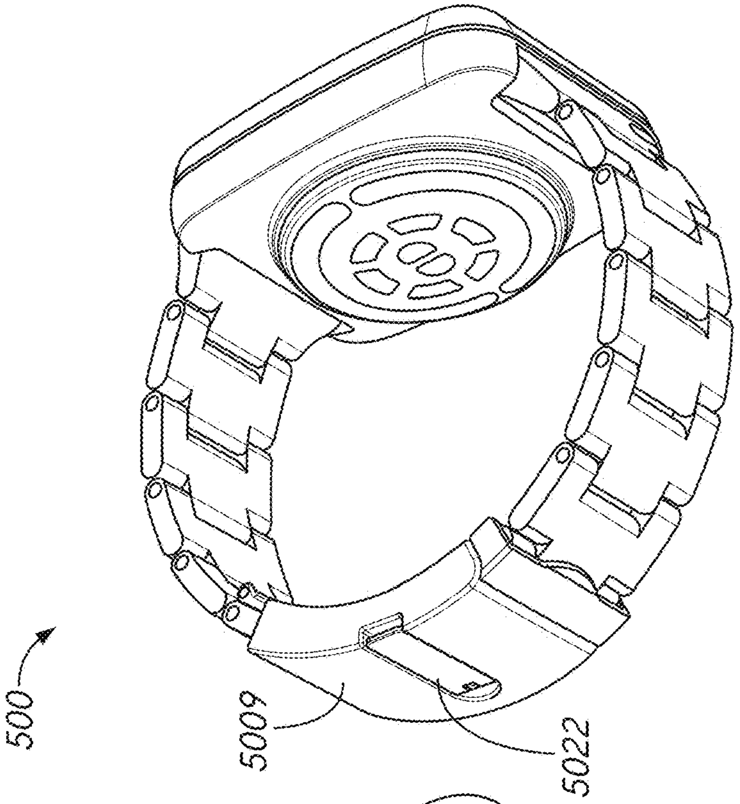
Figure 64:
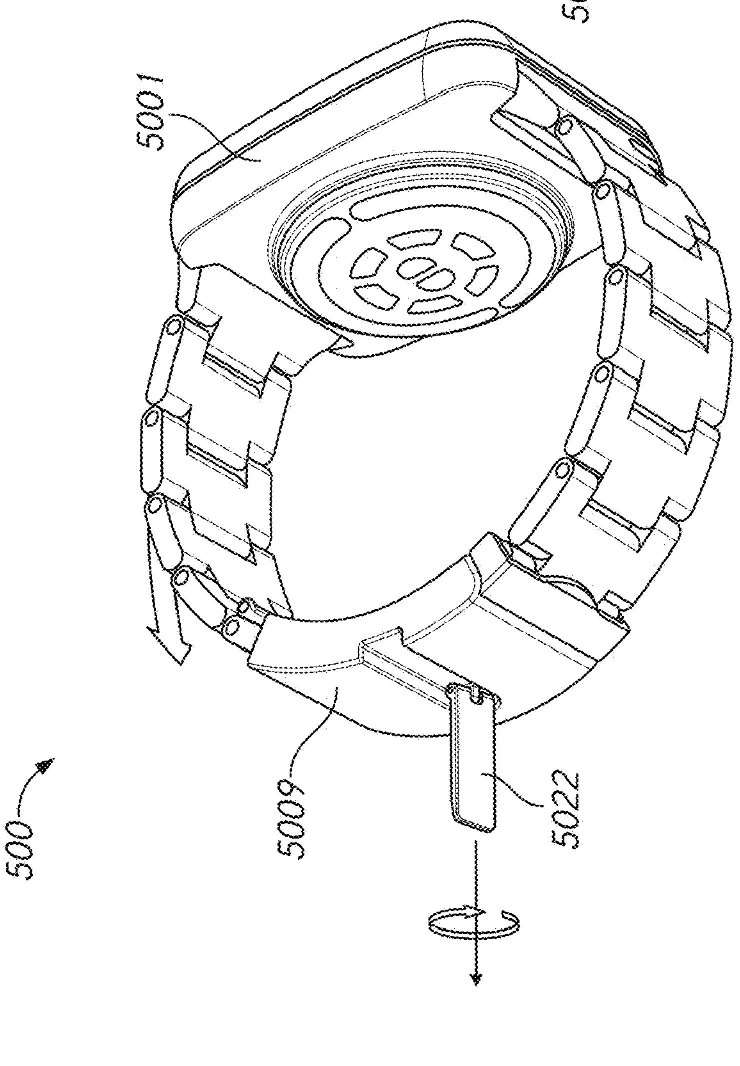

At least some of the components of the mechanical adjustment mechanism 5020 can be coupled with or integrated into the clasp 5009 of the first strap portion 5008 of the strap 5004. In some examples, the mechanical adjustment mechanism 5020 can include a rack and pinion system including at least a support body 5021, a dial or tightening bar 5022, a first gear 5023, a pinion gear 5024, and a rack 5026. In some examples, a shaft can be coupled with the first gear 5023 or integrally formed with the first gear 5023 and can be coupled with the dial or tightening bar 5022. The first gear 5023 can be configured to be rotated by the dial or tightening bar 5022 or the shaft, if any, coupled with the dial or tightening bar 5022. With reference to FIG. 63, the support body 5021 can be configured to support some of the other components of the mechanical adjustment mechanism 5020, including for example and without limitation, the first gear 5023 and/or the pinion gear 5024 so that these components can be coupled with and supported by the support body 5021.

The dial or tightening bar 5022, first gear 5023, and pinion gear 5024 can be configured to freely rotate relative to the support body 5021, but for the interaction of the pinion gear 5024 and the first gear 5023 with the rack 5026. In some examples, the pinion gear 5024 can be coupled with and freely rotate about a shaft that can be supported by or coupled with the support body 5021. In this arrangement, a rotation of the dial or tightening bar 5022 in either direction can cause the simultaneous and equal rotation of the first gear 5023, which is engaged with and configured to rotate the pinion gear 5024. The first gear 5023 can be configured to engage with a plurality of teeth or protrusions on a first portion 5026*a* of the rack 5026 such that a rotation of the first gear 5023 can move the rack 5026 relative to the support body 5021 and the body portion 5001.

As mentioned, the first gear 5023 can also be engaged with and configured to rotate the pinion gear 5024 such that a rotation of the dial or tightening bar 5022 can cause a rotation of the pinion gear 5024 relative to a second portion 5026*b* of the rack 5026 to thereby move the rack 5026 relative to the support body 5021 and the body portion 5001. The dial or tightening bar 5022 can be configured to be rotated by a user in either direction, thereby rotating the first gear 5023 and the pinion gear 5024 in either direction, to either tighten or loosen the mechanical adjustment mechanism 5020.

In some examples, an end portion of the rack 5026 can be coupled with an end portion 5008*a* of the first strap portion 5008. For example, a special link 5011 can be connected with the end portion of the rack 5026 to couple the first strap portion 5008 with the rack 5026. The rack 5026 can be configured to translate relative to the support body 5021 by the action of the mechanical adjustment mechanism 5020. Because the support body 5021 can be rigidly coupled with the clasp 5009 or integrally formed with the clasp 5009, translational movement of the rack 5026 relative to the support body 5021 can cause the simultaneous and equal translational movement of the first strap portion 5008 that can be coupled with the rack 5026. This can be achieved by rotating the dial or tightening bar 5022.

The dial or tightening bar 5022 can be configured to be rotated by a user in either direction, thereby rotating the first gear 5023 and the pinion gear 5024 in either direction, to either tighten or loosen the mechanical adjustment mechanism 5020. For example and without limitation, the first gear 5023 and the pinion gear 5024 can be configured to engage or mesh with the rack 5026, which can have a linear arrangement of teeth on a first and a second portion 5026*a*, 5026*b* thereof that are configured to engage with or mesh with the plurality of teeth on the first gear 5023 and the pinion gear 5024. In this arrangement, the rotational movement of the first gear 5023 and the pinion gear 5024 can translate into and/or can cause a linear movement of the rack 5026 relative to the clasp 5009. For example and without limitation, a rotation of the pinion gear 5024 in a first direction can cause the rack 5026 to move in a first linear direction relative to the clasp 5009 (such as, without limitation, in a direction away from a distal end portion 5009*a* of the clasp 5009) to thereby increase a length of the strap 5004, and a rotation of the pinion gear 5024 in a second direction can cause the rack 5026 to move in a second linear direction relative to the clasp 5009 (such as, without limitation, in a direction toward from a distal end portion 5009*a* of the clasp 5009) to thereby decrease a length of the strap 5004 and tighten the strap 5004. In some examples, the rack 5026 can be configured to translate out of and into of a space 5028 formed in the clasp 5009 as the dial or tightening bar 5022 and the pinion gear 5024 are rotated in the first and second directions, respectively. In this arrangement, the strap 5004 can be loosened or tightened by the rotation of the dial or tightening bar 5022 in the first direction or second direction, respectively.

Figure 62:
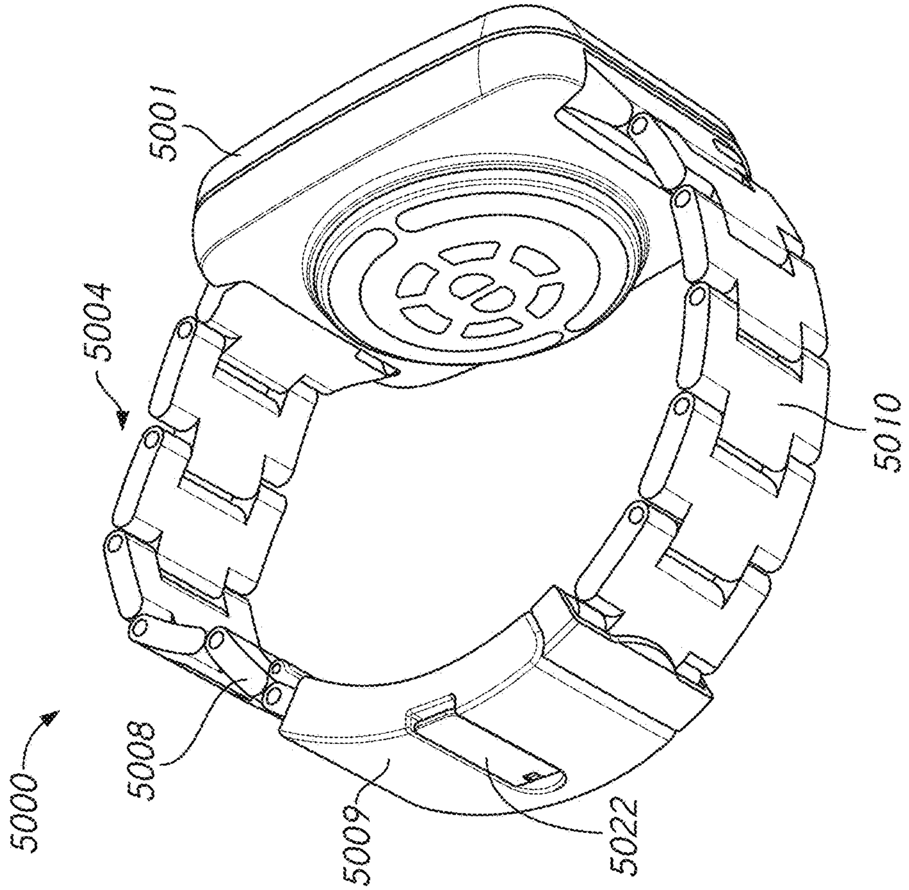
Figure 61:
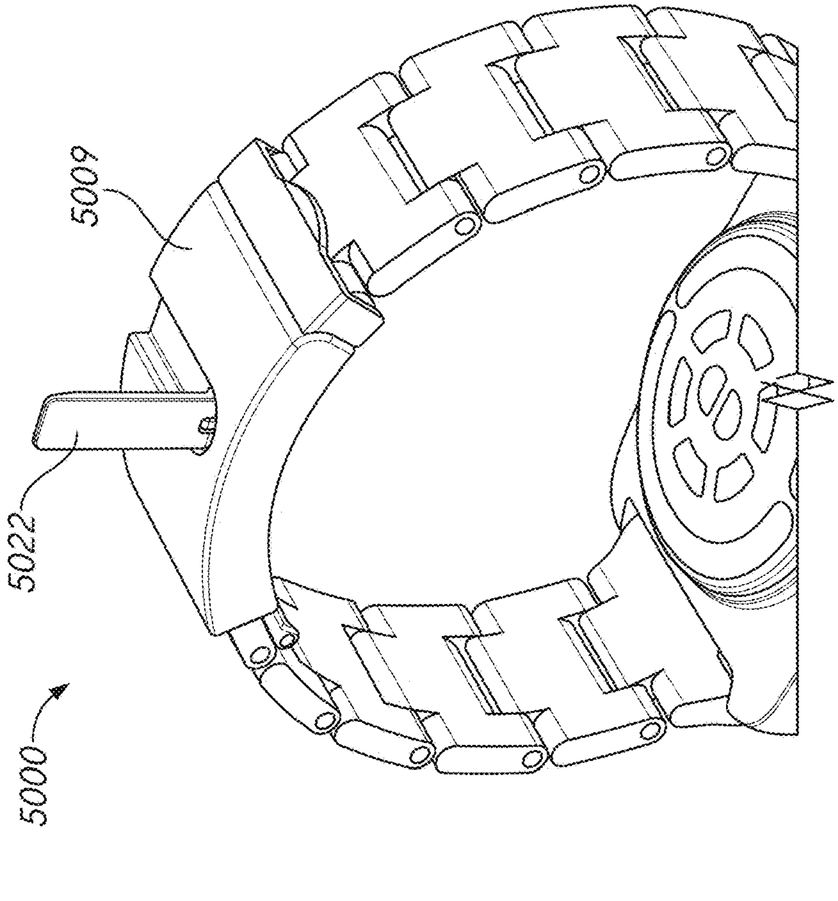

In some examples, the dial or tightening bar 5022 can be configured to move between a first, extended or open position (as shown in FIG. 61) in which a user can grasp and turn the dial or tightening bar 5022 and a second, closed position (as shown in FIG. 62) in which the dial or tightening bar 5022 is stowed in a recess formed in the clasp 5009. Additionally, in some examples, when the dial or tightening bar 5022 is in the second, closed position, the dial or tightening bar 5022 can be prevented from rotating such that moving the dial or tightening bar 5022 to the second position can effectively lock the mechanical adjustment mechanism 5020 to prevent the rack 5026 from moving relative to the support body 5021 (i.e., to prevent the loosening of the strap 5004).

Figure 66:
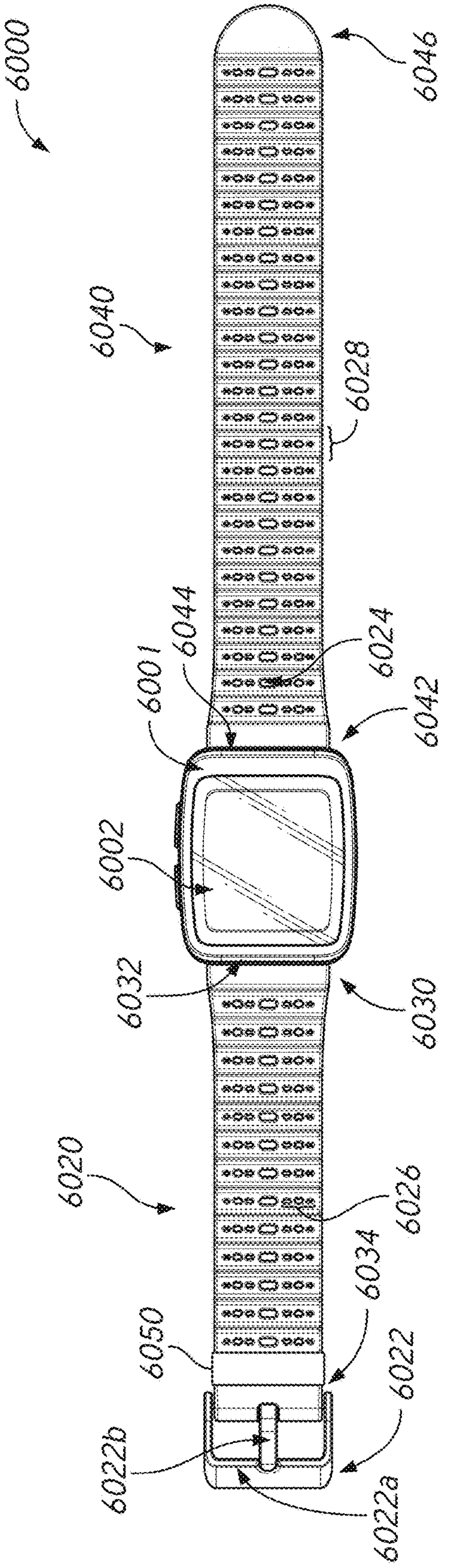
FIGS. 66-68 show another example of wearable device that can be configured to be secured to a wrist of a user.
Figure 67:
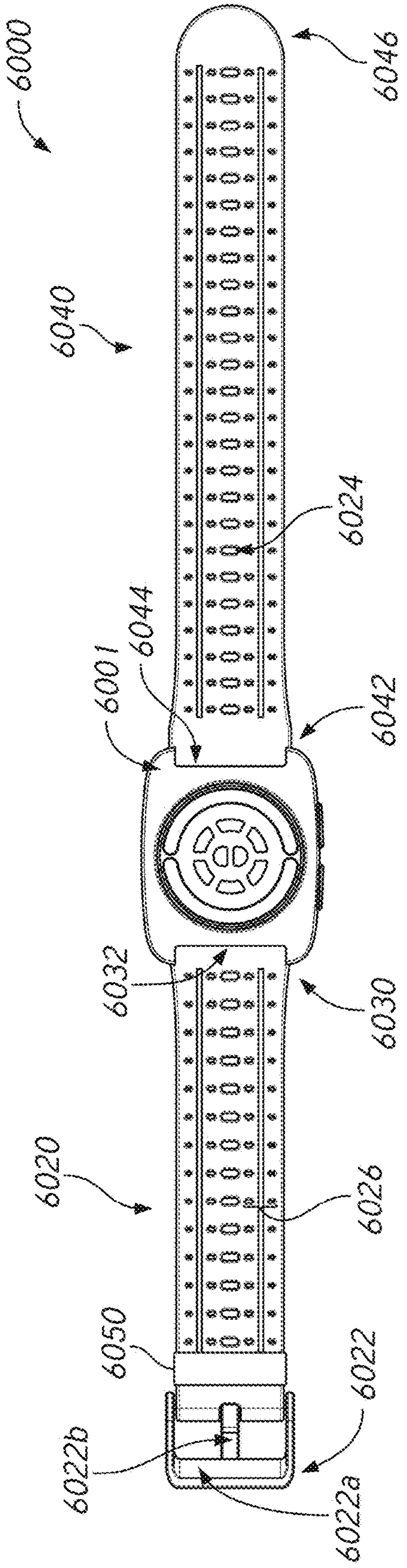
Figure 68:
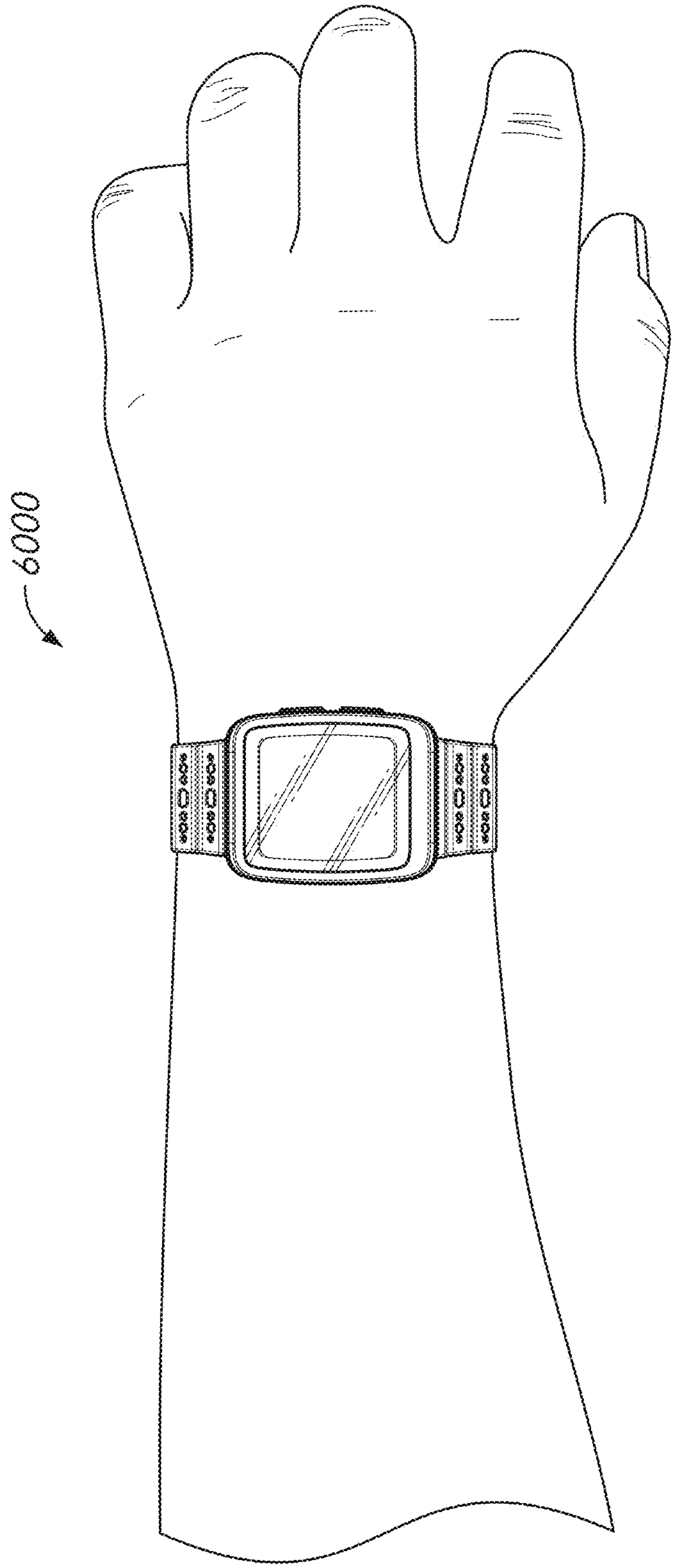

FIGS. 66-68 show another example of wearable device 6000 that can be configured to be secured to a wrist of a user. The wearable device 6000 can have a body portion 6001 having a graphical interface or display screen 6002. The body portion 6001 can, in some examples, have a case or housing that houses or supports the electronic components of the wearable device 6000, including one or more sensors, a processor, a power supply, and the display screen 6002. The wearable device 6000 can also have a set of straps 6020, 6040 (also referred to as a band) that can be used to secure the body portion 6001 of the wearable device 6000 to a wrist of the user (as shown in FIG. 68). The wearable device 6000 can include a securing mechanism that can facilitate securement of the straps 6020, 6040 to one another. For, example strap 6020 can include a buckle 6022 that can facilitate securement of the straps 6020, 6040 to one another. Buckle 6022 can include a buckle body 6022*a* and a tongue 6022*b* (which can also be referred to as a "buckle tongue"). Straps 6020, 6040 can be secured to one another via insertion of at least a portion of strap 6040 through an opening defined by buckle body 6022*a* and insertion of tongue 6022*b* through one of a plurality of openings 6024 in strap 6040. As discussed, in some examples, optimizing a tightness of the straps 6020, 6040 around the user's wrist and, hence, the contact pressure between the body portion 6001 and the skin of the user can improve the quality and accurateness of the signal(s) from the sensor(s) of the wearable device significantly.

In any example disclosed herein, the wearable device 6000 can have any of the components, features, or other details of any other examples of wearable devices disclosed herein, including without limitation any of the examples of the wearable device 10 shown in FIGS. 1A-1H and/or the examples of the wearable devices 4500, 4600, 4700, 4800, 4900, 5000 in any combination with any of the components, features, or details described below. For example and without limitation, any examples of the wearable device 6000 disclosed herein can include any of the examples of the optical physiological sensors (also referred to as physiological parameter measurement sensors or merely sensors) and/or components or features thereof, any examples of the processors disclosed herein, and/or any examples of the displays and/or components or features thereof in combination with any of the other components and/or features described or shown herein. Similarly, any examples of wearable devices disclosed herein can have any of the components, features, or other details of any examples of the wearable device 6000 disclosed herein in any combination with any of the components, features, or details of the other wearable devices.

The strap 6020 can include a first end 6030 configured to be secured to a first portion 6032 of the body portion 6001 of the wearable device 6000. The strap 6020 can also include a second end 6034 opposite the first end 6030, and a length extending between the first end 6030 and the second end 6034. The strap 6040 can include a first end 6042 configured to be secured to a second portion 6044 of the body portion 6001 of the wearable device 6000. The strap 6040 can also include a second end 6046 opposite the first end 6042, and a length extending between the first and second ends. The strap 6020 can also include a strap loop 6050. Strap 6020 and/or 6040 can comprise a material (for example, an elastic material) that allows a length of strap 6020 and/or 6040 to vary. The elastic material of strap 6020 and/or 6040 can comprise a plurality of holes 6026 and/or a plurality of ridges 6028 configured to allow the strap 6020 and/or 6040 to stretch evenly across its length when the strap 6020 is secured to strap 6040 around a portion of a user's body (for example, a wrist). The plurality of ridges and holes can also allow for greater stretch across the length of the strap. In some examples, the plurality of holes 6026 and/or the plurality of ridges 6028 of the straps 6020, 6040 extend along substantially an entirety of a length of the straps 6020, 6040. In some examples, the plurality of holes 6026 and/or the plurality of ridges 6028 of the straps 6020, 6040 are spaced evenly. In other examples, the plurality of holes 6026 and/or the plurality of ridges 6028 of the straps 6020, 6040 extend along substantially a portion of the length of the straps 6020, 6040. In some examples, at least a portion of the plurality of holes 6026 of the straps 6020, 6040 are covered.

Figure 69:
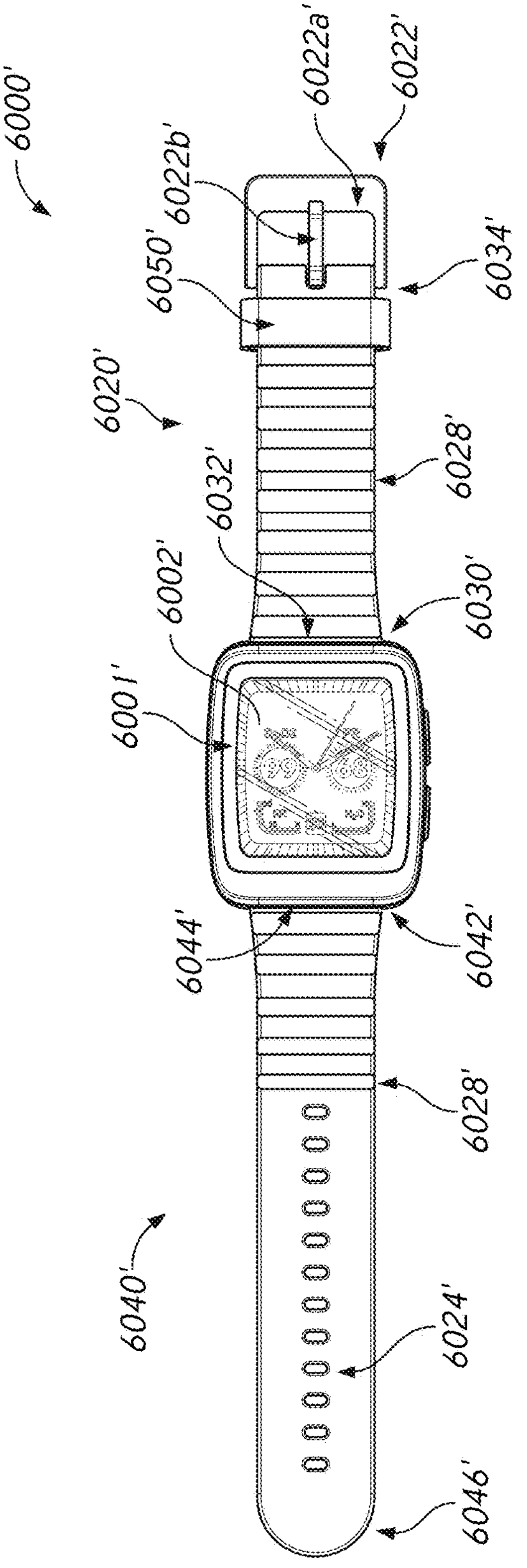
FIGS. 69 and 70 show another example of wearable device that can be configured to be secured to a wrist of a user.
Figure 70:
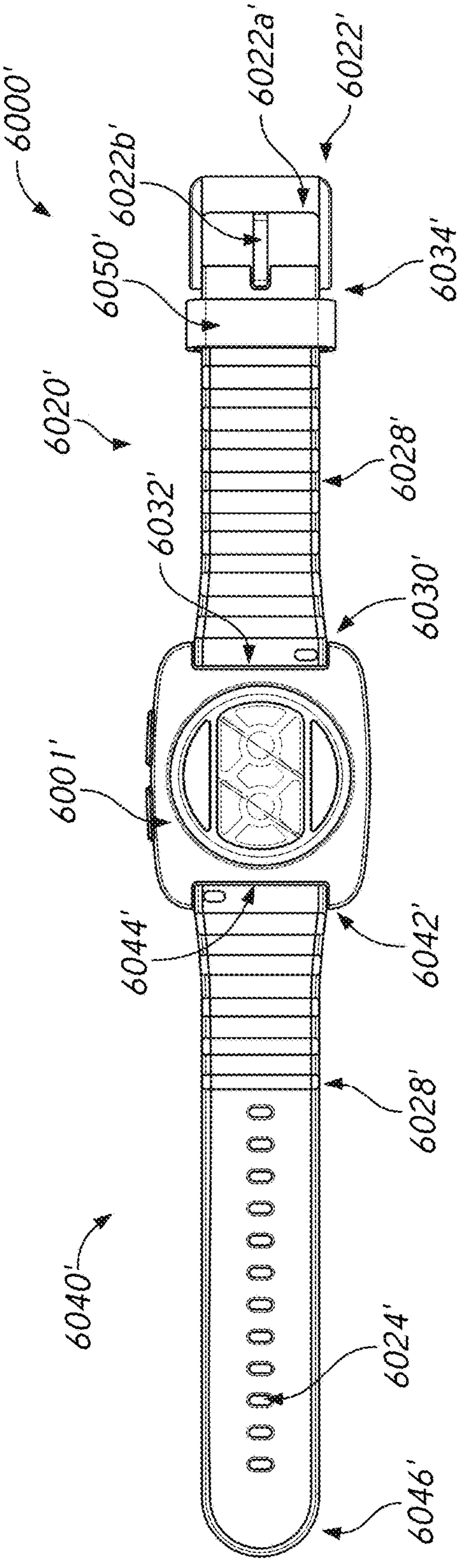

FIGS. 69 and 70 show another example of wearable device 6000' that can be configured to be secured to a wrist of a user. The wearable device 6000' can have a body portion 6001' having a graphical interface or display screen 6002'. The body portion 6001' can, in some examples, have a case or housing that houses or supports the electronic components of the wearable device 6000', including one or more sensors, a processor, a power supply, and the display screen 6002'. The wearable device 6000' can also have a set of straps 6020', 6040' (also referred to as a band) that can be used to secure the body portion 6001' of the wearable device 6000' to a wrist of the user. The wearable device 6000' can include a securing mechanism that can facilitate securement of the straps 6020', 6040' to one another. For, example strap 6020' can include a buckle 6022' that can facilitate securement of the straps 6020', 6040' to one another. Buckle 6022' can include a buckle body **6022*a*' and a tongue 6022*b*' (which can also be referred to as a "buckle tongue"). Straps 6020', 6040' can be secured to one another via insertion of at least a portion of strap 6040' through an opening defined by buckle body 6022*a*' and insertion of tongue 6022*b*' through one of a plurality of openings 6024' in strap 6040'. As discussed, in some examples, optimizing a tightness of the straps 6020', 6040' around the user's wrist and, hence, the contact pressure between the body portion 6001'** and the skin of the user can improve the quality and accurateness of the signal(s) from the sensor(s) of the wearable device significantly.

In any example disclosed herein, the wearable device 6000 can have any of the components, features, or other details of any other examples of wearable devices disclosed herein, including without limitation any of the examples of the wearable device 10 shown in FIGS. 1A-1H and/or the examples of the wearable devices 4500, 4600, 4700, 4800, 4900, 5000 in any combination with any of the components, features, or details described below. For example and without limitation, any examples of the wearable device 6000' disclosed herein can include any of the examples of the optical physiological sensors (also referred to as physiological parameter measurement sensors or merely sensors) and/or components or features thereof, any examples of the processors disclosed herein, and/or any examples of the displays and/or components or features thereof in combination with any of the other components and/or features described or shown herein. Similarly, any examples of wearable devices disclosed herein can have any of the components, features, or other details of any examples of the wearable device 6000' disclosed herein in any combination with any of the components, features, or details of the other wearable devices.

The strap 6020' can include a first end 6030' configured to be secured to a first portion 6032' of the body portion 6001' of the wearable device 6000'. The strap 6020' can also include a second end 6034' opposite the first end 6030', and a length extending between the first end 6030' and the second end 6034'. The strap 6040' can include a first end 6042' configured to be secured to a second portion 6044' of the body portion 6001' of the wearable device 6000'. The strap 6040' can also include a second end 6046' opposite the first end 6042', and a length extending between the first and second ends. The strap 6020' can also include a strap loop 6050'. Strap 6020' and/or 6040' can comprise a material (for example, an elastic material) that allows a length of strap 6020' and/or 6040' to vary. The elastic material of strap 6020' and/or 6040' can comprise a plurality of ridges 6028' configured to allow the strap 6020' and/or 6040' to stretch evenly across its length when the strap 6020' is secured to strap 6040' around a portion of a user's body (for example, a wrist). The plurality of ridges can also allow for greater stretch across the length of the strap. In some examples, the plurality of ridges 6028' of the straps 6020', 6040' extend along substantially an entirety of a length of the straps 6020', 6040'. In some examples, the plurality of ridges 6028' of the straps 6020', 6040' are spaced evenly. In other examples, the plurality of ridges 6028' of the straps 6020', 6040' extend along substantially a portion of the length of the straps 6020', 6040'.

Figure 71:
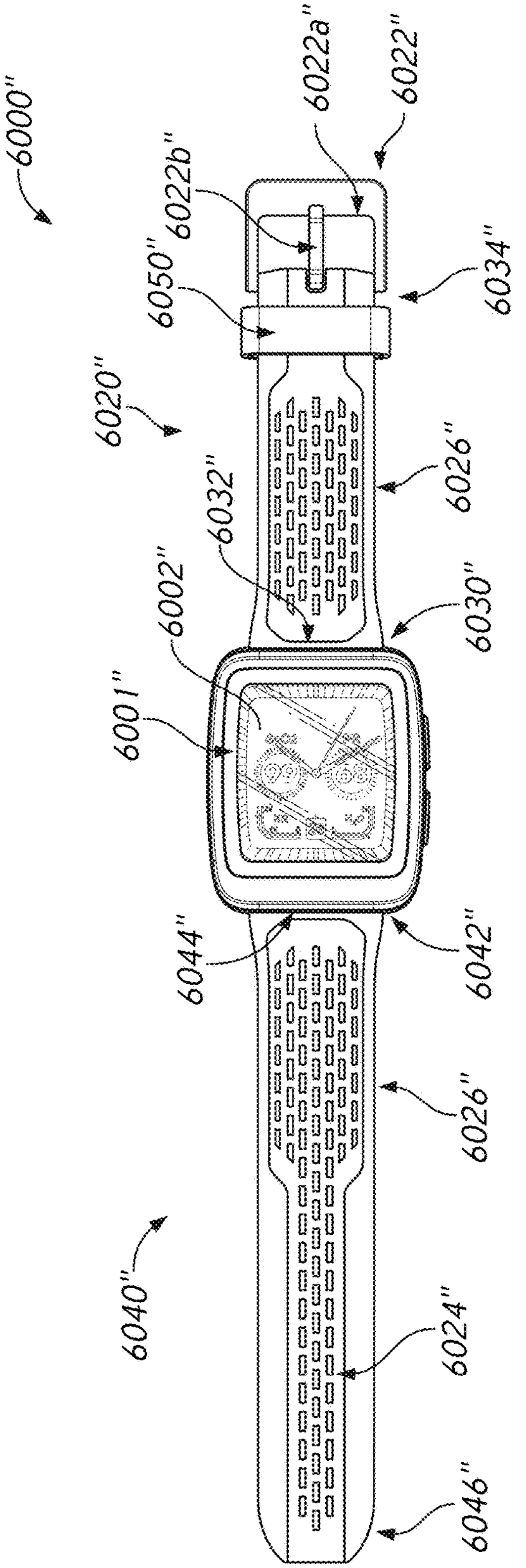
FIGS. 71 and 72 show another example of wearable device that can be configured to be secured to a wrist of a user.
Figure 72:
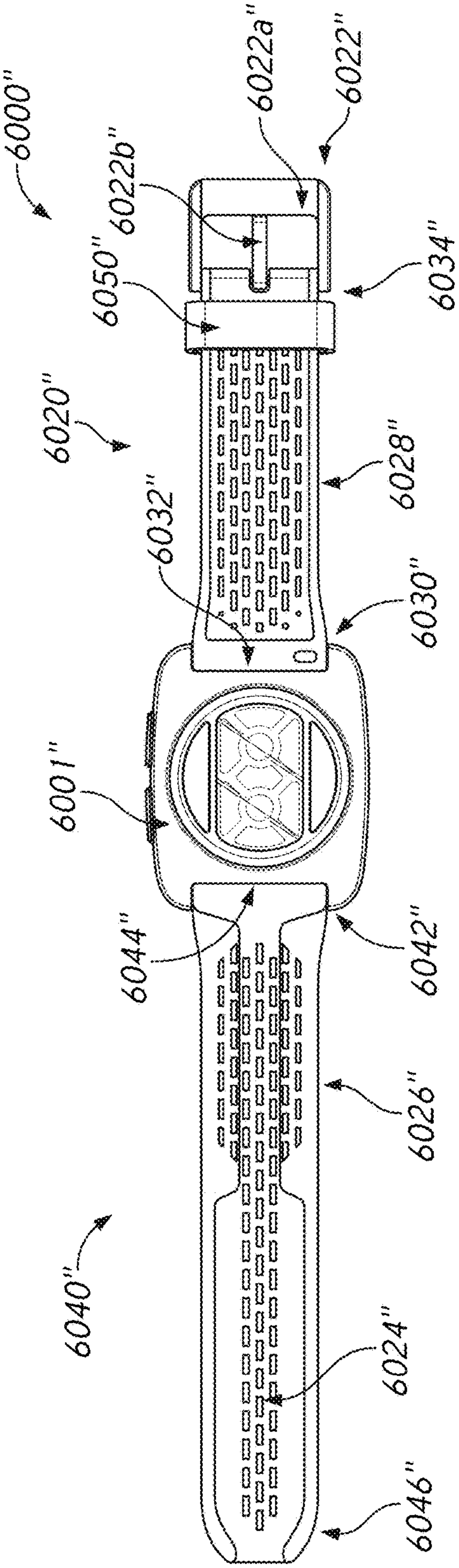

FIGS. 71 and 72 show another example of wearable device 6000" that can be configured to be secured to a wrist of a user. The wearable device 6000" can have a body portion 6001" having a graphical interface or display screen 6002". The body portion 6001" can, in some examples, have a case or housing that houses or supports the electronic components of the wearable device 6000", including one or more sensors, a processor, a power supply, and the display screen 6002". The wearable device 6000" can also have a set of straps 6020", 6040" (also referred to as a band) that can be used to secure the body portion 6001" of the wearable device 6000" to a wrist of the user (as shown in FIG. 68). The wearable device 6000" can include a securing mechanism that can facilitate securement of the straps 6020", 6040" to one another. For, example strap 6020" can include a buckle 6022" that can facilitate securement of the straps 6020", 6040" to one another. Buckle 6022" can include a buckle body **6022*a*" and a tongue 6022*b*" (which can also be referred to as a "buckle tongue"). Straps 6020", 6040" can be secured to one another via insertion of at least a portion of strap 6040" through an opening defined by buckle body 6022*a*" and insertion of tongue 6022*b*" through one of a plurality of openings 6024" in strap 6040". As discussed, in some examples, optimizing a tightness of the straps 6020", 6040" around the user's wrist and, hence, the contact pressure between the body portion 6001"** and the skin of the user can improve the quality and accurateness of the signal(s) from the sensor(s) of the wearable device significantly.

In any example disclosed herein, the wearable device 6000" can have any of the components, features, or other details of any other examples of wearable devices disclosed herein, including without limitation any of the examples of the wearable device 10 shown in FIGS. 1A-1H and/or the examples of the wearable devices 4500, 4600, 4700, 4800, 4900, 5000, 6000, 6000' in any combination with any of the components, features, or details described below. For example and without limitation, any examples of the wearable device 6000" disclosed herein can include any of the examples of the optical physiological sensors (also referred to as physiological parameter measurement sensors or merely sensors) and/or components or features thereof, any examples of the processors disclosed herein, and/or any examples of the displays and/or components or features thereof in combination with any of the other components and/or features described or shown herein. Similarly, any examples of wearable devices disclosed herein can have any of the components, features, or other details of any examples of the wearable device 6000" disclosed herein in any combination with any of the components, features, or details of the other wearable devices.

The strap 6020" can include a first end 6030" configured to be secured to a first portion 6032" of the body portion 6001" of the wearable device 6000". The strap 6020" can also include a second end 6034" opposite the first end 6030", and a length extending between the first end 6030" and the second end 6034". The strap 6040" can include a first end 6042" configured to be secured to a second portion 6044" of the body portion 6001" of the wearable device 6000". The strap 6040" can also include a second end 6046" opposite the first end 6042", and a length extending between the first and second ends. The strap 6020" can also include a strap loop 6050". Strap 6020" and/or 6040" can comprise a material (for example, an elastic material) that allows a length of strap 6020" and/or 6040" to vary. The elastic material of strap 6020" and/or 6040" can comprise a plurality of holes 6026" configured to allow the strap 6020" and/or 6040" to stretch across its length when the strap 6020" is secured to strap 6040" around a portion of a user's body (for example, a wrist). The plurality holes can also allow for greater stretch across a portion of the length with more holes to provide greater comfort around certain portions of the wrist. In some examples, the plurality of holes 6026" of the straps 6020", 6040" extend along substantially an entirety of a length of the straps 6020", 6040" to provide more even stretch across the length of the strap. In some examples, the plurality of holes 6026" of the straps 6020", 6040" are spaced evenly. In other examples, the plurality of holes 6026" of the straps 6020", 6040" extend along substantially a portion of the length of the straps 6020", 6040". In some examples, at least a portion of the plurality of holes 6026" of the straps 6020", 6040" are covered.

Figure 73:
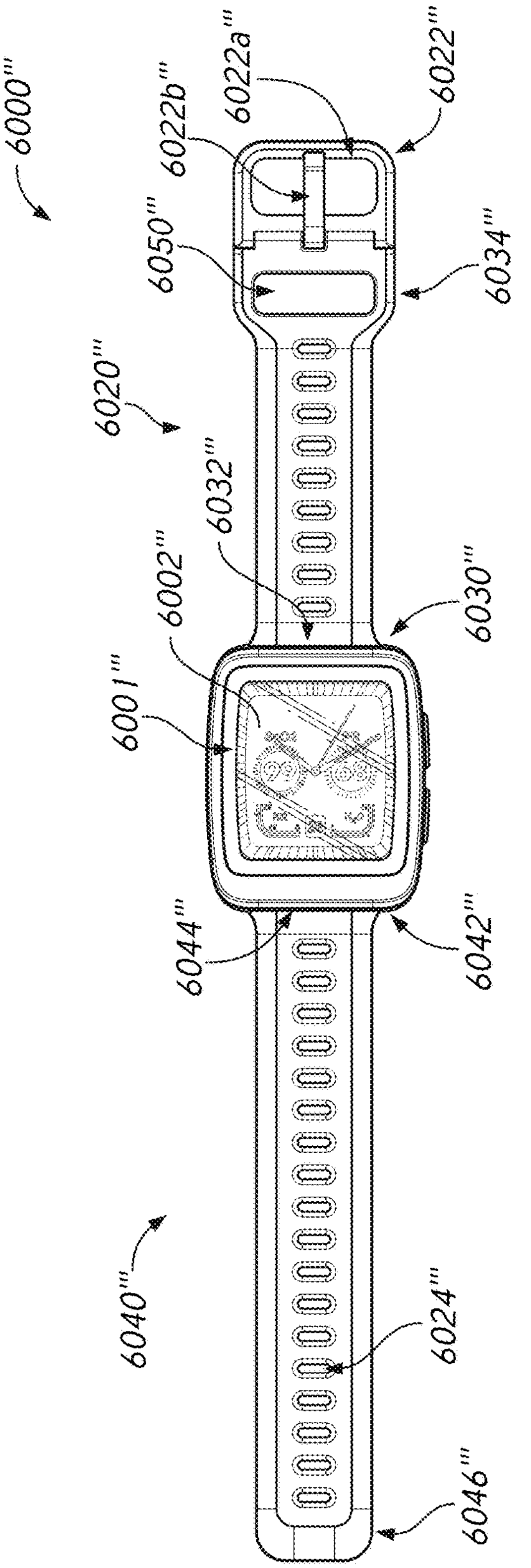
FIGS. 73 and 74 show another example of wearable device that can be configured to be secured to a wrist of a user.
Figure 74:
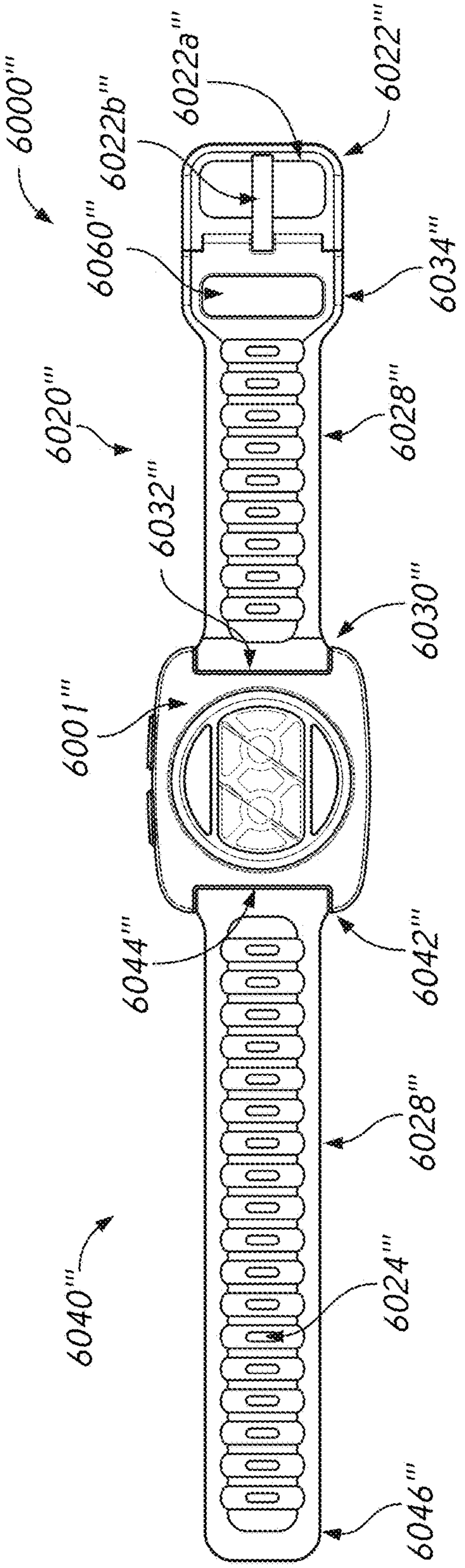

FIGS. 73 and 74 show another example of wearable device 6000'" that can be configured to be secured to a wrist of a user. The wearable device 6000'" can have a body portion 6001' having a graphical interface or display screen 6002'". The body portion 6001'" can, in some examples, have a case or housing that houses or supports the electronic components of the wearable device 6000'", including one or more sensors, a processor, a power supply, and the display screen 6002'. The wearable device 6000'" can also have a set of straps 6020', 6040' (also referred to as a band) that can be used to secure the body portion 6001' of the wearable device 6000' to a wrist of the user. The wearable device 6000'" can include a securing mechanism that can facilitate securement of the straps 6020'", 6040'" to one another. For, example strap 6020' can include a buckle 6022'" that can facilitate securement of the straps 6020'", 6040'" to one another. Buckle 6022' can include a buckle body **6022*a*'" and a tongue 6022*b*'" (which can also be referred to as a "buckle tongue"). Straps 6020'", 6040' can be secured to one another via insertion of at least a portion of strap 6040' through an opening defined by buckle body 6022*a*'" and insertion of tongue 6022*b*'" through one of a plurality of openings 6024' in strap 6040'". As discussed, in some examples, optimizing a tightness of the straps 6020', 6040' around the user's wrist and, hence, the contact pressure between the body portion 6001'** and the skin of the user can improve the quality and accurateness of the signal(s) from the sensor(s) of the wearable device significantly.

In any example disclosed herein, the wearable device 6000' can have any of the components, features, or other details of any other examples of wearable devices disclosed herein, including without limitation any of the examples of the wearable device 10 shown in FIGS. 1A-1H and/or the examples of the wearable devices 4500, 4600, 4700, 4800, 4900, 5000, 6000, 6000', 6000" in any combination with any of the components, features, or details described below. For example and without limitation, any examples of the wearable device 6000' disclosed herein can include any of the examples of the optical physiological sensors (also referred to as physiological parameter measurement sensors or merely sensors) and/or components or features thereof, any examples of the processors disclosed herein, and/or any examples of the displays and/or components or features thereof in combination with any of the other components and/or features described or shown herein. Similarly, any examples of wearable devices disclosed herein can have any of the components, features, or other details of any examples of the wearable device 6000'" disclosed herein in any combination with any of the components, features, or details of the other wearable devices.

The strap 6020' can include a first end 6030' configured to be secured to a first portion 6032''' of the body portion 6001''' of the wearable device 6000'''. The strap 6020' can also include a second end 6034' opposite the first end 6030', and a length extending between the first end 6030''' and the second end 6034'. The strap 6040''' can include a first end 6042''' configured to be secured to a second portion 6044' of the body portion 6001' of the wearable device 6000'''. The strap 6040' can also include a second end 6046' opposite the first end 6042''', and a length extending between the first and second ends. The strap 6020' can also include an aperture 6060''' configured to receive the second end 6046''' of strap 6040' when the strap 6020' is secured to strap 6040''' around a portion of a user's body (for example, a wrist). Strap 6020''' and/or 6040''' can comprise a material (for example, an elastic material) that allows a length of strap 6020''' and/or 6040' to vary. The elastic material of strap 6020''' and/or 6040''' can comprise a plurality of ridges 6028''' configured to allow the strap 6020''' and/or 6040' to stretch evenly across its length when the strap 6020''' is secured to strap 6040''' around a portion of a user's body (for example, a wrist). The plurality of ridges can also allow for greater stretch across the length of the strap. In some examples, the plurality of ridges 6028''' of the straps 6020''', 6040''' extend along substantially an entirety of a length of the straps 6020', 6040'''. In some examples, the plurality of ridges 6028''' of the straps 6020', 6040' are spaced evenly. In other examples, the plurality of ridges 6028''' of the straps 6020', 6040''' extend along substantially a portion of the length of the straps 6020, 6040.

Figure 75A:
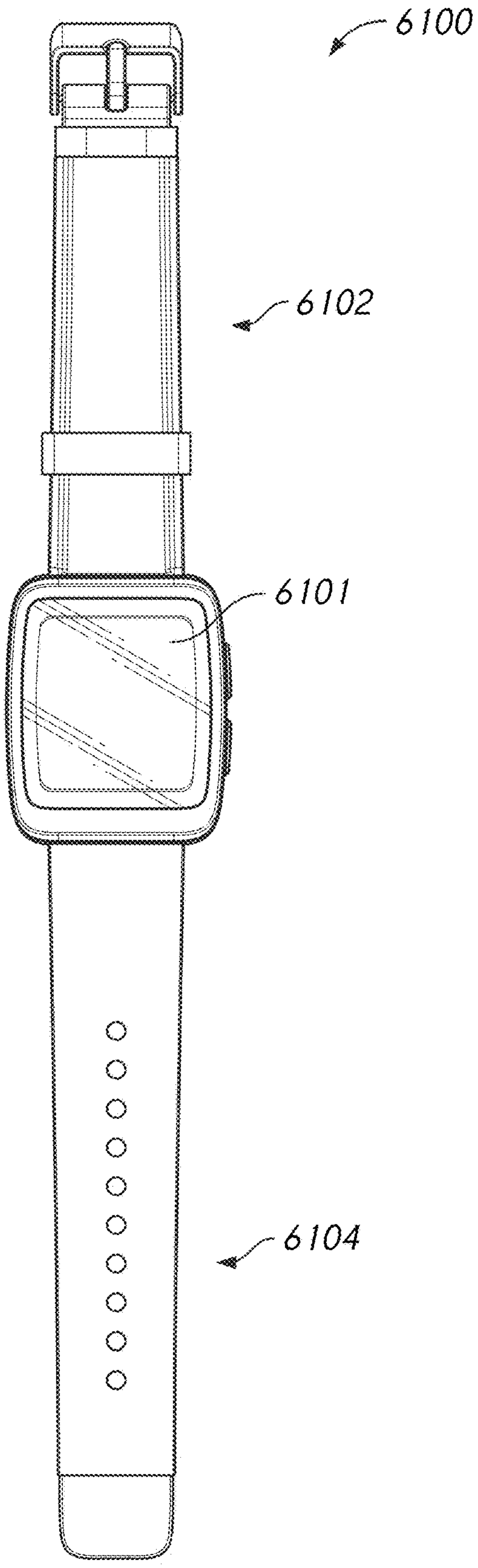
FIGS. 75A-75B illustrate top and bottom views of a wearable device in accordance with aspects of this disclosure.
Figure 75B:
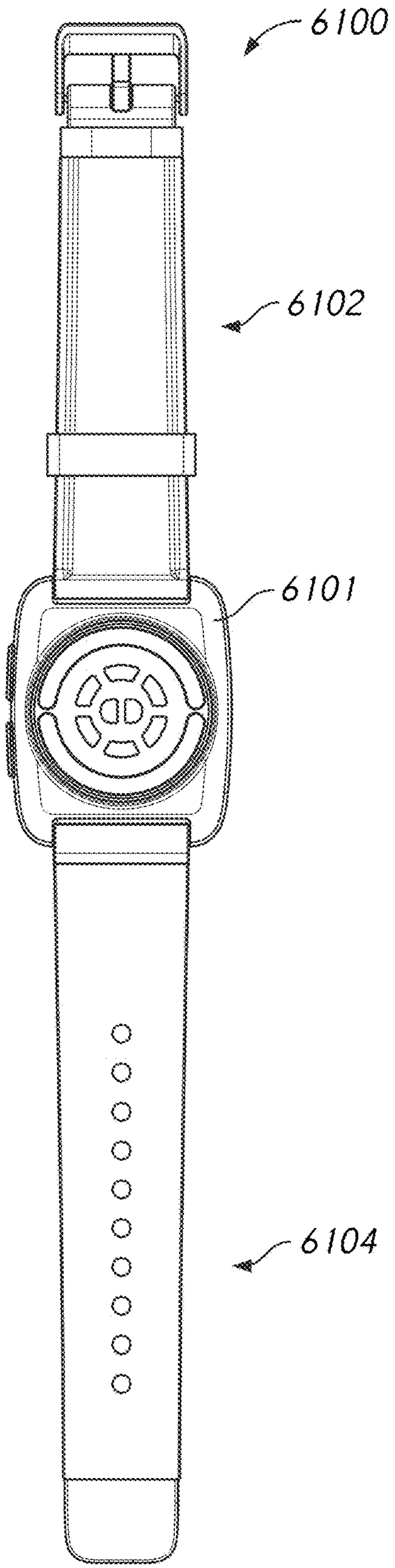
Figure 75C:
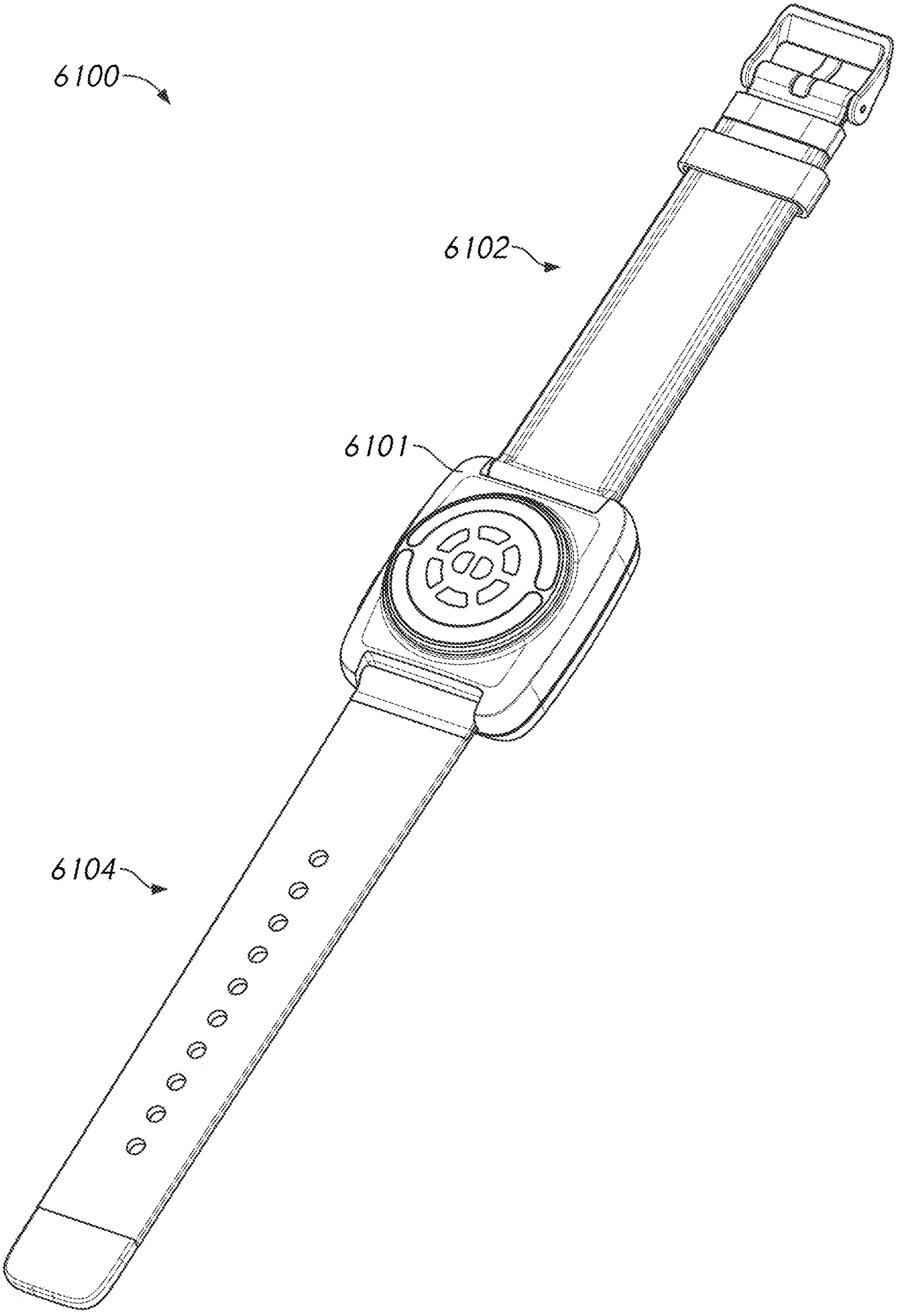
FIG. 75C illustrates a bottom perspective view of the wearable device of FIGS. 75A-75B in accordance with aspects of this disclosure.
Figure 75D:
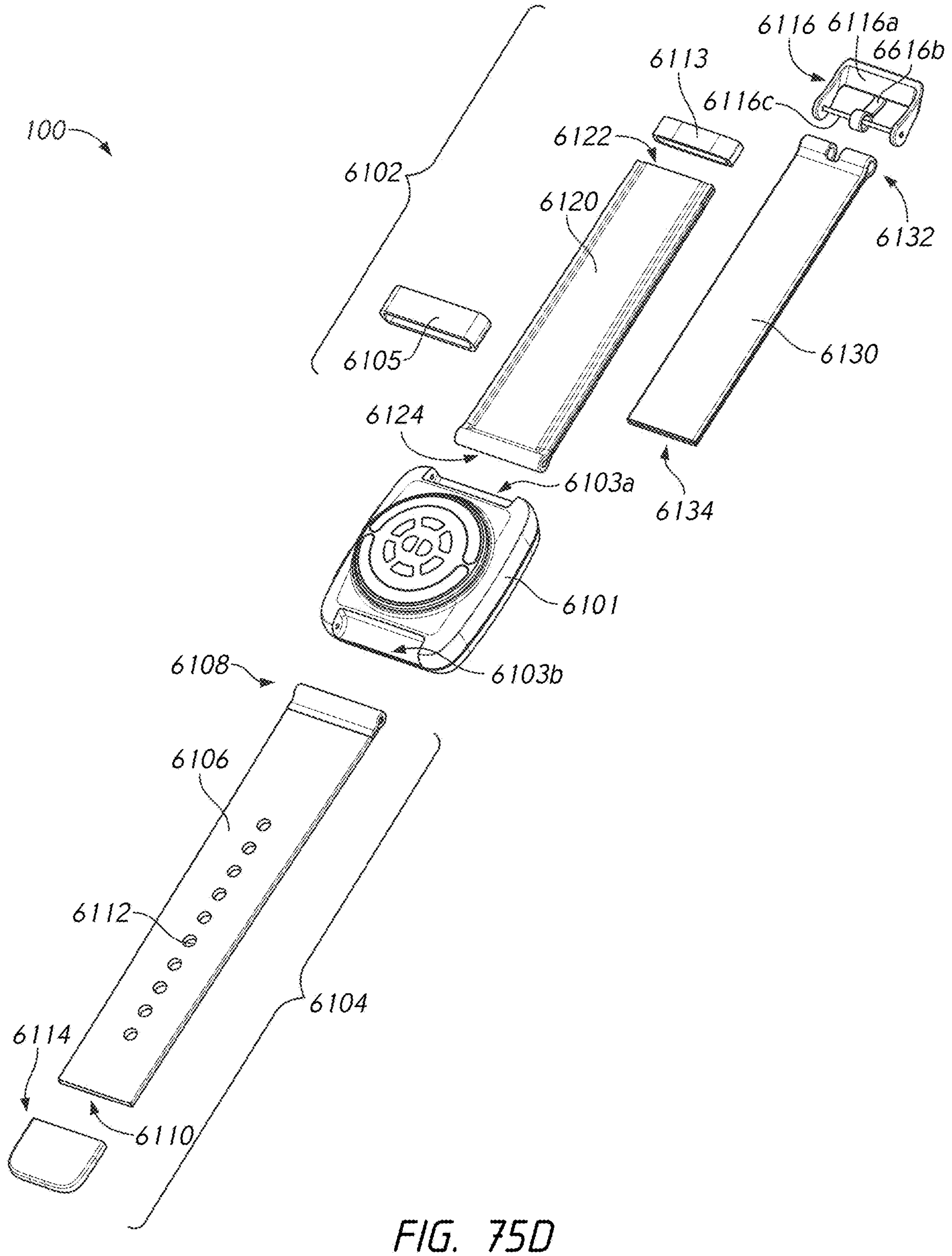
FIG. 75D illustrates an exploded view of the wearable device of FIGS. 75A-75B in accordance with aspects of this disclosure.

FIGS. 75A-75B illustrate top and bottom views of a wearable device 6100. FIG. 75C illustrates a bottom perspective view of the wearable device 6100 and FIG. 75D illustrates an exploded view of the wearable device 6100. The wearable device 6100 can include one or more straps. For example, the wearable device 6100 can include strap 6102 and strap 6104. Straps 6102, 6104 can be configured to secure to one another and/or to a portion of a user's body (for example, around a wrist of the user). While straps disclosed herein may be described and/or shown with reference to a wearer's wrist, any of the straps disclosed herein can be configured to secure to other portions of a wearer's body, such as an ankle, leg, arm, chest, among other locations.

Wearable device 6100 can be a wristwatch incorporating a plethysmograph sensor (which may also be referred to as a "pulse oximeter" or "oximetry sensor" or "optical sensor") with built-in watch and/or time-indicating functions. As described in more detail below, strap 6102 can be configured to allow the wearable device 6100 to accommodate a greater variety of sizes and/or shapes of wrists. For example, at least a portion of strap 6102 can be made of an elastic (for example, stretchable) material that allows a length of strap 6102 to vary, for example, before, during, and/or after securement to a user's wrist. This can advantageously provide, among other things, optimal contact between the plethysmograph sensor and the wrist while not compromising the comfort of the wearer and/or reducing the blood flow across the wrist in a way that reduces the accuracy of physiological parameter measurement by the plethysmograph sensor of the wearable device 6100. Accordingly, in some implementations, the wearable device 6100 can eliminate the need to wear an additional sensor (for example, a pulse oximetry sensor) when going about daily activities. Incorporation of an oximetry sensor in wearable device 6100 can provide the benefits of physiological information monitoring in a discrete (for example, hidden) form. A wearer of the wearable device 6100 can be informed of physiological parameters, such as vital signs including but not limited to heart rate and oxygen saturation. This information can be helpful in providing feedback to the wearer and/or a third party user, for example, a healthcare professional or the wearer's family member, when the wearer is exercising, or otherwise for warning the wearer of possible health-related conditions, including but not limited to changes in the wearer's physiological parameters in response to medication that is being administered to the wearer.

Wearable device 6100 (for example, strap 6102 and/or strap 6104) can include a mechanism configured to allow the straps 6102, 6104 to secure around a portion of the user's body (for example, wrist). For example, with reference to FIGS. 75D-75F, the wearable device 6100 can include a buckle 6116 that can facilitate securement of the straps 6102, 6104 to one another. Buckle 6116 can include a buckle body **6116*a* and a tongue 6116*b* (which can also be referred to as a "buckle tongue"). Straps 6102, 6104 can be secured to one another via insertion of at least a portion of strap 6104 through an opening defined by buckle body 6116*a* and insertion of tongue 6116*b* through one of a plurality of openings 6112 in strap 6104**.

Figure 75E:
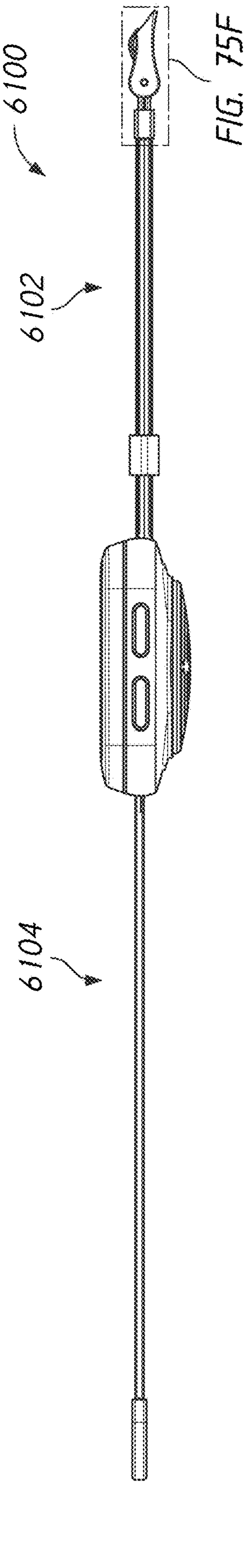
FIG. 75E illustrates a side view of the wearable device of FIGS. 75A-75B in accordance with aspects of this disclosure.
Figure 75F:
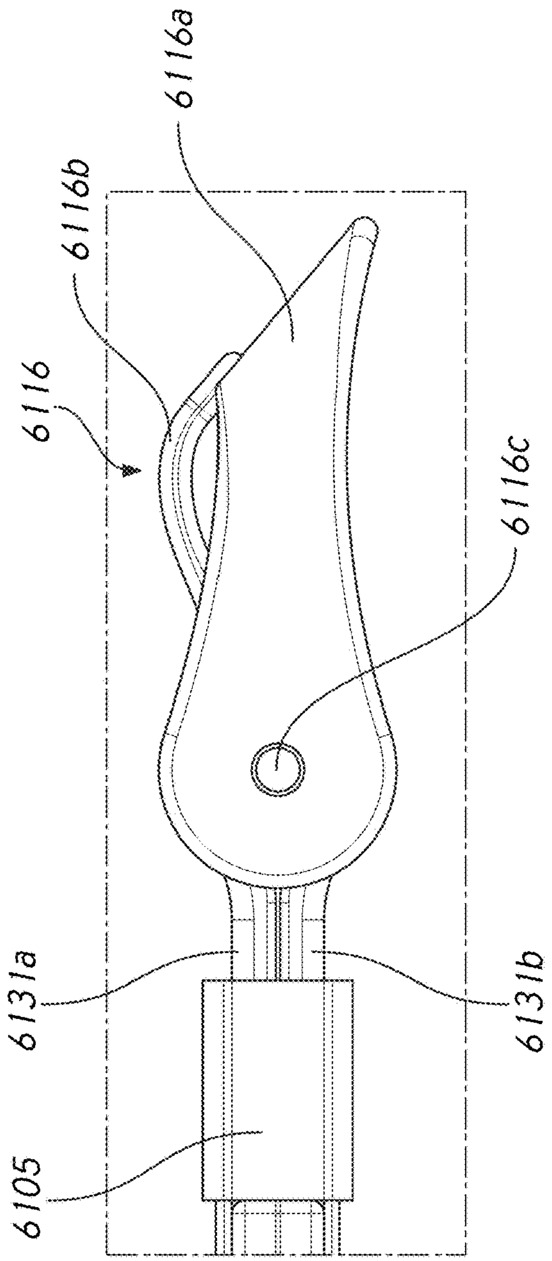
FIG. 75F illustrates an enlarged view of a portion of the wearable device as shown in FIG. 75E in accordance with aspects of this disclosure.

As discussed in more detail below, in some implementations, strap 102 comprises an outer band 6120 and an inner band 6130. In such implementations, buckle 6116 can be coupled with an end 6132 of inner band 6130. For example, buckle 6116 can be coupled to an end 6132 of inner band 6130 via a pin **6116*c* that extends through an opening at end 6132 of inner band 6130. FIG. 75E illustrates a side view of wearable device 6100 and strap 6102 and FIG. 75F illustrates an enlarged view of a portion of strap 6102 and buckle 6116. In some implementations, such opening is defined as a through-hole extending through all or a portion of a width of the inner band 6130 at end 6132. In some implementations, an opening at end 6132 is defined by portions 6131*a*, 6131*b* of the inner band 6130 that are wrapped and/or folded upon each other (see FIG. 75F). Pin 6116*c* can extend through any of such above-described openings of inner band 6130 and can be coupled to portions of buckle body 6116*a* so as to couple buckle 6116 to inner band 6130. Such securement can also couple buckle 6116 to strap 6102 (for example, to outer band 6120) and module 6101 of wearable device 6100 (discussed further below) when inner band 6130 and outer band 6120 are secured to one another. In some implementations, as shown in FIG. 75D, end 6132 of inner band 6130 includes a slot that accommodates a portion of buckle tongue 6116*b* when buckle 6116 is secured to end 6132 of inner band 6130**.

Buckle 6116 can be secured to inner band 6130 so as to allow buckle body **6116*a* to rotate relative to end 6132. In some implementations, tongue 6116*b* can be coupled (for example, rotatably coupled) to an end 6132 of inner band 6130, for example, via the above-described pin 6116*c*. As shown, buckle body 6116*a* can define an opening (for example, when coupled to an end 6132 of inner band 6130) that can be configured to receive an end of strap 6104 to facilitate securement of straps 6102, 6104** and/or formation of a closed loop around a portion of the wearer's body.

With reference to FIG. 75D, strap 6104 can include a band 6106 having ends 6108, 6110 opposite one another. In some implementations, strap 6104 includes one or more or a plurality of openings 6112 that can be sized and/or shaped to receive buckle tongue **6116*b* as discussed above. End 6108 can be configured to be secured to a strap connection 6103*b* (discussed further below) to secure strap 6104 to module 6101 of wearable device 6100 which is described further below. In some implementations, strap 6104 includes an end piece 6114 secured to end 6110 of band 6104**.

Strap 6102 and/or 6104 can include one or more members comprising a material (for example, an elastic material) that allows a length of strap 6102 and/or 6104 to vary. For example, strap 6102 and/or 6104 can include two members connected to one another, and one or both of such two members can be made of an elastic (for example, stretchable) material that allows a length of strap 6102 and/or 6104 to vary when a force is applied to one or both of such two members. In some implementations, strap 6102 and/or strap 6104 can include a first member made of a first material and a second member made of a second material and connected to the first member, wherein the first material is different than (for example, more stretchable) the second material. Such first and second members can be, for example, inner band 6130 and outer band 6120 discussed further below.

As mentioned above and with reference to FIG. 75D, in some implementations, strap 6102 includes an outer band 6120 and an inner band 6130. Inner band 6130 can include an end 6132 that can be connected to buckle 6116 as discussed above and an end 6134 opposite end 6132. Outer band 6120 can include an end 6124 configured to be secured to a strap connection 6103*a* of module 6101 and an end 6122 opposite such first end. Inner band 6130 and outer band 6120 can be secured to one another. In some implementations, outer band 6120 includes a hollow interior that is sized and/or shaped to receive at least a portion of inner band 6130. For example, a cross-section of inner band 6130 can be smaller than a cross-section of a hollow interior defined by outer band 6120. The hollow interior of outer band 6120 can extend along all or a portion of a length of the outer band 6120 that extends between ends 6122, 6124. In some implementations, the hollow interior of outer band 6120 extends substantially the entirety of the length of outer band 6120 between ends 6122, 6124. FIG. 75H illustrates how the inner band 6130 can be positioned within and/or secured to outer band 6120, where a portion of inner band 6130 is shown in dotted lines. Various portions of inner band 6130 can be secured to (for example, permanently secured to) and/or within the hollow interior of outer band 6120. For example, end 6134 (or a portion thereof) can be secured to a portion of outer band 6120. Additionally or alternatively, a top surface and/or bottom surface which extend between ends 6132, 6134 of inner band 6130 (or portions thereof) can be secured to portions of outer band 6120. Additionally or alternatively, sides of inner band 6130 extending between ends 6132, 6134 (or portions thereof) can be secured to outer band 6120. In some implementations, such top and bottom surfaces are not secured portions of outer band 6120 and/or such sides are not secured portions of outer band 6120. In some implementations, only end 6134 is secured (for example, permanently secured) to and/or within outer band 6120.

In some implementations, inner band 6130 extends within an entirety of the hollow interior of outer band 6120 and/or along substantially an entirety of the length of outer band 6120. Alternatively, in some implementations, inner band 6130 extends within less than an entirety of the hollow interior and/or length of outer band 6120, for example, less than 90%, less than 80%, less than 70%, less than 60%, less than 50%, less than 40%, less than 30%, less than 20%, less than 10%, of an entirety of the hollow interior of outer band 6120 and/or the length of outer band 6120. As shown in the FIGS., a portion of inner band 6130 can be positioned within the hollow interior of outer band 6120 and another portion of inner band 6130 can be positioned outside such hollow interior. For example, a portion of inner band 6130 proximate end 6132 can be positioned outside such hollow interior of outer band 6120 and can extend beyond end 6122 of outer band 6120.

With reference to FIG. 75D, in some implementations, strap 6102 includes a collar 6113 connected to and/or around end 6122 of outer band 6120. In some implementations, wearable device 6100 includes a strap loop 6105. Strap loop 6105 can be positioned around outer band 6120 and can receive a portion of strap 6104 when straps 6102, 6104 form a closed loop.

Straps 6102, 6104 can be made of a variety of materials. Strap 6104 (for example, band 6106) or portions thereof can be made of leather (for example, suede) and/or fabric among other materials. Outer band 6120 (or portions thereof) of strap 6102 can be made of leather (for example, suede), fabric, and/or silicone among other materials. Inner band 6130 (or portions thereof) of strap 6102 can be made of silicone and/or fabric among other materials. Inner band 6130 (or a portion thereof) can be made of a material that is different than a material that outer band 6120 is made of. In some implementations, inner band 6130 (or a portion thereof) is made of an elastic material that allows a length of inner band 6130 to be extended when a force is applied to inner band 6130 and retracted when such force is removed. In some implementations, inner band 6130 (or a portion thereof) is made of a material that is more stretchable than a material of the outer band 6120. Such configurations can allow inner band 6130 to stretch relative to outer band 6120 when connected thereto, thereby allowing a total length of strap 6102 to increase, for example, to accommodate varying sizes and/or shapes of wrists of different users. In some implementations, inner band 6130 (or a portion thereof) is made of silicone and/or fabric that is stretchable.

Figure 75G:
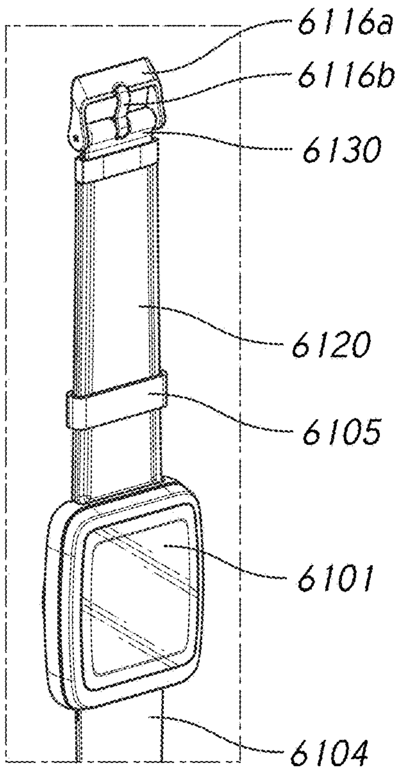
FIGS. 75G-75H illustrates views of a strap of the wearable device of FIGS. 75A-75B in a first state in accordance with aspects of this disclosure.
Figure 75H:
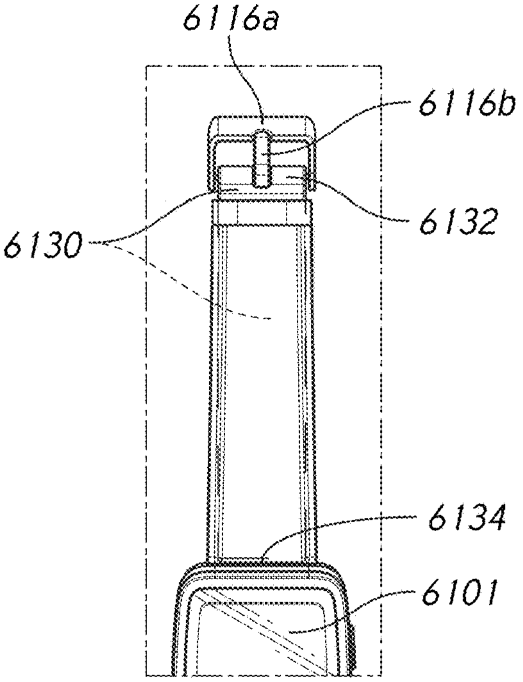
Figure 75I:
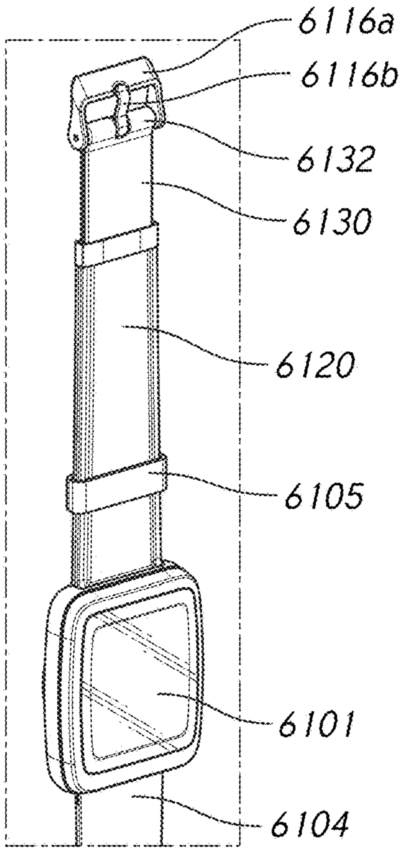
Figure 75J:
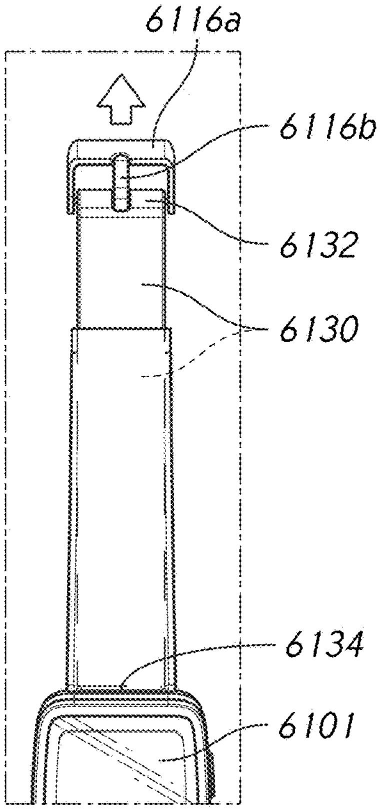

FIGS. 75G-75H illustrate strap 6102 in a first state and FIGS. 75I-75J illustrate strap 6102 in a second state. A portion of inner band 6130 that is within an interior and/or enclosed by outer band 6120 is shown in dotted lines in FIGS. 75H and 75J, and strap loop 6105 is not shown for purposes of clarity. Such first state (FIGS. 75G-75H) can be a neutral and/or unstretched state of strap 6102 and such second state (FIGS. 75I-75J) can be a stretched state. As shown, inner band 6130 can be extended (for example, stretched) farther when strap 6102 is in the second state than when in the first state. Application of opposing forces on inner band 6130 (one of which is shown in FIG. 75J), for example, relative to outer band 6120 can cause the strap 6102 to transition from and/or between such first and second states. Such force can be applied before, during, and/or after securement of strap 6102 and strap 6104, for example, around a user's wrist. Such force can result when strap 6102 is secured around a portion of a user's body (for example, a wrist) and/or when strap 6102 is secured to strap 6104 (for example, via buckle 6116). With reference to FIGS. 75H and 75J, a total length of strap 6102 can be larger when strap 6102 is in the second state (FIG. 75J) than when in the first state (FIG. 75H). Such total length of strap 6102 can be that measured between a portion of the module 6101 to which an end of strap 6102 (for example, end 6124 of outer band 6120) connects to an opposite end of strap 6102 and/or to a portion of buckle 6116 connected to such opposite end (which can be included in wearable device 6100 in some implementations). A length of inner band 6130 can be larger when strap 6102 is in the second state (FIG. 75J) than when in the first state (FIG. 75H). In some implementations, a length of outer band 6120 does not change or changes minimally when strap 6102 transitions from the first and second states. As discussed above, inner band 6130 can be made of a material that allows inner band 6130 to stretch. As also discussed, outer band 6120 can be made of a material that is different than a material of inner band 6130.

Figure 75K:
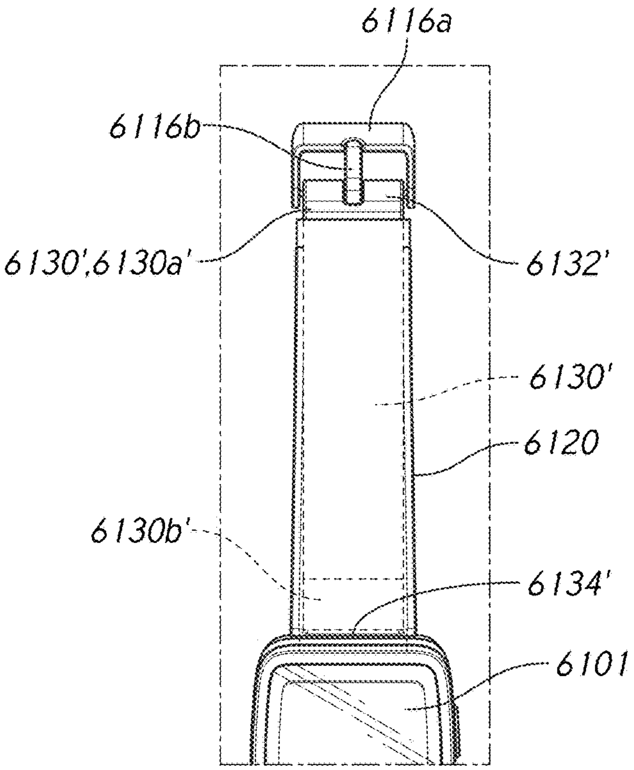
Figure 75L:
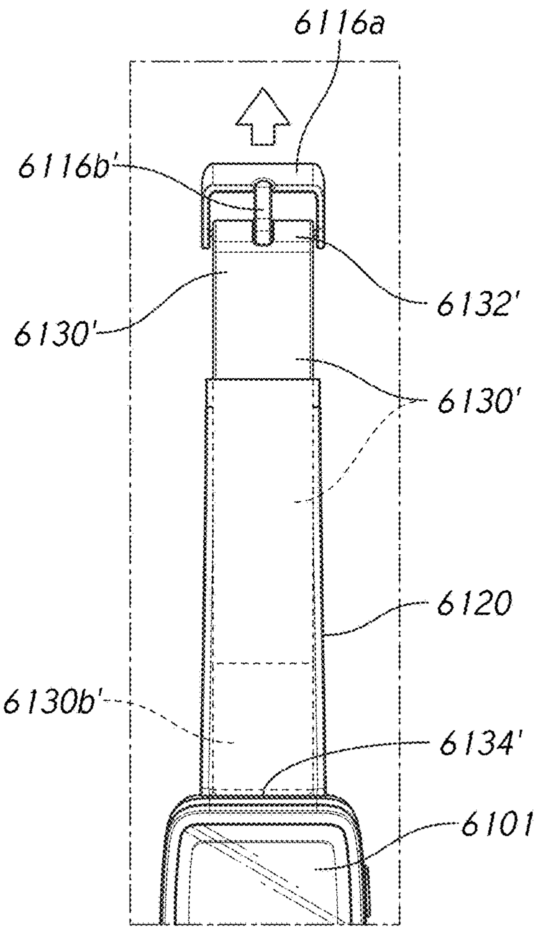

FIGS. 75K-75L illustrate an alternative implementation for an inner band 6130' that can be used with outer band 6120 in place of inner band 6130. Inner band 6130' includes ends 6132', 6134' opposite one another. FIG. 75K illustrates inner band 6130' in a first state (for example, an unstretched state) and FIG. 75L illustrates inner band 6130' in a second state (for example, a stretched state). FIGS. 75K-75L illustrate a portion of inner band 6130' in dotted line so as to illustrate the securement and/or positioning of inner band 6130' within the interior of outer band 6120. Ends 6132', 6134' can be similar or identical to ends 6132, 6134 discussed above and therefore the discussion above with respect to ends 6132, 6134 is equally applicable to ends 6132', 6134'. Inner band 6130' can include top and bottom surfaces and sides extending between ends 6132', 6134' similar to the top and bottom surfaces and sides of inner band 6130. All or portions of end 6134', such top and/or bottom surfaces, and/or such sides can be secured (for example, permanently secured) to and/or within outer band 6120 similar to as discussed above with respect to inner band 6130.

Inner band 6130' includes a first portion 6130*a*' and a second portion 6130*b*'. In some implementations, portions 6130*a*', 6130*b*' are made of different materials. A portion of first portion 6130*a*' that is within an interior of and/or surrounded by outer band 6120 is illustrated in dotted lines in FIGS. 75K-75L. Second portion 6130*b*', being within an interior of and/or surrounded by outer band 6120, is also illustrated in dotted lines in FIGS. 75K-75L. For example, in some implementations, portion 6130*a*' comprises a material that is less stretchable than portion 6130*b*'. Alternatively, in some implementations, portion 6130*a*' comprises a material that is more stretchable than portion 6130*b*'. In some implementations, portion 6130*a*' comprises leather and/or fabric and portion 6130*b*' comprises a stretchable material such as silicone and/or a stretchable fabric. Alternatively, in some implementations, portion 6130*b*' comprises leather and/or fabric and portion 6130*a*' comprises a stretchable material such as silicone and/or a stretchable fabric. In some implementations, portion 6130*a*' comprises a different material than portion 6130*b*' but the same material as outer band 6120. In some implementations, portion 6130*a*', portion 6130*b*', and outer band 66120 all comprise materials different from one another. In some implementations, portions 6130*a*', 6130*b*' are integrally formed with one another. For example, ends of portions 6130*a*', 6130*b*' can be permanently secured to one another to form inner band 6130'.

In some implementations, portion 6130*a*' comprises a greater portion of inner band 6130' than portion 6130*b*'. For example, portion 6130*a*' can extend for a greater portion of a length of inner band 6130' than portion 6130*b*'. Alternatively, in some implementations, portion 6130*b*' comprises a greater portion of inner band 6130' than portion 6130*a*'. For example, portion 6130*b*' can extend for a greater portion of a length of inner band 6130' than portion 6130*a*'.

Inner band 6130' (and therefore strap 6102 that includes inner band 6130' along with outer band 6120) can have a first state (for example, a neutral and/or unstretched state) as shown by FIG. 75K and a second state (for example, a stretched state) as shown in FIG. 75L. In some implementations, when inner band 6130' is in both of such first and second states, portion 6130*b*' of inner band 6130' is within the interior of outer band 6120, for example, is hidden. Alternatively, in some implementations, portion 6130*b*' is at least partially outside the interior of outer band 6120 when inner band 6130' is in the second state (FIG. 75L) but is positioned within such interior when inner band 6130' is in the first state (FIG. 75K) such that portion 6130*b*' is not visible.

Figure 76A:
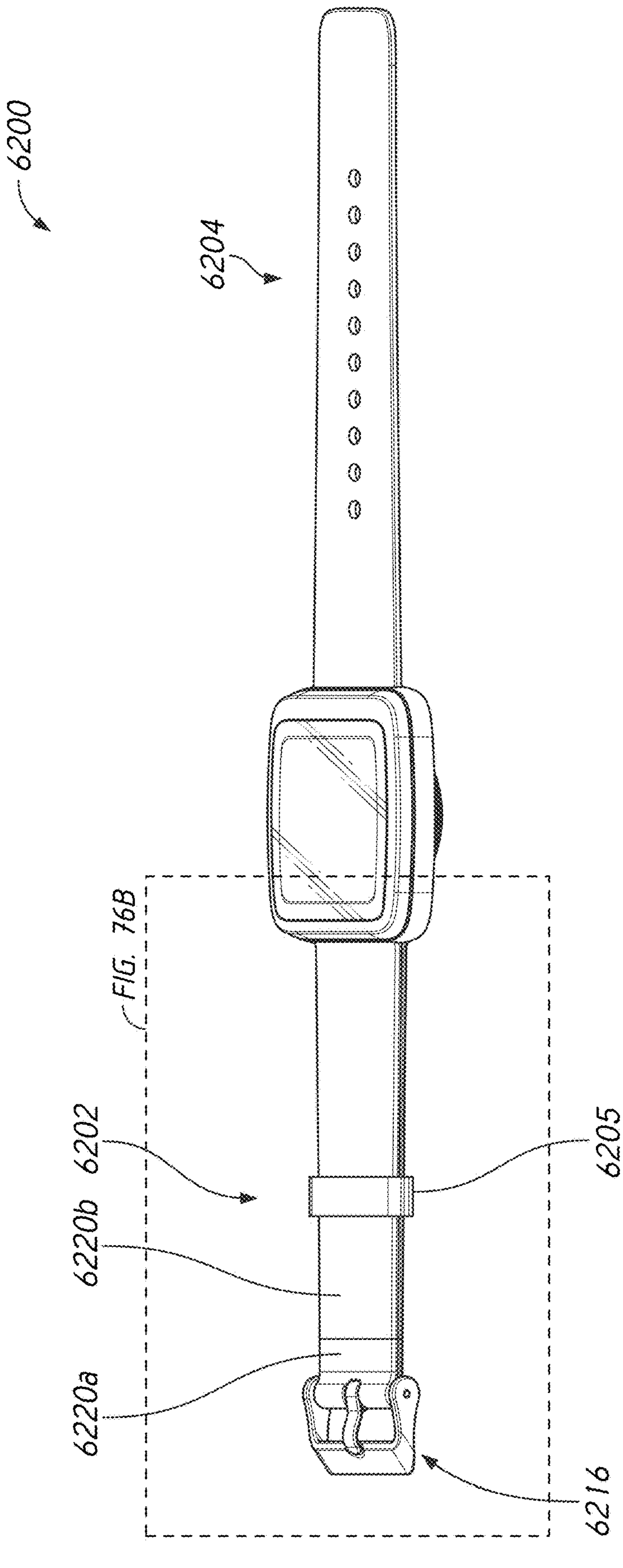

FIG. 76A illustrates another implementation of a wearable device 6200. Wearable device 6200 can be similar to wearable device 6100 in some or many respects. Wearable device 6200 can include a strap 6202, module 6101 (discussed in more detail elsewhere herein), and strap 6204. Wearable device 6200 can include a fastening mechanism that can allow straps 6202, 6204 to secure to one another to form a closed loop around a portion of a user's body (for example, a wrist). For example, wearable device 6200 can include a buckle 6216 connected to a portion of strap 6202, and buckle 6216 can be similar or identical to buckle 6116 discussed previously. For example, buckle 6216 can include a buckle body 6216*a* and a buckle tongue 6216*b* which can be similar or identical to buckle body 6116*a* and buckle tongue 6116*b*, respectively. In some implementations, wearable device 6200 includes a strap loop 6205. Strap loop 6205 can be similar or identical to strap loop 6105 discussed above.

Figure 76B:
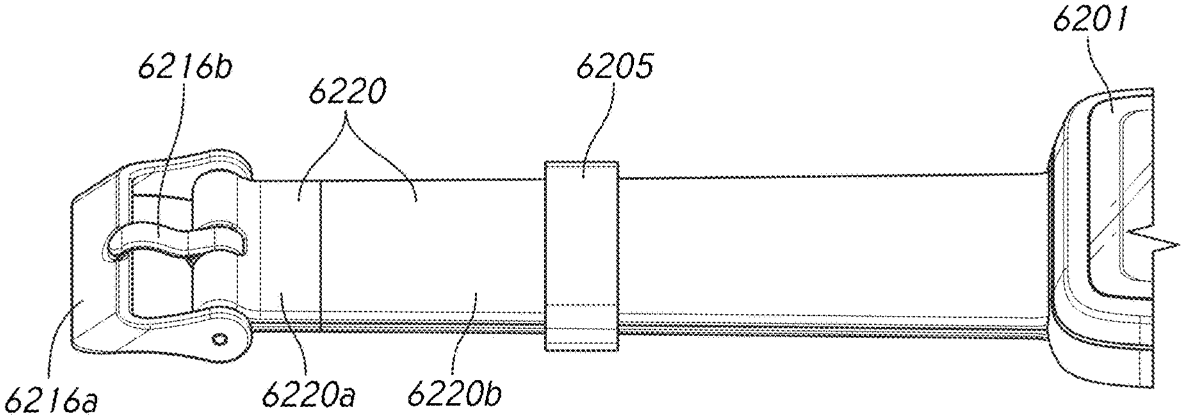
Figure 76C:
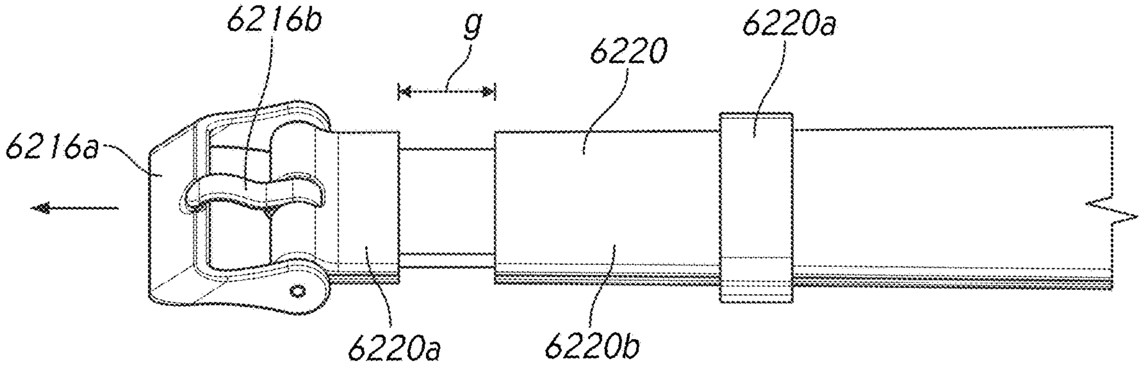

FIGS. 76B-76C illustrate enlarged views of strap 6202. Specifically, FIG. 76B illustrates strap 6202 in a first state and FIG. 76C illustrates strap 6202 in a second state. Such first state (FIG. 76B) can be a neutral and/or unstretched state of strap 6202 and such second state (FIG. 76C) can be a stretched state. Strap 6202 can include an inner band 6230 (see FIG. 76C) and an outer band 6220. Outer band 6220 can comprise a first portion 6220*a* and a second portion 6220*b*, each of which can be connected to the inner band 6230. Inner band 6230 can be secured to portions 6220*a*, 6220*b* and portions 6220*a*, 6220*b* can be indirectly connected to one another via inner band 6230. In some implementations, portion 6220*a* and portion 6220*b* each include a hollow interior. In some implementations, a first portion of inner band 6230 is positioned and/or secured within an interior of portion 6220*a* and a second portion of inner band 6230 is positioned and/or secured within an interior of portion 6220*b*. Inner band 6230 can include a first end secured to portion 6220*a* (for example, secured within an interior of portion 6220*a*) and a second end opposite the first end of the inner band 6230 that is secured to portion 6220*b* (for example, secured within an interior of portion 6220*b*). In some implementations, inner band 6230 includes top and/or bottom surfaces and/or sides that extend between opposite ends of inner band 6230. In some implementations, portions of such top surface, bottom surface, and/or sides are secured (for example, permanently secured) to and/or within the first portion 6220*a* and/or second portion 6220*b*.

Inner band 6230 can be made of a material that is different than (for example, more elastic than) a material that portions 6220*a*, 6220*b* of outer band 6220 are made of. Inner band 6230 (or portions thereof) can be made of an elastic material. In some implementations, inner band 6230 comprises a material that is more stretchable than a material that portions 6220*a*, 6220*b* of outer band 6220 are made of. Such implementations can allow the inner band 6230 to stretch relative to outer band 6220, thereby varying a total length of strap 6202. Such total length of strap 6202 can be measured from an end of strap 6202 (for example, an end of portion 6220*b* of outer band 6220) that connects to module 6101 to an opposite end of strap 6202 (for example, an end of portion 6220*a*) and/or to buckle 6216 which may be connected to portion 6220*a* in some implementations. In some implementations, inner band 6230 comprises silicone and/or stretchable fabric and outer band 6220 (for example, portion 6220*a* and/or portion 6220*b*) comprises leather and/or fabric.

When strap 6202 is in a first state as shown in FIG. 76B, portions 6220*a*, 6220*b* can be positioned closer to one another than when strap 6202 is in a second state as shown in FIG. 76C. As discussed above, such first state (FIG. 76B) can be a neutral and/or unstretched state of strap 6202 (for example, of inner band 6230) and such second state (FIG. 76C) can be a stretched state of strap 6202 (for example, of inner band 6230). In some implementations, when strap 6202 is in the first state, there is no gap between the portions 6220*a*, 6220*b*. In some implementations, portions 6220*a*, 6220*b* contact one another when strap 6202 is in such first state and do not contact one another when strap 6202 is in such second state. Portions 6220*a*, 6220*b* can be closer to one another when strap 6202 is in the first state than when strap 6202 is in the second state. Such implementations can advantageously allow the inner band 6230 to be substantially hidden from view when strap 6202 is in such first state, which may increase aesthetic appearance of strap 6202 where outer band 6220 is more aesthetically appealing (for example, in color, material, and/or texture) than inner band 6230. In some alternative implementations, portions 6220*a*, 6220*b* are separated from one another by a gap when strap 6202 (for example, inner band 6230) is in such first state, and such gap can be less than about 0.5 inch, less than about 0.4 inch, less than about 0.3 inch, less than about 0.2 inch, less than about 0.1 inch, less than about 0.05 inch, less than about 0.04 inch, less than about 0.03 inch, less than about 0.02 inch, or less than about 0.01 inch. Such optional gap between portions 6220*a*, 6220*b* when strap 6202 is in such first state can be less than a gap between portions 6220*a*, 6220*b* when strap 6202 is in such second state (FIG. 76C).

FIG. 76C shows an illustrative position of strap 6202 in such above-described second state when inner band 6230 is extended (for example, stretched). However, the size of gap g and therefore overall appearance and amount of the visible portion of inner band 6230 can be variable depending upon the implementation and depending upon the amount by which inner band 6230 is extended.

Figure 76D:
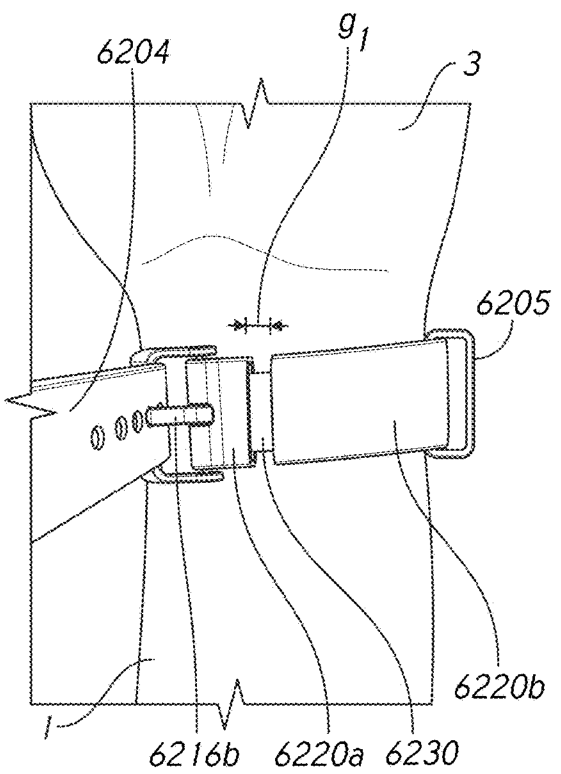
Figure 76E:
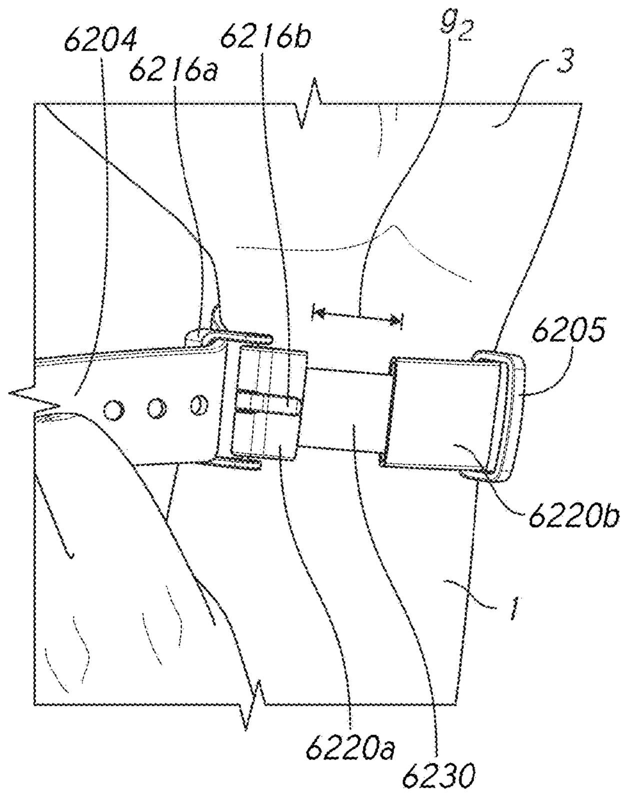
Figure 76F:
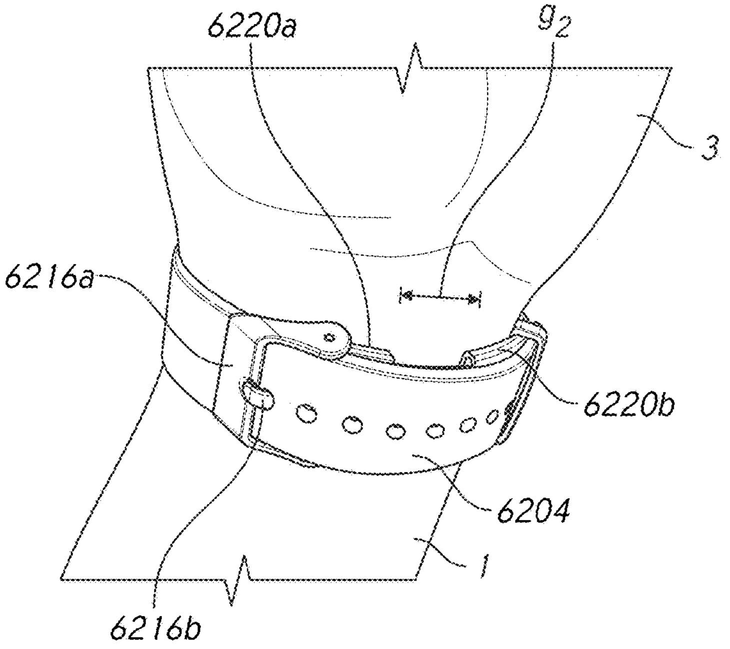

FIGS. 76D-76F illustrate how wearable device 6200 can be secured to a user's wrist 1 (for example, near a hand 3 of the user). With reference to FIG. 76D, straps 6202, 6204 can be wrapped around the wrist 1 and strap 6204 can be inserted through an opening defined by buckle 6216 (for example, by buckle body 216*a*). When strap 6202 is in the position shown in FIG. 76D, inner band 6230 can be stretched such that a gap g1 separates portions 6220*a*, 6220*b* of outer band 6220. Inner band 6230 can be stretched from a state shown in FIG. 76D to the state shown in FIG. 76E where a gap g2, greater than gap g1, separates portions 6220*a*, 6220*b* from one another. The stretching of inner band 6230 from a state where there is no gap between portions 6220*a*, 6220*b* to either of the states shown in FIGS. 76D-76D (where gaps g1, g2 are present between portions 6220*a*, 6220*b*) allows a total length of strap 6202 to be increased to accommodate a size and/or shape of the user's wrist when a particular size increment is selected by the user, for example, when the user inserts a buckle tongue 6216*b* of buckle 6216 through one of a plurality of openings in strap 6204. Accordingly, FIGS. 76D-76E illustrate how inner band 6230 advantageously allows the strap 6202 to provide greater "fine tuning" of size adjustment and comfort during securement of the wearable device 6200 to the user 1. FIG. 76F illustrates how the straps 6202, 6204 can be secured to one another, for example, after a final step whereby an end of strap 6204 is inserted through the strap loop 6205 along strap 6202 of wearable device 6200. In some implementations, when straps 6202, 6204 are secured, for example, as shown in FIG. 76F, strap 6204 is adjacent and/or covers gap g2 such that inner band 6230 is not visible or less visible. In such implementations, a portion of inner band 6230 that is positioned between portions 6220*a*, 6220*b* is positioned between the user's skin and strap 6204.

Figure 77A:
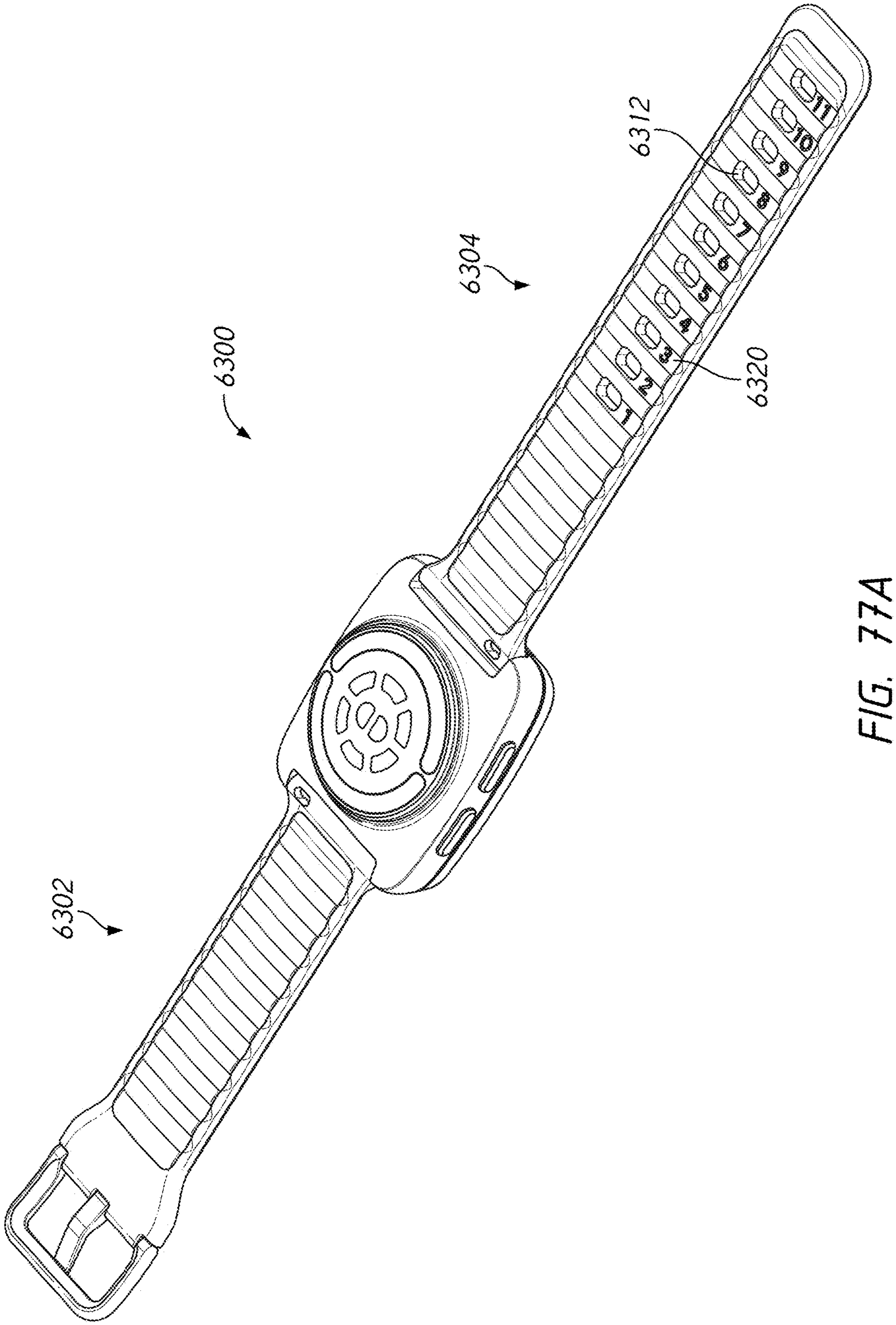
Figure 77B:
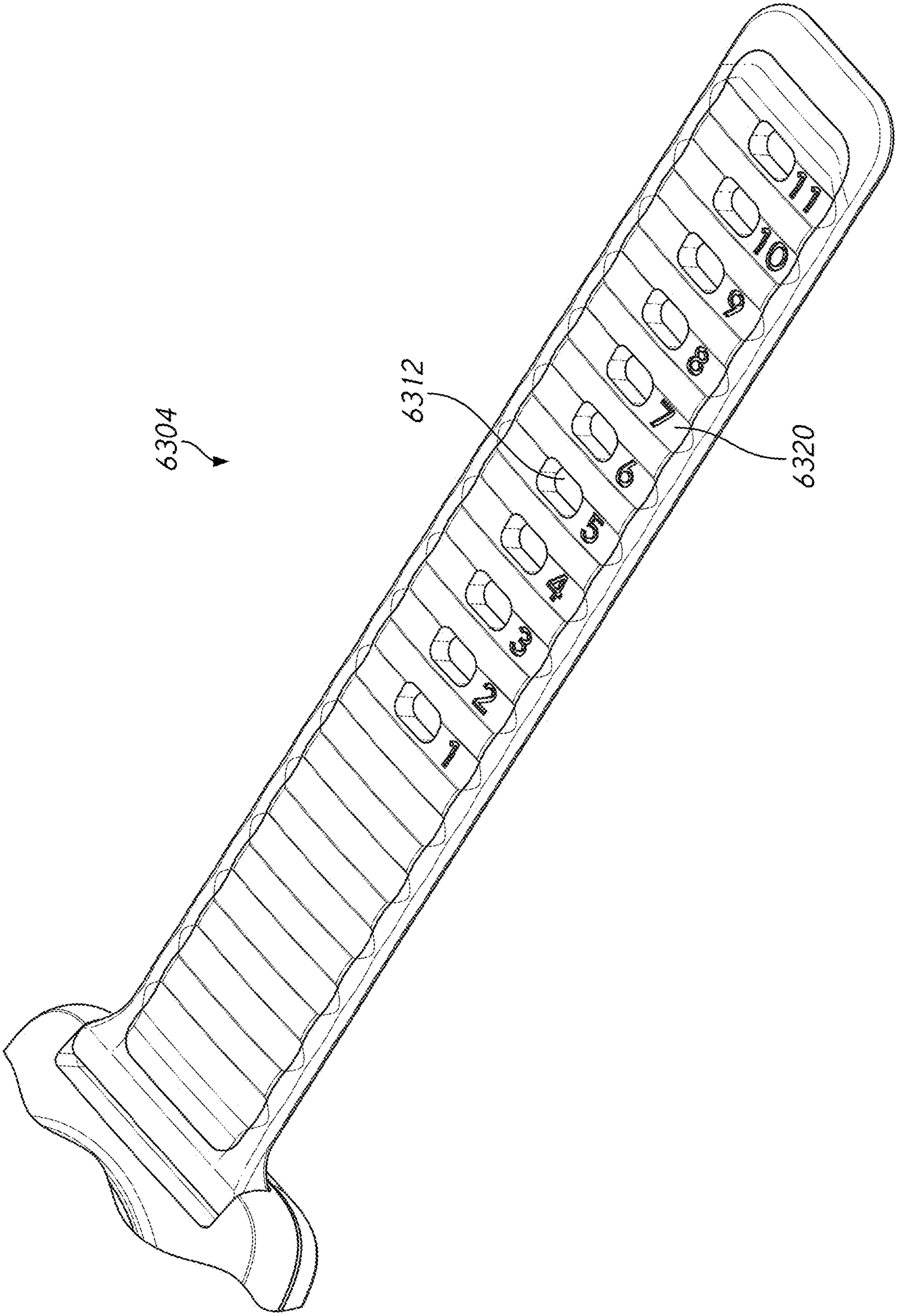

In some cases, any of the bands disclosed herein can include a plurality of characters 6320, as shown in FIGS. 77A-77B. For example, a wearable device 6300 can include a strap 6302, and a strap 6304. At least one of the straps 6302, 6304 can include a plurality of characters 6320. The plurality of characters 6320 can be positioned on a bottom surface of the band strap 6304. Each of the plurality of characters 6320 can be positioned adjacent to a plurality of openings 6312. Although the wearable device 6300 shown in FIGS. 77A and 77B includes a plurality of numbers ranging from 1 to 11, the plurality of characters can include letters, symbols, any other suitable characters, or a combination thereof. Further, the plurality of characters 6320 can include more than or less than eleven characters, and the plurality of openings 6312 along the band strap 6304 can include less than or more than eleven openings. For example, a band strap can include eight openings and eight characters, wherein each character is associated to each opening. Each of the plurality of characters 6320 can provide an indication to a user of the tightness of the wearable device 6300. For example, and without limitation, each of the plurality of characters 6320 can be associated to an opening in a plurality of openings 6312 on the band strap 6304.

In addition to instructing a user to increase or decrease the level of tightness of the strap and determining if the quality of the signal data has improved or degraded, in some cases, the device can also instruct the user to wear the device using a specific notch or opening of the strap. For example, if a user secures the device to her wrist using opening associated to character "5", and the device determines, after analyzing the quality level of the signals from the optical physiological sensor, that the quality level of the signals is below a threshold quality level, the device can instruct the user to try a different opening or notch and/or instruct the user to try, for example, the opening associated to characters "4" or "6". In some cases, the instruction can include an instruction to try one or more openings or notches (e.g., openings "6-7" and/or "3-4"). If the quality of the signal data has improved and the quality level of signal data meets or exceeds the threshold or desired value, then no further adjustments may be needed. If the quality of the signal data has improved but the quality level of signal data is below the threshold or desired value, then the device can be configured to instruct the user to continue tightening the strap if the strap was tightened in the previous step or continue loosening the strap if the strap was loosened in the previous step, and instruct the user to wear the device using specific openings and/or notches of the strap. The device can instruct the user to wear the device using a specific opening or notch by displaying to the user on the display (e.g., display 12) the characters associated to that specific notch or opening and an instruction to try such openings or notches. In some examples, and without limitation, the device can be configured to instruct a user to tighten the strap until the band does not slide or move around with respect to skin, and then to tighten the strap one notch further.

Figure 78A:
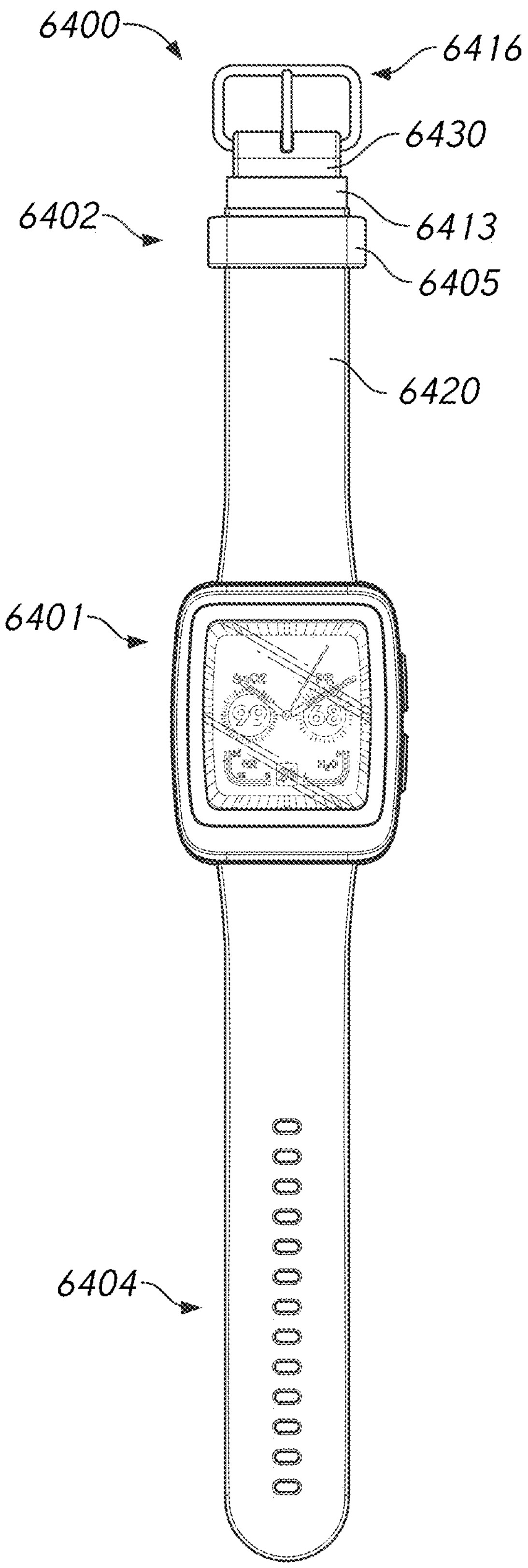
Figure 78B:
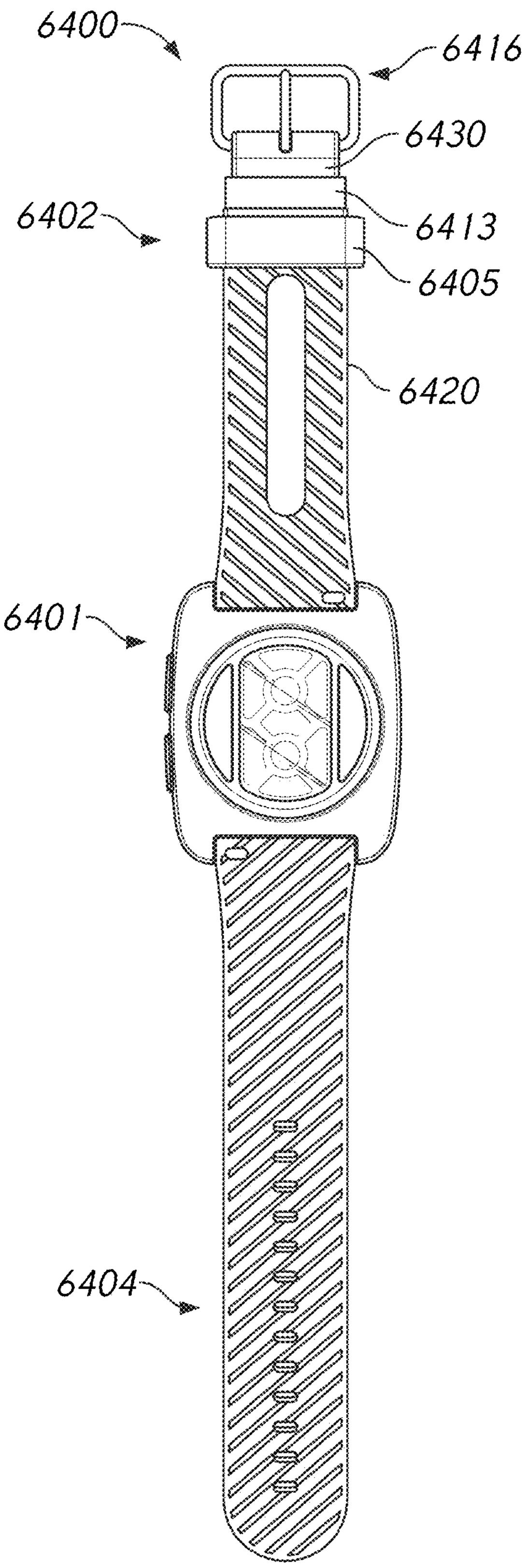
Figure 78C:
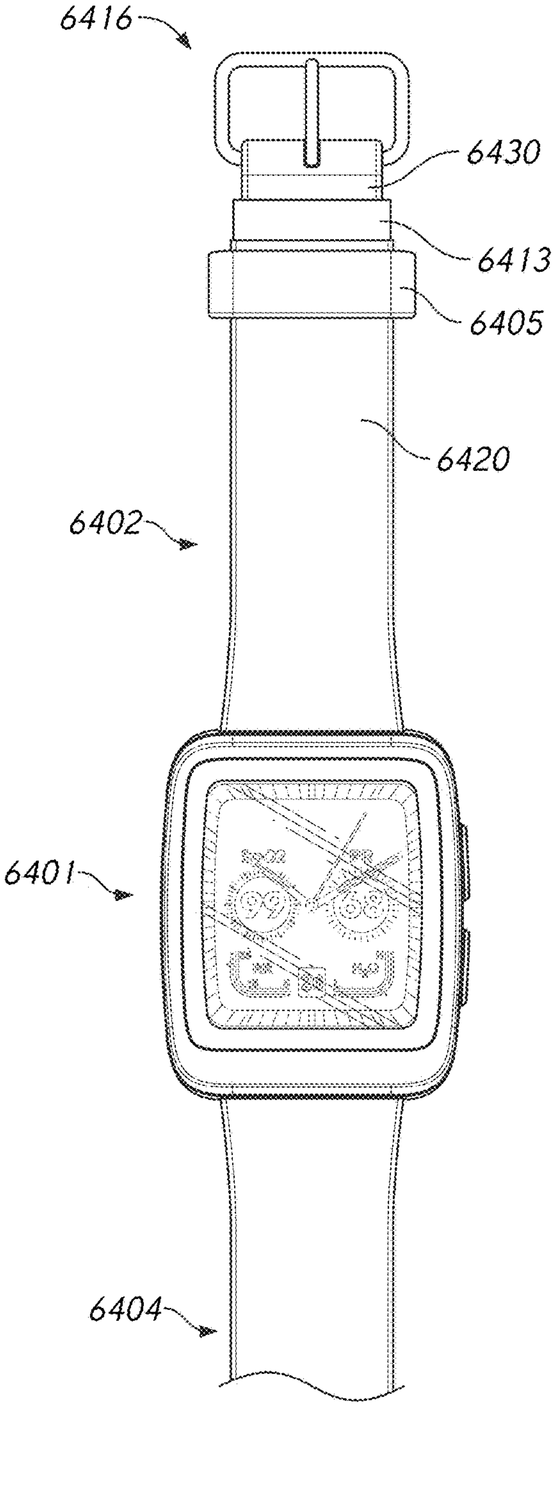
Figure 78D:
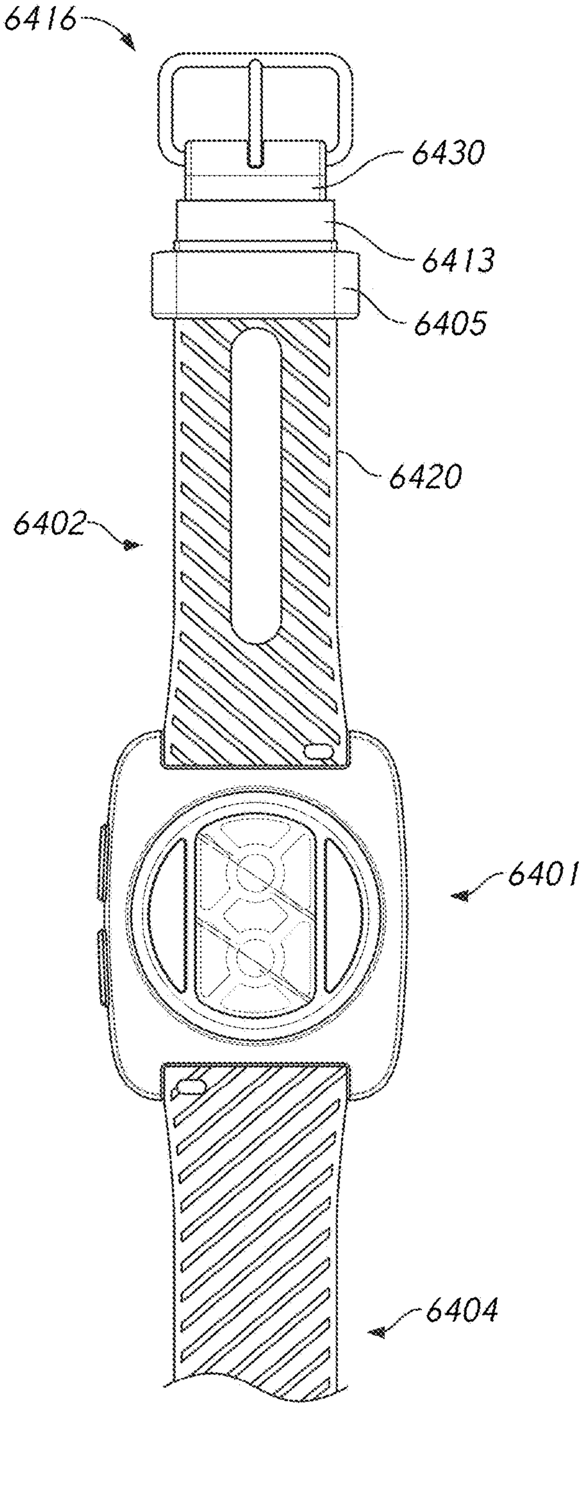
Figure 78E:
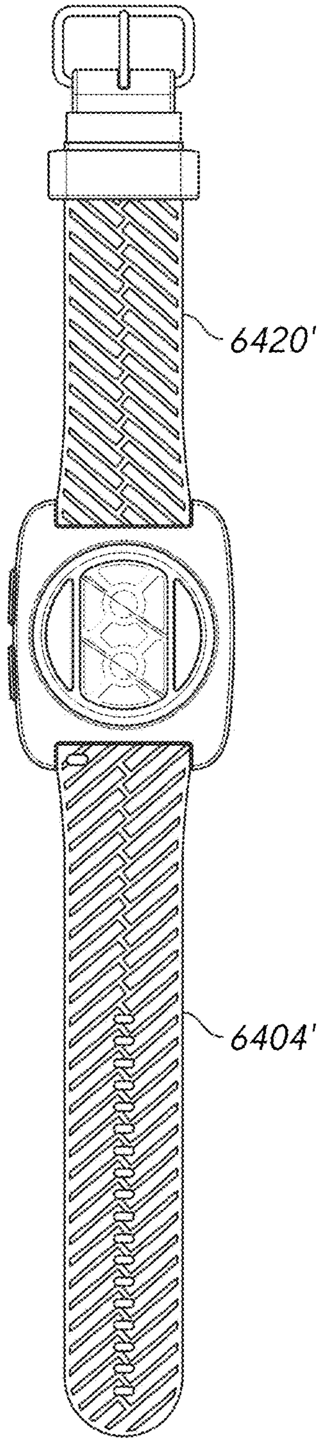
Figure 78F:
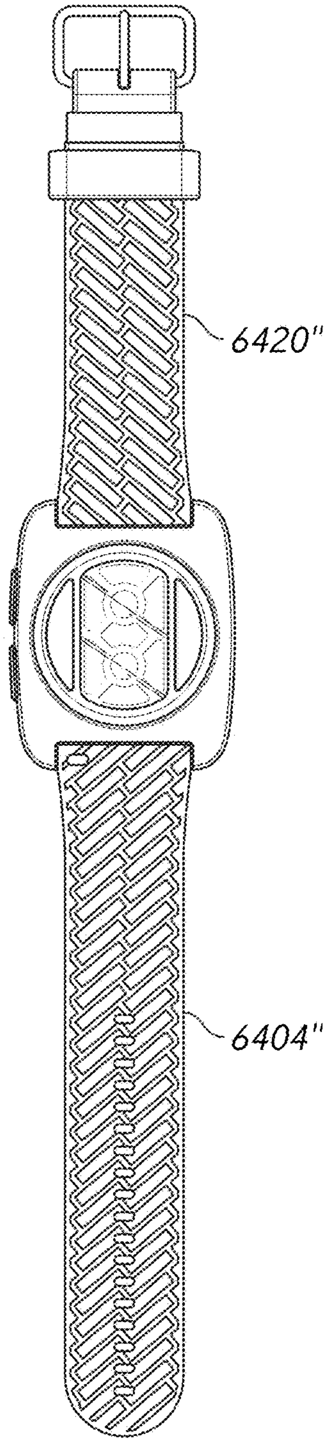
Figure 78G:
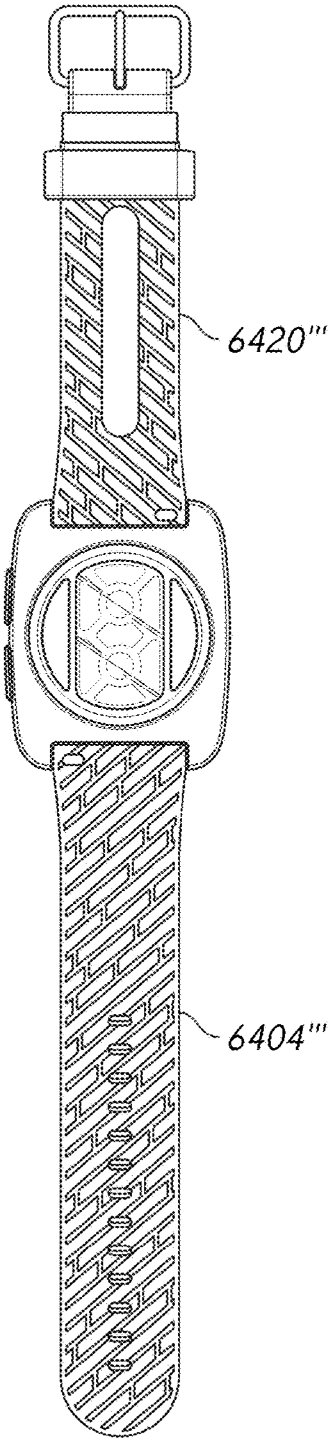
Figure 79A:
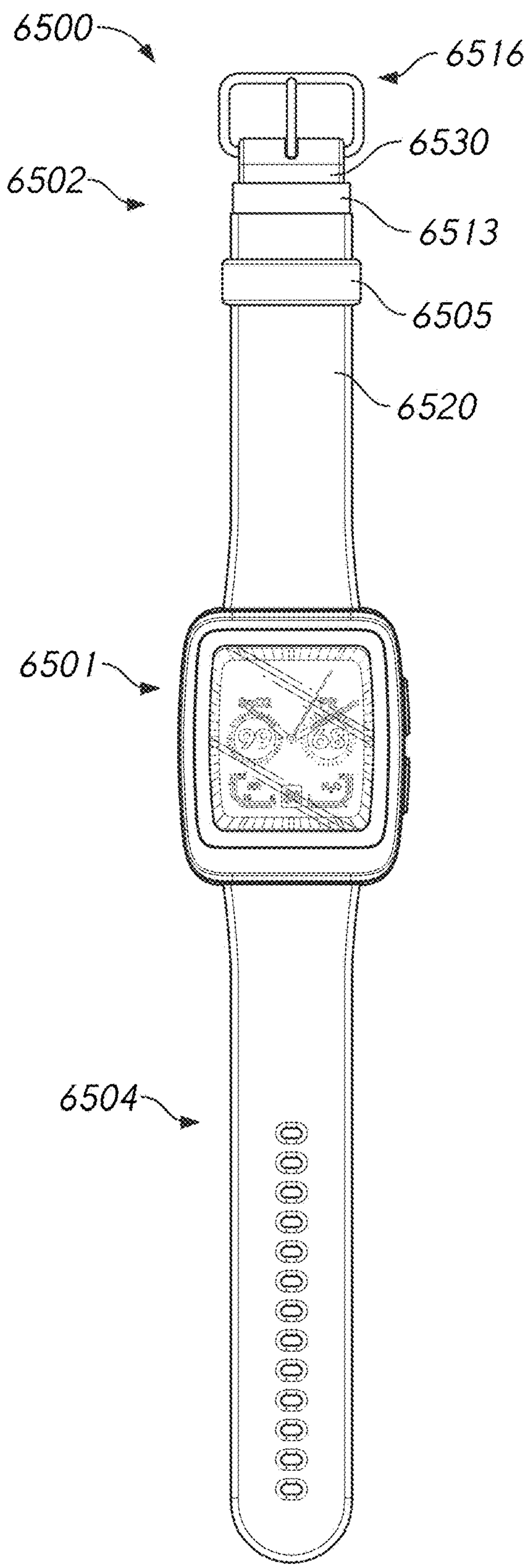
Figure 79B:
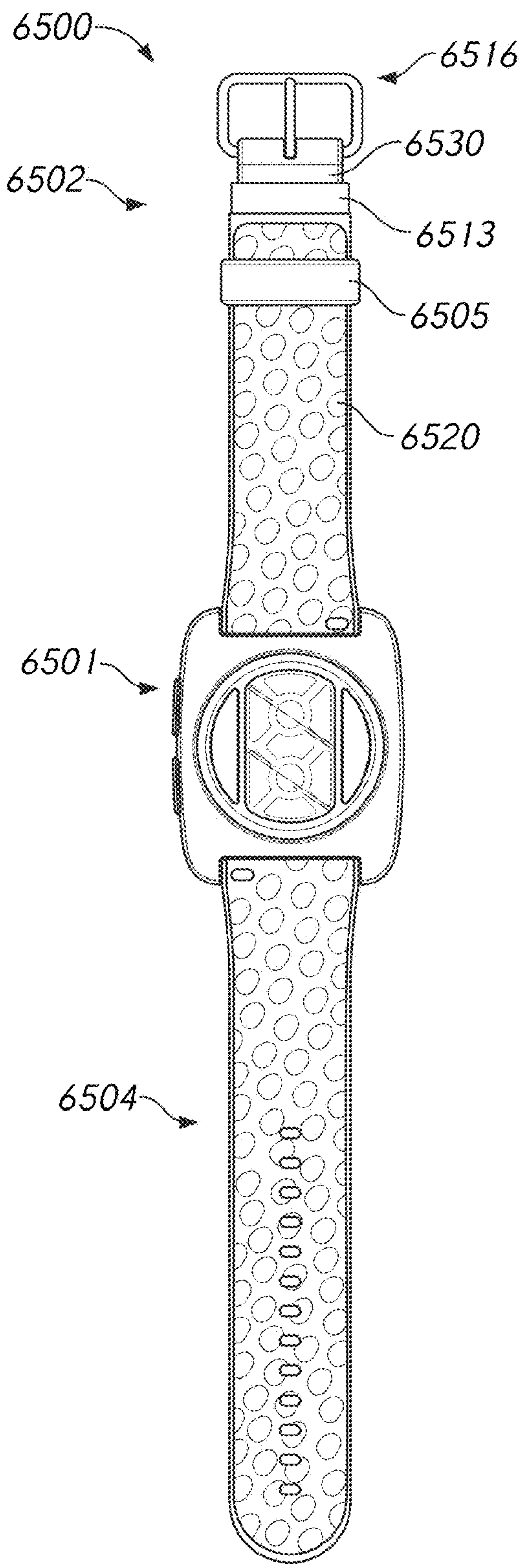
Figure 79C:
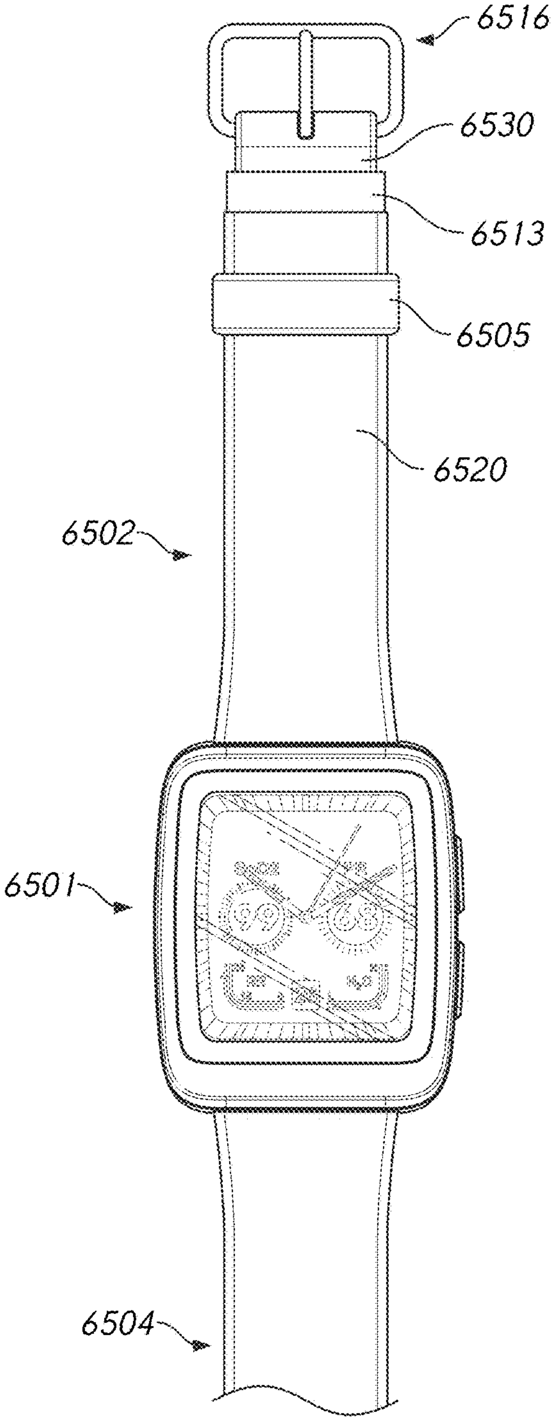
Figure 79D:
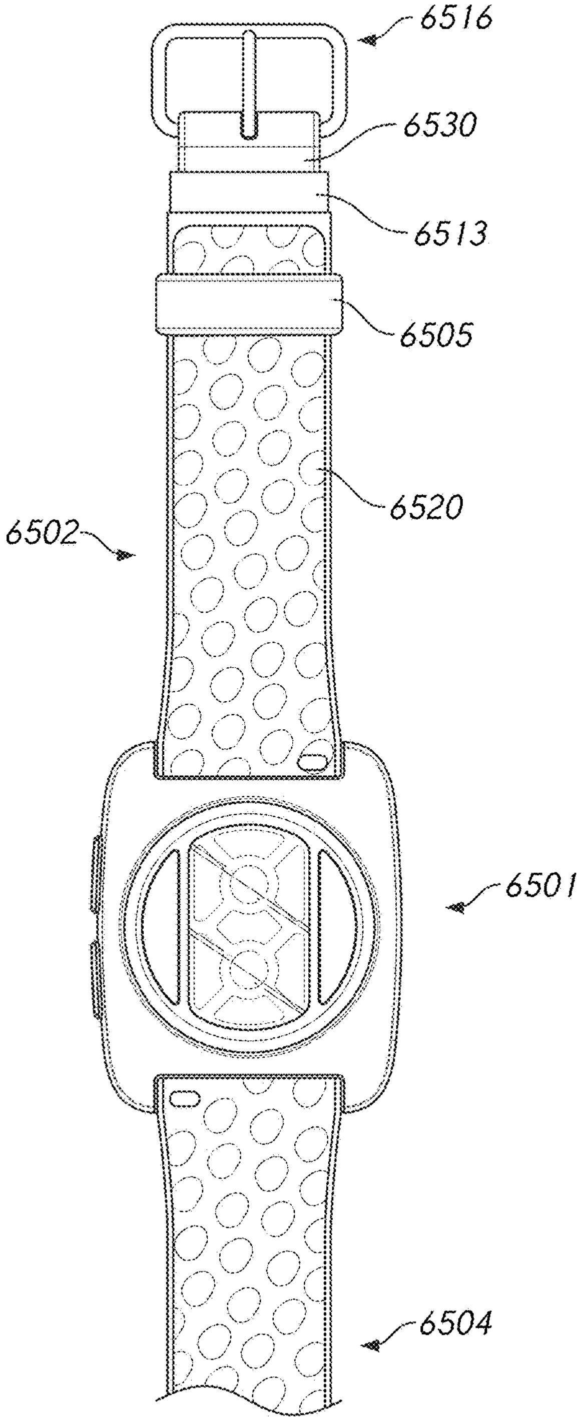

FIGS. 78A-78D illustrate a wearable device 6400. Wearable device 6400 can include a strap 6402, a strap 6404, and a watch module 6401. Watch module 6401 can be similar or identical to watch module 6101 in some or many respects. Strap 6402 can be similar or identical to strap 6102 in some or many respects. For example, strap 6402 can include an outer band 6420, an inner band 6430, a strap loop 6405, a collar 6413, and/or a buckle 6416 that can be similar or identical to outer band 6120, inner band 6130, strap loop 6105, collar 6113, and/or buckle 6116 (respectively) as described herein. Strap 6404 can be similar or identical to strap 6104 in some or many respects. For example, strap 6404 can include a plurality of openings similar or identical to openings 6112 discussed above. Strap 6402 and/or 6404 can be connected to watch module 6401 in a similar or identical manner as that described elsewhere herein with resect to straps 6102, 6104 and watch module 6101. With reference to FIGS. 78A-78D, a surface (for example, a surface configured to face towards the subject's skin when the wearable device 6400 is worn) can include ornamentation. FIGS. 78E-78G illustrate additional implementations of outer bands 6420', 6420", 6420' and straps 6404', 6404", 6404'" that can be utilized in wearable device 6400. Straps 6402, 6404 can comprise any of the materials described elsewhere herein with respect to, for example, straps 6102, 6104. For example, outer band 6420 can comprise leather, fabric, and/or plastic among other materials, and inner band 6430 can comprise silicone and/or fabric, among other materials. In some implementations, inner band 6430 comprises a material that is more stretchable than a material of the outer band 6420.

FIGS. 79A-79D illustrate a wearable device 6500. Wearable device 6500 can include a strap 6502, a strap 6504, and a watch module 6501. Watch module 6501 can be similar or identical to watch module 6101 in some or many respects. Strap 6502 can be similar or identical to strap 6102 in some or many respects. For example, strap 6502 can include an outer band 6520, an inner band 6530, a strap loop 6505, a collar 6513, and/or a buckle 6516 that can be similar or identical to outer band 6120, inner band 6130, strap loop 6105, collar 6113, and/or buckle 6116 (respectively) as described herein. Strap 6504 can be similar or identical to strap 6104 in some or many respects. For example, strap 6504 can include a plurality of openings similar or identical to openings 6112 discussed above. Strap 6502 and/or 6504 can be connected to watch module 6501 in a similar or identical manner as that described elsewhere herein with respect to straps 6102, 6104 and watch module 6101. With reference to FIGS. 79A-79D, a surface (for example, a surface configured to face towards the subject's skin when the wearable device 6500 is worn) can include ornamentation. Straps 6502, 6504 can comprise any of the materials described elsewhere herein with respect to, for example, straps 6102, 6104. For example, outer band 6520 can comprise leather, fabric, and/or plastic among other materials, and inner band 6530 can comprise silicone and/or fabric, among other materials. In some implementations, inner band 6530 comprises a material that is more stretchable than a material of the outer band 6520.

Figure 80A:
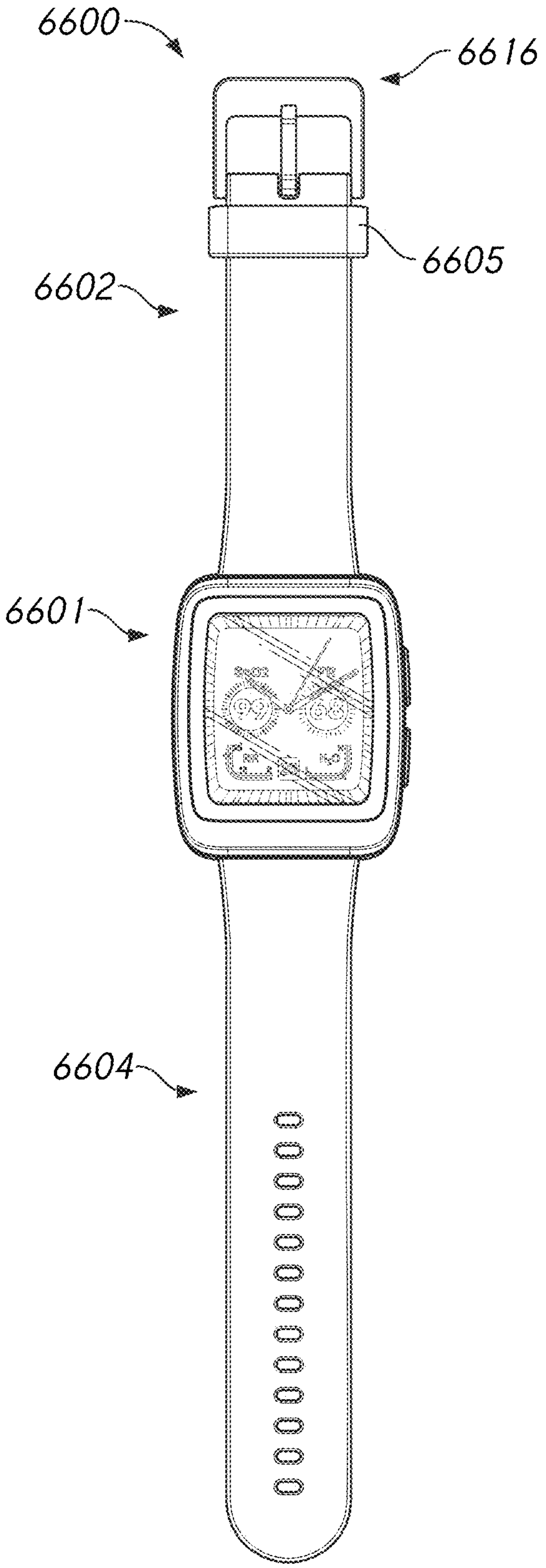
Figure 80B:
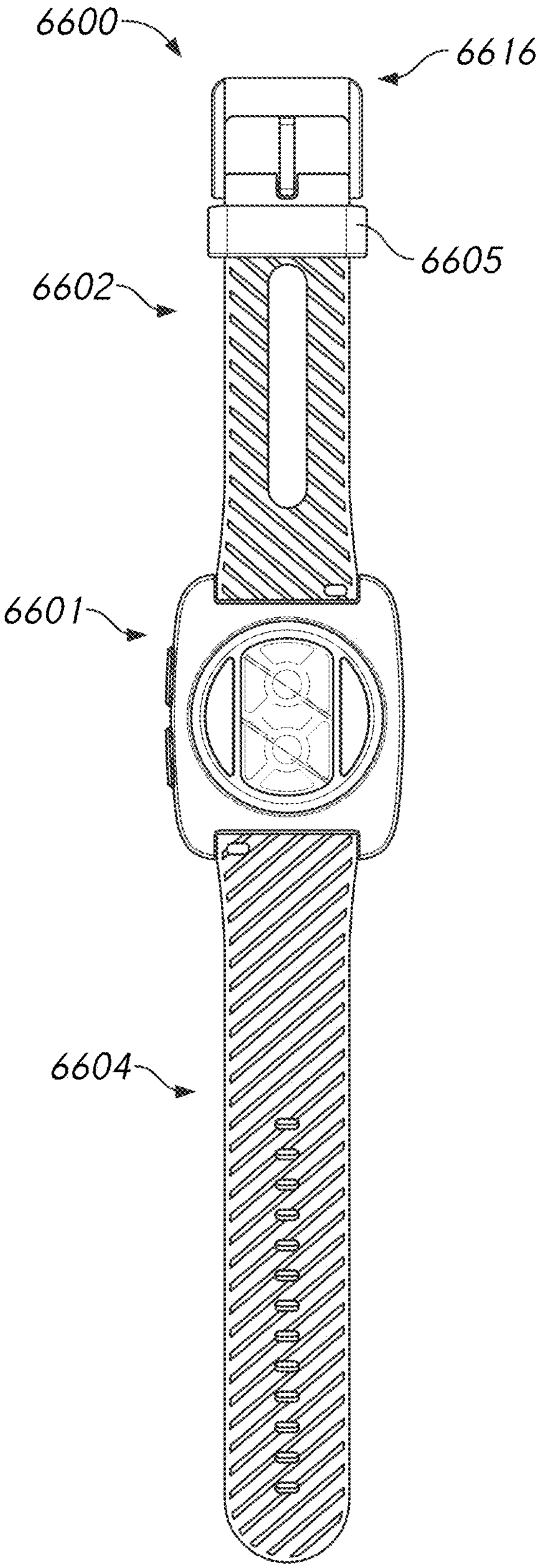
Figure 80C:
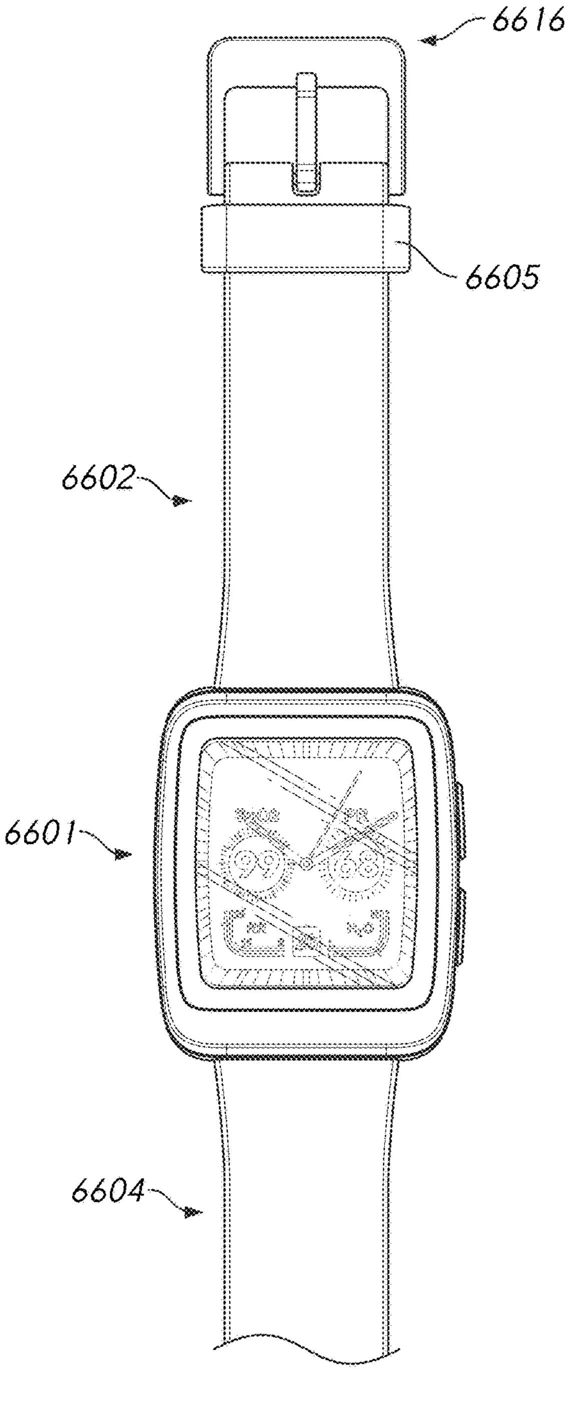
Figure 80D:
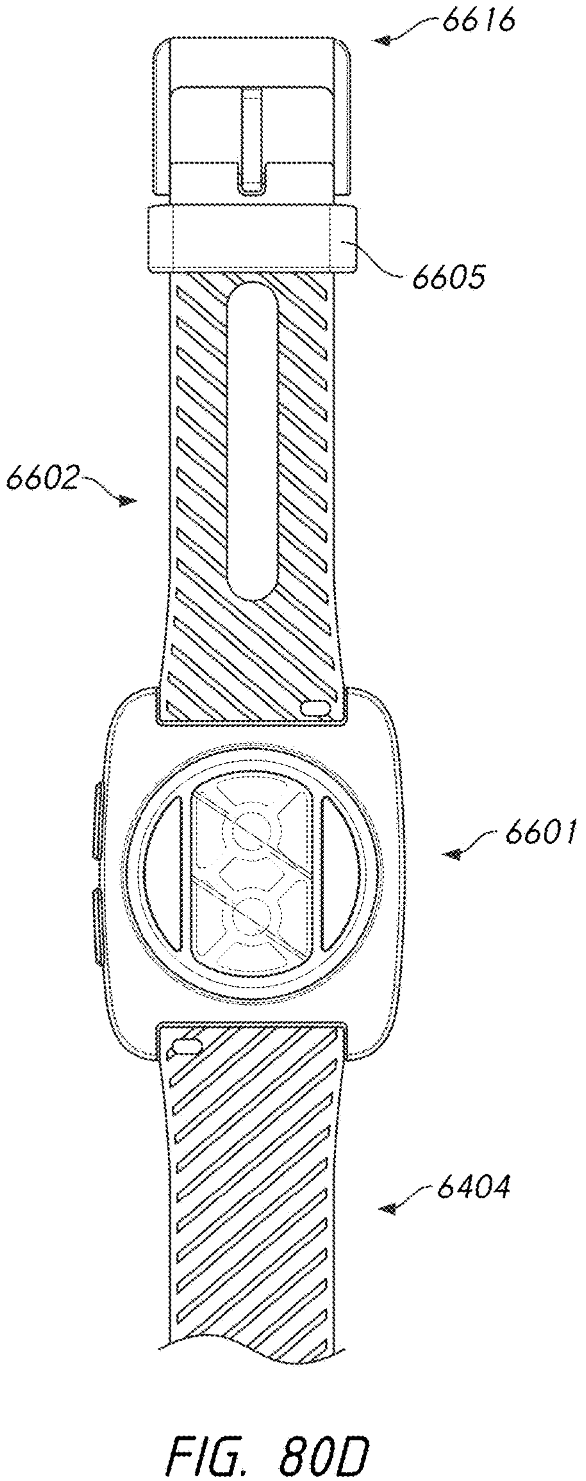
Figure 80E:
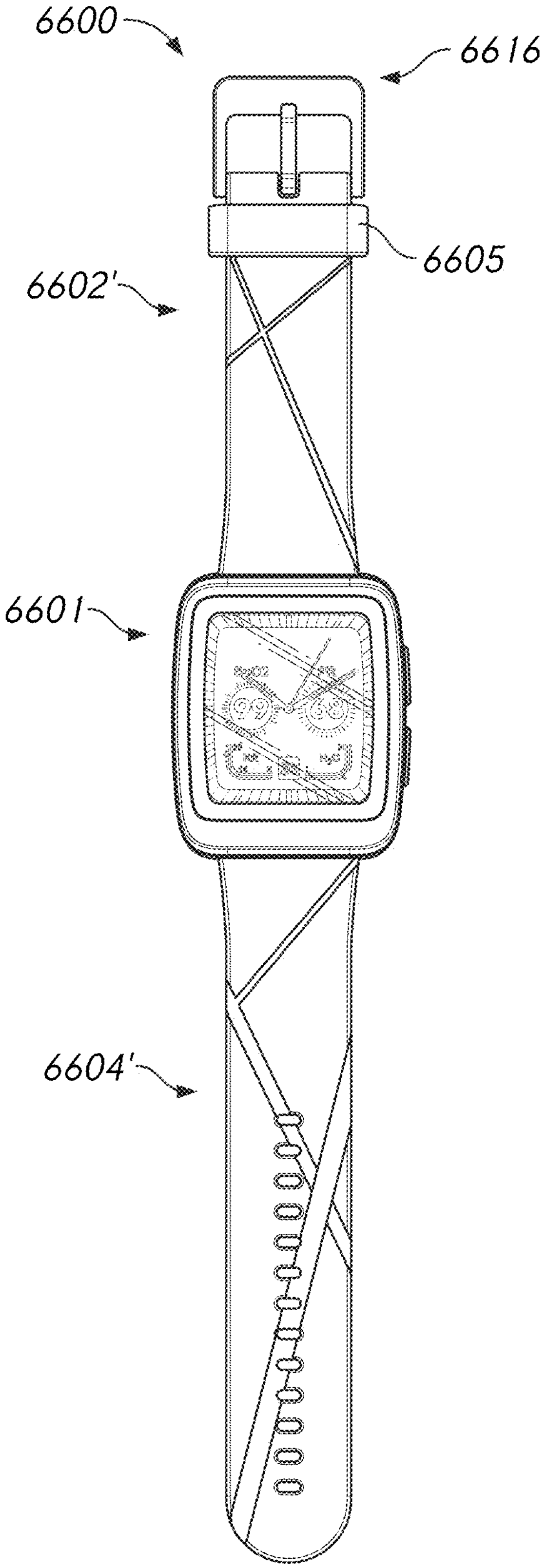

FIGS. 80A-80D illustrate a wearable device 6600. Wearable device 6600 can include a strap 6602, a strap 6604, and a watch module 6601. Watch module 6601 can be similar or identical to watch module 6101 in some or many respects. Strap 6602 can be similar or identical to strap 6102 in some or many respects. In some implementations, strap 6602 includes a single band instead of inner and outer bands like inner and outer bands 6130, 6120 of strap 6102. Strap 6602 can include a strap loop 6605 and/or a collar 6613 that can be similar or identical to strap loop 6105 and collar 6113 (respectively). Strap 6604 can be similar or identical to strap 6104 in some or many respects. For example, strap 6504 can include a plurality of openings similar or identical to openings 6112 discussed above. Strap 6602 and/or 6604 can be connected to watch module 6601 in a similar or identical manner as that described elsewhere herein with resect to straps 6102, 6104 and watch module 6101. With reference to FIGS. 80B and 80D, a surface (for example, a surface configured to face towards the subject's skin when the wearable device 6600 is worn) can include ornamentation. FIG. 80E illustrates straps 6602', 6604' having surface ornamentation. Straps 6602, 6604 can comprise any of the materials described elsewhere herein with respect to, for example, straps 6102, 6104. For example, strap 6602 and/or strap 6604 can comprise leather, fabric, silicone, and/or plastic among other materials. In some implementations, straps 6602, 6604 comprises a stretchable material, such as any of those described herein.

Example Additional Features of the Wearable Device

The wearable device examples disclosed herein can provide protection of the wearer's safety by sending an alert to a first responder (for example, a hospital emergency room, a firefighter, 911, security at the facility where the wearer is located, or otherwise) and/or the wearer's family or guardian when the wearer is in danger, for example, when the wearer is drowning. The wearable device can include a swim mode, which the wearer can activate when going swimming. The physiological parameter measurement module of the wearable device can monitor one or more parameters to determine that the wearer is likely drowning (such as drowning of a child in water), for example, by determining that the wearer's respiratory rate has become irregular (such as showing fluctuations greater than a predetermined number per minute), or the wearer's SpO2 value declines by a predetermined amount, or otherwise. Alternatively, the module processor can determine that wearer is likely drowning based on the gyroscope and/or accelerometer readings, which can further be combined with the parameters monitored by the other sensors. In response to determining that the wearer is likely drowning, the module can send a notification to the processor of the wearable device, which can send an alert to a first responder and/or the wearer's family or guardian. Additionally or alternatively, the wearable device can include a distress button that the wearer can push in an emergency, such as when the wearer is drowning, has sustained a fall (which can alternatively or additionally be determined using the gyroscope and/or accelerometer readings, which can further be combined with the parameters monitored by the other sensors) while being alone, or otherwise.

The physiological parameters (for example but not limited to, SpO2, PR, PI, PVI, RR, Hydration, ECG-related parameters, etc.) measured by the module disclosed herein can be reliable enough for healthcare or medical purposes, for example, in hospitals. The module can be configured to take measurements at the same time every day. The wearable device (or the physiological parameter measurement module of the device) can further include a hospital patient ID tag on a near-field communication (NFC) or Bluetooth chip, or a watch strap or band. Essential patient information, such as the patient's name, admission date, reason for admission, blood type, drug allergies, etc. can be stored on the memory device of the watch or the physiological parameter measurement module. The patient ID tag cannot be easily removed and/or may include special tools like theft prevention devices, for example, requiring the patient to cut the watch strap off. Alternatively, the wearable device can display the patient information (for example, name, admission date, etc.) on the screen when the patient is admitted to the hospital. The patient ID tag can be either disposable after the patient is discharged or reusable after disinfection. The physiological parameter measurement module can be removed and replaced when the patient ID tag (for example, the watch band) is changed. If the wearable device is worn by a caregiver, the caregiver can use the wearable device for communications with other caregivers (for example, to share critical, real-time information about patients, update changes in patient status, and/or the like), replacing the need for specialized communication tools, for example, Vocera®, Spok®, etc.

Terminology

Many other variations than those described herein will be apparent from this disclosure. For example, certain acts, events, or functions of any of the algorithms described herein can be performed in a different sequence, can be added, merged, or left out altogether (for example, not all described acts or events are necessary for the practice of the algorithms). Moreover, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

It is to be understood that not necessarily all such advantages can be achieved in accordance with any particular example of the examples disclosed herein. Thus, the examples disclosed herein can be embodied or carried out in a manner that achieves or optimizes one advantage or group of advantages as taught herein without necessarily achieving other advantages as may be taught or suggested herein.

The various illustrative logical blocks, modules, and algorithm steps described in connection with the examples disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the examples disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry or digital logic circuitry configured to process computer-executable instructions. In another example, a processor can include an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the examples disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "for example," and the like, unless specifically stated otherwise, or otherwise understood within the context as used, is generally intended to convey that certain examples include, while other examples do not include, certain features, elements and/or states. Thus, such conditional language is not generally intended to imply that features, elements and/or states are in any way required for one or more examples or that one or more examples necessarily include logic for deciding, with or without author input or prompting, whether these features, elements and/or states are included or are to be performed in any particular example. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain examples require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "approximately," "about," "generally," and "substantially"

as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 10 degrees, 5 degrees, 3 degrees, or 1 degree. As another example, in certain embodiments, the terms "generally perpendicular" and "substantially perpendicular" refer to a value, amount, or characteristic that departs from exactly perpendicular by less than or equal to 10 degrees, 5 degrees, 3 degrees, or 1 degree.

While the above detailed description has shown, described, and pointed out novel features as applied to various examples, it will be understood that various omissions, substitutions, and changes in the form and details of the devices or algorithms illustrated can be made without departing from the spirit of the disclosure. As will be recognized, the inventions described herein can be embodied within a form that does not provide all of the features and benefits set forth herein, as some features can be used or practiced separately from others.

Additionally, all publications, patents, and patent applications mentioned in this specification are herein incorporated by reference to the same extent as if each individual publication, patent, or patent application was specifically and individually indicated to be incorporated by reference.

What is claimed is:

1. A wearable device configured to monitor physiological parameters of a wearer, the wearable device comprising:

a physiological parameter measurement sensor configured to monitor a plurality of physiological parameters;

a hardware processor;

a power source configured to power at least the wearable device and the physiological parameter measurement sensor;

a display in communication with the hardware processor, the display configured to display the plurality of physiological parameters monitored by the physiological parameter measurement sensor; and a band comprising a plurality of characters and configured to secure the physiological parameter measurement sensor to the wearer;

wherein the hardware processor is configured to:

obtain a first plurality of signals from the physiological parameter measurement sensor when the band is secured to the wearer at a first tightness;

determine a signal quality responsive to the first plurality of signals; and output an indication on the display to adjust tightness of the band with respect to a wrist from the first tightness to a second tightness based on the determined signal quality;

wherein the indication comprises displaying at least one of the plurality of characters on the display.

2. The wearable device of claim 1, wherein the band is adjustable.

3. The wearable device of claim 1, wherein each of the plurality of characters comprise at least one of a number, a letter, a symbol, or a combination thereof.

4. The wearable device of claim 1, wherein the band comprises a first strap and a second strap, at least one of the first strap and the second strap comprising a plurality of holes configured to receive a securing mechanism.

5. The wearable device of claim 4, wherein the hardware processor is further configured to provide an indication to a user to secure the securing mechanism to at least one of the plurality of holes.

6. The wearable device of claim 4, wherein the plurality of holes extend along a length of the first strap and second strap, and wherein each of the plurality of characters is positioned adjacent to each of the plurality of holes.

7. The wearable device of claim 1, wherein each of the plurality of characters is displayed adjacent to each one of the plurality of holes of the first strap and the second strap.

8. A method of analyzing and notifying a user of a tension level of a strap of a wearable device configured to monitor physiological parameters of a wearer, comprising:

providing a strap having a plurality of holes and a plurality of characters associated to each of the plurality of holes;

obtaining a first plurality of signals from a physiological parameter measurement sensor when the strap is secured to the user at a first tightness;

determining a signal quality responsive to the first plurality of signals using a hardware processor; and outputting a message to a user to adjust the tightness of the strap from the first tightness to a second tightness based on the determined signal quality and displaying, on a display of the wearable device, at least one of the plurality of characters.

9. The method of claim 8, wherein the plurality of characters comprises at least one of a number, a letter, a symbol, or a combination thereof.

10. The method of claim 8, further comprising instructing the user to secure the strap to a specific hole of the plurality of holes associated to a specific character of the plurality of characters.

11. The method of claim 8, further comprising:

obtaining a second plurality of signals from the physiological parameter measurement sensor when the strap is secured to the user at the second tightness; and determining the signal quality responsive to the second plurality of signals using the hardware processor.

* * * * *